United States Patent [19]

Marchionni

[11] Patent Number: 5,876,973
[45] Date of Patent: Mar. 2, 1999

[54] METHOD FOR MAKING ANTIBODIES WHICH SPECIFICALLY BIND TO GLIAL GROWTH FACTORS

[75] Inventor: Mark Marchionni, Arlington, Mass.

[73] Assignee: Cambridge NeuroScience, Inc., Cambridge, Mass.

[21] Appl. No.: 469,660

[22] Filed: Jun. 6, 1995

Related U.S. Application Data

[60] Division of Ser. No. 11,396, Jan. 29, 1993, abandoned, which is a continuation-in-part of Ser. No. 984,085, Dec. 1, 1992, abandoned, which is a continuation-in-part of Ser. No. 951,747, Sep. 25, 1992, abandoned, which is a continuation-in-part of Ser. No. 927,337, Aug. 10, 1992, abandoned.

[51] Int. Cl.$^6$ .................................................. A61K 39/395
[52] U.S. Cl. .................. 435/70.21; 435/332; 424/152.1; 424/184.1; 530/388.2; 530/389.1
[58] Field of Search ........................... 435/70.21, 240.22, 435/332; 530/387.1, 388.2, 389.1; 424/184.1, 152.1

[56] References Cited

U.S. PATENT DOCUMENTS

| | | |
|---|---|---|
| 4,935,341 | 6/1990 | Bargmann et al. . |
| 4,968,603 | 11/1990 | Slamon et al. . |
| 5,367,060 | 11/1994 | Vandlen et al. . |
| 5,530,109 | 6/1996 | Goodearl et al. ...................... 536/23.5 |

FOREIGN PATENT DOCUMENTS

| | | |
|---|---|---|
| 0 246 753 | 4/1987 | European Pat. Off. . |
| PCT/US89/00051 | 7/1989 | WIPO . |
| PCT/US90/02697 | 11/1990 | WIPO . |
| PCT/US91/02331 | 10/1991 | WIPO . |
| PCT/US91/03443 | 12/1991 | WIPO . |
| WO 92/05184 | 4/1992 | WIPO . |
| PCT/US92/00329 | 7/1992 | WIPO . |
| PCT/WO92/12174 | 7/1992 | WIPO . |
| WO 92/12174 | 7/1992 | WIPO . |
| WO 92/18627 | 10/1992 | WIPO . |
| WO 94/00140 | 1/1994 | WIPO . |

OTHER PUBLICATIONS

Brockes et al., "The neuron as a source of mitogen", Development in the Nervous System, Garrod and Feldman, eds., pp. 309–327 (1980).

Davis et al., "Isolation and characterization of a neu protein–specific activating factor from human ATL–2 cell conditioned medium" Biochem. Biophys. Res. Communications 179:1536–1542 (1991).

Holmes et al., "Identification of Heregulin, a Specific Activator of p185erbB2" Science 256:1205–1210 (1992).

Huang et al., "Purification and Characterization of the neu/erb B2 Ligand–Growth Factor from Bovine Kidney" J. Biol. Chem. 257:11508–11512 (1992).

Lemke et al., "An immunochemical approach to the purification and characterization of glial growth factor", Monoclonal Antibodies to Neural Antigens, McKay et al., eds. 133–140 (1981).

Lupu et al., "Direct Interaction of a Ligand for the erbB2 Oncogene Product with the EGF Receptor and p185 erb2", Science 249:1552–1555 1990).

Tarakhovsky et al., "A 25 kDa polypeptide is the ligand for p185neu and is secreted by activated macrophages" Oncogene 6:2187–2196 (1991).

Brockes et al., "Assay and Isolation of Glial Growth Factor from the Bovine Pituitary", Methods In Enzym. 147:217–225, 1987.

Jeong et al., Dialog Medline Abs., J. Neurobiol. 22:462–74, 1991.

Jessel et al., "Induction of acetylcholine receptors on cultured skeletal muscle by a factor extracted from brain and spinal cord" PNAS USA 76:5397–5401, 1979.

Lentz et al., "Partial purification and characterization of a nerve trophic factor regulating muscle acetylcholinesterase activity" Exper. Neurology 73:542–557, 1981.

Markelonis et al., "Purification of sciatin using affinity chromatography on concanavalin A–Agarose" J. Neurochemistry 37:95–99., 1981.

Markelonis et al., Dialog Medline Abs. J. Cell Bio. 100:8–17, 1985.

Markelonis et al., Dialog Medline Abs. J. Neurochem 39:315–20, 1982.

Markelonis et al., Dialog Medline Abs. J. Biol. Chem. 255:8967–70, 1980.

Markelonis et al., Dialog Medline Abs. Dev. Biol. 89:353–61, 1982.

Markelonis et al., Dialog Medline Abs. Exp. Neurol. 58:285–95, 1978.

Markelonis et al., Dialog Medline Abs. J. Neurochem. 37:95–9, 1981.

Markelonis et al., Dialog Medline Abs. Exp. Neurol. 70:598–612, 1980.

Oh, "Neurotrophic effects of sciatic nerve extracts on muscle development in culture" Exp. Neurology 50:376–386, 1976.

Oh et al., Dialog Medline Abs. Dev. Biology 127:88–98, 1988.

(List continued on next page.)

*Primary Examiner*—Lila Feisee
*Assistant Examiner*—Julie E Reeves
*Attorney, Agent, or Firm*—Clark & Elbing LLP

[57] ABSTRACT

Disclosed is the characterization and purification of DNA encoding numerous polypeptides factors useful for the inhibition of cell (particularly, Schwann cell) proliferation. These factors are useful for the treatment of neural tumors. Also disclosed are the DNA sequences encoding novel polypeptides which may have use as agents which inhibit cell proliferation. Methods for the synthesis, purification, and testing of both known and novel polypeptides for their use as therapeutic and diagnostic aids in the treatment of diseases are also provided. Methods are also provided for the use of these polypeptides for the preparation of antibody probes. Such probes have diagnostic and therapeutic use in diseases involving neural and glial cells.

1 Claim, 68 Drawing Sheets

OTHER PUBLICATIONS

Oh et al., Dialog Medline Abs. J. Histochem Cytochem 29:1205–12, 1981.

Oh et al., Dialog Medline Abs. J. Neuros. Res. 8:535–45, 1982.

Oh et al., Dialog Medline Abs. PNAS USA 77:6922–5, 1980.

Oh et al., Dialog Medline Abs. Exp. Neurol. 67:646–54, 1980.

Oh et al., Dialog Medline Abs. Science 200:337–9, 1978.

Oh et al., Dialog Medline Abs. Exp. Neurol. 46:432–8, 1975.

Podleski et al., "Nerve extract induces increase and redistribution of acetylcholine receptors on cloned muscle cells" PNAS USA 75:2035–2039, 1978.

Thibault et al., "Trophic effect of a sciatic nerve extract on fast and slow myosin heavy chain synthesis" Am. Physiological Society 0363/6143; C269–C272, 1981.

Benveniste et al., Purification and Characterization of a Human T–lymphocyte–derived Glial Growth–Promoting Factor, Proc. Natl. Acad. Sci USA 82:3930–3934, 1985.

Brockes, Assay and Isolation of Glial Growth Factor from the Bovine Pituitary, Methods in Enzymology 147:217–225, 1987.

Brockes et al., Purification and Preliminary Characterization of a Glial Growth Factor from the Bovine Pituitary, The Journal of Biological Chemistry 255:8374–8377, 1980.

Davis et al., Platelet–derived Growth Factors and Fibroblast Growth Factors are Mitogens for Rat Schwann Cells, The Journal of Cell Biology 110:1353–1360, 1990.

Dobashi et al., Characterization of a neu/c–erbB–2 Protein–Specific Activating Factor, Proc. Natl. Acad. Sci. USA 88:8582–8586, 1991.

Kimura et al., Structure, expression and function of a schwannoma–derived growth factor, Nature 348:257–260, 1990.

Lemke et al., Identification and Purification of Glial Growth Factor, The Journal of Neuroscience 4:75–83, 1984.

Lupu et al., Characterization of a Growth Factor that Binds Exclusively to the erbB–2 Receptor and Induces Cellular Responses, Proc. Natl. Acad. Sci. USA 89:2287–2291, 1992.

Peles et al., Isolation of the Neu/HER–2 Stimulatory Ligand: A 44 kd Glycoprotein That Induces Differentiation of Mammary Tumor Cells, Cell 69:205–216, 1992.

Wen et al., Neu Differentiation Factor: A Transmembrane Glycoprotein Containing an EGF Domain and an Immunoglobulin Homology Unit, Cell 69:559–572, 1992.

Yarden et al., Biochemical Analysis of the Ligand for the neu Oncogenic Receptor, Biochemistry 30:3543–3550, 1991.

Yarden et al., Growth Factor Receptor Tyrosine Kinases, Ann. Rev. Biochem. 57:443–478, 1988.

Falls et al., "ARIA, a Protein That Stimulates Acetylcholine Receptor Synthesis, Is a Member of the Neu Ligand Family", Cell, 72:801–815, 1993.

Chan et al., "Identification of a Competative HGF Antagonist Encoded by an Alternative Transcript" Science 254:1382–1385, 1991.

Goodearl et al., "Identification and Purification of Glial Growth Factor–II" J. Cell. Biochem., Supp. 0, (16 part F) 79 abstract, 1992.

CM Cellulose

Hydroxylapatite HPLC

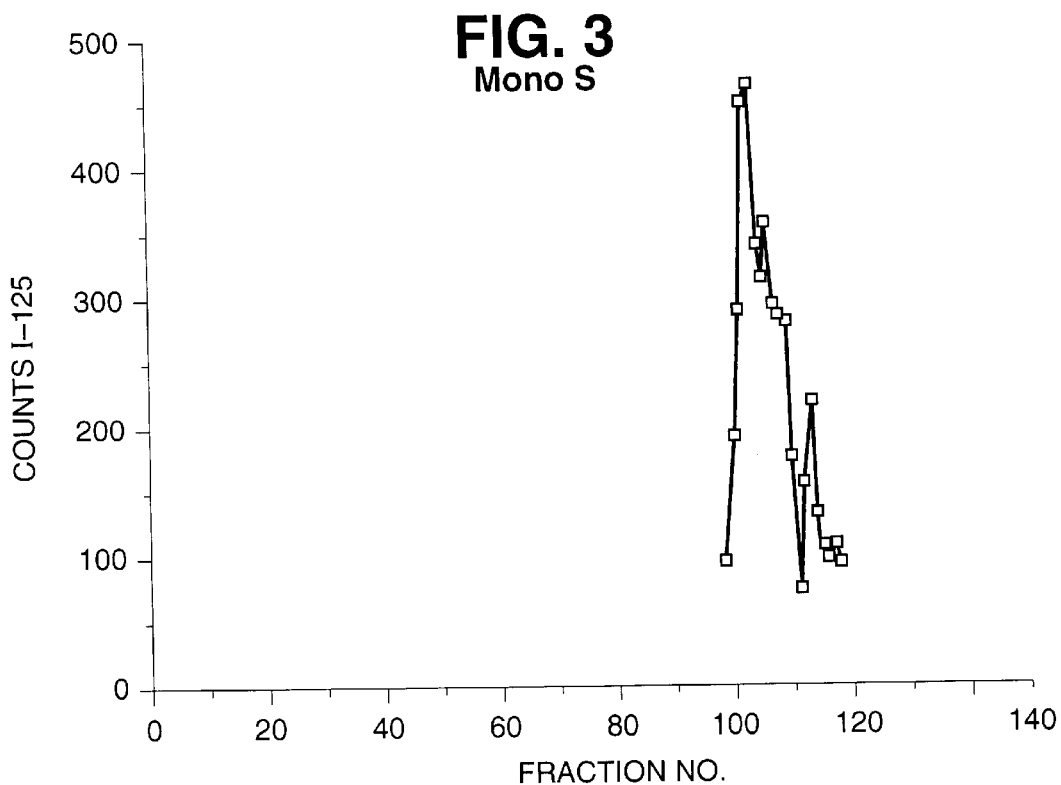
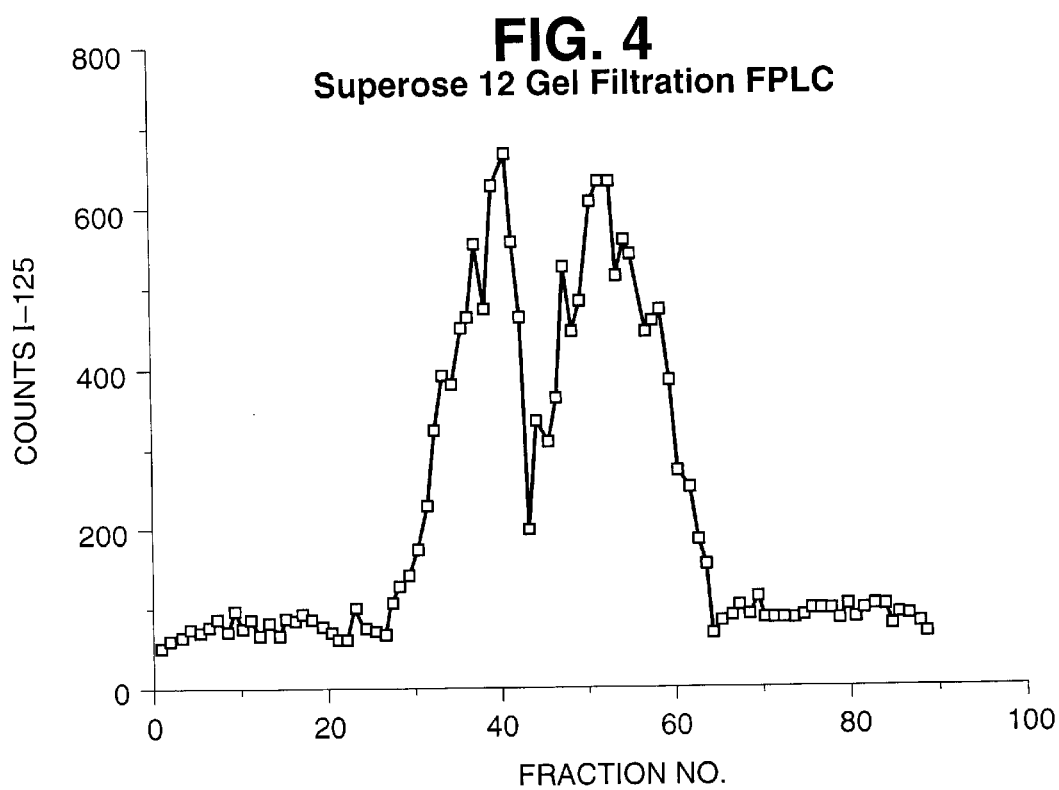

Reversed Phase HPLC

Reversed Phase HPLC

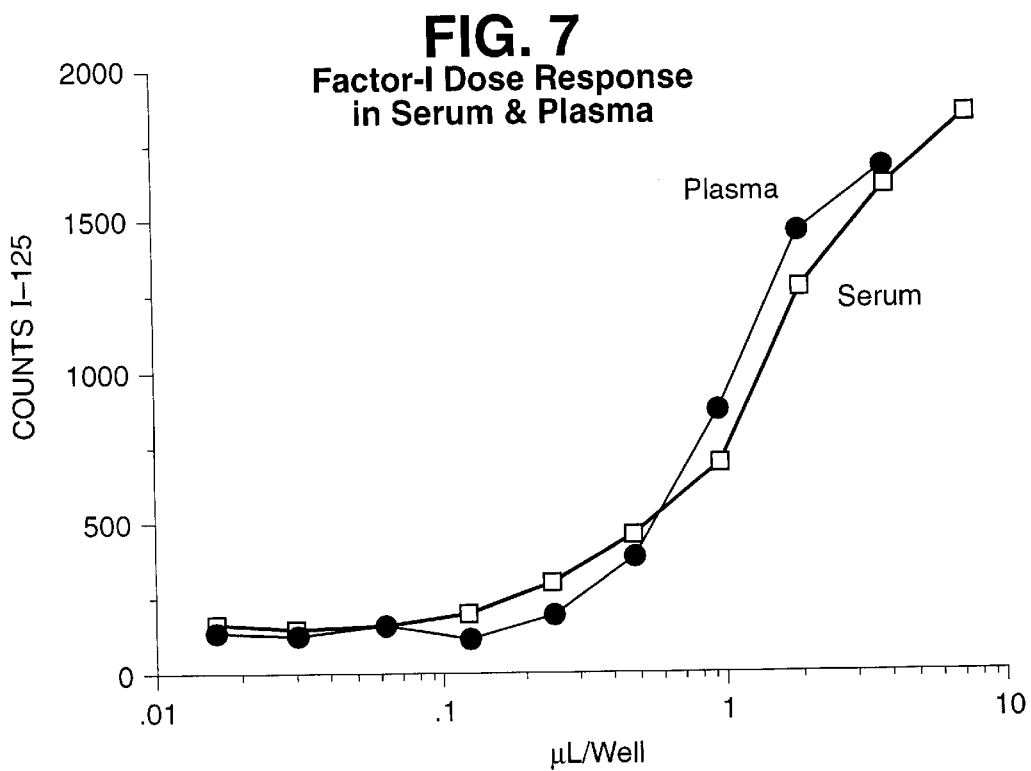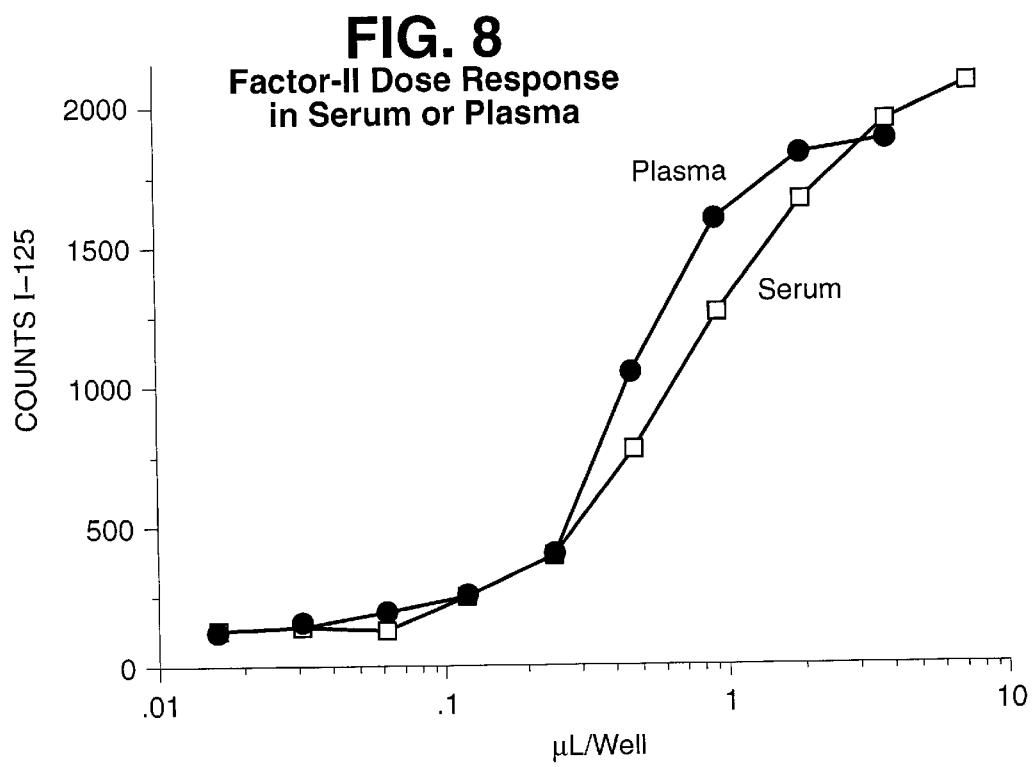

FIG. 9

```
           N-terminus
GGF-I 01   F K G D A H T E                            (SEQ ID NO: 1)

Trypsin peptides
GGF-I 02   K/R A S L A D E Y E Y M X K *              (SEQ ID NO: 2)
GGF-I 03   K/R T E T S S S G L X L K *                (SEQ ID NO: 3)
GGF-I 04   K/R K L G E M W A E                        (SEQ ID NO: 4)   HMG-1
GGF-I 05   K/R L G E K R A                            (SEQ ID NO: 5)   HMG-1?
GGF-I 06   K/R I K S E H A G L S I G D T A K *        (SEQ ID NO: 6)   HMG-2
GGF-I 07   K/R A S L A D E Y E Y M R K *              (SEQ ID NO: 7)
GGF-I 08   K/R I K G E H P G L S I G D V A K *        (SEQ ID NO: 8)   HMG-1
GGF-I 09   K/R M S E Y A F F V Q T X R *              (SEQ ID NO: 9)   HMG-2
GGF-I 10   K/R S E H P G L S I G D T A K *            (SEQ ID NO: 10)  HMG-1
GGF-I 11   K/R A G Y F A E X A R *                    (SEQ ID NO: 11)
GGF-I 12   K/R K L E F L X A K *                      (SEQ ID NO: 12)
GGF-I 13   K/R T T E M A S E Q G A                    (SEQ ID NO: 13)
GGF-I 14   K/R A K E A L A A L K *                    (SEQ ID NO: 14)
GGF-I 15   K/R F V L Q A K K *                        (SEQ ID NO: 15)
GGF-I 16   K/R L G E M W                              (SEQ ID NO: 16)  HMG-1

Protease V8 peptides
GGF-I 17   E T Q P D P G Q I L K K V P M V I G A Y T  (SEQ ID NO: 169)
GGF-I 18   E Y K C L K F K W F K K A T V M            (SEQ ID NO: 17)
GGF-I 19   E A K Y F S K X D A                        (SEQ ID NO: 18)  LH-alpha
GGF-I 20   E X K F Y V P                              (SEQ ID NO: 19)
GGF-I 21   E L S F A S V R L P G C P P P G V D P M V S F P V A L  (SEQ ID NO: 20)  LH-beta
```

| | | |
|---|---|---|
| GGF-I 01 | F K G D A H T E | (SEQ ID NO: 1) |
| GGF-I 02 | A S L A D E Y E Y M X K | (SEQ ID NO: 22) |
| GGF-I 03 | T E T S S G L X L K | (SEQ ID NO: 23) |
| GGF-I 07 | A S L A D E Y E Y M R K | (SEQ ID NO: 24) |
| GGF-I 11 | A G Y F A E X A R | (SEQ ID NO: 25) |
| GGF-I 13 | T T E M A S E Q G A | (SEQ ID NO: 26) |
| GGF-I 14 | A K E A L A A L K | (SEQ ID NO: 27) |
| GGF-I 15 | F V L Q A K K | (SEQ ID NO: 28) |
| GGF-I 17 | E T Q P D P G Q I L K K V P M V I G A Y T | (SEQ ID NO: 29) |
| GGF-I 18 | E Y K C L K F K W F K K A T V M | (SEQ ID NO: 17) |

B

| | | |
|---|---|---|
| GGF-I 20 | E X K F Y V P | (SEQ ID NO: 19) |
| GGF-I 12 | K L E F L X A K | (SEQ ID NO: 32) |

FIG. 11

Trypsin peptides

| | | |
|---|---|---|
| GGF-II 01 | K/R V H Q V W A A K * | (SEQ ID NO: 33) |
| GGF-II 02 | K/R Y I F F M E P E A X S S G | (SEQ ID NO: 34) |
| GGF-II 03 | K/R L G A W G P P A F P V X Y | (SEQ ID NO: 35) |
| GGF-II 04 | K/R W F V V I E G K * | (SEQ ID NO: 36) |
| GGF-II 05 | K/R A L A A A G Y D V E K * | (SEQ ID NO: 164) |
| GGF-II 06 | K/R L V L R * | (SEQ ID NO: 165) |
| GGF-II 07 | K/R X X Y P G Q I T S N | (SEQ ID NO: 166) Histone H1 |
| GGF-II 08 | K/R A S P V S V G S V Q E L V Q R * | (SEQ ID NO: 37) Trypsin |
| GGF-II 09 | K/R V C L L T V A A L P P T | (SEQ ID NO: 38) |
| GGF-II 10 | K/R D L L L X V | (SEQ ID NO: 39) |

Lysyl Endopeptidase-C peptides

| | | |
|---|---|---|
| GGF-II 11 | K V H Q V W A A K * | (SEQ ID NO: 51) |
| GGF-II 12 | K A S L A D S G E Y M X K* | (SEQ ID NO: 52) |

| | | | | | | | | | | | | | | |
|---|---|---|---|---|---|---|---|---|---|---|---|---|---|---|
| GGF-II 01 | V | H | Q | V | W | A | A | K | | | | | | (SEQ ID NO: 45) |
| GGF-II 02 | Y | I | F | F | M | E | P | E | A | X | S | S | G | (SEQ ID NO: 46) |
| GGF-II 03 | L | G | A | W | G | P | P | A | F | P | V | X | Y | (SEQ ID NO: 47) |
| GGF-II 04 | W | F | V | V | I | E | G | K | | | | | | (SEQ ID NO: 48) |
| GGF-II 08 | A | S | P | V | S | V | G | S | V | Q | E | L | V | Q R (SEQ ID NO: 49) |
| GGF-II 09 | V | C | L | L | T | V | A | A | L | P | P | T | | (SEQ ID NO: 50) |
| GGF-II 11 | K | V | H | Q | V | W | A | A | K | | | | | (SEQ ID NO: 51) |
| GGF-II 12 | K | A | S | L | A | D | S | G | E | Y | M | X | K | (SEQ ID NO: 52) |

B    Novel Factor II Peptides - others

GGF-II 10    D L L L X V      (SEQ ID NO: 53)

Comparison of BrdU-ELISA and [125 I]UdR Counting Method for the DNA Synthesis Assay in Schwann Cell Cultures

Comparison of Br-UdR Immunoreactivity and Br-UdR Labelled Cell Number

Comparison of Br-UdR Immunoreactivity and Br-UdR Labelled Cell Number

Mitogenic Response of Rat Sciatic Nerve Schwann Cell to GGFs

DNA Synthesis in Rat Sciatic Nerve Schwann Cells and 3T3 Fibroblasts in the Presence of GGFs

Mitogenic Response of BHK21 C13 Cells to FCS and GGFs

Survival and Proliferation of BHK21 C13 Cell Microcultures After 48 Hours in Presence of GGFs Mitogenic Response
of C6 Cells to FCS

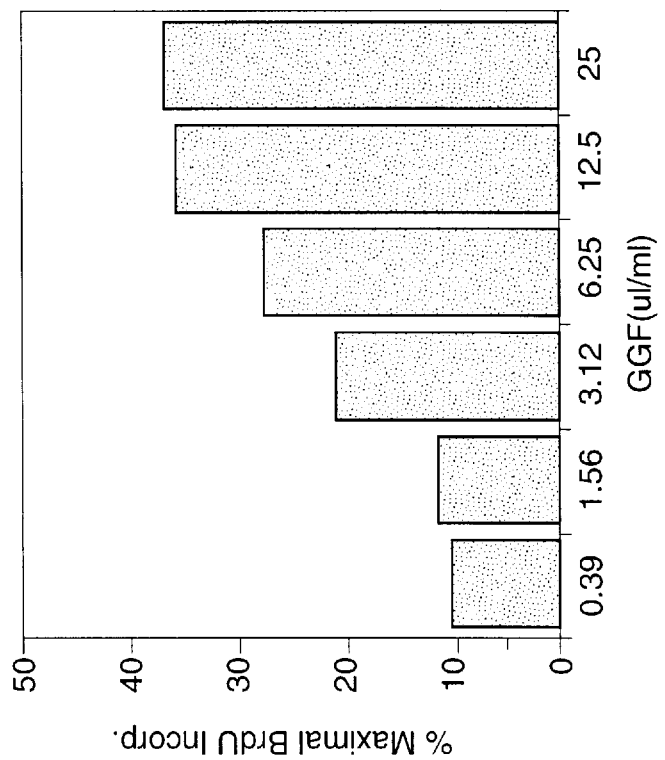
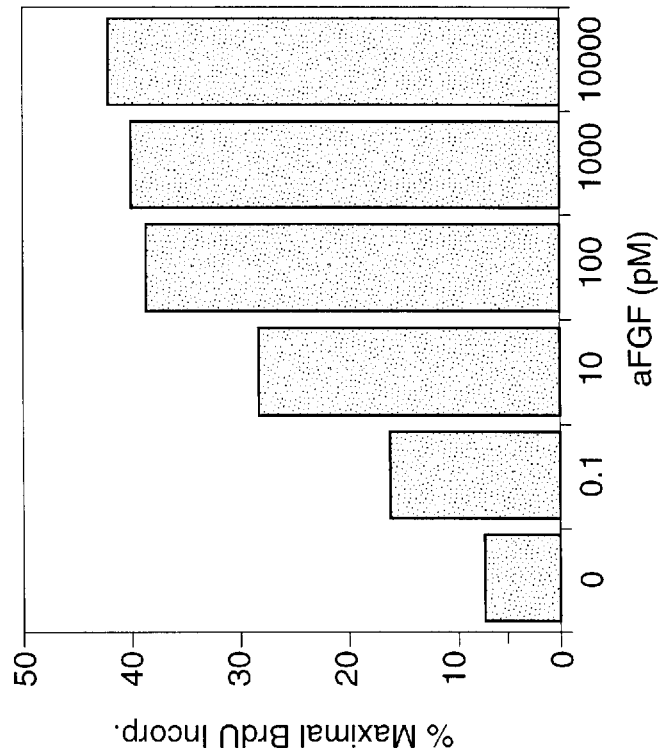

FIG. 21

Degenerate Oligonucleotide Probes for Factor I & Factor II

| Oligo | Sequence | Peptide | | |
|-------|----------|---------|---|---|
| 535 | TTYAARGGNGAYGCNCAYAC! | GGFI-1 | (SEQ ID NO: | 54) |
| 536 | CATRTAYTCRTAYTCRTCNGC! | GGFI-2 | (SEQ ID NO: | 55) |
| 537 | TGYTCNGANGCCATYTCNGT! | GGFI-13 | (SEQ ID NO: | 56) |
| 538 | TGYTCRCTNGCCATYTCNGT! | GGFI-13 | (SEQ ID NO: | 57) |
| 539 | CCDATNACCATNGGNACYTT! | GGFI-17 | (SEQ ID NO: | 58) |
| 540 | GCNGCCCANACYTGRTGNAC! | GGFII-1 | (SEQ ID NO: | 59) |
| 541 | GCYTCNGGYTCCATRAARAA! | GGFII-2 | (SEQ ID NO: | 60) |
| 542 | CCYTCDATNACNACRAACCA! | GGFII-4 | (SEQ ID NO: | 61) |
| 543 | TCNGCRAARTANCCNGC! | GGFI-11 | (SEQ ID NO: | 62) |
| 544 | GCNGCNAGNGCYTCYTTNGC! | GGFI-14 | (SEQ ID NO: | 63) |
| 545 | GCNGCYAANGCYTCYTTNGC! | GGFI-14 | (SEQ ID NO: | 64) |
| 546 | TTYTTNGCYTGNAGNACRAA! | GGFI-15 | (SEQ ID NO: | 65) |
| 551 | TTYTTNGCYTGYAANACRAA! | GGFI-15 | (SEQ ID NO: | 66) |
| 568 | TGNACNAGYTCYTGNAC! | GGFII-8 | (SEQ ID NO: | 67) |
| 569 | TGNACYAAYTCYTGNAC! | GGFII-8 | (SEQ ID NO: | 68) |
| 609 | CATRTAYTCNCCNGARTCNGC! | GGFII-12 | (SEQ ID NO: | 69) |
| 610 | CATRTAYTCNCCRCTRTCNGC! | GGFII-12 | (SEQ ID NO: | 70) |
| 649 | NGARTCNGCYAANGANGCYTT! | GGFII-12 | (SEQ ID NO: | 71) |
| 650 | NGARTCNGCNAGNGANGCYTT! | GGFII-12 | (SEQ ID NO: | 72) |
| 651 | RCTRTCNGCYAANGANGCYTT! | GGFII-12 | (SEQ ID NO: | 73) |
| 652 | RCTRTCNGCNAGNGANGCYTT! | GGFII-12 | (SEQ ID NO: | 74) |
| 653 | NGARTCNGCYAARCTNGCYTT! | GGFII-12 | (SEQ ID NO: | 75) |
| 654 | NGARTCNGCNAGRCTNGCYTT! | GGFII-12 | (SEQ ID NO: | 76) |
| 655 | RCTRTCNGCYAARCTNGCYTT! | GGFII-12 | (SEQ ID NO: | 78) |
| 656 | RCTRCTNGCNAGRCTNGCYTT! | GGFII-12 | (SEQ ID NO: | 79) |
| 659 | ACNACNGARATGGCTCNNGA! | GGFI-13 | (SEQ ID NO: | 80) |
| 660 | ACNACNGARATGGCAGYNGA! | GGFI-13 | (SEQ ID NO: | 81) |
| 661 | CAYCARGTNTGGGCNGCNAA! | GGFII-1 | (SEQ ID NO: | 82) |
| 662 | TTYGTNGTNATHGARGGNAA! | GGFII-4 | (SEQ ID NO: | 83) |
| 663 | AARGGNGAYGCNCAYACNGA! | GGFI-1 | (SEQ ID NO: | 84) |
| 664 | GARGCNYTNGCNGCNYTNAA! | GGDI-14 | (SEQ ID NO: | 85) |
| 665 | GTNGGNTCNGTNCARGARYT! | GGFII-8 | (SEQ ID NO: | 86) |
| 666 | GTNGGNAGYGTNCARGARYT! | GGFII-8 | (SEQ ID NO: | 87) |
| 694 | NACYTTYTTNARHATYTGNCC! | GGFI-17 | (SEQ ID NO: | 88) |

FIG. 22
Putative Bovine Factor II Gene Sequences

SEQ ID NO: 89:

```
TC TAA AAC TAC AGA GAC TGT ATT TTC ATG ATC ATC ATA GTT CTG TGA AAT ATA          53
   Xaa Asn Tyr Arg Asp Cys Ile Phe Met Ile Ile Ile Val Leu Xaa Asn Ile

CTT AAA CCG CTT TGG TCC TGA TCT TGT AGG AAG TCA GAA CTT CGC ATT               101
Leu Lys Pro Leu Trp Ser Xaa Ser Cys Arg Lys Ser Glu Leu Arg Ile

AGC AAA GCG TCA CTG GCT GAT TCT GGA GAA TAT ATG TGC AAA GTG ATC               149
Ser Lys Ala Ser Leu Ala Asp Ser Gly Glu Tyr Met Cys Lys Val Ile

AGC AAA CTA GGA AAT GAC AGT GCC TCT GCC AAC ATC ACC ATT GTG GAG               197
Ser Lys Leu Gly Asn Asp Ser Ala Ser Ala Asn Ile Arg Ile Val Glu

TCA AAC GGT AAG AGA TGC CTA CTG CGT GCT ATT TCT CAG TCT CTA AGA               245
Ser Asn Gly Lys Arg Cys Leu Leu Arg Ala Ile Ser Gln Ser Leu Arg

GGA GTG ATC AAG GTA TGT GGT CAC ACT TGA ATC ACG CAG GTG TGT GAA               293
Gly Val Ile Lys Val Cys Gly His Thr Xaa Ile Thr Gln Val Cys Glu

ATC TCA TTG TGA ACA AAT CAT GAA AGG AAA ACT CTA TGT TTG                       341
Ile Ser Cys Xaa Thr Asn Lys Asn His Glu Arg Lys Thr Leu Cys Leu

AAA TAT CTT ATG GGT CCT CCT GTA AAG CTC TTC ACT CCA TAA GGT GAA               389
Lys Tyr Leu Met Gly Pro Pro Val Lys Leu Phe Thr Pro Xaa Gly Glu

ATA GAC CTG AAA TAT ATA TAG ATT ATT T                                         417
Ile Asp Leu Lys Tyr Ile Xaa Ile Ile
```

FIG. 23A
PCR Primers for Factor I & Factor II

Degenerate PCR Primers

| Oligo | Sequence | Peptide | |
|---|---|---|---|
| 657 | CCGAATTCTGCAGGARACNCARCCNGAYCCNGG! | GGFI-17 | (SEQ ID NO: 90) |
| 658 | AAGGATCCTGCAGNGTRTANGCNCCHATNACCATNGG! | GGFI-17 | (SEQ ID NO: 91) |
| 667 | CCGAATTCTGCAGGCNGAYTCNGGNGARTAYATG! | GGFII-12 | (SEQ ID NO: 92) |
| 668 | CCGAATTCTGCAGGCNGAYATYGGNGARTAYAT! | GGFII-12 | (SEQ ID NO: 93) |
| 669 | AAGGATCCTGCAGNNNCATRTAYTCNCCNGARTC! | GGFII-12 | (SEQ ID NO: 94) |
| 670 | AAGGATCCTGCAGNNNCATRTAYTCNCCRRTRTC! | GGFII-12 | (SEQ ID NO: 95) |
| 671 | CCGAATTCTGCAGCAYCARGTNTGGCNGCNAA! | GGFII-1 | (SEQ ID NO: 96) |
| 672 | CCGAATTCTGCAGATRTTYTTYATGGARCCNGARG! | GGFII-2 | (SEQ ID NO: 97) |
| 673 | CCGAATTCTGCAGGGGNCCNCCNGCNTTYCCNGT! | GGFII-3 | (SEQ ID NO: 98) |
| 674 | CCGAATTCTGCAGTGGTTYGTNGTNATHGARGG! | GGFII-4 | (SEQ ID NO: 99) |
| 677 | AAGGATCCTGCAGYTTNGCNGCCCANACYTGRTG! | GGFII-1 | (SEQ ID NO: 100) |
| 678 | AAGGATCCTGCAGGCYTCNGGYTCCATRAARAA! | GGFII-2 | (SEQ ID NO: 101) |
| 679 | AAGGATCCTGCAGACNGGRAANGCNGNGGNCC! | GGFII-3 | (SEQ ID NO: 102) |
| 680 | AAGGATCCTGCAGYTTNCCYTCDATNACNACRAAC! | GGFII-4 | (SEQ ID NO: 103) |
| 681 | CATRTAYTCRTAYTCTCNGCAAGGATCCTGCAG! | GGFI-2 | (SEQ ID NO: 104) |
| 682 | CCGAATTCTGCAGAARGGNGAYGCNCAYACNGA! | GGFI-1 | (SEQ ID NO: 105) |
| 683 | GCNGCYAANGCYRCYTTNGCAAGGATCCTGCAG! | GGFI-14 | (SEQ ID NO: 106) |
| 684 | GCNGCNAGNGCYTCYTTNGCAAGGATCCTGCAG! | GGFI-14 | (SEQ ID NO: 107) |
| 685 | TCNGCRAARTANCCNGCAAGGATCCTGCAG! | GGFII-1 | (SEQ ID NO: 108) |

FIG. 23B

PCR Primers for Factor I & Factor II

Unique PCR Primers for Factor II

| Oligo | Sequence | Comment | |
|---|---|---|---|
| 711 | CATCGATCTGCAGGCTGATTCTGGAGAATATATGTGCA! | 3' RACE | (SEQ ID NO: 109) |
| 712 | AAGGATCCTGCAGCCACATCTGAGTCGACATCGATT! | 3' RACE | (SEQ ID NO: 110) |
| 713 | CCGAATTCTGCAGTGATCAGCAAACTAGGAAATGACA! | 3' RACE | (SEQ ID NO: 111) |
| 721 | CATCGATCTGCAGCCTAGTTTGCTGATCACTTTGCAC! | 5' RACE | (SEQ ID NO: 112) |
| 722 | AAGGATCCTGCAGTATATTCTCCAGAATCAGCCAGTG! | 5' RACE; ANCHORED | (SEQ ID NO: 113) |
| 725 | AAGGATCCTGCAGGCACGCAGTAGGCATCTCTTA! | EXON A | (SEQ ID NO: 114) |
| 726 | CCGAATTCTGCAGCAGAACTTCGCATTAGCAAAGC! | EXON A | (SEQ ID NO: 115) |
| 771 | CATCCCGGGATGAAGAGTCAGGAGTCTGTGGCA! | EXONS B+A | (SEQ ID NO: 116) |
| 772 | ATACCCGGGCTGCAGACAATGAGATTTCACACACCTGCG! | | (SEQ ID NO: 117) |
| 773 | AAGGATCCTGCAGTTTGGAACCTGCCACAGACTCCT! | ANCHORED | (SEQ ID NO: 118) |
| 776 | ATACCCGGGCTGCAGATGAGATTTCACACACCTGCGTGA! | EXONS B+A | (SEQ ID NO: 119) |

Summary of Contiguous GGF-II
cDNA Structures & Sequences

Alternative Gene Products of Putative Bovine GGF-II

FIG. 27

GGF-II Peptides Identified in Deduced Amino Acid Sequences of Putative Bovine GGF-II Proteins

| Peptide | Pos. | Sequence match | ID Sequences |
|---|---|---|---|
| II-1 |  | VHQVWAAK |  |
|  | 1: | HQVWAAK AAGLK | (SEQ ID NO:120) |
| II-10 |  | DLLLXV |  |
|  | 14: | GGLKK dslltv RLGAW | (SEQ ID NO:121) |
| II-03 |  | LGAWGPPAFPVXY | (SEQ ID NO:122) |
|  | 21: | LLTVR lgawghpafpscg RLKED | (SEQ ID NO:123) |
| II-02 |  | YIFFMEPEAXSSG | (SEQ ID NO:124) |
|  | 41: | KEDSR YIFFMEPEANSSG GPGRL | (SEQ ID NO:125) |
| II-6 |  | LVLR |  |
|  | 103: | VAGSK LVLR CETSS | (SEQ ID NO:126) |
| I-18 |  | EYKCLKFKWFKKATVM | (SEQ ID NO:127) |
|  | 112: | CETSS eysslkfkwfkngsel SRKNK | (SEQ ID NO:128) |
| II-12 |  | KASLADSGEYMXK | (SEQ ID NO:129) |
|  | 151: | ELRIS KASLADSGEYMCK VISKL | (SEQ ID NO:130) |
| I-07 |  | ASLADEYEYMRK | (SEQ ID NO:131) |
|  | 152: | LRISK asladsgeymck VISKL | (SEQ ID NO:132) |

FIG. 28A

SEQ ID NO: 133:

```
CCTGCAG CAT CAA GTG TGG GCG AAA GCC GGG GGC TTG AAG GAC TCG CTG      55
        His Gln Val Trp Ala Lys Ala Gly Gly Leu Lys Asp Ser Leu

CTC ACC GTG CGC CTG GGC GCC TGG GGC CAC CCC GCC TTC CCC TCC TGC     103
Leu Thr Val Arg Leu Gly Ala Trp Gly His Pro Ala Phe Pro Ser Cys

GGG CGC CTC AAG GAG GAC GAC AGC AGG TAC ATC TTC TTC ATG GAG CCC GAG 151
Gly Arg Leu Lys Glu Asp Asp Ser Arg Tyr Ile Phe Phe Met Glu Pro Glu

GCC AAC AGC AGC GGG GGG CCC GGC CGC CTT CCG AGC CTC CTT CCC CCC     199
Ala Asn Ser Ser Gly Gly Pro Gly Arg Leu Pro Ser Leu Leu Pro Pro

TCT CGA GAC GGG CCG GAA CCT CAA GAA GGT CAG CCG GGT GCT GTG         247
Ser Arg Asp Gly Pro Glu Pro Gln Glu Gly Gln Pro Gly Ala Val

CAA CGG TGC GCC TTG CCT CCC CGC TTG AAA GAG ATG AAG CAG GAG         295
Gln Arg Cys Ala Leu Pro Pro Arg Leu Lys Glu Met Lys Gln Glu

TCT GTG GCA GGT TCC AAA CTA GTG CTT CGG TGC GAG ACC AGT TCT GAA     343
Ser Val Ala Gly Ser Lys Leu Val Leu Arg Cys Glu Thr Ser Ser Glu

TAC TCC TCT CTC AAG TTC TGG TTC AAG AAT GGG AGT GAA TTA AGC         391
Tyr Ser Ser Leu Lys Phe Trp Phe Lys Asn Gly Ser Glu Leu Ser

CGA AAC AAC CCA GAA AAC ATC GCG CAG ATA CAG AAA AGG CCG AAG         439
Arg Asn Asn Pro Glu Asn Ile Ala Gln Ile Gln Lys Arg Pro Lys

TCA GAA CTT CGC ATT AGC ATC AAA CTG GCT GAT TCT GGA GAA TAT         487
Ser Glu Leu Arg Ile Ser Ile Lys Leu Ala Asp Ser Gly Glu Tyr

ATG TGC AAA GTG GAG ATC AGC AGG CTA GGA GAT GAC AGT TCT GCC AAC     535
Met Cys Lys Val Glu Ile Ser Arg Leu Gly Asp Asp Ser Ser Ala Asn

ATC ACC ATT GTG GAG TCA AAC AAG GGT AAG AGA TGC CTA CTG CGT ATT     583
Ile Thr Ile Val Glu Ser Asn Lys Gly Arg Cys Leu Leu Arg Ile

TCT CAG TCT CTA AGA GGA ATC GTG AAG GTA TGT GGT CAC ACT             625
Ser Gln Ser Leu Arg Gly Ile Val Lys Val Cys Gly His Thr

TGAATCACGC AGGTGTGTGA AATCTCATTG TGAACAAATA AAAATCATGA AAGGAAAAAA   685

AAAAAAAAAA AATCGATGTC GACTCGAGAT GTGGCTGCAG GTCGACTCTA GAGGATCCC   744
```

FIG. 28B

Nucleotide Sequences & Deduced Amino Acid Sequences of GGF2BPP2

SEQ ID NO: 134:

| | | | | | | | | | | | | | | | | | |
|---|---|---|---|---|---|---|---|---|---|---|---|---|---|---|---|---|---|
| CCTGCAG | CAT | CAA | GTG | TGG | GCG | GCC | AAA | GCC | GGG | GGC | TTG | AAG | AAG | GAC | TCG | CTG | 55 |
| | His | Gln | Val | Trp | Ala | Ala | Lys | Ala | Gly | Gly | Leu | Lys | Lys | Asp | Ser | Leu | |
| CTC | ACC | GTG | CGC | CTG | GGC | CTG | GCC | TGG | GGC | CAC | CCC | GCC | TTC | CCC | TCC | TGC | 103 |
| Leu | Thr | Val | Arg | Leu | Gly | Leu | Ala | Trp | Gly | His | Pro | Ala | Phe | Pro | Ser | Cys | |
| GGG | CGC | CTC | AAG | GAG | GAC | AGC | AGG | TAC | ATC | TTC | TTC | ATG | GAG | CCC | GAG | | 151 |
| Gly | Arg | Leu | Lys | Glu | Asp | Ser | Arg | Tyr | Ile | Phe | Phe | Met | Glu | Pro | Glu | | |
| GCC | AAC | AGC | AGC | GGC | GGG | CCC | CGC | GGC | CTT | CCG | AGC | CTC | CTT | CCC | CCC | | 199 |
| Ala | Lys | Ser | Ser | Gly | Gly | Pro | Arg | Gly | Leu | Pro | Ser | Leu | Leu | Pro | Pro | | |
| TCT | CGA | GAC | GGG | CCG | GAA | CCT | CAA | GGA | GGT | CAG | CCG | GGT | GCT | GTG | | | 247 |
| Ser | Arg | Asp | Gly | Pro | Glu | Pro | Gln | Glu | Gly | Gln | Pro | Gly | Ala | Val | | | |
| CAA | CGG | TGC | GCC | TTG | CCT | CCC | CGC | TTG | AAA | GAG | ATG | AAG | AGT | CAG | GAG | | 295 |
| Gln | Arg | Cys | Ala | Leu | Pro | Pro | Arg | Leu | Lys | Glu | Met | Lys | Ser | Gln | Glu | | |
| TCT | GTG | GCA | GGT | TCC | AAA | CTA | GTG | CTT | CGG | TGC | GAG | ACC | AGT | TCT | GAA | | 343 |
| Ser | Val | Ala | Gly | Ser | Lys | Leu | Val | Leu | Arg | Cys | Glu | Thr | Ser | Ser | Glu | | |
| TAC | TCC | TCT | CTC | AAG | TTC | AAG | TGG | TTC | AAG | AAT | GGG | AGT | GAA | TTA | AGC | | 391 |
| Tyr | Ser | Ser | Leu | Lys | Phe | Lys | Trp | Phe | Lys | Asn | Gly | Ser | Glu | Leu | Ser | | |
| CGA | AAG | AAC | AAA | CCA | GAA | AAC | ATC | AAG | ATA | CAG | AAA | AGG | CCG | GGG | AAG | | 439 |
| Arg | Lys | Asn | Lys | Pro | Glu | Asn | Ile | Lys | Ile | Gln | Lys | Arg | Pro | Gly | Lys | | |
| TCA | GAA | CTT | CGC | ATT | AGC | AAA | GCG | TCA | CTG | GCT | GAT | TCT | GGA | GAA | TAT | | 487 |
| Ser | Glu | Leu | Arg | Ile | Ser | Lys | Ala | Ser | Leu | Ala | Asp | Ser | Gly | Glu | Tyr | | |
| ATG | TGC | AAA | GTG | ATC | AGC | AAA | CTA | GGA | AAT | GAC | AGT | GCC | TCT | GCC | AAC | | 535 |
| Met | Cys | Lys | Val | Ile | Ser | Lys | Leu | Gly | Asn | Asp | Ser | Ala | Ser | Ala | Asn | | |

FIG. 28C

Nucleotide Sequences & Deduced Amino Acid Sequences of GG2BPP2

```
ATC ACC ATT GTG GAG TCA AAC GCC ACA TCC ACA TCT ACA GCT GGG ACA   583
Ile Thr Ile Val Glu Ser Asn Ala Thr Ser Thr Ser Thr Ala Gly Thr

AGC CAT CTT GTC AAG TGT GCA GAG AAG GAG AAA ACT TTC TGT GTG AAT   631
Ser His Leu Val Lys Ser Ala Glu Lys Glu Lys Thr Phe Cys Val Asn

GGA GGC GAG TGC TTC ATG GTG AAA GAC CTT TCA AAT CCC TCA AGA TAC   679
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   727
Leu Cys Lys Cys Gln Pro Gly Phe Thr Gly Ala Arg Cys Thr Glu Asn

GTG CCC ATG AAA GTC CAA ACC CAA GAA AGT GCC CAA ATG AGT TTA CTG   775
Val Pro Met Lys Val Gln Thr Gln Glu Ser Ala Gln Met Ser Leu Leu

GTG ATC GCT GCC AAA ACT ACG TAATGGCCAG CTTCTACAGT ACGTCCACTC     826
Val Ile Ala Ala Lys Thr Thr

CCTTTCTGTC TCTGCCTGAA TAGGCGCATCT CAGTCGGTGC CGCTTTCTTG TTGCCGCATC   886

TCCCCTCAGA TTCCTCCTAG AGCTAGATGC GTTTTACCAG GTCTAACATT GACTGCCTCT     946

GCCTGTCGCA TGAGAACATT AACACAAGCG ATTGTATGAC TTCCTCTGTC CGTGACTAGT    1006

GGGCTCTGAG CTACTCGTAG GTGCGTAAGG CTCCAGTGTT TCTGAAATTG ATCTTGAATT    1066

ACTGTGATAC GACATGATAG TCCCTCTCAC CCAGTGCAAT GACAATAAAG GCCTTGAAAA    1126

GTCAAAAAAA AAAAAAAAAA AAAAAATCGA TGTCGACTCG AGATGTGGCT GCAGGTCGAC    1186

TCTAGAG                                                              1193
```

FIG. 28D

Nucleotide Sequences & Deduced Amino Acid Sequences of GGF2BPP3

SEQ ID NO: 135:

```
CCTGCAG CAT CAA GTG TGG GCG AAA GCC GGG GGC TTG AAG AAG GAC TCG CTG  55
        His Gln Val Trp Ala Lys Ala Gly Gly Leu Lys Lys Asp Ser Leu

CTC ACC GTG CGC CTG GGC GCC TGG GGC CAC CCC TTC CCC TCC TGC          103
Leu Thr Val Arg Leu Gly Ala Trp Gly His Pro Phe Pro Ser Cys

GGG CGC AAG GAG CTC AAG GAC AGC AGG TAC TTC TTC ATG GAG CCC GAG      151
Gly Arg Lys Glu Leu Lys Asp Ser Arg Tyr Phe Phe Met Glu Pro Glu

GCC AAC AGC AGC GGC GGG CCC CGC GGC CTT CCG AGC CTC CTT CCC CCC      199
Ala Asn Ser Ser Gly Gly Pro Arg Gly Leu Pro Ser Leu Leu Pro Pro

TCT CGA GAC GGG CCG GAA CCT CAA GGA GGT CAG CCG GGT GCT GTG          247
Ser Arg Asp Gly Pro Glu Pro Gln Gly Gly Gln Pro Gly Ala Val

CAA CGG TGC GCC TTG CCT CCC CGC TTG AAA GAG ATG AAG AGT CAG GAG      295
Gln Arg Cys Ala Leu Pro Pro Arg Leu Lys Glu Met Lys Ser Gln Glu

TCT GTG GCA GGT TCC AAA CTA GTG CTT CGG TGC GAG AGT TCT GAA          343
Ser Val Ala Gly Ser Lys Leu Val Leu Arg Cys Glu Thr Ser Ser Glu

TAC TCC TCT CTC AAG TTC TTC TGG TTC AAG AAT GGG AGT GAA TTA AGC      391
Tyr Ser Ser Leu Lys Phe Phe Trp Phe Lys Asn Gly Ser Glu Leu Ser

CGA AAG AAC CCA GAA ATC AAC ATA AAG ATA CAG AGG CCG GGG AAG          439
Arg Lys Asn Pro Glu Ile Asn Ile Lys Ile Gln Arg Pro Gly Lys

TCA GAA CTT CGC ATT AGC AAA GCG TCA CTG GCT GAT TCT GGA GAA TAT      487
Ser Glu Leu Arg Ile Ser Lys Ala Ser Leu Ala Asp Ser Gly Glu Tyr
```

FIG. 28E

Nucleotide Sequences & Deduced Amino Acid Sequences of GGF2BPP3

```
ATG TGC AAA GTG ATC AGC AAA CTA GGA AAT GAC AGT GCC TCT GCC AAC      535
Met Cys Lys Val Ile Ser Lys Leu Gly Asn Asp Ser Ala Ser Ala Asn

ATC ACC ATT GTG GAG TCA AAC GCC ACA TCC ACA TCT ACA GCT GGG ACA      583
Ile Arg Ile Val Glu Ser Asn Ala Thr Ser Thr Ser Thr Ala Gly Thr

AGC CAT GTC AAG TGT GCA GAG AAG ACT TTC TGT GTG AAT                  631
Ser His Val Lys Cys Ala Glu Lys Thr Phe Cys Val Asn

GGA GGC GAG TGC TTC ATG GTG AAA GAC CTT TCA AAT CCC TCA AGA TAC      679
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC      727
Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT      775
Val Met Ala Ser Phe Tyr Ser Thr Ser Thr Pro Phe Leu Ser Leu Pro

GAA TAGCGCATCT CAGTCGGTGC CGCTTTCTTG TTGCCGCATC TCCCCTCAGA TTCCGCCTAG    838
Glu

AGCTAGATGC GTTTTACCAG GTCTAACATT GACTGCCTCT GCCTGTCGCA TGAGAACATT       898

AACACAAGCG ATTGTATGAC TTCCTCTGTC CGTGACTAGT GGGCTCTGAG CTACTCGTAG        958

GTGCGTAAGG CTCCAGTGTT TCTGAAATTG ATCTTGAATT ACTGTGATAC GACATGATAG       1018

TCCCTCTCAC CCAGTGCAAT GACAATAAAG GCCTTGAAAA GTCAAAAAAA AAAAAAAAAA       1078

AAAAATCGAT GTCGACTCGA GATGTGGCTG                                        1108
```

FIG. 31A

Coding Segments of Glial Growth Factor/Heregulin Gene

```
CODING SEGMENT F: (SEQ ID NO: 136 (bovine) and 173 (human))

AGTTTCCCCC CCCAACTTGT CGGAACTCTG GGCTCGCGCG CAGGGCAGGA GCGGAGCGGC        60

GGCGGCTGCC CAGGCGATGC GAGCGCGGGC CGGACGGTAA TCGCCTCTCC CTCCTCGGGC       120

TGCCAGCGCG CCGGACCGAG GCAGCGACAG GAGCGGACCG CGGCGGGAAC CGAGGACTCC       180

CCAGCGGCGC GCCAGCAGGA GCCACCCCGC GAGNCGTGCG ACCGGGACGG AGCGCCCGCC       240

AGTCCCAGGT GGCCCGGACC GCACGTTGCG TCCCCGCGCT CCCCGCCGGC GACAGGAGAC       300

GCTCCCCCCC ACGCCGCGCG CGCCTCGGCC CGGTCGCTGG CCCGCCTCCA CTCCGGGGAC       360
                                 |||||||||| |||||||||| |||||| ||||
                                 CGGCGAG CGCCTCAGCG CGGCCGCTCG CTCTC..CCC CTCGAGGGAC

AAACTTTTCC CGAAGCCGAT CCCAGCCCTC GGACCCAAAC TTGTCGCGCG TCGCCTTCGC       420
|||||||||| | ||||||||  |||||||||                      ||| |||
AAACTTTTCC CAAACCCGAT CCGAGCCCTT GGACCAAA..  ..........C TCGCCTGCGC

Met Ser Glu Arg Arg
CGGGAGCCGT CCGCGCAGAG CGTGCACTTC TCGGGCGAG ATG TCG GAG CGC AGA        474
|||||||||| |||| ||||| ||||| |||| |||||||||  |||  ||  ||  ||  |||
CGAGAGCCGT CCGCGTAGAG CGCTC.CGTC TCCGGCGAG ATG TCC GAG CGC AAA
                                                                K

Glu Gly Lys Gly Lys Gly Lys Gly Lys Gly Lys Asp Arg Gly Ser Gly
GAA GGC AAA GGC AAG GGG AAA GGG AAG GGC AAG GAC CGA GGC TCC GGG        522
||| |||  || ||| ||| ||   || ||   || ||| ||| ||| ||| ||| ||| ||
GAA GGC AGA GGC AAA GGC AAG GGC AAG GAG GAG CGA GGA GGC TCC GGC
        R                                   E

Lys Lys Pro Val Pro Ala Ala Gly Pro Ser Pro Ala
AAG AAG CCC GTG CCC GCT GGC GCG CCG AGC CCA G                          559
||| ||| |||  || |||  || ||| ||| ||  ||| ||| |
AAG AAG CCG GAG TCC GCG GCG GCC CAG AGC CCA G
            E   S
```

FIG. 31B

CODING SEGMENT E: (SEQ ID NO: 137)

```
CC CAT CAN GTG TGG GCG AAA GCC GGG GGC TTG AAG AAG GAC TCG       47
   His Gln Val Trp Ala Lys Ala Gly Gly Leu Lys Lys Asp Ser

CTG CTC ACC GTG CGC GGC CTG GGC GCC TGG GGC CAC CCC TTC CCC TCC  95
Leu Leu Thr Val Arg Gly Leu Gly Ala Trp Gly His Pro Ala Phe Pro Ser

TGC GGG CGC CTC AAG GAG GAC AGC AGG TAC ATC TTC ATG GAG CCC    143
Cys Gly Arg Leu Lys Glu Asp Ser Arg Tyr Ile Phe Met Glu Pro

GAG GCC AAC AGC GGG GGT CCC CGC CTT CCG AGC CTC CTT CCC        191
Glu Ala Asn Ser Gly Gly Pro Arg Leu Pro Ser Leu Leu Pro

CCC TCT CGA GAC GGG CCG GAA CCT CAA GGA GGT CAG CCG GGT GCT   239
Pro Ser Arg Asp Gly Pro Glu Pro Gln Gly Gly Gln Pro Gly Ala

GTG CAA CGG TGC G                                              252
Val Gln Arg Cys
```

FIG. 31C

CODING SEGMENT B: (SEQ ID NO: 138 (bovine) and 174 (human))

```
    Leu Pro Pro Arg Leu Lys Glu Met Lys Ser Gln Glu Ser Val Ala
CC  TTG CCT CCC CGC TTG AAA GAG ATG AAG AGT CAG GAG TCT GTG GCA      47
    |||  |   |   |   |   |   |   |   |   |   |   |   |   |   |
CC  TTG CCT CCC CGA TTG AAA GAG ATG AAA AGC CAG GAA TCG GCT GCA
                 Q                           A

Gly Ser Lys Leu Val Leu Arg Cys Glu Thr Ser Ser Glu Tyr Ser Ser
    GGT TCC AAA CTA GTG CTT CGG TGC GAG ACC AGT TCT GAA TAC TCC TCT   95
     |   |   |   |   |   |   |   |   |   |   |   |   |   |   |   |
    GGT TCC AAA CTA GTC CTT CGG TGT GAA ACC AGT TCT GAA TAC TCC TCT

Leu Lys Phe Lys Trp Phe Lys Asn Gly Ser Glu Leu Ser Arg Lys Asn
    CTC AAG TTC AAG TGG TTC AAG AAT GGG AGT GAA TTA AGC CGA AAG AAC   143
     |   |   |   |   |   |   |   |   |   |   |   |   |   |   |   |
    CTC AGA TTC AAG TGG TTC AAG AAT GGG AAT GAA TTG AAT CGA AAA AAC
            R                           N               N

Lys Pro Gln Asn Ile Lys Ile Gln Lys Arg Pro Gly
    AAA CCA CAA AAC ATC AAG ATA CAG AAA AGG CCG GG                    178
     |   |   |   |   |   |   |   |   |   |   |   |
    AAA CCA CAA AAT ATC AAG ATA CAA AAA AAG CCA GG
                                             K
```

FIG. 31D

CODING SEGMENT A: (SEQ ID NO: 139 (bovine) and 175 (human))

```
    Lys Ser Glu Leu Arg Ile Ser Lys Ala Ser Leu Ala Asp Ser Gly
  G AAG TCA GAA CTT CGC ATT AGC AAA GCG TCA CTG GCT GAT TCT GGA
    ||| ||| ||| ||| ||| ||| | | ||| | | ||| ||| ||| ||| ||| |||                                    46
  G AAG TCA GAA CTT CGC ATT AAC AAA GCA TCA CTG GCT GAT TCT GGA
                            N

Glu Tyr Met Cys Lys Val Ile Ser Lys Leu Gly Asn Asp Ser Ala Ser
    GAA TAT ATG TGC AAA GTG ATC AGC AAA CTA GGA AAT GAC AGT GCC TCT
    ||| ||| ||| ||| ||| ||| ||| ||| ||| | | ||| ||| ||| ||| ||| |||                                94
    GAG TAT ATG TGC AAA GTG ATC AGC AAA TTA GGA AAT GAC AGT GCC TCT

Ala Asn Ile Thr Ile Val Glu Ser Asn Ala
    GCC AAC ATC ACC ATT GTG GAG TCA AAC G
    ||| | | ||| ||| ||| ||| ||| ||| ||| |                                                            122
    GCC AAT ATC ACC ATC GTG GAA TCA AAC G
```

FIG. 31E

CODING SEGMENT A': (SEQ ID NO: 140)

```
TCTAAAACTA CAGAGACTGT ATTTTCATGA TCATCATAGT TCTGTGAAAT ATACTTAAAC                    60

CGCTTTGGTC CTGATCTTGT AGG AAG TCA GAA CTT CGC ATT AGC AAA GCG                       110
                         Lys Ser Glu Leu Arg Ile Ser Lys Ala

TCA CTG GCT GAT TCT GGA GAA TAT ATG TGC AAA GTG ATC AGC AAA CTA                     158
Ser Leu Ala Asp Ser Gly Glu Tyr Met Cys Lys Val Ile Ser Lys Leu

GGA AAT GAC AGT GCC TCT GCC AAC ATC ACC ATT GTG GAG TCA AAC GGT                     206
Gly Asn Asp Ser Ala Ser Ala Asn Ile Thr Ile Val Glu Ser Asn Gly

AAG AGA TGC CTA CTG CGT GCT ATT TCT CAG TCT CTA AGA GGA GTG ATC                     254
Lys Arg Cys Leu Leu Arg Ala Ile Ser Gln Ser Leu Arg Gly Val Ile

AAG GTA TGT GGT CAC ACT TGAATCACGC AGGTGTGTGA AATCTCATTG                            302
Lys Val Cys Gly His Thr

TGAACAAATA AAAATCATGA AAGGAAAACT CTATGTTTGA AATATCTTAT GGGTCCTCCT                   362

GTAAAGCTCT TCACTCCATA AGTGAAATA GACCTGAAATA ATATATAGAT TATTT                        417
```

FIG. 31F

CODING SEGMENT G: (SEQ ID NO: 141 (bovine) and 176 (human))

```
    Glu Ile Thr Thr Gly Met Pro Ala Ser Thr Glu Thr Ala Tyr Val Ser
    AG ATC ACC ACT GGC ATG CCA GCC TCA ACT GAG ACA GCG TAT GTG TCT    47
       |||  |  ||| ||| ||| ||| ||| ||| ||| ||| ||| -|| ||| ||| |||
    AG ATC ACT GGT ATG CCA GCC TCA ACT GAA GGA GCA TAT GTG TCT
        I                                    G
    Ser Glu Ser Pro Ile Arg Ile Ser Val Ser Thr Glu Gly Thr Asn Thr
    TCA GAG TCT CCC ATT AGA ATA TCA GTA TCA ACA GAA GGA ACA AAT ACT    95
    ||| ||| ||| ||| ||| ||| -|| ||| ||| ||| ||| ||| ||| ||| ||| |||
    TCA GAG TCT CCC ATT AGA ATA TCA GTA TCC ACA GAA GGA GCA AAT ACT
                                                          A
    Ser Ser Ser
    TCT TCA T                                                         102
    ||| ||| |
    TCT TCA T
```

FIG. 31G

CODING SEGMENT C: (SEQ ID NO: 160 (bovine) and 177 (human))

```
    Thr Ser Thr Ala Gly Thr Ser His Leu Val Lys Cys Ala
 CC ACA TCC ACA TCT ACA GCT GGG ACA AGC CAT CTT GTC AAG TGT GCA        47
    ||| ||| ||| ||  ||| ||| ||| ||| ||| ||| ||| ||| ||| |||
                       T
 CT ACA TCT ACA TCC ACC ACT GGG ACA AGC CAT CTT GTA AAA TGT GCG

Glu Lys Thr Phe Cys Val Asn Gly Gly Glu Cys Phe Met Val
    GAG AAG ACT TTC TGT GTG AAT GGA GGC GAG TGC TTC ATG GTG           95
    ||| ||| ||| ||| ||| ||| ||| ||| ||| ||| ||| ||| ||| |||
    GAG AAG ACT TTC TGT GTG AAT GGA GGG GAG TGC TTC ATG GTG

Lys Asp Leu Ser Asn Pro Ser Arg Tyr Leu Cys
    AAA GAC CTT TCA AAT CCC TCA AGA TAC TTG TGC                       128
    ||| ||| ||| ||| ||| ||| ||| ||| ||| ||| |||
    AAA GAC CTT TCA AAC CCC TCG AGA TAC TTG TGC
```

FIG. 31H

CODING SEGMENT C/D: (SEQ ID NO: 142 (bovine) and 178 (human))

```
        Lys Cys Gln Pro Gly Phe Thr Gly Ala Arg Cys Thr Glu Asn Val Pro
        AAG TGC CAA CCT GGA TTC ACT GGA GCG AGA TGT ACT GAG AAT GTG CCC    48
        ||| ||| ||| ||| ||| ||| ||| ||| ||  ||| ||| ||| ||| ||| ||| |||
        AAG TGC CAA CCT GGA TTC ACT GGA GCA AGA TGT ACT GAG AAT GTG CCC

Met Lys Val Gln Thr Gln Glu
        ATG AAA GTC CAA ACC CAA GAA                                        69
        ||| ||| ||| ||| ||  ||| |||
        ATG AAA GTC CAA AAC CAA GAA
                          N
```

FIG. 31I

CODING SEGMENT C/D': (SEQ ID NO: 143 (bovine) and 179 (human))

```
Lys Cys Pro Asn Glu Phe Thr Gly Asp Arg Cys Gln Asn Tyr Val Met
AAG TGC CCA AAT GAG TTT ACT GGT GAT CGC TGC CAA AAC TAC GTA ATG    48
||| ||| ||| ||| ||| ||| ||| ||| ||| ||| ||| ||| ||| ||| ||| |||
AAG TGC CCA AAT GAG TTT ACT GGT GAT CGC TGC CAA AAC TAC GTA ATG

Ala Ser Phe Tyr
GCC AGC TTC TAC                                                    60
||| ||| ||| |||
GCC AGC TTC TAC
```

FIG. 31J

CODING SEGMENT D: (SEQ ID NO: 144 (bovine) and 180 (human))

```
Ser Thr Ser Thr Pro Phe Leu Ser Leu Pro Glu *
AGT ACG TCC ACT CCC TTT CTG TCT CTG CCT GAA TAG                    36
||| ||| ||| ||| ||| ||| ||| ||| ||| ||| ||| |||
AGT ACG TCC ACT CCC TTT CTG TCT CTG CCT GAA TAG
```

FIG. 31K

CODING SEGMENT D': (SEQ ID NO: 145 (human))

```
Lys His Leu Gly Ile Glu Phe Met Glu
AAG CAT CTT GGG ATT GAA TTT ATG GAG                                27
```

FIG. 31L

```
CODING SEGMENT H: (SEQ ID NO: 146 (bovine) and 181 (human))

Lys Ala Glu Glu Leu Tyr Gln Lys Arg Val Leu Thr Ile Thr Gly Ile
      AAA GCG GAG GAG CTC TAC CAG AAG AGA GTG CTC ACC ATT ACC GGC ATT       48
      ||  ||| ||| ||| ||| ||| ||| ||| ||| ||| ||| ||| ||  ||| ||| ||
      AAG GCG GAG GAG CTG TAC CAG AAG AGA GTG CTG ACC ATA ACC GGC ATC

Cys Ile Ala Leu Leu Val Val Gly Ile Met Cys Val Val Val Tyr Cys
      TGC ATC GCG CTG CTC GTT GGC ATC ATG TGT GTG GTC GTG GTG TAC TGC       96
      ||| ||| ||  ||| ||| ||  ||| ||| ||| ||| ||| ||  ||| ||| ||| |||
      TGC ATC GCC CTC CTT GTG GTC GGC ATG TGT GTG GTG GTG GTG TAC TGC
                                                      A

Lys Thr Lys Lys Gln Arg Lys Leu His Asp Arg Leu Arg Gln Ser
      AAA ACC AAG AAA CAA CGG AAG CTT CAT GAC CGG CTT CGG CAG AGC          144
      ||| ||| ||| ||| ||  ||| ||| ||| ||| ||| ||  ||| ||| ||| |||
      AAA ACC AAG AAA CAG CGG AAG CTG CAT GAC CGT CTT CGG CAG AGC

Leu Arg Ser Glu Arg Asn Thr Met Met Asn Val Ala Asn Gly Pro His
      CTT CGG TCT GAA AGA AAC ACC ATG ATG AAC GTA GCC AAC GGG CCC CAC      192
      ||| ||| ||| ||| ||  ||| ||  ||| ||| ||  ||  ||| ||  ||| ||| |||
      CTT CGG TCT GAA CGA AAC CGA ATG ATG AAT GTT GCC AAT GGG CCT CAC
                            N                  I

His Pro Asn Pro Pro Glu Asn Val Gln Leu Val Asn Gln Tyr Val
      CAC CCC AAT CCG CCC GAG AAC GTG CAG CTG GTG AAT CAA TAC GTA          240
      ||| ||| ||  ||  ||| ||| ||| ||| ||| ||| ||| ||  ||| ||| |||
      CAT CCT AAC CCA CCC GAG AAC GTC CAG CTC GTG AAT CAA TAC GTA

Ser Lys Asn Val Ile Ser Ser Glu His Ile Val Glu Arg Glu Ala Glu
      TCT AAA AAT GTC ATC TCT AGC GAG CAT ATT GTT GAG AGA GAG GCG GAG      288
      ||| ||| ||| ||| ||| ||  ||| ||| ||| ||| ||| ||| ||| ||| ||  |||
      TCT AAA AAC GTC ATC TCC AGT GAG CAT ATT GTT GAG AGA GAG GCA GAG
```

FIG. 31M

```
Ser Ser Phe Ser Thr Ser His Tyr Thr Ser Thr Ala His His Ser Thr
AGC TCT TTT TCC ACC AGT CAC TAC ACT TCG ACA GCT CAT CAT TCC ACT       336
    ---     --- --- --- --- --- --- --- --- --- --- --- --- ---
ACA TCC TTT TCC ACC AGT CAC TAT ACT TCC ACA GCC CAT CAC TCC ACT
T

Thr Val Thr Gln Thr Pro Ser His Ser Trp Ser Asn Gly His Thr Glu
ACT GTC ACT CAG ACT CCC AGT CAC AGC TGG AGC AAT GGA CAC ACT GAA       384
--- --- --- --- --- ---     --- --- --- --- --- --- --- --- ---
ACT GTC ACC CAG ACT CCT AGC CAC AGC TGG AGC AAC GGA CAC ACT GAA

Ser Ile Ile Ser Glu Ser His Val Ile Val Met Ser Ser Val Glu
AGC ATC ATT TCG GAA AGC CAC TCT GTC ATC GTG ATG TCA TCC GTA GAA       432
--- --- --- ---     --- --- --- --- --- --- --- --- --- --- ---
AGC ATC ATC CTT TCC GAA AGC CAC TCT GTA ATC GTG ATG TCA TCC GTA GAA
         L

Asn Ser Arg His Ser Ser Pro Thr Gly Gly Pro Arg Glu Cys Asn Ser Phe Leu Arg His Ala Arg
AAC AGT AGG CAC AGC AGC CCG ACT GGG GGC CCG CGT GAA TGT AAC AGC TTC CTC AGG CAT GCC AGA       480
--- --- --- --- --- ---     --- --- --- --- --- --- --- --- --- --- --- --- --- --- ---
AAC AGT AGG CAC AGC AGC CCA ACT GGG GGC CCA CGT GAA TGT AAC AGC TTC CTC AGG CAT GCC AGA

Gly Leu Gly Gly Pro Arg His Ser Ser Pro Thr Gly Gly Pro Arg Glu Cys Asn Ser Pro His Ser Glu Arg
GGC TTG GGA GGC CCT CGT AGG AGC TCT CCT CAT AGT GAA AG                                        528
--- --- ---     --- --- --- --- --- --- --- --- ---  —
GGC ACA GGA GGC CCT CGT AGG AGC TCT CCT CAT AGT GAA AG
    T

Glu Thr Pro Asp Ser Tyr Arg Asp Ser Pro His Ser Glu Arg
GAA ACC CCT GAC TCC CGA TCC CAT AGT GAA AG                                                    569
--- --- --- --- --- --- --- --- --- --- --- —
GAA ACC CCT GAT TCC CGA TCC CAT AGT GAA AG
```

FIG. 31N

CODING SEGMENT K: (SEQ ID NO: 161)

```
A CAT AAC CTT ATA GCT GAG CTA AGG AGA AAC AAG GCC CAC AGA TCC          46
  His Asn Leu Ile Ala Glu Leu Arg Arg Asn Lys Ala His Arg Ser

AAA TGC ATG ATC CAG CTT TCC GCA ACT CAT CTT AGA GCT TCT TCC            94
Lys Cys Met Ile Gln Leu Ser Ala Thr His Leu Arg Ala Ser Ser

ATT CCC CAT TGG GCT TCA TTC TCT AAG ACC CCT TGG CCT TTA GGA AG        141
Ile Pro His Trp Ala Ser Phe Ser Lys Thr Pro Trp Pro Leu Gly Arg
```

FIG. 31O

CODING SEGMENT L: (SEQ ID NO: 147 (bovine) and 182 (human))

```
    Tyr Val Ser Ala Met Thr Thr Pro Ala Arg Met Ser Pro Val Asp
  G TAT GTA TCA GCA ATG ACC ACC CCG GCT CGT ATG TCA CCT GTA GAT          46
    ||| ||| ||  ||| ||| ||| ||| ||| ||| ||| ||| ||| ||| ||| |||
  G TAT GTG TCA GCC ATG ACC ACC CCG GCT CGT ATG TCA CCT GTA GAT

Phe His Thr Pro Ser Ser Pro Lys Ser Pro Pro Ser Glu Met Ser Pro
    TTC CAC ACG CCA AGC TCC CCC AAG TCA CCC CCT TCG GAA ATG TCC CCG      94
    ||| ||| ||| ||| ||| ||| ||| ||  ||| |||  || ||| ||| ||| ||   ||
    TTC CAC ACG CCA AGC TCC CCC AAA TCG CCC CCT TCG GAA ATG TCT CCA

Pro Val Ser Ser Thr Thr Thr Val Ser Met Pro Ser Met Ala Val Ser Pro
    CCC GTG TCC AGC ACG ACG GTC TCC ATG CCC ATG TCC AGT CCC          142
    ||| ||| ||| ||| ||| ||  ||| ||| ||| ||| ||| ||| |||  || |||
    CCC GTG TCC AGC ACG GTG TCC ATG CCT ATG TCC ATG GCG GTC AGC CCC
                    M

Phe Val Glu Glu Arg Pro Leu Leu Val Thr Pro Pro Arg Leu
    TTC GTG GAA GAG AGA CCC CTG CTC GTG ACG CCA CCA CGG CTG          190
    ||| ||| ||| ||| ||| ||| ||| ||  ||| ||  ||| ||| ||| |||
    TTC ATG GAA GAA GAG AGA CCT CTA CTT CTC GTG ACA CCA CCA AGG CTG
        M

Arg Glu Lys       Tyr Asp His His Ala Gln Gln Phe Asn Ser Phe His
    CGG GAG AAG ...   TAT GAC CAC CAC GCC CAG CAA TTC AAC TCG TTC CAC   238
    ||| ||| |||       ||  ||| ||  ||| ||| ||| ||| ||  ||  ||| ||| |||
    CGG GAG AAG AAG   TTT GAC CAT CAC GCC CAG CAG TTC AGC TCC TTC CAC
                K       F                                S

Cys Asn Pro Ala His Glu Ser Asn Ser Leu Pro Pro Ser Pro Leu Arg
    TGC AAC CCC GCG CAT GAG AGC AGC CTG CCC AGC TCC TTC AGG         286
    ||| ||| ||| ||  ||| ||| ||  ||| ||  ||| ||| ||| |||  || |||
    CAC AAC CCC GCG CAT GAC AGT AAC AGC CTC CCT GCT AGC CCC TTG AGG
    H                       D                         P    A
```

FIG. 31P

```
                                                                              334
Ile Val Glu Asp Glu Glu Tyr Glu Thr Thr Gln Glu Tyr Glu Pro Ala
ATA GTG GAG GAT GAG GAA TAT GAA ACG CAG GAG TAC GAA CCA GCT
||| ||| ||| ||| ||| ||| ||| ||| ||| ||| ||| ||| ||| ||| |||
ATA GTG GAG GAT GAG GAG TAT GAA ACG CAG GAG TAC GAG CCA GCC

382
Gln Glu Pro Val Lys Lys Leu Thr Asn Ser Ser Arg Arg Ala Lys Arg
CAA GAG CCG GTT AAG AAA CTC ACC AAC AGC AGC CGG CGG GCC AAA AGA
||| ||| ||| ||| ||| ||| ||| ||| ||| ||| ||| ||| ||| ||| ||| |||
CAA GAG CCT GTT AAG AAA CTC GCC AA. ..T AGC CGG CGG GCC AAA AGA
                                    A

430
Thr Lys Pro Asn Gly His Ile Ala His Arg Leu Glu Met Asp Asn Asn
ACC AAG CCC AAT GGT CAC ATT GCC CAC AGG TTG GAA ATG GAC AAC AAC
||| ||| ||| ||| ||| ||| ||| ||| ||| ||| ||| ||| ||| ||| ||| |||
ACC AAG CCC AAT GGC CAC ATT GCT AAC AGA TTG GAA GTG GAC AGC AAC
                                  N                     V       S

478
Thr Gly Ala Asp Ser Ser Asn Ser Glu Ser Glu Thr Glu Asp Glu Arg
ACA GGC GCT GAC AGC AGT AAC TCA GAG AGC GAA ACA GAG GAT GAA AGA
||| ||| ||| ||| ||| ||| ||| ||| ||| ||| ||| ||| ||| ||| ||| |||
ACA AGC TCC CAG — AGC AGT AAC TCA GAG AGT GAA ACA GAG GAT GAA AGA
    S   S   Q
```

FIG. 31Q

```
        Val Gly Glu Asp Thr Pro Phe Leu Ala Ile Gln Asn Pro Leu Ala Ala
        GTA GGA GAA GAT ACG CCT TTC CTG GCC ATA CAG AAC CCC CTG GCA GCC    526
        ||| ||  ||| ||| ||| ||| ||| ||| ||  ||| ||| ||| ||| ||| ||| |||
        GTA GGT GAA GAT ACG CCT TTC CTG GGC ATA CAG AAC CCC CTG GCA GCC
                                            G

Ser Leu Glu Ala Ala Pro Ala Phe Arg Leu Val Asp Ser Arg Thr Asn
        AGT CTC GAG GCG GCC CCT GCC TTC CGC CTG GTC GAC AGC AGG ACT AAC    574
        ||| ||| ||| ||  ||  ||| ||| ||| ||| ||| ||  ||| ||| ||| ||| |||
        AGT CTT GAG GCA ACA CCT GCC TTC CGC CTG GTT GAC AGC AGG ACT AAC
                        T

Pro Thr Gly Gly Phe Ser Pro Gln Glu Leu Val Asp Ser Arg Leu Ser
        CCA ACA GGC GGC TTC TCT CCG CAG GAA CTG GTC GAC AGC AGG CTC TCC    622
        ||  ||| ||| ||| ||| ||  ||  ||| ||| ||| ||  ||| ||| ||| ||| |||
        CCA GCA GGC CGC TTC TCC TCG ACA CAG GAA CTG GTT GAC AGC AGG CTG TCT
            R                   T

Gly Val Ile Ala Asn Gln Asp Pro Ile Ala Val *
        GGT GTA ATC GCT AAC CAA GAC CCT ATC GCT GTC TAA AAC CGA AAT ACA    670
        ||  ||  ||| ||| ||| ||| ||| ||| ||  ||| ||| ||| ||| ||  ||| |||
        AGT GTA ATT GCT AAC CAA GAC CCT ATT GCT GTC TAA AAC CTA AAT AAA
        S

CCC ATA GAT TCA CCT GTA AAA CTT TAT TTT ATA TAA AGT ATT CCA         718
        ||  ||| ||| ||| ||| ||| ||| ||| ||| ||| ||| ||| ||| ||| |||
        CAC ATA GAT TCA CCT GTA AAA CTT TAT TTT ATA TAA AGT ATT CCA

CCT TAA ATT AAA CAA                                                733
        ||| ||| ||| ||| |||
        CCT TAA ATT AAA CAA
```

FIG. 31R

HUMAN CODING SEGMENT E:
(SEQ ID NO: 163)

```
ATG AGA TGG CGA CGC GCC CCG CGC CGC TCC GGG CGT CCC GGC CCC CGG    48
Met Arg Trp Arg Arg Ala Pro Arg Arg Ser Gly Arg Pro Gly Pro Arg

GCC CAG CGC CCC CTG CTG TCC GCC GCC CGC TCG TCG CCG CCG CTG CTG    96
Ala Gln Arg Pro Leu Leu Ser Ala Ala Arg Ser Ser Pro Pro Leu Leu

CTG CCA CTA CTG CTG CTG CTG GGG GCC ACC ACC GCC CTG GCC CCG GGG GCG   144
Leu Pro Leu Leu Leu Leu Leu Gly Ala Thr Thr Ala Leu Ala Pro Gly Ala

GCG GCC GGC GAG GAG GCT GCG GGA GGG GGA GCG GCC GCG GCC GCC GGG GCG   192
Ala Ala Gly Glu Glu Ala Ala Gly Gly Gly Ala Ala Ala Ala Ala Gly Ala

TCC CCG CCC AGC AGC GGA TCG TCG GTG CAG GAG CTA GCT CAG CGC GCC GCA   240
Ser Pro Pro Ser Ser Gly Ser Ser Val Gln Glu Leu Ala Gln Arg Ala Ala

GTG GTG ATC GAG GGA AAG GTG CAC CCG GTG CAG CGG GAG CGG CAG GGG GCA   288
Val Val Ile Glu Gly Lys Val His Pro Val Gln Arg Glu Arg Gln Gly Ala

CTC GAC AGG AAG GCG GCG ALA GCG GCG GCG GAG GCA GGG GCG TGG GGC GGG   336
Leu Asp Arg Lys Ala Ala Ala Ala Ala Ala Glu Ala Gly Ala Trp Gly Gly

GGC GAT GAG CGC CCG GAG CCA CCG GGC CCA CGG GGC CGG CTG GGG CTG CCC   384
Gly Asp Glu Arg Pro Glu Pro Pro Gly Pro Arg Gly Arg Leu Gly Leu Pro

GCC GAG GAG CTG CTC GAG CTC AAC AAC ACC GTG GAG CCC TCT TGG TGG CCC   432
Ala Glu Glu Leu Leu Glu Leu Asn Asn Thr Val Glu Pro Ser Trp Pro

ACC GCC CCG CCG CTC CAG AGC AGC CAG GTG TGG GGG GCA GCC GAG GCG GCG TAT   480
Thr Ala Pro Pro Leu Gln Ser Ser Gln Val Trp Gly Ala Ala Glu Ala Tyr

CTG GTG AAG GTG GTG CAC CAC GTG ACC GTG CGC TGG CCC AAA AAA GCC GGG GGG TTG AAG   528
Leu Val Lys Val Val His His Val Thr Val Arg Trp Pro Lys Lys Ala Gly Gly Leu Lys

AAG GAC TCG CTG GGG AGG CTC ACC GAG GAG ACC TGG CAC TAC TGC CCC GCC   576
Lys Asp Ser Leu Gly Arg Leu Thr Glu Glu Thr Trp His Tyr Pro Ala

TTT CCC TGC TGT GAC GCC CCC AAC AGC GAC ACG AGC AGC AGG ATC ATC TTC TTC   624
Phe Pro Cys Cys Asp Ala Pro Asn Ser Asp Thr Ser Ser Arg Ile Ile Phe Phe

ATG GAG GAC GAC CCC CCT CTG CTC GAG ACG CGG CCG GCC GCC TTC CGA   672
Met Glu Asp Asp Pro Pro Leu Leu Glu Thr Arg Pro Ala Ala Phe Arg

GCC TCT TTC TGC CCT CTG GAG GGC CGG CTC AAG AAG AAG CTC GAG GTC   720
Ala Ser Phe Cys Pro Leu Glu Gly Arg Gly Arg Leu Lys Lys Leu Glu Val

AGC CGG GTG CTG TGC AAG AAG CGG TGC G                              745
Ser Arg Val Leu Cys Lys Lys Arg Cys
```

FIG. 31S

HUMAN GGF CODING SEGMENT A': (SEQ ID NO: 185)

```
GAAGTCAGAACTTCGCATTAACAAAGCATCACTGGCTGATTCTGGAGAGTATATGTGCAA    60
 K  S  E  L  R  I  N  K  A  S  L  A  D  S  G  E  Y  M  C  K
AGTGATCAGCAAATTAGGAAATGACAGTGCCTCTGCCAATATCACCATCGTGGAATCAAA   120
 V  I  S  K  L  G  N  D  S  A  S  A  N  I  T  I  V  E  S  N
CGGTAAGAGATACCTACGGTATTCTGTTCCTCAATCTGTAACAAGAGTAATCAAAACATG   180
 G  K  R  Y  L  R  Y  S  V  P  Q  S  V  T  R  V  I  K  T  C
TGGTAAGACTCATAATAGACTGGTGTCTTAA                                 211
 G  K  T  H  N  R  L  V  C  *
```

FIG. 32A

GGF2BPP5 Nucleotide Sequence & Deduced Protein Sequence

SEQ ID NO: 148:

```
AGTTTCCCCC CCCAACTTGT CGGAACTCTG GGCTCGCGCG CAGGGCAGGA GCGGAGCGGC    60
GGCGGCTGCC CAGGCGATGC GAGCGCGGGC CGGACGGTAA TCGCCTCTCC CTCCTCGGGC   120
TGCGAGCGCG CCGGACCGAG GCAGCGACAG GAGCGGACCG CGGCGGGAAC CGAGGACTCC   180
CCAGCGGGCG GCCAGCAGGA GCCACCCCGC GAGNCGTGCG ACCGGGACGG AGCGCCCGCC   240
AGTCCCAGGT GGCCCGGACC GCACGTTGCG TCCCCGCGCT CCCCGCCGGC GACAGGAGAC   300
GCTCCCCCCC ACGCCGGCGC CGCCTCGGCC CGGTCGCTGG CCCGCCTCCA CTCCGGGGAC   360
AAACTTTTCC CGAAGCCGAT CCCAGCCCTC GGACCCAAAC TTGTCGCGCG TCGCCTTCGC   420
CGGGAGCCGT CCGCGCAGAG CGTGCACTTC TCGGGCGAG ATG TCG GAG CGC AGA     474
                                           Met Ser Glu Arg Arg

GAA GGC AAA GGC AAG GGG AAG GGC GGC AAG AAG GAC CGA GGC TCC GGG     522
Glu Gly Lys Gly Lys Gly Lys Gly Gly Lys Lys Asp Arg Gly Ser Gly

AAG AAG CCC GTG CCC GCG GCT GGC GGC GGC AGC CCG GCC TTG CCT CCC     570
Lys Lys Pro Val Pro Ala Ala Gly Gly Gly Ser Pro Ala Leu Pro Pro

CGC TTG AAA GAG ATG AAG AGT CAG GAG TCT GTG GCA GGT TCC AAA CTA     618
Arg Leu Lys Glu Met Lys Ser Gln Glu Ser Val Ala Gly Ser Lys Leu

GTG CTT CGG TGC GAG ACC AGT TCT GAA TAC TCC TCT CTC AAG TTC AAG     666
Val Leu Arg Cys Glu Thr Ser Ser Glu Tyr Ser Ser Leu Lys Phe Lys

TGG TTC AAG AAT GGG AGT GAA TTA AGC CGA AAG AAA CCA CAA AAC         714
Trp Phe Lys Asn Gly Ser Glu Leu Ser Arg Lys Lys Pro Gln Asn

ATC AAG ATA CAG AAA AGG CCG GGG AAG TCA GAA CTT CGC ATT AGC AAA     762
Ile Lys Ile Gln Lys Arg Pro Gly Lys Ser Glu Leu Arg Ile Ser Lys

GCG TCA CTG GCT GAT TCT GGA GAA TAT ATG TGC AAA GTG ATC AGC AAA     810
Ala Ser Leu Ala Asp Ser Gly Glu Tyr Met Cys Lys Val Ile Ser Lys
```

FIG. 32B

GGF2BPP5 Nucleotide Sequence & Deduced Protein Sequence

```
CTA GGA AAT GAC AGT GCC TCT GCC AAC ATC ACC ATT GTG GAG TCA AAC      858
Leu Gly Asn Asp Ser Ala Ser Ala Asn Ile Thr Ile Val Glu Ser Asn

GAG ATC ACC ACT GGC ATG CCA GCC ATG TCA ACT GAG ACA GCG TAT GTG TCT  906
Glu Ile Thr Thr Gly Met Pro Ala Met Ser Thr Glu Thr Ala Tyr Val Ser

TCA GAG TCT CCC ATT AGA ATA TCA GTA TCA GAA GGA ACA AAT ACT          954
Ser Glu Ser Pro Ile Arg Ile Ser Val Ser Glu Gly Thr Asn Thr

TCT TCA TCC ACA TCC ACA TCT ACA GCT GGG ACA AGC CAT CTT GTC AAG     1002
Ser Ser Ser Thr Ser Thr Ser Thr Ala Gly Thr Ser His Leu Val Lys

TGT GCA GAG AAG GAG AAA ACT TTC TGT GTG AAT GGA GGC GAG TGC TTC     1050
Cys Ala Glu Lys Glu Lys Thr Phe Cys Val Asn Gly Gly Glu Cys Phe

ATG GTG AAA GAC CTT TCA AAT CCC TCA AGA TAC TTG TGC AAG TGC CCA     1098
Met Val Lys Asp Leu Ser Asn Pro Ser Arg Tyr Leu Cys Lys Cys Pro

AAT GAG TTT ACT GGT GAT CGC TGC CAA AAC TAC GTA ATG GCC AGC TTC     1146
Asn Glu Phe Thr Gly Asp Arg Cys Gln Asn Tyr Val Met Ala Ser Phe

TAC AGT ACG TCC ACT CCC TTT CTG TCT CCT GAA TAGGCGCATG              1192
Tyr Ser Thr Ser Thr Pro Phe Leu Ser Pro Glu

CTCAGTCGGT GCCGCTTTCT TGTTGCCGCA TCTCCCCTCA GATTCAACCT AGAGCTAGAT   1252
GCGTTTTACC AGTCTAACA TTGACTGCCT CTGCCTGTCG CATGAGAACA TTAACACAAG    1312
CGATTGTATG ACTTCCTCTG TCCCGTGACTA GCTACTCGT AGGTGCGTAA              1372
GGCTCCAGTG TTTCTGAAAT TGATCTTGAA TTACTGTGAT ACGACATGAT AGTCCCTCTC   1432
ACCCAGTGCA ATGACAATAA AGGCCTTGAA AAGTCTCACT TTTATTGAGA AAATAAAAAT   1492
CGTTCCACGG GACAGTCCCT CTTCTTTATA AAATGACCCT ATCCTTGAAA AGGAGGTGTG   1552
TTAAGTTGTA ACCAGTACAC ACTTGAAATG ATGGTAAGTT CGCTTCGGTT CAGAATGTGT   1612
TCTTTCTGAC AAATAAACAG AATAAAAAAA AAAAAAAAAA A                       1653
```

FIG. 33A

GGF2BPP2 Nucleotide Sequence & Deduced Protein Sequence

SEQ ID NO: 149:

```
CAT CAN GTG TGG GCG GCG AAA GCC GGG TTG AAG AAG GAC TCG CTG      48
His Gln Val Trp Ala Ala Lys Ala Gly Leu Lys Lys Asp Ser Leu

CTC ACC GTG CGC CTG GGC GGC TGG GGC CAC CCC GCC TTC CCC TGC      96
Leu Thr Val Arg Leu Gly Gly Trp Gly His Pro Ala Phe Pro Cys

GGG CGC AAG GAG GAC AGC AGG AGG TAC ATC TTC TTC ATG GAG CCC GAG  144
Gly Arg Lys Glu Asp Ser Arg Arg Tyr Ile Phe Phe Met Glu Pro Glu

GCC AAC AGC AGC GGC GGG CCC CTT CGC AGC CTC CCG GGT GCT CCC      192
Ala Asn Ser Ser Gly Gly Pro Leu Arg Ser Leu Pro Gly Ala Pro

TCT CGA GAC GGG CCG GAA CCT CAA GGA GGT CAG CCG GTG GCT GTG      240
Ser Arg Asp Gly Pro Glu Pro Gln Gly Gly Gln Pro Val Ala Val

CAA CGG TGC GCC TTG CCT AAA CTA GTG TTG AAA GAG ATG CCG CAG GAG  288
Gln Arg Cys Ala Leu Pro Lys Leu Val Leu Lys Glu Met Pro Gln Glu

TCT GTG GCA GGT TCC AAA TTC CGC CTT TTC TGC GAG ACC AGT TCT GAA  336
Ser Val Ala Gly Ser Lys Phe Arg Leu Phe Cys Glu Thr Ser Ser Glu

TAC TCC TCT CTC AAG TTC TGG TTC AAG AAT GGG AGT GAA TTA AGC      384
Tyr Ser Ser Leu Lys Phe Trp Phe Lys Asn Gly Ser Glu Leu Ser

CGA AAG AAC CCA GAA ATC ATA CAG CTG AAA AGG CCG GGG AAG          432
Arg Lys Asn Pro Glu Ile Ile Gln Leu Lys Arg Pro Gly Lys

TCA GAA CTT CGC ATT AGC GCG TCA CTG GCT GAT TCT GGA GAA TAT      480
Ser Glu Leu Arg Ile Ser Ala Ser Leu Ala Asp Ser Gly Glu Tyr

ATG TGC AAA GTG ATC AGC AAA CTA GGA AAT GAC AGT TCT GCC AAC      528
Met Cys Lys Val Ile Ser Lys Leu Gly Asn Asp Ser Ser Ala Asn
```

FIG. 33B

GGF2BPP2 Nucleotide Sequence & Deduced Protein Sequence

```
ATC ACC ATT GTG GAG TCA AAC GCC ACA TCC ACA TCT ACA GCT GGG ACA      576
Ile Thr Ile Val Glu Ser Asn Ala Thr Ser Thr Ser Thr Ala Gly Thr

AGC CAT CTT GTC AAG TGT GCA GAG AAG GAG AAA ACT TTC TGT GTG AAT      624
Ser His Leu Val Lys Cys Ala Glu Lys Glu Lys Thr Phe Cys Val Asn

GGA GGC TGC GAG TTC ATG GTG AAA GAC CTT TCA AAT CCC TCA AGA TAC      672
Gly Gly Cys Glu Phe Met Val Lys Asp Leu Ser Asn Pro Ser Arg Tyr

TTG TGC TGC CAA CCT GGA TTC ACT GGA GCG AGA TGT ACT GAG AAT          720
Leu Cys Cys Gln Pro Gly Phe Thr Gly Ala Arg Cys Thr Glu Asn

GTC CCC ATG AAA GTC CAA ACC CAA GAA AAG TGC CCA AAT GAG TTT ACT      768
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC      816
Gly Asp Arg Cys Gln Asn Tyr Val Met Ala Ser Phe Tyr Ser Thr Ser

ACT CCC TTT CTG TCT CTG CCT GAA TAGCGCATCT CAGTCGGTGC CGCTTTCTTG     870
Thr Pro Phe Leu Ser Leu Pro Glu

TTGCCGCATC TCCCCCTCAGA TTCCNCCTAG AGCTAGATGC GTTTTACCAG GTCTAACATT   930

GACTGCCTCT GCCTGTCGCA TGAGAACATT AACACAAGCG ATTGTATGAC TTCCTCTGTC    990

CGTGACTAGT GGGCTCTGAG CTACTCGTAG GTGCGTAAGG CTCCAGTGTT TCTGAAATTG   1050

ATCTTGAATT ACTGTGATAC GACATGATAG TCCCCTCTCAC CCAGTGCAAT GACAATAAAG  1110

GCCTTGAAAA GTCAAAAAAA AAAAAAAAAA                                    1140
```

FIG. 34A

GGF2BPP4 Nucleotide Sequence & Deduced Protein Sequence

SEQ ID NO: 150:

```
  G AAG TCA GAA CTT CGC ATT AGC AAA GCG TCA CTG GCT GAT TCT GGA GAA      49
    Lys Ser Glu Leu Arg Ile Ser Lys Ala Ser Leu Ala Asp Ser Gly Glu

TAT ATG TGC AAA GTG ATC GAG AAA CTA GGA AAT GAC GCC AGT TCT GCC          97
Tyr Met Cys Lys Val Ile Glu Lys Leu Gly Asn Asp Ala Ser Ser Ala

AAC ATC ACC ATT GTG TCA AAC GCC ACA TCC ACA TCT ACA GCT GGG             145
Asn Ile Thr Ile Val Ser Asn Ala Thr Ser Thr Ser Thr Ala Gly

ACA AGC CAT CTT GTC AAG TGT GCA GAG AAG GAG AAA ACT TTC TGT GTG         193
Thr Ser His Leu Val Lys Cys Ala Glu Lys Glu Lys Thr Phe Cys Val

AAT GGA GGC TGC GAC ATG GTG AAA GAC CTT TCA AAT CCC TCA AGA             241
Asn Gly Gly Cys Asp Met Val Lys Asp Leu Ser Asn Pro Ser Arg

TAC TTG TGC AAG TGC CAA CCT GGA TTC ACT GGA GCG AGA TGT ACT GAG         289
Tyr Leu Cys Lys Cys Gln Pro Gly Phe Thr Gly Ala Arg Cys Thr Glu

AAT GTG CCC ATG AAA GTC CTC CAA ACC CAA GAA AAA GCG GAG GAG CTC TAC     337
Asn Val Pro Met Lys Val Leu Gln Thr Gln Glu Lys Ala Glu Glu Leu Tyr

CAG AAG AGA ATG TGT CTC ACC ATT ACC GGC TAC TGC AAA ACC CTG CTC GTG     385
Gln Lys Arg Met Cys Leu Thr Ile Thr Gly Tyr Cys Lys Thr Leu Leu Val

GTT GGC ATC ATG ATG TGT GTG GTG GTC CAG CTT CGG AAA AAG CAA CGG         433
Val Gly Ile Met Met Cys Val Val Val Gln Leu Arg Leu Lys Gln Arg

AAA AAG CTT CAT GAC CGG CTT CGG CAG AGC CTT GAA TCT GAA AGA AAC         481
Lys Lys Leu His Asp Arg Leu Arg Gln Ser Leu Glu Ser Glu Arg Asn

ACC ATG ATG AAC GTA GCC AAC GGG CCC CAC CAC AAT CCG CCC CCC CCC         529
Thr Met Met Asn Val Ala Asn Gly Pro His His Asn Pro Pro Pro Pro

GAG AAC GTG CAG CTG GTG AAT CAA TAC GTA TCT AAA AAT GTC ATC TCT         577
Glu Asn Val Gln Leu Val Asn Gln Tyr Val Ser Lys Asn Val Ile Ser
```

FIG. 34B

GGF2BPP4 Nucleotide Sequence & Deduced Protein Sequence

```
AGC GAG CAT ATT GTT GAG AGA GAG GCG GAG AGC TCT TTT TCC ACC AGT    625
Ser Glu His Ile Val Glu Arg Glu Ala Glu Ser Ser Phe Ser Thr Ser

CAC TAC ACT TCG ACA GCT CAT CAT TCC ACT GTC ACT CAG ACT CCC        673
His Tyr Thr Ser Thr Ala His His Ser Thr Val Thr Gln Thr Pro

AGT CAC AGC TGG AGC AAT GGA CAC ACT GAA AGC ATT TCG GAA AGC        721
Ser His Ser Trp Ser Asn Gly His Thr Glu Ser Ile Ser Glu Ser

CAC TCT GTC ATC GTG ATG TCA GAA GTA GAA AGT AGG CAC AGC AGC        769
His Ser Val Ile Val Met Ser Glu Val Glu Ser Arg His Ser Ser

CCG ACT GGG GGC CCG AGA GGA CGT CTC AAT GGC TTG GGA CCT CGT        817
Pro Thr Gly Gly Pro Arg Gly Arg Leu Asn Gly Leu Gly Pro Arg

GAA TGT AAC AGC TTC CTC CAT GCC AGA GAA ACC CCT GAC TCC TAC        865
Glu Cys Asn Ser Phe Leu His Ala Arg Glu Thr Pro Asp Ser Tyr

CGA GAC TCT CCT CAT AGT GAA CAT AAC CTT ATA GCT GAG CTA AGG        913
Arg Asp Ser Pro His Ser Glu His Asn Leu Ile Ala Glu Leu Arg

AGA AAC AAG GCC CAC AGA TCC AAA TGC ATG CAG ATC CAG CTT TCC GCA    961
Arg Asn Lys Ala His Arg Ser Lys Cys Met Gln Ile Gln Leu Ser Ala

ACT CAT CTT AGA GCT TCT CCC ATT CCC CAT TGG GCT TCA TTC AAG        1009
Thr His Leu Arg Ala Ser Pro Ile Pro His Trp Ala Ser Phe Lys

ACC CCT TGG CCT TTA GGA AGG TAT GTA TCA GCA ATG ACC CCG GCT        1057
Thr Pro Trp Pro Leu Gly Arg Tyr Val Ser Ala Met Thr Pro Ala

CGT ATG TCA CCT GTA GAT TTC CAC ACG AGC TCC CCC AAG TCA CCC        1105
Arg Met Ser Pro Val Asp Phe His Thr Ser Ser Pro Lys Ser Pro

CCT TCG GAA ATG TCC CCG GTG CCC AGC ACG GTC TCC ATG CCC            1153
Pro Ser Glu Met Ser Pro Val Pro Ser Thr Val Ser Met Pro
```

FIG. 34C

GGF2BPP4 Nucleotide Sequence & Deduced Protein Sequence

```
TCC ATG GCG GTC AGT CCC TTC GTG GAA GAG AGA CCC CTG CTC CTT   1201
Ser Met Ala Val Ser Pro Phe Val Glu Glu Arg Pro Leu Leu Leu

GTG ACG CCA CCA CGG CTG GAG AAG TAT GAC CAC CAC GCC CAG CAA   1249
Val Thr Pro Pro Arg Leu Glu Lys Tyr Asp His His Ala Gln Gln

TTC AAC TCG TTC CAC TGC AAC CCC GCG CAT GAG AGC AGC CTG CCC   1297
Phe Asn Ser Phe His Cys Asn Pro Ala His Glu Ser Asn Leu Pro

CCC AGC CCC TTG AGG ATA GTG GAG GAT GAG GAA TAT GAA ACC CAG   1345
Pro Ser Pro Leu Arg Ile Val Glu Asp Glu Glu Tyr Glu Thr Gln

GAG TAC GAA CCA GCT CAA GAG CCG GTT AAG AAA CTC ACC AGC AGC   1393
Glu Tyr Glu Pro Ala Gln Glu Pro Val Lys Lys Leu Thr Asn Ser

CGG GCC AAA AGA ACC AAG CCC AAT GGT CAC ATT GCC CAC AGG TTG   1441
Arg Ala Lys Arg Thr Lys Pro Asn Gly His Ile Ala His Arg Leu

GAA ATG GAC AAC AAC ACA GGC GCT GAC AGC AGT AAC TCA GAG AGC GAA   1489
Glu Met Asp Asn Asn Thr Gly Ala Asp Ser Ser Asn Ser Glu Glu

ACA GAT GAA AGA GTA GGA GAA GAT ACG GAT CCT TTC CTG GCC ATA CAG   1537
Thr Asp Glu Arg Val Gly Glu Asp Thr Asp Pro Phe Leu Ala Ile Gln

AAC CCC CTG GCA GCC AGT CTC GAG GCG CCT TTC CGC CTG GTC   1585
Asn Pro Leu Ala Ala Ser Leu Glu Ala Pro Ala Phe Arg Leu Val

GAC AGC AGG ACT AAC CCA GGC GGC TTC TCT CAA CCG CAG GAA TTG   1633
Asp Ser Arg Thr Asn Pro Gly Gly Phe Ser Gln Pro Gln Glu Leu

CAG GCC AGG CTC TCC GGT GTA ATC GCT AAC CAA GAC CCT ATC GCT GTC   1681
Gln Ala Arg Leu Ser Gly Val Ile Ala Asn Gln Asp Pro Ile Ala Val

TAAAACCGAA ATACACCCAT AGATTCACCT GTAAAACTTT ATTTTATATA ATAAAGTATT   1741

CCACCTTAAA TTAAACAAAA AAA                                        1764
```

FIG. 35

```
GGF2bpp5 (SEQ ID NO: 151)  KCAEKEKTFCVNGGECFMVKDLSNPSRYLCKCPNEFTGDRCQNYVMASFY
GGF2bpp4 (SEQ ID NO: 152)  KCAEKEKTFCVNGGDCFMVKDLSNPSRYLCKCQPGFTGARCTENVPMKVQ
hEGF     (SEQ ID NO: 153)  ECLRKYKDFCIH-GECKYVKELRAPS---CKCQQEYFGERCGEKSNKTHS
```

200 kDa Tyrosine Phosphorylation
Compared with Mitogenic Activity

FIG. 37A  GGF/Heregulin Splicing Variants

```
F-B-A'                              F-E-B-A'

F-B-A-C-C/D-D                       F-E-B-A-C-C/D-D
F-B-A-C-C/D-H                       F-E-B-A-C-C/D-H
F-B-A-C-C/D-H-L                     F-E-B-A-C-C/D-H-L
F-B-A-C-C/D-H-K-L                   F-E-B-A-C-C/D-H-K-L
F-B-A-C-C/D-D'-H                    F-E-B-A-C-C/D-D'-H
F-B-A-C-C/D-D'-H-L                  F-E-B-A-C-C/D-D'-H-L
F-B-A-C-C/D-D'-H-K-L                F-E-B-A-C-C/D-D'-H-K-L
F-B-A-C-C/D'-D                      F-E-B-A-C-C/D'-D
F-B-A-C-C/D'-H                      F-E-B-A-C-C/D'-H
F-B-A-C-C/D'-H-L                    F-E-B-A-C-C/D'-H-L
F-B-A-C-C/D'-H-K-L                  F-E-B-A-C-C/D'-H-K-L
F-B-A-C-C/D'-D'-H                   F-E-B-A-C-C/D'-D'-H
F-B-A-C-C/D'-D'-H-L                 F-E-B-A-C-C/D'-D'-H-L
F-B-A-C-C/D'-D'-H-K-L               F-E-B-A-C-C/D'-D'-H-K-L
F-B-A-C-C/D-C/D'-D                  F-E-B-A-C-C/D-C/D'-D
F-B-A-C-C/D-C/D'-H                  F-E-B-A-C-C/D-C/D'-H
F-B-A-C-C/D-C/D'-H-L                F-E-B-A-C-C/D-C/D'-H-L
F-B-A-C-C/D-C/D'-H-K-L              F-E-B-A-C-C/D-C/D'-H-K-L
F-B-A-C-C/D-C/D'-D'-H               F-E-B-A-C-C/D-C/D'-D'-H
F-B-A-C-C/D-C/D'-D'-H-L             F-E-B-A-C-C/D-C/D'-D'-H-L
F-B-A-C-C/D-C/D'-D'-H-K-L           F-E-B-A-C-C/D-C/D'-D'-H-K-L

F-B-A-G-C-C/D-D                     F-E-B-A-G-C-C/D-D
F-B-A-G-C-C/D-H                     F-E-B-A-G-C-C/D-H
F-B-A-G-C-C/D-H-L                   F-E-B-A-G-C-C/D-H-L
F-B-A-G-C-C/D-H-K-L                 F-E-B-A-G-C-C/D-H-K-L
F-B-A-G-C-C/D-D'-H                  F-E-B-A-G-C-C/D-D'-H
F-B-A-G-C-C/D-D'-H-L                F-E-B-A-G-C-C/D-D'-H-L
F-B-A-G-C-C/D-D'-H-K-L              F-E-B-A-G-C-C/D-D'-H-K-L
F-B-A-G-C-C/D'-D                    F-E-B-A-G-C-C/D'-D
F-B-A-G-C-C/D'-H                    F-E-B-A-G-C-C/D'-H
F-B-A-G-C-C/D'-H-L                  F-E-B-A-G-C-C/D'-H-L
F-B-A-G-C-C/D'-H-K-L                F-E-B-A-G-C-C/D'-H-K-L
F-B-A-G-C-C/D'-D'-H                 F-E-B-A-G-C-C/D'-D'-H
F-B-A-G-C-C/D'-D'-H-L               F-E-B-A-G-C-C/D'-D'-H-L
F-B-A-G-C-C/D'-D'-H-K-L             F-E-B-A-G-C-C/D'-D'-H-K-L
F-B-A-G-C-C/D-C/D'-D                F-E-B-A-G-C-C/D-C/D'-D
F-B-A-G-C-C/D-C/D'-H                F-E-B-A-G-C-C/D-C/D'-H
F-B-A-G-C-C/D-C/D'-H-L              F-E-B-A-G-C-C/D-C/D'-H-L
F-B-A-G-C-C/D-C/D'-H-K-L            F-E-B-A-G-C-C/D-C/D'-H-K-L
F-B-A-G-C-C/D-C/D'-D'-H             F-E-B-A-G-C-C/D-C/D'-D'-H
F-B-A-G-C-C/D-C/D'-D'-H-L           F-E-B-A-G-C-C/D-C/D'-D'-H-L
F-B-A-G-C-C/D-C/D'-D'-H-K-L         F-E-B-A-G-C-C/D-C/D'-D'-H-K-L
```

FIG. 37B
GGF/Heregulin Splicing Variants

E-B-A'

E-B-A-C-C/D-D
E-B-A-C-C/D-H
E-B-A-C-C/D-H-L
E-B-A-C-C/D-H-K-L
E-B-A-C-C/D-D'-H
E-B-A-C-C/D-D'-H-L
E-B-A-C-C/D-D'-H-K-L
E-B-A-C-C/D'-D
E-B-A-C-C/D'-H
E-B-A-C-C/D'-H-L
E-B-A-C-C/D'-H-K-L
E-B-A-C-C/D'-D'-H
E-B-A-C-C/D'-D'-H-L
E-B-A-C-C/D'-D'-H-K-L
E-B-A-C-C/D-C/D'-D
E-B-A-C-C/D-C/D'-H
E-B-A-C-C/D-C/D'-H-L
E-B-A-C-C/D-C/D'-H-K-L
E-B-A-C-C/D-C/D'-D'-H
E-B-A-C-C/D-C/D'-D'-H-L
E-B-A-C-C/D-C/D'-D'-H-K-L

E-B-A-G-C-C/D-D
E-B-A-G-C-C/D-H
E-B-A-G-C-C/D-H-L
E-B-A-G-C-C/D-H-K-L
E-B-A-G-C-C/D-D'-H
E-B-A-G-C-C/D-D'-H-L
E-B-A-G-C-C/D-D'-H-K-L
E-B-A-G-C-C/D'-D
E-B-A-G-C-C/D'-H
E-B-A-G-C-C/D'-H-L
E-B-A-G-C-C/D'-H-K-L
E-B-A-G-C-C/D'-D'-H
E-B-A-G-C-C/D'-D'-H-L
E-B-A-G-C-C/D'-D'-H-K-L
E-B-A-G-C-C/D-C/D'-D
E-B-A-G-C-C/D-C/D'-H
E-B-A-G-C-C/D-C/D'-H-L
E-B-A-G-C-C/D-C/D'-H-K-L
E-B-A-G-C-C/D-C/D'-D'-H
E-B-A-G-C-C/D-C/D'-D'-H-L
E-B-A-G-C-C/D-C/D'-D'-H-K-L

GGF2HBS5

FIG. 39
EGFL1

SEQ ID NO: 154:

```
AGC CAT CTT GTC AAG TGT GCA GAG AAG GAG AAA ACT TTC TGT GTG AAT   48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC   96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC  144
Leu Cys Lys Cys Pro Asn Glu Phe Thr Gly Asp Arg Cys Gln Asn Tyr

GTA ATG GCC AGC TTC TAC AGT ACG TCC ACT CCC TTT CTG TCT CTG CCT  192
Val Met Ala Ser Phe Tyr Ser Thr Ser Thr Pro Phe Leu Ser Leu Pro

GAA TAG                                                          198
Glu
```

FIG. 40
EGFL2

SEQ ID NO: 155:

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAA GCG GAG GAG CTC TAC TAA   192
Val Pro Met Lys Val Gln Thr Gln Glu Lys Ala Glu Glu Leu Tyr
```

FIG. 41
EGFL3

SEQ ID NO: 156:

| AGC | CAT | CTT | GTC | AAG | TGT | GCA | GAG | AAG | GAG | AAA | ACT | TTC | TGT | GTG | AAT | 48 |
|---|---|---|---|---|---|---|---|---|---|---|---|---|---|---|---|---|
| Ser | His | Leu | Val | Lys | Cys | Ala | Glu | Lys | Glu | Lys | Thr | Phe | Cys | Val | Asn | |

| GGA | GGC | GAG | TGC | TTC | ATG | GTG | AAA | GAC | CTT | TCA | AAT | CCC | TCA | AGA | TAC | 96 |
|---|---|---|---|---|---|---|---|---|---|---|---|---|---|---|---|---|
| Gly | Gly | Glu | Cys | Phe | Met | Val | Lys | Asp | Leu | Ser | Asn | Pro | Ser | Arg | Tyr | |

| TTG | TGC | AAG | TGC | CCA | AAT | GAG | TTT | ACT | GGT | GAT | CGC | TGC | CAA | AAC | TAC | 144 |
|---|---|---|---|---|---|---|---|---|---|---|---|---|---|---|---|---|
| Leu | Cys | Lys | Cys | Pro | Asn | Glu | Phe | Thr | Gly | Asp | Arg | Cys | Gln | Asn | Tyr | |

| GTA | ATG | GCC | AGC | TTC | TAC | AAA | GCG | GAG | GAG | CTC | TAC | TAA | | | | 183 |
|---|---|---|---|---|---|---|---|---|---|---|---|---|---|---|---|---|
| Val | Met | Ala | Ser | Phe | Tyr | Lys | Ala | Glu | Glu | Leu | Tyr | | | | | |

FIG. 42
EGFL4

SEQ ID NO: 157:

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CCA AAT GAG TTT ACT GGT GAT CGC TGC CAA AAC TAC   144
Leu Cys Lys Cys Pro Asn Glu Phe Thr Gly Asp Arg Cys Gln Asn Tyr

GTA ATG GCC AGC TTC TAC AAG CAT CTT GGG ATT GAA TTT ATG GAG AAA   192
Val Met Ala Ser Phe Tyr Lys His Leu Gly Ile Glu Phe Met Glu Lys

GCG GAG CTC TAC TAA                                                210
Ala Glu Leu Tyr
```

FIG. 43
EGFL5

SEQ ID NO: 158:

```
AGC CAT CTT GTC AAG TGT GCA GAG AAG GAG AAA ACT TTC TGT GTG AAT    48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC    96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT   144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT   192
Val Pro Met Lys Val Gln Thr Gln Glu Lys Cys Pro Asn Glu Phe Thr

GGT GAT CGC TGC CAA AAC TAC GTA ATG GCC AGC TTC TAC AGT ACG TCC   240
Gly Asp Arg Cys Gln Asn Tyr Val Met Ala Ser Phe Tyr Ser Thr Ser

ACT CCC TTT CTG TCT CTG CCT GAA TAG                               267
Thr Pro Phe Leu Ser Leu Pro Glu
```

FIG. 44
EGFL6

SEQ ID NO: 159:

| | | | | | | | | | | | | | | | | |
|---|---|---|---|---|---|---|---|---|---|---|---|---|---|---|---|---|
|AGC|CAT|CTT|GTC|AAG|TGT|GCA|GAG|AAG|GAG|AAA|ACT|TTC|TGT|GTG|AAT|48|
|Ser|His|Leu|Val|Lys|Cys|Ala|Glu|Lys|Glu|Lys|Thr|Phe|Cys|Val|Asn||
|GGA|GGC|GAG|TGC|TTC|ATG|GTG|AAA|GAC|CTT|TCA|AAT|CCC|TCA|AGA|TAC|96|
|Gly|Gly|Glu|Cys|Phe|Met|Val|Lys|Asp|Leu|Ser|Asn|Pro|Ser|Arg|Tyr||
|TTG|TGC|AAG|TGC|CAA|CCT|GGA|TTC|ACT|GGA|GCG|AGA|TGT|ACT|GAG|AAT|144|
|Leu|Cys|Lys|Cys|Gln|Pro|Gly|Phe|Thr|Gly|Ala|Arg|Cys|Thr|Glu|Asn||
|GTG|CCC|ATG|AAA|GTC|CAA|ACC|CAA|GAA|AAG|TGC|CCA|AAT|GAG|TTT|ACT|192|
|Val|Pro|Met|Lys|Val|Gln|Thr|Gln|Glu|Lys|Cys|Pro|Asn|Glu|Phe|Thr||
|GGT|GAT|CGC|TGC|CAA|AAC|TAC|GTA|ATG|GCC|TTC|TAC|AAA|GCG|GAG|  |240|
|Gly|Asp|Arg|Cys|Gln|Asn|Tyr|Val|Met|Ala|Ser|Phe|Lys|Ala|Glu|  |   |
|GAG|CTC|TAC|TAA| | | | | | | | | | | | |252|
|Glu|Leu|Tyr| | | | | | | | | | | | | | |

FIG. 45A

Nucleotide Sequence & Deduced Amino Acid Sequence of GGF2HBS5

SEQ ID NO: 21:

```
GGAATCCTT TTTTTTTTT TTTTTTCTT NNTTTTTTT TGCCCTTATA CCTCTTCGCC     60
TTTCTGTGGT TCCATCCACT TCTTCCCCCT CCTCCTCCCA TAAACAACTC TCCTACCCCT    120
GCACCCCCAA TAAATAAATA AAAGGAGGAG GGCAAGGGGG GAGGAGGAGG AGTGGTGCTG    180
CGAGGGGAAG GAAAAGGGAG GCAGCGCGAG AAGAGCCGGG CAGAGTCCGA ACCGACAGCC    240
AGAAGCCCGC ACGCACCTCG CACC ATG AGA TGG CGA CGC GCC CCG CGC CGC      291
                            Met Arg Trp Arg Arg Ala Pro Arg Arg

TCC GGT CCC GGC CCC CGG GCC CAG CGC CCC GGC TCC GCC GCC CGC         339
Ser Gly Pro Gly Pro Arg Ala Gln Arg Pro Gly Ser Ala Ala Arg
                                                    GGF-II 09

TCG CCG CCG CTG CCG CTA CTG CCA CTG CTG CTG CTG CTG GGG ACC         387
Ser Pro Pro Leu Pro Leu Leu Pro Leu Leu Leu Leu Leu Gly Thr
                                  Val Cys Leu Leu Leu Thr Val
                                                       GGF-II 09

GCG GCC CTG GCG GCG CCG GGG GCG GCC AAC GAG GCG GCT CCC GCG         435
Ala Ala Leu Ala Ala Pro Gly Ala Ala Gly Asn Glu Ala Ala Pro Ala
Ala Ala Leu Pro Pro Thr

GGG GCC TCG TGC TAC TCG TCC CCG CCC AGC GTG GGA TCG GTG CAG         483
Gly Ala Ser Val Cys Tyr Ser Ser Pro Pro Ser Val Gly Ser Val Gln
                        Ala Ser Pro Val Ser Pro Val Ser Val Gln
                                                    GGF-II 08

GAG CTA GCT CAG CGC GCC GCG GTG GTG ATC GAG GGA AAG GTG CAC CCG     531
Glu Leu Ala Gln Arg Ala Ala Val Val Ile Glu Gly Lys Val His Pro
Glu Leu Val Gln Arg Trp Phe Val Val Ile Glu Gly Lys
                  GGF-II 04
```

FIG. 45B

Nucleotide Sequence & Deduced Amino Acid Sequence of GGF2HBS5

```
CAG CGG CAG CAG GGG GCA CTC GAC AGG AAG GCG GCG GCG GCG GCG        579
Gln Arg Gln Gln Gly Ala Leu Asp Arg Lys Ala Ala Ala Ala Ala

GGC GAG GCA GGG GCG TGG GGC GAT CGC GAG GAG CCA GCC GCG GGC        627
Gly Glu Ala Gly Ala Trp Gly Asp Arg Glu Glu Pro Pro Ala Gly

CCA CGG GCG CTG GGG CCG CCC GCC GAG CCG CTG CTC GCC GCC AAC        675
Pro Arg Ala Leu Gly Pro Pro Ala Glu Pro Leu Leu Ala Ala Asn

GGG ACC GTG CCC TCT TGG CCC ACC GCC CCG GTG CCC AGC GGC GAG        723
Gly Thr Val Pro Ser Trp Pro Thr Ala Pro Val Pro Ser Ala Gly Glu

CCC GGG GAG GAG GCG CCC TAT CTG GTG AAG GTG CAC CAG GTG TGG GCG    771
Pro Gly Glu Glu Ala Pro Tyr Leu Val Lys Val His Gln Val Trp Ala
                                        Lys Val His Glu Val Trp Ala
                                        GGF-II 01 & GGF-II 11

GTG AAA GCC GGG GGC TTG AAG AAG GAC TCG CTG CTC ACC GTG CGC CTG    819
Val Lys Ala Gly Gly Leu Lys Lys Asp Ser Leu Leu Thr Val Arg Leu
Ala Lys                       Asp Leu Leu Leu Xaa Val     Leu
                              GGF-II 10

GGG ACC TGG GGC CAC CCC GCC TTC CCC TCC TGC GGG AGG CTC AAG GAG    867
Gly Thr Trp Gly His Pro Ala Phe Pro Ser Cys Gly Arg Leu Lys Glu
Gly Ala Trp Gly Pro Pro Ala Phe Pro Val Xaa Tyr
GGF-II 03

GAC AGC AGG TAC ATC TTC ATG GAG CCC GAC GCC AAC AGC ACC AGC        915
Asp Ser Arg Tyr Ile Phe Met Glu Pro Asp Ala Asn Ser Thr Ser
Tyr Ile Phe Met Glu Pro Glu Ala Xaa Ser Ser Gly
GGF-II 02
```

FIG. 45C

Nucleotide Sequence & Deduced Amino Acid Sequence of GGF2HBS5

```
CGC GCG CCG GCC TTC CGA GCC TCT CCC CCT CTG GAG ACG GGC        963
Arg Ala Pro Ala Phe Arg Ala Ser Phe Pro Leu Glu Thr Gly

CGG AAC CTC AAG GAG AAG GTC AGC CGG CTG TGC AAG TGC GCC       1011
Arg Asn Leu Lys Glu Lys Val Ser Arg Leu Cys Lys Cys Ala

TTG CCT CCC CAA TTG AAA GAG ATG AAA AGC CAG GAA TCG GCA GGT   1059
Leu Pro Pro Gln Leu Lys Glu Met Lys Ser Gln Glu Ala Ala Gly

TCC AAA CTA GTC CTT CGG TGT GAA ACC AGT TCT GAA TAC TCC CTC   1107
Ser Lys Leu Val Leu Arg Cys Glu Thr Ser Ser Glu Tyr Ser Leu
         Leu Val Leu Arg
          GGF-II 06

AGA TTC AAG TGG TTC AAG AAT AAT GAA TTG AAT CGA AAA AAC AAA   1155
Arg Phe Lys Trp Phe Lys Asn Asn Gly Asn Glu Leu Asn Arg Lys Asn Lys

CCA CAA AAT ATC AAG ATA CAA AAG AAG CCA GGG AAG TCA GAA CTT CGC   1203
Pro Gln Asn Ile Lys Ile Gln Lys Lys Pro Gly Lys Ser Glu Leu Arg

ATT AAC AAA GCA TCA CTG GCT GAT TCT GGA GAG TAT ATG TGC AAA GTG   1251
Ile Asn Lys Ala Ser Leu Ala Asp Ser Gly Glu Tyr Met Cys Lys Val
Lys Ala Ser Leu Ala Asp Ser Gly Glu Tyr Met Xaa Lys
                 GGF-II 12

ATC AGC AAA TTA GGA AAT GAC AGT GCC TCT GCC AAT ATC ACC ATC GTG   1299
Ile Ser Lys Leu Gly Asn Asp Ser Ala Ser Ala Asn Ile Thr Ile Val

GAA TCA AAC GCT ACA TCT ACA TCC ACT ACT GGG ACA AGC CAT CTT GTA   1347
Glu Ser Asn Ala Thr Ser Thr Ser Thr Thr Gly Thr Ser His Leu Val
```

FIG. 45D

Nucleotide Sequence & Deduced Amino Acid Sequence of GGF2HBS5

```
AAA TGT GCG GAG AAG GAG AAA ACT TTC TGT GTG AAT GGA GGG GAG TGC          1395
Lys Cys Ala Glu Lys Glu Lys Thr Phe Cys Val Asn Gly Gly Glu Cys

TTC ATG GTG AAA GAC CTT TCA AAC CCC TCG AGA TAC TTG TGC AAG TGC          1443
Phe Met Val Lys Asp Leu Ser Asn Pro Ser Arg Tyr Leu Cys Lys Cys

CCA AAT GAG TTT ACT GGT GAT CGC TGC CAA AAC TAC GTA ATG GCC AGC          1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                      1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCCTCA GATTCCACCT       1590

AGAGCTAGAT GTGTCTTACC AGATCTAATA TTGACTGCCT CTGCCTGTCG CATGAGAACA        1650

TTAACAAAAG CAATTGTATT ACTTCCTCTG TTCGCGACTA GTTGGCTCTG AGATACTAAT        1710

AGGTGTGTGA GGCTCCGGAT GTTTCTGGAA TTGATATTGA ATGATGTGAT ACAAATTGAT        1770

AGTCAATATC AAGCAGTGAA ATATGATAAT AAAGGCATTT CAAAGTCTCA CTTTTATTGA        1830

TAAAATAAAA ATCATTCTAC TGAACAGTCC ATCTTCTTTA TACAATGACC ACATCCTGAA        1890

AAGGGTGTTG CTAAGCTGTA ACCGATATGC ACTTGAAATG ATGGTAAGTT AATTTTGATT        1950

CAGAATGTGT TATTTGTCAC AAATAAACAT AATAAAAGGA AATAAAAGGA AAAAAAAAAA AAA   2003
```

METHOD FOR MAKING ANTIBODIES WHICH SPECIFICALLY BIND TO GLIAL GROWTH FACTORS

This is a divisional application Ser. No. 08/011,396, filed Jan. 29, 1993, now abandoned, which is a continuation-in-part of application Ser. No. 07/984,085, filed Dec. 1, 1992, now abandoned which is a continuation-in-part of application Ser. No. 07/951,747, filed Sep. 25, 1992, now abandoned which is a continuation-in-part of application Ser. No. 07/927,337 filed Aug. 10, 1992 now abandoned.

BACKGROUND OF THE INVENTION

The invention relates to compounds which are inhibitors of cell proliferation, having antiproliferative activity on a variety of cell types.

Many vertebrate cell types respond to diffusible growth factors as stimuli which regulate proliferation. A number of these growth factors and their cognate receptors have been purified, and the genes encoding them have been cloned and characterized (Sporn and Roberts eds. (1991) Peptide Growth Factors and their Receptors I and II. Springer-Verlaz, New York). Many cancers, which are diseases of cell proliferation, involve genetic modifications which affect the nature of the growth factor-receptor interaction. Such modifications can result in unregulated stimulation of proliferation in the receptor bearing target cell. Additionally, certain tumors of the nervous system involve the regulation of proliferation of cells from both the central and peripheral nervous systems.

The glial cells of vertebrates constitute the specialized connective tissue of the central and peripheral nervous systems. Important glial cells include the peripheral Schwann cells which provide both the metabolic support for neurons and the myelin sheathing around the axons of certain peripheral neurons, thereby forming individual nerve fibers. Schwann cells support neurons and provide a sheath effect by forming concentric layers of membrane around adjacent neuron axons, twisting as they develop around the axons. These myelin sheaths are a susceptible element of many nerve fibers. Damage to Schwann cells, or failure in growth and development, can be associated with significant demyelination or nerve degeneration characteristic of a number of peripheral nervous system diseases and disorders. In the development of the nervous system, it has become apparent that cells require various factors to regulate their division and growth. Several regulators of Schwann cell proliferation and differentiation have been identified. Such factors play an important role in both the development and the regeneration (following injury) of the peripheral nervous system.

Brockes et al. ((1984) J. Neuroscience 4:75–83) describe a protein growth factor present in extracts from bovine brain and pituitary tissue, termed Glial Growth Factor (GGF). This factor stimulates cultured rat Schwann cells to divide against a background medium containing ten percent fetal calf serum. GGF has been described as having a molecular weight of 31 KD and readily forming dimers. Brockes ((1987) Meth. Enz. 147:217–225) describes a Schwann cell-based assay for 31 kD GGF and purification using reversed phase HPLC.

The J. Neuroscience article of Brockes et al., supra, describes methods of purification of GGF to apparent homogeneity. In brief, one large-scale purification method described involves extraction of the lyophilized bovine anterior lobes and chromatography of material obtained thereby, using NaCl gradient elution from CM cellulose. Gel filtration is then carried out with an Ultrogel column, followed by elution from a phosphocellulose column, and finally, small-scale SDS gel electrophoresis. Alternatively, the CM-cellulose material was applied directly to a phosphocellulose column, fractions from the column were pooled and purified by preparative native gel electrophoresis, followed by a final SDS gel electrophoresis.

Brockes et al. ((1980) J. Biol. Chem. 255:8374–8377) observe that in gel filtration experiments the major peak of growth factor activity is observed to migrate with a molecular weight of 56 KD, whereas in the first of the above-described procedures activity was predominantly observed at molecular weight 31 KD. They report that the GGF dimer is largely removed as a result of the gradient elution from CM-cellulose in this procedure.

Benveniste et al. ((1985) PNAS 82:3930–3934) describe a T lymphocyte-derived glial growth promoting factor. This factor, under reducing conditions, exhibits a change in apparent molecular weight on SDS gels.

Kimura et al. ((1990) Nature 348:257–260) describe a factor they term Schwannoma-derived growth factor (SDGF) obtained from a sciatic nerve sheath tumor. The authors state that SDGF does not stimulate the incorporation of tritium-labelled TdR into cultured Schwann cells under conditions where, in contrast, partially purified pituitary fraction containing GGF is active. SDGF has an apparent molecular weight between 31 KD and 35 KD.

Davis et al. ((1990) J. Cell. Biol. 110:1353–1360) describe the screening of a number of candidate mitogens. The chosen candidate substances being examined for their ability to stimulate DNA synthesis in Rat Schwann cells in the presence of 10% FCS (fetal calf serum), with and without forskolin. One of the factors tested, GGF-carboxymethyl cellulose fraction (GGF-CM), was mitogenic in the presence of FCS, with and without forskolin. It was also observed that in the presence of forskolin platelet derived growth factor (PDGF) is a potent mitogen for Schwann cells. Previous to this finding, PDGF was not thought to have a mitogenic effect on Schwann cells.

Holmes et al. ((1992) Science 256:1205) and Wen et al. ((1992) Cell 69:559) demonstrate that DNA sequences which encode proteins which bind to a receptor (p185$^{erbB2}$) are associated with several human tumors.

The p185$^{erbB2}$ protein is a 185 kilodalton membrane spanning protein with tyrosine kinase activity. The protein is encoded by the erbB2 proto-oncogene (Yarden and Ullrich. (1988) Ann. Rev. Biochem. 57:443). The erbB2 gene, also referred to as HER-2 (in human cells) and neu (in rat cells), is closely related to the receptor for epidermal growth factor (EGF). Recent evidence indicates that proteins which interact with (and activate the kinase of) p185$^{erbB2}$ induce proliferation in the cells bearing p185$^{erbB2}$ (Holmes et al. (1992) Science 256:1205; Dobashi et al. (1991) Proc. Natl. Acad. Sci. 88:8582; and Lupu et al. (1992) Proc. Natl. Acad. Sci. 89:2287).

Although ligands have been identified which stimulate proliferation of cells with certain receptors (e.g., the p185$^{erbB2}$ receptor), there exists a need to identify and isolate factors which act as inhibitors of cell proliferation at these receptor sites. Such inhibitors could be used for the purpose of treating cell proliferative disorders (e.g., neoplasms).

SUMMARY OF THE INVENTION

In general, the invention provides methods for inhibiting proliferation of cells, including cells of the nervous system.

The antiproliferative factors of the invention are alternative splicing products and fragments thereof of the DNA encoding the GGF/p185$^{erbB2}$ family of proteins.

The invention also provides a DNA sequence encoding a glial growth inhibitory factor; the sequence is included in the clone pGGF2HBS11 (ATCC Deposit No. 75347).

The peptide encoded by this clone is also a part of the invention. The invention further includes a peptide comprising a peptide encoded by the E sequence (SEQ ID Nos. 137 and 163) and at least a portion of the peptides encoded by brain derived DNA sequences flanking the E encoding sequences on clone pGGF2HBS11 (ATCC Deposit No. 75347). Preferably, the E encoded polypeptide sequence lacks 48 amino acids on the amino-terminal end and includes between 20 and 100 or, more preferably, between 25 and 70 amino acids of flanking the E encoded polypeptide. In addition, the E encoded polypeptide may be flanked by between 30 and 50, or, more preferably, between 35 and 45 amino acids on the carboxy terminal side of the E encoded segment. The sequences flanking the E encoded polypeptide are encoded by the DNA sequences flanking the E sequence present in clone pGGF2HBS11 (ATCC Deposit No. 75347).

Specifically, the invention also provides a method for inhibiting cell proliferation in vitro or in vivo comprising contacting the cell with
a) a polypeptide defined by the formula

VYBAZWX wherein VYBAZWX is composed of the polypeptide segments shown in FIG. 31 (SEQ ID Nos. 136–139, 141–147, 160, 161); wherein V comprises F, or is absent; wherein Y comprises polypeptide segment E, or is absent; wherein Z comprises polypeptide segment G or is absent; wherein W comprises C or is absent; and wherein X comprises polypeptide segments C/D HKL, C/D H, C/D HL, C/D D, C/D' HL, C/D' HKL, C/D' H, C/D' D, C/D C/D' HKL, C/D C/D' H, C/D C/D' HL, C/D C/D' D, C/D D' H, C/D D' HL, C/D D' HKL, C/D' D' H, C/D' D' HL, C/D' D' HKL, C/D C/D' D' H, C/D C/D' D' HL, H, HK, HKL, or C/D C/D' D' HKL;
b) a polypeptide comprising FBA polypeptide segments having the amino acid sequences shown in FIG. 31 (SEQ ID Nos. 136, 138, 139);
c) a polypeptide comprising FBA' polypeptide segments having the amino acid sequences shown in FIG. 31 (SEQ ID Nos. 136, 138, 140, 168);
d) a polypeptide comprising FEBA polypeptide segments having the amino acid sequences shown in FIG. 31 (SEQ ID Nos. 136–139); or
e) a polypeptide comprising FEBA' polypeptide segments having the amino acid sequences corresponding to polypeptide segments shown in FIG. 31 (SEQ ID Nos. 136–138, 140, 168);
f) a polypeptide comprising EBA' polypeptide segments having the amino acid sequences corresponding to polypeptide segments shown in FIG. 31 (SEQ ID Nos. 136, 138, 140, 168); or
g) a polypeptide comprising a portion of the E sequence (SEQ ID Nos. 137 and 163) and flanked by new sequence not contained in F, B, A, C/D, C/D', D, D', HK or L and contained in clone pGGF2HBS11, ATCC Deposit No. 75347; or to glial cells (i.e., astrocytes and microglial cells of the central and peripheral nervous system and Schwann cells of the peripheral nervous system).

The invention also provides a method of inhibiting proliferation of cells, including cells of the nervous system, by a method which consists of contacting the cells with a compound which specifically binds the p185$^{erbB2}$ receptor of the cell type.

Also included is the method comprising the administration of any of the above mentioned peptides when the peptides are administered in the treatment or prophylaxis of a nervous disease or disorder. Further included in the invention is the method of administering any of the above mentioned peptides when the cell is present in a mammal and the contacting of the cell is carried out by the administration of the peptide to the mammal for the prophylaxis or treatment of a pathophysiological condition in the mammal which involves the stated cell. Also included is the use of the method, as stated above, wherein the condition involves a disease of cell proliferation, such as a tumor, and more specifically, where the condition involves peripheral nerve damage caused by a tumor of the nervous system. Also a part of the invention is the administration of the inhibitory factors for the purpose of increasing myelination of existing or regenerated neural tissue.

Further included as a part of the invention are methods comprising administration of any of the above mentioned polypeptides to a cell when the cell is present in a mammal and the contacting of the cell is carried out by administering the peptide to the mammal for the prophylaxis or treatment of a condition which involves one of the following conditions: a tumor of the Schwann cells, for example, neurofibromatosis, malignant Schwannomas or neurofibrosarcomas; a meningioma; a bilateral acoustic neuroma; an astrocytoma; a retinoblastoma; a neuroglioma; a neuroblastoma; an adenocarcinoma; or a glioma, by the method comprising administering to the mammal an effective amount of a polypeptide, as defined above.

The invention also includes a method for producing an antibody specific for a polypeptide, consisting of immunizing a mammal with a polypeptide selected from the above listed polypeptides, or a fragment thereof, and purifying the antibody from the tissue of the animal, or from a hybridoma made using the tissue.

Furthermore, the invention provides a method for detecting, in a sample, the presence of a molecule capable of binding to a receptor which binds to a polypeptide selected from the above mentioned polypeptides, and contacting the sample with the polypeptide together with the receptor, and detecting inhibition of the binding of the polypeptide to the receptor as an indication of the presence of a receptor binding molecule in the sample. The invention also provides methods for determining whether such a competitive inhibitor is an antagonist or agonist of receptor function.

Thus, factors useful in the methods of the invention are:
(a) basic polypeptide factors having antiproliferative activity when contacted with cells, including cells of the nervous system and specifically Schwann cells, and containing within their amino acid sequences one or more of the following peptide sequences:
F K G D A H T E (SEQ ID NO: 1)
A S L A D E Y E Y M X K (SEQ ID NO: 2)
T E T S S S G L X L K (SEQ ID NO: 3)
A S L A D E Y E Y M R K (SEQ ID NO: 7)
A G Y F A E X A R (SEQ ID NO: 11)
T T E M A S E Q G A (SEQ ID NO: 13)
A K E A L A A L K (SEQ ID NO: 14)
F V L Q A K K (SEQ ID NO: 15)
E T Q P D P G Q I L K K V P M V I G A Y T (SEQ ID NO: 169) and (b) basic polypeptide factors capable of inhibiting the division of cells, including cells of the nervous system and particularly Schwann cells, and containing within their amino acid sequences, respectively, one or more of the following peptide sequences:
V H Q V W A A K (SEQ ID NO: 33)
Y I F F M E P E A X S S G (SEQ ID NO: 34)
L G A W G P A F P V X Y (SEQ ID NO: 35)
W F V V I E G K (SEQ ID NO: 36)
A S P V S V G S V Q E L Q R (SEQ ID NO: 37)
V C L L T V A A L P P T (SEQ ID NO: 38)
K V H Q V W A A K (SEQ ID NO: 51)
K A S L A D S G E Y M X K (SEQ ID NO: 52)
D L L L X V (SEQ ID NO: 39)

The peptide sequences set out above, derived from lower and higher molecular weight polypeptide factors described in detail below, are also aspects of this invention in their own right. These sequences are potentially useful as therapeutics, probes for large polypeptide factors, for investigating, isolating or preparing such factors (or corresponding gene sequences) from a range of different species, or preparing such factors by recombinant technology, and in the generation of antibodies (preferably monoclonal), by conventional technologies, which are themselves useful as investigative tools and potential medicaments. Such antibodies are included within this invention. The invention also includes inhibitors of cell proliferation encoded by gene sequences obtainable using the peptide sequences of the invention.

The invention further includes methods for use of a polypeptide factor having cell, including cells of the nervous system, antiproliferative activity and including an amino acid sequence encoded by:

(a) a DNA sequence shown in any one of FIGS. 28a, 28b or 28c (SEQ ID Nos. 133–135 respectively);

(b) a DNA sequence shown in FIG. 22 (SEQ ID No. 89);

(c) the DNA sequence represented by nucleotides 281–557 of the sequence shown in FIG. 28a (SEQ ID No. 133); or (d) a DNA sequence hybridizable to any one of the DNA sequences according to (a), (b) or (c).

While the present invention is not limited to a particular set of hybridization conditions, the following protocol gives general guidance which may, if desired, be followed:

Thus, DNA probes may be labelled to high specific activity (approximately $10^8$ to $10^9$ dpm $^{32}$p per $\mu$g) by nick-translation or by PCR reactions according to Schowalter and Sommer ((1989) Anal. Biochem. 177:90–94) and purified by desalting on G-150 Sephadex columns. Probes may be denatured (10 minutes in boiling water followed by immersion into ice water), then added to hybridization solutions of 80% buffer B (2 g polyvinylpyrolidine, 2 g Ficoll-400, 2 g bovine serum albumin, 50 $\mu$l 1M Tris HCL (pH 7.5), 58 g NaCl, 1 g sodium pyrophosphate, 10 g sodium dodecyl sulfate, 950 $\mu$l H$_2$O) containing 10% dextran sulfate at $10^6$ dpm 32p per $\mu$l and incubated overnight (say, 16 hours) at 60° C. The filters may then be washed at 60° C., first in buffer B for 15 minutes followed by three 20-minute washes in 2× SSC, 0.1% SDS then one for 20 minutes in 1× SSC, 0.1% SDS.

The methods of the invention take advantage of the fact that a Glial Growth Factor and the p185$^{erbB2}$ ligand protein are encoded by the same gene. A variety of messenger RNA splicing variants (and their resultant proteins) are derived from this gene, and many of these products exhibit p185$^{erbB2}$ binding. This binding may result in either cell proliferation or cessation of cell division. At least two of the gene products (GGFI and GGFII) have been used to induce Schwann cell mitogenic activity. This invention employs some of the known products of the GGF/p185$^{erbB2}$ ligand gene (described in the references listed above) as inhibitors of cell proliferation and, more specifically, as inhibitors of glial cell proliferation.

This invention also relates to other, not yet naturally isolated splicing variants of the Glial Growth Factor gene. FIG. 30 shows the known patterns of splicing derived from polymerase chain reaction experiments (on reverse transcribed RNA) and analysis of cDNA clones (as presented within) and derived from what has been published as sequences encoding p185$^{erbB2}$ ligands (Peles et al. (1992) Cell 69:205 and Wen et al. (1992) Cell 69:559). These patterns, as well as additional patterns disclosed herein, represent probable existing splicing variants.

Thus other aspects of the invention are Methods for the use of a series of human and bovine polypeptide factors having cell antiproliferative activity, including the inhibition of the division of cells of the nervous system, such as Schwann cells. Such peptide sequences are shown in FIG. 31–34, (SEQ ID Nos. 136–137, 173–179), respectively.

The human peptide sequences described above and presented in FIGS. 31–34, SEQ ID Nos. 136–137 respectively, represent a series of splicing variants which can be isolated as full length complementary DNA's (cDNA's) from natural sources (cDNA libraries prepared from the appropriate tissues) or assembled as DNA constructs with individual exons (e.g., derived as separate exons) by one skilled in the art.

Other compounds, in particular, peptides, which bind specifically to the p185$^{erbB2}$ receptor can also be used according to the invention as inhibitors of glial cell proliferation. A candidate compound can be routinely screened for p185$^{erbB2}$ binding, and, if it binds, can be screened for inhibition of cell proliferation using the methods described herein.

The invention includes the use of any modifications or equivalents of the above polypeptide factors which do not exhibit a significant reduction in the stated inhibitory activity. For example, modifications in which amino acid content or sequence is altered without substantially adversely affecting inhibitory activity are included. By way of illustration, in EP-A 109748 muteins of native proteins are disclosed in which the possibility of unwanted disulfide binding is avoided by replacing any cysteine in the native sequence which is not necessary for biological activity with a neutral amino acid. The statements of effect and use contained herein are therefore to be construed accordingly, with such uses and effects employing modified or equivalent factors as aforesaid being part of the invention.

The peptides useful in the invention can be made recombinantly using DNA constructs comprising DNA sequences, as defined above, in operable reading frame position in vectors under the control of control sequences so as to permit expression of the sequences in suitable host cells after transformation thereof by said constructs (preferably the control sequence includes a regulatable promoter, e.g. Trp)—it will be appreciated that the selection of a promoter and regulatory sequences (if any) are matters of choice for those of ordinary skill in the art.

The factors of the invention can be formulated for pharmaceutical or veterinary use by combination with an acceptable diluent, carrier or excipient and/or in unit dosage form. In using the factors of the invention, conventional pharmaceutical or veterinary practice may be employed to provide suitable formulations or compositions.

Thus, the formulations of this invention can be applied to parenteral administration, for example, intravenous, subcutaneous, intramuscular, intraorbital, ophthalmic, intraventricular, intracranial, intracapsular, intraspinal, intracisternal, intraperitoneal, topical, intranasal, aerosol, scarification, and also oral, buccal, rectal or vaginal administration.

The formulations of the invention may also be administered by the transplantation into the patient of host cells expressing the DNA of the instant invention or by the use of surgical implants which release the formulations of the invention.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are to be found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The present factors can be used as the sole active agents or can be used in combination with other active ingredients.

The concentration of the present factors in the formulations of the invention will vary depending upon a number of issues, including the dosage to be administered, and the route of administration.

In general terms, the factors of this invention may be provided in an aqueous physiological buffer solution containing about 0.1 to 10% w/v compound for parenteral administration. General dose ranges are from about 1 $\mu$g/kg to about 1 g/kg of body weight per day; a preferred dose range is from about 0.01 mg/kg to 100 mg/kg of body weight per day. The preferred dosage to be administered is likely to depend upon the type and extent of progression of the pathophysiological condition being addressed, the overall health of the patient, the make up of the formulation, and the route of administration.

As indicated above, cell proliferation, particularly that of Schwann cells (the glial cells of the peripheral nervous system) and other cells of the nervous system is inhibited in the presence of the factors of the invention.

There are a variety of tumors of glial cells, the most common of which is probably neurofibromatosis, which is a patchy small tumor created by overgrowth of glial cells. Also, it has been found that an activity very much like GGF can be found in some Schwann cell tumors (Brockes et al., Ann. Neurol. 20:317 (1986)). Therefore inhibitors of GGF action on their receptors provides a therapy of a glial tumor. This therapy comprises administering an effective amount of a substance which inhibits the binding of a stimulatory factor as defined above to its receptor. Additionally, given the association of GGF receptor amplification with human adenocarcinomas (Kraus et al., (1987) EMBO J. 6:605; Slamon et al. (1987) Science 235:177; Varley et al. (1987) Oncogene 1:423; and van de Vijver et al. (1987) Mol Cell Biol 7:2019) and tumors of the breast and ovary (Slamon et al. supra; Varley et al. supra: Venter et al. (1987) Lancet ii:67; Zhou et al. (1987) Cancer Res. 47:6123; Berger et al. (1988) Cancer Res. 48:1238; Tsuda et al. (1989) Cancer Res. 49:3104; Slamon et al. (1989) Science 244:707), a similar therapeutic approach may be taken with adenocarcinomas and tumors of breast and ovarian tissues.

In general, the invention includes the use of present polypeptide factors in the prophylaxis or treatment of any pathophysiological condition in which a factor-sensitive or factor-responsive cell type is involved.

The polypeptide factors of the invention can also be used as immunogens for making antibodies, such as monoclonal antibodies, following standard techniques. Such antibodies are included within the present invention. These antibodies can be used for therapeutic or diagnostic purposes. Thus, conditions associated with abnormal levels of the factor may be tracked by using such antibodies. In vitro techniques can be used, employing assays on isolated samples using standard methods. Imaging methods can also be employed in which the antibodies are, for example, tagged with radioactive isotopes which can be remotely imaged from outside the body using techniques employed in the art of, for example, tumour imaging.

Such antibodies, as described above, may also be used for therapeutic purposes. Anti-idiotypic antibodies raised against the polypeptide factors of the invention or idiotypic antibodies raised against their cognate receptor can be used as antagonists of GGF/erbB2 ligand induced proliferation of p185$^{erbB2}$ bearing cells.

The invention also includes the general use of the present factors as inhibitors of cell proliferation in vivo or in vitro, and the methods for such use. One embodiment is thus a method for producing a tumor cell antiproliferative effect in a vertebrate by administering an effective amount of a factor of the invention. An example of such a method is the treatment or prophylaxis of nervous system tumors or tumors of other tissues.

A further general aspect of the invention is the use of a factor of the invention in the manufacture of a medicament, preferably for the treatment of a nervous disease or disorder.

Also included in the invention are the use of the factors of the invention in competitive assays to identify or quantify molecules having receptor binding characteristics corresponding to those of said polypeptides. The polypeptides may be labelled, optionally with a radioisotope and these labelled products may be used to determine if receptor binding exists. A competition assay can identify both antagonists and agonists of the relevant receptor. Any competition for receptor binding between a known agonist and an antagonist (shown to bind the receptor) in a bioassay would be reflected by a decrease in biological activity with in an increase in concentration of antagonist.

In another aspect, the invention provides the use of the factors in an affinity isolation process, e.g., affinity chromatography, for the separation of a respective corresponding receptor. Such processes for the isolation of receptors corresponding to particular proteins are known in the art, and a number of techniques are available and can be applied to the factors of the present invention. For example, in relation to IL-6 and IFN-gamma, the reader is referred to Novick et al. ((1990) J. Chromatogr. 510:331–7), in relation to gonadotropin releasing hormone, reference is made to Hazum ((1990) J. Chromatogr. 510:233–8), in relation to G-CSF, reference is made to Fukunaga et al. ((1990) J. Biol. Chem. 265:13386–13390), in relation to IL-2, reference is made to Smart et al. ((1990) J. Invest. Dermatol. 94:158S–163S), and in relation to human IFN-gamma, reference is made to Stefanos et al. ((1989) J. Interferon Res. 9:719–30)

The following examples are not intended to limit the invention, but are intended to usefully illustrate the same, and provide specific guidance for effective preparative techniques. Examples 1–4 teach the purification and consequent cloning of bovine DNA sequences encoding GGF Examples 5 and 7 demonstrate the isolation of human DNA sequences encoding GGF. Examples 8 and 9 demonstrate the isolation of splicing variants. Examples 10 and 11 show specific antiproliferative variants and examples of their function. Examples 12 and 13 demonstrate the production and testing of antiproliferative molecules.

BRIEF DESCRIPTION OF THE DRAWINGS

The drawings will first be described.

Drawings

FIGS. 1 to 8 relate to Example 1 hereinafter, and are briefly described below:

FIG. 1 is the profile for product from carboxymethyl cellulose chromatography;

FIG. 2 is the profile for product from hydroxylapatite HPLC;

FIG. 3 is the profile for product from Mono S FPLC;

FIG. 4 is the profile for product from Gel filtration FPLC;

FIGS. 5 and 6 depict the profiles for the two partially purified polypeptide products from reversed-phase HPLC; and FIGS. 7 and 8 depict dose response curves for the GGF-I and GGF-II fractions from reversed-phase HPLC using either a fetal calf serum or a fetal calf plasma background;

FIGS. 9 to 12 depict peptides derived from GGF-I and GGF-II, (SEQ ID Nos. 1–53, 164–166 and 169) (see Example 2, hereinafter), FIGS. 10 and 12 specifically depict novel sequences:

FIG. 9 shows the N-terminus of GGF-I and various trypsin and V8 protease peptides derived from GGF-I.

In FIG. 10, Panel A, the sequences of GGF-I peptides used to design degenerate oligonucleotide probes and degenerate PCR primers are listed (SEQ ID Nos. 20–30). Some of those sequences in Panel A were also used to design synthetic peptides. Panel B shows the novel peptides that were too short (less than 6 amino acids) for the design of degenerate probes or degenerate PCR primers (SEQ ID Nos. 19 and 32)

FIG. 11 shows various trypsin and lysyl endopeptidase-C peptides derived from GGF2.

In FIG. 12, Panel A, the sequences of GGF-II peptides used to design degenerate oligonucleotide probes and degenerate PCR primers are listed (SEQ ID Nos. 45–52). Some of these sequences in Panel A were also used to design synthetic peptides. Panel B shows the novel peptides that were too short (less than 6 amino acids) for the design of degenerate probes or degenerate PCR primers (SEQ ID No. 53);

FIGS. 13 to 20 relate to Example 3 hereinafter, and show various aspects of the mitogenic activity of factors related to the invention;

FIG. 13 shows a graph comparing BrUdR-ELISA and [$^{125}$I]UdR counting methods for the DNA synthesis assay in Schwann cell cultures.

FIG. 15 shows the mitogenic response of rat sciatic nerve Schwann cells to GGFs.

FIG. 16 shows a graph quantifying DNA synthesis in rat sciatic nerve Schwann cells and 3T3 fibroblasts in the presence of GGFs.

FIG. 17 shows a graph of the mitogenic response of BHK21 C13 cells to FCS and GGFs.

FIG. 18 shows a graph of survival and proliferation of BHK21 C13 cell microcultures after 48 hours in the presence of GGFs.

FIG. 19 shows a graph of the mitogenic response of C6 cells to FCS.

FIG. 20 shows graphs of the mitogenic response of C6 cells to aFGF (left panel) and GGFs (right panel).

FIGS. 21 to 28 (a, b and c) relate to Example 4 hereinafter, and are briefly described below:

FIG. 21 lists the degenerate oligonucleotide probes (SEQ ID Nos. 54–88) designed from the novel peptide sequences listed in FIG. 10, Panel A and FIG. 12, Panel A;

FIG. 22 (SEQ ID No. 89) depicts a stretch of the putative bovine GGF-II gene sequence from the recombinant bovine genomic phage GGF2BG1, which contains the binding site of degenerate oligonucleotide probes 609 and 650 (see FIG. 21, SEQ ID Nos. 69 and 72, respectively).

Figure 24:
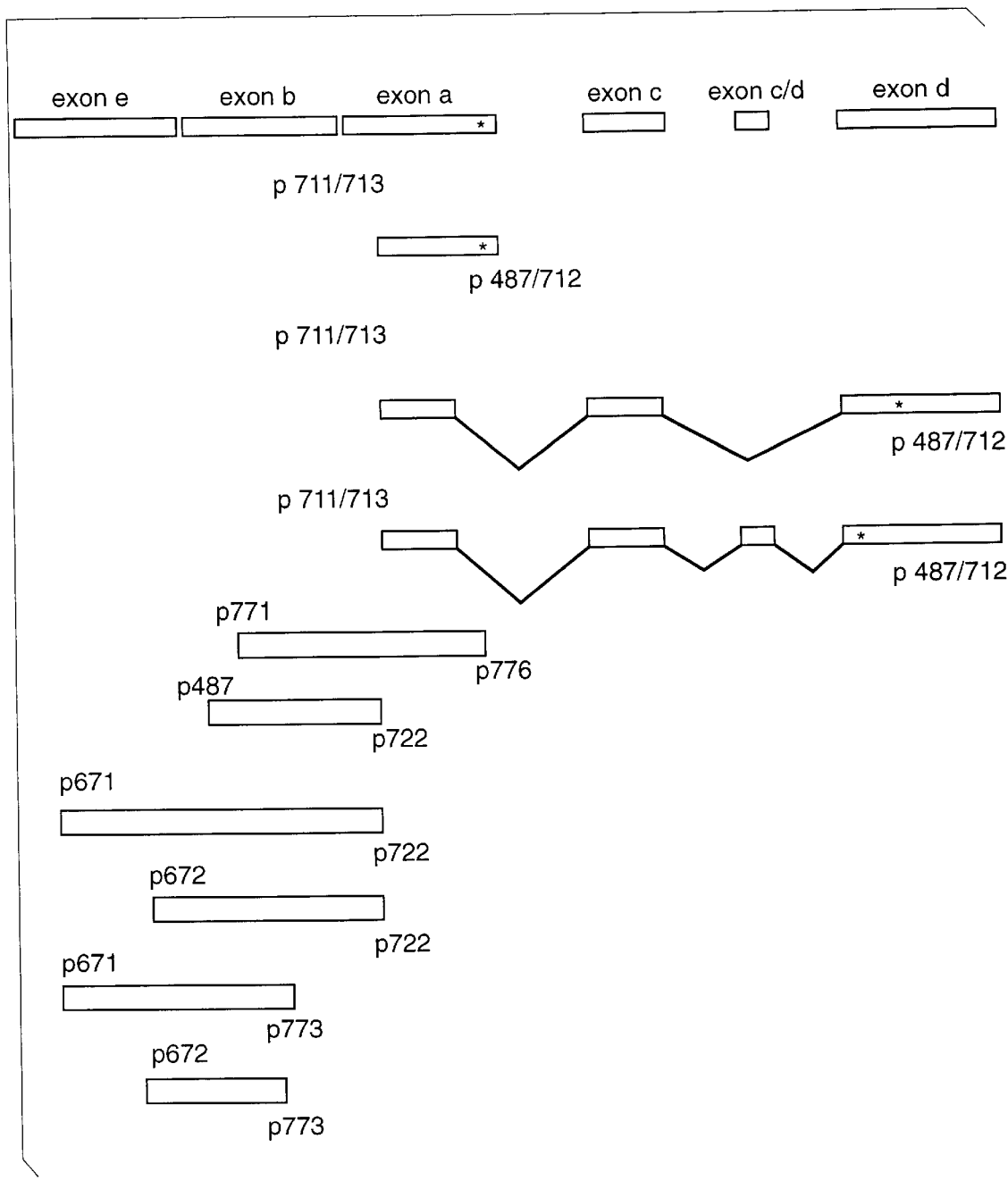
Figure 25:
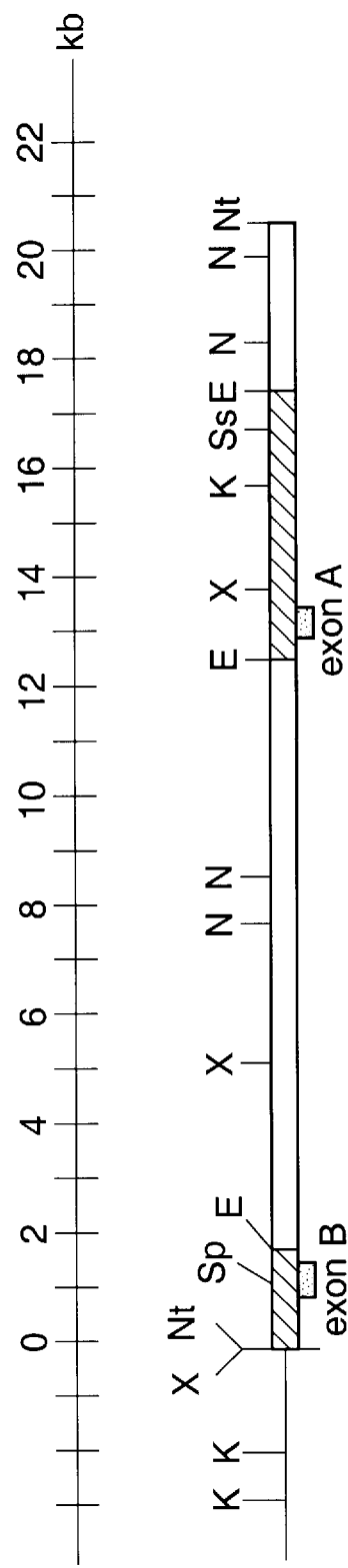
Figure 26:
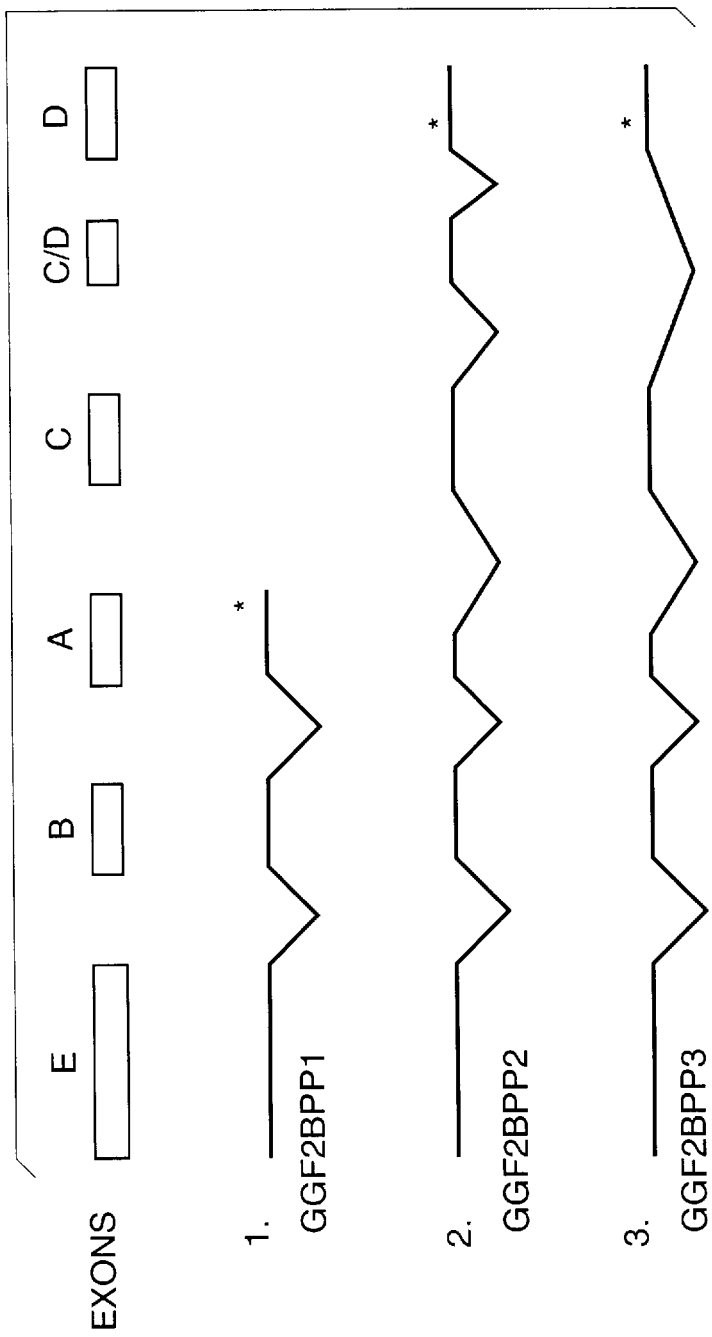
Figure 29:
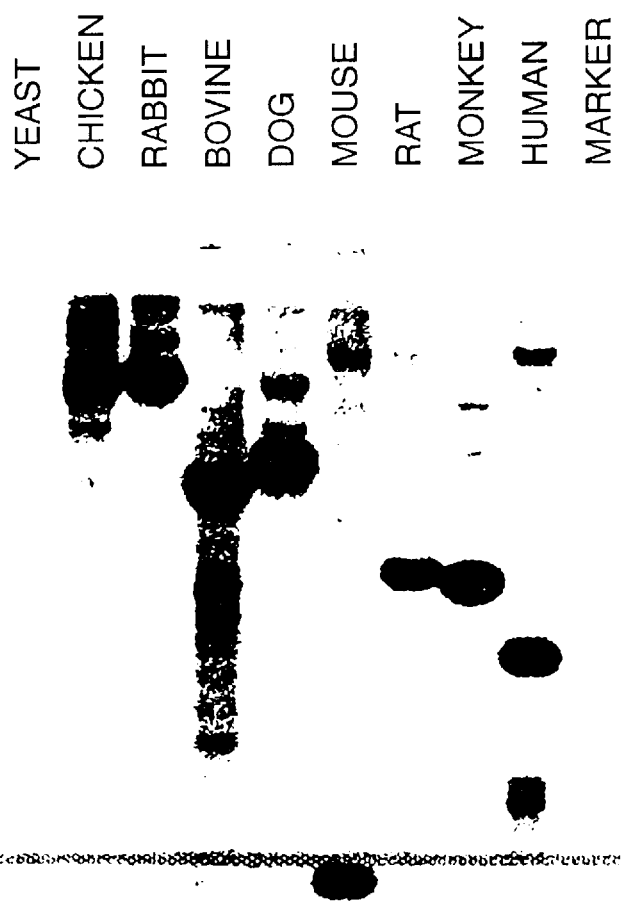

Shown are the coding strand of the DNA sequence and the deduced amino acid sequence in the third reading frame. The sequence of peptide 12 from GGF-2 (shown in bold) is part of a 66 amino acid open reading frame (nucleotides 75272);

FIG. 23A lists the degenerate PCR primers (SEQ ID No. 90–108) and unique PCR primers FIG. 23B (SEQ ID Nos. 109–119) used in experiments to isolate segments of the bovine GGF-II coding sequences present in RNA from posterior pituitary;

FIG. 24 summarizes the nine distinct contiguous bovine GGF-II cDNA structures and sequences that were obtained in PCR amplification experiments using the list of primers in FIG. 7, Panels A and B, on RNA from posterior pituitary. The top line of the Figure shows a schematic of the exon sequences which contribute to the cDNA structures that were characterized;

FIG. 25 is a physical map of bovine recombinant phage GGF2BG1. The bovine DNA fragment is roughly 20 kb in length and contains two exons (bold) of the bovine GGFII gene. Restriction sites for the enzymes XbaI, Spe I, NdeI, EcoRI, Kpn1, and SstI have been placed on this physical map. Shaded portions correspond to fragments which were subcloned for sequencing;

FIG. 26 shows schematically the structure of three alternative gene products of the putative bovine GGF-II gene. Exons are listed A through E in the order of their discovery. The alternative splicing patterns 1, 2 and 3 generate three overlapping deduced protein structures (GGF2BPP1, 2, and 3), which are displayed in the various FIGS. 28;

FIG. 27 compares the GGF-I and GGF-II sequences identified in the deduced protein sequences (SEQ ID Nos. 120–132) shown in FIGS. 28A, 28B, and 28C with the novel peptide sequences listed in FIGS. 10 and 12. The Figure shows that six of the nine novel GGF-II peptide sequences are accounted for in these deduced protein sequences. Two peptide sequences similar to GGF-I sequences are also found;

FIG. 28A shows the coding strand DNA sequence and deduced amino acid sequence of the cDNA (SEQ ID No. 133) obtained from splicing pattern number 1 shown in FIG. 26. This partial cDNA of the putative bovine GGF-II gene encodes a protein of 206 amino acids in length. Peptides shown in bold were those identified from the lists presented in FIGS. 10 and 12. Potential glycosylation sites are underlined (along with polyadenylation signal AATAAA);

FIGS. 28B and 28C show the coding strand DNA sequence and deduced amino acid sequence of the cDNA (SEQ ID No. 134) obtained from splicing pattern number 2 shown in FIG. 26. This partial cDNA of the putative bovine GGF-II gene encodes a protein of 281 amino acids in length. Peptides shown in bold were those identified from the lists presented in FIGS. 10 and 12. Potential glycosylation sites are underlined (along with polyadenylation signal AATAAA);

FIGS. 28D and 28E show the coding strand DNA sequence and deduced amino acid sequence of the cDNA (SEQ ID No. 135) obtained from splicing pattern number 3 shown in FIG. 26. This partial cDNA of the putative bovine GGF-II gene encodes a protein of 257 amino acids in length. Peptides shown in bold were those identified from the lists presented in FIGS. 10 and 12. Potential glycosylation sites are underlined (along with polyadenylation signal AATAAA); and the DNA sequences shown in FIGS. 28a, 28b and 28c are themselves further aspects of this invention; and the invention further includes polypeptides encoded by said sequences;

FIG. 29 relates to Example 7, hereinafter, and shows an autoradiogram of a cross hybridization analysis of putative bovine GGF-II gene sequences to a variety of mammalian DNAs on a Southern blot. The filter contains lanes of EcoRI-digested DNA (5 Mg per lane) from the species listed in the Figure. The probe detects a single strong band in each DNA sample, including a four kb fragment in the bovine DNA as anticipated by the physical map in FIG. 25. Bands of relatively minor intensity are observed as well, which could represent related DNA sequences. The strong hybridizing band from each of the other mammalian DNA samples presumably represents the GGF-II homologue of those species.

In Example 1 hereinafter, unless otherwise indicated, all operations were conducted at 40° C., and, with reference to FIGS. 1 to 6, activity at each stage was determined using the Brockes (Meth. Enz., supra) techniques with the following modifications. Thus, in preparing Schwann cells, 5 μM forskolin was added in addition to DMEM (Dulbecco's modified Eagle's medium), FCS and GGF. Cells used in the assay were fibroblast-free Schwann cells at passage number less than 10, and these cells were removed from flasks with trypsin and plated into flat-bottomed 96-well plates at 3.3 thousand cells per microwell.

$^{125}$IIUdR was added for the final 24 hours after the test solution addition. The background (unstimulated) incorporation to each assay was less than 100 cpm, and maximal incorporation was 20 to 200 fold over background depending on Schwann cell batch and passage number.

In the case of the GGF-I and GGF-II fractions from reversed-phase HPLC as described below in Example 1, two dose response curves were also produced for each factor, using exactly the above method for one of the curves for each factor, and the above method modified in the assay procedure only by substituting fetal calf plasma for fetal calf serum to obtain the other curve for each factor. The results are in FIGS. 7 and 8.

Figure 30:
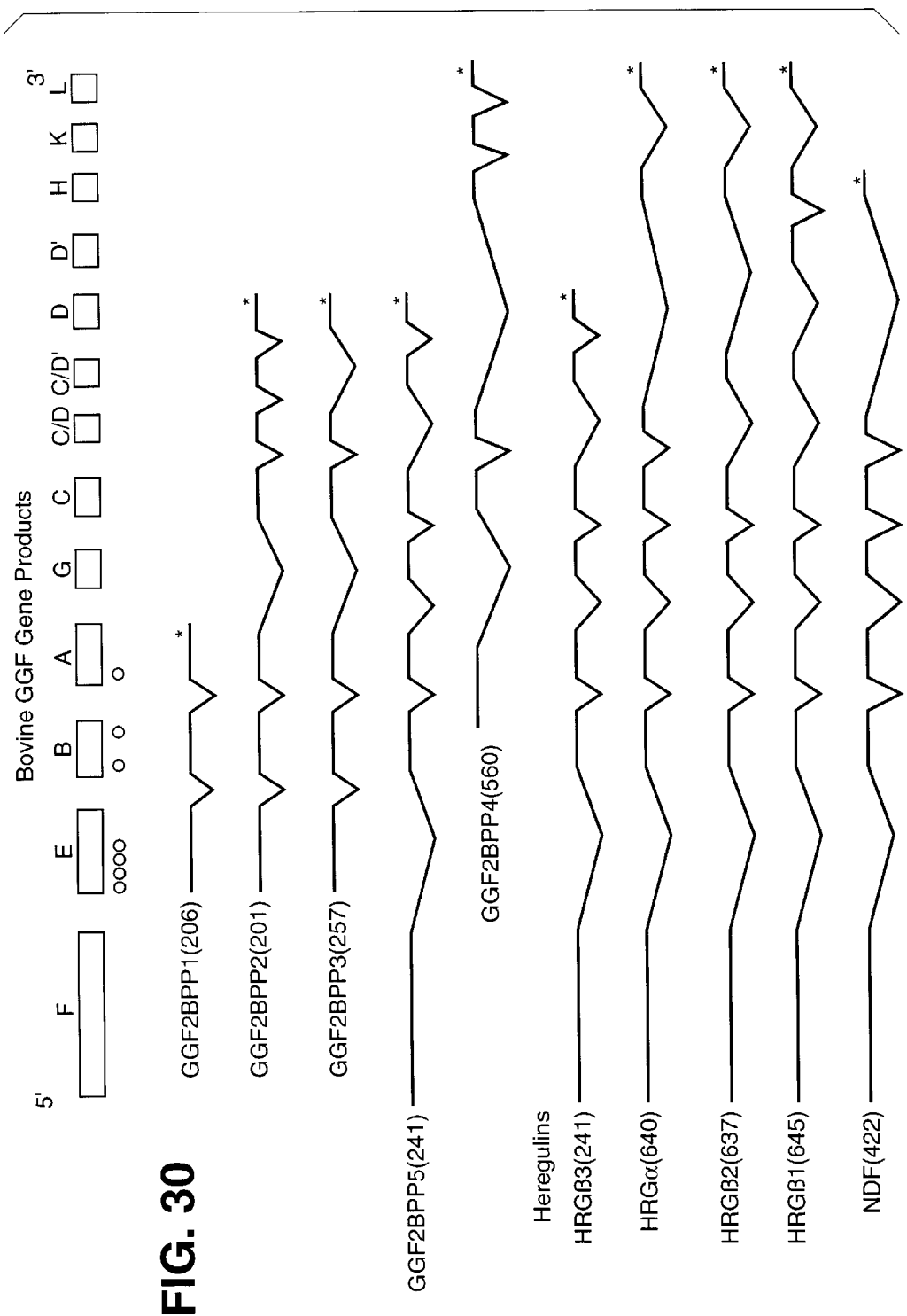

FIG. 30 is a schematic diagram of representative splicing variants. The coding segments are represented by F, E, B, A, G, C, C/D, C/D', D, D', H, K and L. The location of the peptide sequences derived from purified protein are indicated by "o".

FIGS. 31A through 31S (SEQ ID No. 136–147, 173–182, 160, 161 and 163) (is a listing of the DNA sequences and predicted peptide sequences of the coding segments of GGF. Line 1 represents the predicted amino acid sequence of bovine GGF, line 2 represents the nucleotide sequence of bovine GGF, line 3 represents the nucleotide sequence of human GGF (heregulin) (nucleotide base matches are indicated with a vertical line) and line 4 represents the predicted amino acid sequence of human GGF/heregulin where it differs from the predicted bovine sequence. Coding segment K represents only the bovine sequence. The human and bovine coding segments for both E and A' are provided. Coding segment D' represents only the human (heregulin) sequence.

FIGS. 32A and 32B is the predicted GGF2 amino acid sequence and nucleotide sequence of BPP5 (SEQ ID No. 148). The upper line represents the nucleotide sequence and the lower line represents the predicted amino acid sequence.

FIGS. 33A and 33B is the predicted amino acid sequence and nucleotide sequence of GGF2BPP2 (SEQ ID No. 149). The upper line represents the nucleotide sequence and the lower line represents the predicted amino acid sequence.

FIG. 34A through 34C is the predicted amino acid sequence and nucleotide sequence of GGF2BPP4 (SEQ ID NO: 150). The upper line represents the nucleotide sequence and the lower line represents the predicted amino acid sequence.

FIG. 35 (SEQ ID Nos. 151–152) depicts the alignment of two GGF peptide sequences (GGF2bpp4 and GGF2bpp5) with the human EGF (hEGF) peptides sequences. Asterisks indicate positions of conserved cysteines.

Figure 36:
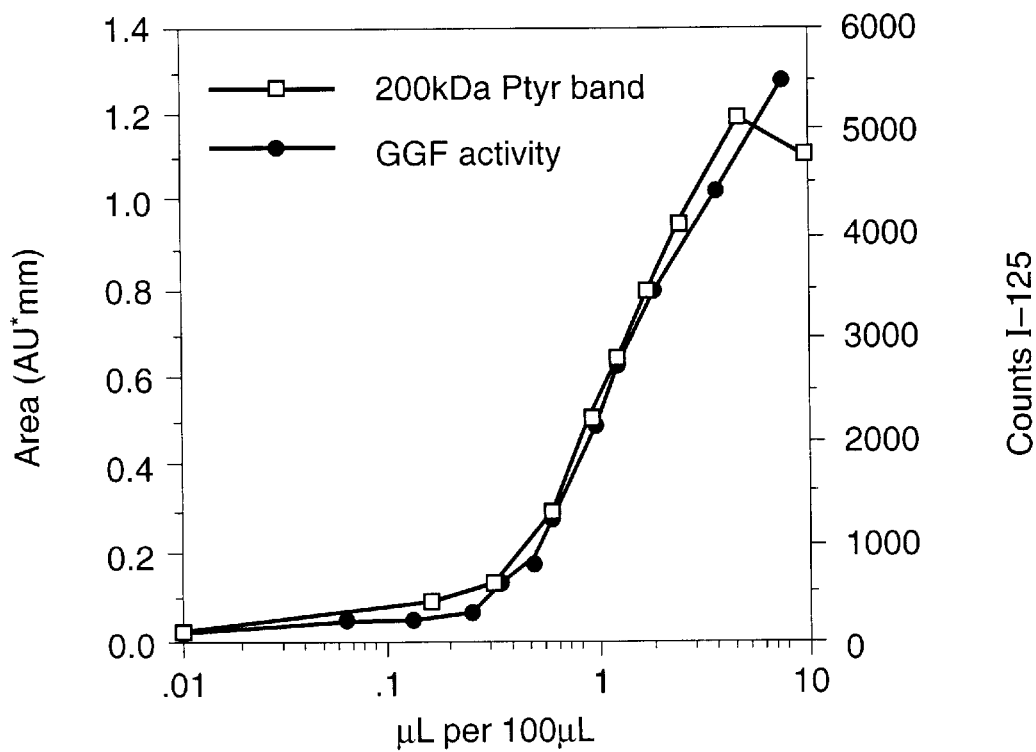

FIG. 36 depicts the level of GGF activity (Schwann cell mitogenic assay) and tyrosine phosphorylation of a ca. 200 kD protein (intensity of a 200 kD band on an autoradiogram of a Western blot developed with an antiphosphotyrosine polyclonal antibody) in response to increasing amounts of GGF.

FIG. 37A and FIG. 37B is a list of splicing variants derived from the sequences shown in FIG. 31.

Figure 38:
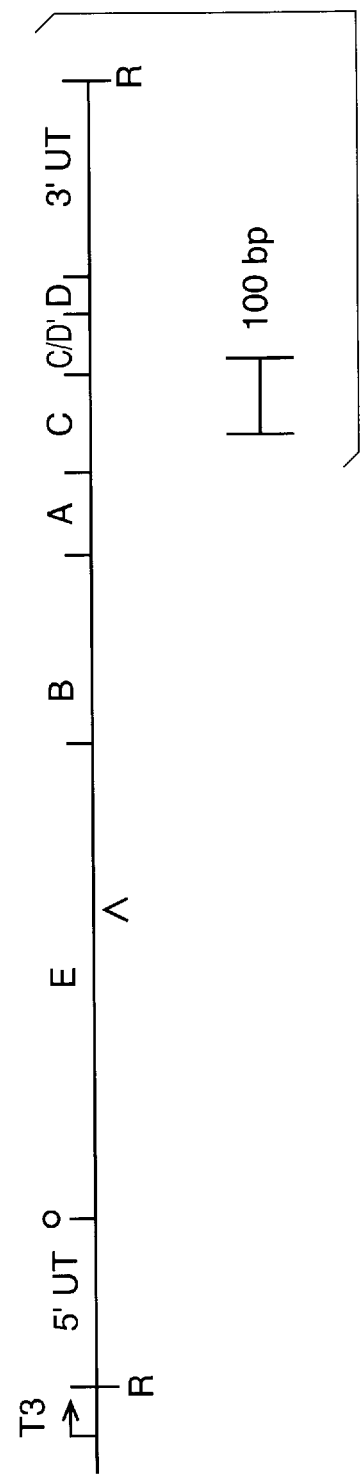

FIG. 38 is a scale coding segment map of the clone. T3 refers to the bacteriophage promoter used to produce mRNA from the clone. R=flanking EcoRI restriction enzyme sites. 5' UT refers to the 5' untranslated region. E, B, A, C, C/D', and D refer to the coding segments. o=the translation start site. Λ=the 5' limit of the region homologous to the bovine E segment (see example 6) and 3' UT refers to the 3' untranslated region.

FIG. 39 is the predicted amino acid sequence, bottom, and nucleic sequence, top, of EGFL1 (SEQ ID No. 154).

FIG. 40 is the predicted amino acid sequence, bottom, and nucleic sequence, top, of EGFL2 (SEQ ID No. 155).

FIG. 41 is the predicted amino acid sequence, bottom, and nucleic sequence, top, of EGFL3 (SEQ ID No. 156).

FIG. 42 is the predicted amino acid sequence, bottom, and nucleic sequence, top, of EGFL4 (SEQ ID No. 157).

FIG. 43 is the predicted amino acid sequence, bottom, and nucleic sequence, top, of EGFL5 (SEQ ID No. 158).

FIG. 44 is the predicted amino acid sequence, bottom, and nucleic sequence, top, of EGFL6 (SEQ ID No. 159).

FIG. 45A through FIG. 45D is the predicted amino acid sequence (middle) and nucleic sequence (top) of GGF2HBS5 (SEQ ID No. 21). The bottom (intermittent sequence represents peptide sequences derived from GGFII preparations (see FIGS. 11, 12).

DETAILED DESCRIPTION

The invention pertains to methods for the use of novel factors which are inhibitors of cell, particularly neural and glial cell proliferation, and the use of DNA sequences encoding these factors. Disclosed are several gene splicing variants of these factors which may encode inhibitors of cell division.

Holmes et al. ((1992) Science 256:1205) and Wen et al. ((1992) Cell 69:559) demonstrate that DNA sequences encoding proteins which bind to a receptor associated with several human tumors ($p185^{erbB2}$) share a great deal of homology with GGF DNA sequences. This provides evidence to indicate that the bovine GGFs and the human and rat $p185^{erbB2}$ ligands are encoded by the same (homologous) gene and that ligand groups both interact with the same receptor ($p185^{erbB2}$).

The $p185^{erbB2}$ protein is a 185 kilodalton membrane spanning protein with tyrosine kinase activity. The protein is encoded by the erbB2 proto-oncogene (Yarden and Ullrich. (1988) Ann. Rev. Biochem. 57:443). The erbB2 gene, also referred to as HER-2 (in human cells) and neu (in rat cells), is closely related to the receptor for epidermal growth factor (EGF). Recent evidence indicates that proteins which interact with (and activate the kinase of) $p185^{erbB2}$ induce proliferation in the cells bearing $p185^{erbB2}$ (Holmes et al. (1992) Science 256:1205; Dobashi et al. (1991) Proc. Natl. Acad. Sci. 88:8582; Lupu et al. (1992) Proc. Natl. Acad. Sci. 89:2287). This evidence supports the conclusion that the gene encoding GGF's and the $p185^{erbB2}$ binding proteins are responsible for the production of a family of growth factors which have pleiotropic effects in that they target both neural cells, particularly Schwann cells, and cells which give rise to human adenocarcinoma and other carcinomas.

Furthermore, it is evident that the gene encoding GGF and $p185^{erbB2}$ binding proteins produces a number of variably-sized, differentially-spliced RNA transcripts that give rise to a series of proteins, which are of different lengths and contain some common peptide sequences and some unique peptide sequences. This is supported by the evidence that differentially spliced sequences are recoverable from bovine posterior pituitary RNA (as presented herein), and human breast cancer cell line (MDA-MB-231) RNA (Holmes et al. (1992) Science 256:1205). Further support for this "one gene: multiple product" conclusion derives from the wide size range of proteins which act as both mitogens for Schwann cells (as disclosed herein) and ligands for the $p185^{erbB2}$ receptor (see below).

Further evidence to support the fact that the genes encoding GGF and $p185^{erbB2}$ receptor ligands are homologous comes from nucleotide sequence comparison. Holmes et al. ((1992) Science, 256:1205–1210) demonstrate the purification of a 45-kilodalton human protein (heregulin) which specifically interacts with the $p185^{erbB2}$ receptor. The predicted sequences of the polypeptides encoded by these human DNA sequences match very closely with the sequences predicted from the Glial Growth Factor sequences. Peles et al. ((1992) Cell 69:205) and Wen et al ((1992) Cell 69:559) describe a complementary DNA isolated from rat cells encoding a protein called neu differentiation factor (NDF), which shares homology with the heregulin sequences described by Holmes et al. In addition, the translation product of the NDF cDNA has $p185^{erbB2}$ binding activity. Several other groups have reported the purification of proteins of various molecular weights with erbB2 binding activity. These groups include Lupu et al. ((1992) Proc. Natl. Acad. Sci. USA 89:2287), Yarden and Peles ((1991) Biochemistry 30:3543), Lupu et al ((1990) Science 249:1552), and Dobashi et al. ((1991) Biochem Biophys. Res. Comm. 179:1536).

It has been established that the $p185^{erbB2}$ oncogene and, by inference, its cognate ligands play a significant role in the development and maintenance of several types of tumors. Amplification and overexpression of erbB2 has been associated with human adenocarcinomas from several tissues (Kraus et al. (1987) EMBO J. 6:605; Slamon et al. (1987) Science 235:177; Varley et al. (1987) Oncogene 1:423; and van de Vijver et al. (1987) Mol Cell Biol 7:2019). An association has also been reported with breast and ovarian cancer (Slamon et al. supra; Varley et al. supra: Venter et al. (1987) Lancet ii:67; Zhou et al. (1987) Cancer Res. 47:6123; Berger et al. (1988) Cancer Res. 48:1238; Tsuda et al. (1989) Cancer Res. 49:3104; Slamon et al. (1989) Science 244:707).

There is also evidence that the erbB2 gene plays a role in oncogenesis of cells of the Schwann cell lineage (Perantoni et al. (1987) Proc. Nat. Acad. Sci. 84:6317; Nikitin et al. (1991) Proc. Nat. Acad. Sci. 88:9939). Several tumor types are a result of abnormal proliferation of Schwann cells and these include neurofibromas, and malignant schwannomas and neurofibrosarcomas.

As candidate ligands for the erbB2 receptor, the GGFs could play a significant role in the development of the tumors described above.

As outlined above, the gene encoding the GGFs and the $p185^{erbB2}$ ligands gives rise to a number of variant transcripts which encode a variety of proteins. Several of these variant proteins bind to the $p185^{erbB2}$ receptor on neural cells, including Schwann cells (described above and disclosed herein), as well as to the same receptor on tumor cell lines as described above. Some of these variant proteins activate cell proliferation in Schwann cells and in tumor cell lines (described above and disclosed herein). Other variants may possibly interfere with the activity of the ligands which stimulate proliferation by competing with those ligands for binding sites on the $p185^{erbB2}$ receptor. Chan et al. ((1991) Science 254:1382) showed that a naturally occurring hepatocyte growth factor (HGF) variant was derived from a smaller transcript encoded by the same gene as the full length molecule. The truncated protein encoded by the variant transcript specifically inhibits HGF induced mitogenesis and was demonstrated to compete with HGF for binding to the HGF receptor. The HGF receptor has been identified as the c-met proto-oncogene product. Thus, these variant versions of growth factor proteins may play a significant regulatory role in the control of cell proliferation. GGF-related factors which inhibit glial proliferation will be therapeutically useful as anti-proliferative compounds for the treatment of tumors of the neural system.

It has been shown that myelination by Schwann cells and oligodendrocytes is regulated by the proliferative state (Jessen et al., 1991 Ann NY Acad Science 633:78–89). When the cell withdraws from the proliferative cycle the myelination process appears to begin. Factors of the invention which induce Schwann cells and oligodendrocytes to exit the proliferative cell cycle and enter the quiescent state may be administered to increase myelination of existing or newly regenerated neural tissue in a mammal suffering from diseases or disorders of demyelination. Examples of diseases and disorders which may be treated using an inhibitor of mutagenesis include Charot-Marie-Tooth disease (particularly type I and type III), peroneal muscular atrophy, Dejerine-Sottos disease (type III hereditary motor and sensory neuropathy), multiple sclerosis, chronic inflammatory demyelinating polyradiculoneuropathy, chronic liver disease, diphtheritic polyneuritis, Guillain-Barre syndrome, hypothyroid polyneuropathy, metachromatic leukodystrophy, type I hereditary motor and sensory neuropathy, type III hereditary motor and sensory neuropathy, and vasculitic neuropathy.

EXAMPLE 1

I. Preparation of Factor-CM Fraction 4,000 frozen whole bovine pituitaries (c.a. 12 kg) were thawed overnight, washed briefly with water and then homogenized in an equal volume of 0.15M ammonium sulphate in batches in a Waring Blender. The homogenate was taken to pH 4.5 with 1.0M HCl and centrifuged at 4,900 g for 80 minutes. Any fatty material in the supernatant was removed by passing it through glass wool. After taking the pH of the supernatant to 6.5 using 1.0M NaOH, solid ammonium sulphate was added to give a 36% saturated solution. After several hours stirring, the suspension was centrifuged at 4,900 g for 80 minutes and the precipitate discarded. After filtration through glass wool, further solid ammonium sulphate was added to the supernatant to give a 75% saturated solution which was once again centrifuged at 4,900 g for 80 minutes after several hours stirring. The pellet was resuspended in c.a. 2 L of 0.1M sodium phosphate pH 6.0 and dialyzed 3×40 L of the same buffer. After confirming that the conductivity of the dialysate was below 20.0 $\mu$Siemens, it was loaded onto a Bioprocess column (120× 113 mm, Pharmacia) packed with carboxymethyl cellulose (CM-52, Whatman) at a flow rate of 2 $\mu$l.min$^{-1}$ The column was washed with 2 volumes of 0.1M sodium phosphate pH 6.0, followed by 2 volumes of 50 mM NaCl, and finally 2 volumes of 0.2M NaCl both in the same buffer. During the final step, 10 $\mu$L (5 minute) fractions were collected. Fractions 73 to 118 inclusive were pooled, dialyzed against the 10 volumes of 10 mM sodium phosphate pH 6.0 twice and clarified by centrifugation at 100,000 g for 60 minutes.

II. Hydroxylapatite HPLC

Hydroxylapatite HPLC is not a technique hitherto used in isolating glial growth factors, but proved particularly efficacious in this invention.

The material obtained from the above CM-cellulose chromatography was filtered through a 0.22 $\mu$m filter (Nalgene), loaded at room temperature on to a high performance hydroxylapatite column (50×50 mm, Biorad) equipped with a guard column (15×25 mm, Biorad) and equilibrated with 10 mM potassium phosphate pH 6.0. Elution at room temperature was carried out at a flow rate of 2 $\mu$l.minute$^{-1}$ using the following programmed linear gradient:

| time (min) | %B | Solvent A: | 10 mM potassium phosphate pH 6.0 |
|---|---|---|---|
| 0.0 | 0 | Solvent B: | 1.0 M potassium phosphate pH 6.0 |
| 5.0 | 0 | | |
| 7.0 | 20 | | |
| 70.0 | 20 | | |
| 150.0 | 100 | | |
| 180.0 | 100 | | |
| 185.0 | 0 | | |

6.0 $\mu$L (3 minutes) fractions were collected during the gradient elution. Fractions 39–45 were pooled and dialyzed against 10 volumes of 50 mM sodium phosphate pH 6.0.

III. Mono S FPLC

Mono S FPLC enabled a more concentrated material to be prepared for subsequent gel filtration.

Any particulate material in the pooled material from the hydroxylapatite column was removed by a clarifying spin at 100,000 g for 60 minutes prior to loading on to a preparative HR10/10 Mono S cation exchange column (100×10 mm, Pharmacia) which was then re-equilibrated to 50 MM sodium phosphate pH 6.0 at room temperature with a flow rate of 1.0 $\mu$uL.minute$^{-1}$. Under these conditions, bound protein was eluted using the following programmed linear gradient:

| time (min) | %B | Solvent A: | 50 mM potassium phosphate pH 6.0 |
|---|---|---|---|
| 0.0 | 0 | Solvent B: | 1.2 M sodium chloride, 50 mm sodium phosphate pH 6.0 |
| 70.0 | 30 | | |
| 240.0 | 100 | | |
| 250.0 | 100 | | |
| 260.0 | 0 | | |

1 $\mu$L (1 minute) fractions were collected throughout this gradient program. Fractions 99 to 115 inclusive were pooled.

IV. Gel Filtration FPLC

This step commenced the separation of the two factors of the invention prior to final purification, producing enriched fractions.

For the purposes of this step, a preparative Superose 12 FPLC column (510×20 mm, Pharmacia) was packed according to the manufacturers' instructions. In order to standardize this column, a theoretical plates measurement was made according to the manufacturers' instructions, giving a value of 9,700 theoretical plates.

The pool of Mono S eluted material was applied at room temperature in 2.5 $\mu$L aliquots to this column in 50 MM sodium phosphate, 0.75 NaCl pH 6.0 (previously passed through a C18 reversed phase column (Sep-pak, Millipore) at a flow rate of 1.0 $\mu$L.minute$^{-1}$. 1 $\mu$L (0.5 minute) fractions were collected from 35 minutes after each sample was applied to the column. Fractions 27 to 41 (GGF-II) and 42 to 57 (GGF-I) inclusive from each run were pooled.

V. Reversed-Phase HPLC

The GGF-I and GGF-II pools from the above Superose 12 runs were each divided into three equal aliquots. Each aliquot was loaded on to a C8 reversed-phase column (Aquapore RP-300 7 $\mu$ C8 220×4.6 mm, Applied Biosystems) protected by a guard cartridge (RP-8, 15×3.2 mm, Applied Biosystems) and equilibrated to 4° C. at 0.5 $\mu$L.minute. Protein was eluted under these conditions using the following programmed linear gradient:

| time (min) | %B | Solvent A: | 0.1% trifluoroacetic acid (TFA) |
|---|---|---|---|
| 0 | | Solvent B: | 90% acetonitrile, 0.1% TFA |
| 60 | 66.6 | | |
| 62.0 | 100 | | |
| 72.0 | 100 | | |
| 75.0 | 0 | | |

200 $\mu$L (0.4 minute) fractions were collected in siliconized tubes (Multilube tubes, Bioquote) from 15.2 minutes after the Beginning of the programmed gradient.

VI. SDS-Polyacrylamide Gel Electrophoresis

In this step, protein molecular weight standards, low range, catalogue no. 161-0304, from Bio-Rad Laboratories Limited, Watford, England were employed. The actual proteins used, and their molecular weight standards, have been listed hereinbefore.

Fractions 47 to 53 (GGF-I) and fractions 61 to 67 (GGF-II) from the reversed-phase runs were individually pooled. 7

μL of the pooled material was boiled in an equal volume of 0.0125M Tris-Cl, 4% SDS, 20% glycerol, and 10% β-mercaptoethanol for GGF-I, for 5 minutes and loaded on to an 11% polyacrylamide Leammli gel with a 4% stacking gel and run at a constant voltage of 50 V for 16 hours. This gel was then fixed and stained using a silver staining kit (Amersham). Under these conditions, the factors are each seen as a somewhat diffuse band at relative molecular weights 30,000 to 36,000 Daltons (GGF-I) and 55,000 to 63,000 Daltons (GGF-II), as defined by molecular weight markers. From the gel staining, it is apparent that there are a small number of other protein species present at equivalent levels to the GGF-I and GGF-II species in the material pooled from the reversed-phase runs.

VII. Stability in Trifluoroacetic Acid

Stability data were obtained for the present Factors in the presence of trifluoroacetic acid, as follows:

GGF-I

Material from the reversed-phase HPLC, in the presence of 0.1% TFA and acetonitrile, was assayed within 12 hours of the completion of the column run and then after 10 weeks incubation at 40° C. Following incubation, the GGF-I had at least 50% of the activity of that material assayed directly off the column.

GGF-II

Material from the reversed-phase HPLC, in the presence of 0.1% TFA and acetonitrile, and stored at −20° C., was assayed after thawing and then after 4 days incubation at 40° C. Following incubation, the GGF-II had at least 50% of the activity of that material freshly thawed.

It will be appreciated that the trifluoroacetic acid concentration used in the above studies is that most commonly used for reversed-phase chromatography.

EXAMPLE 2

Amino Acid Sequences Purified GGF-I and GGF-II

Amino acid sequence analysis studies were performed using highly purified bovine pituitary GGF-I and GGF-II. The conventional single letter code was used to describe the sequences. Peptides were obtained by lysyl endopeptidase and protease V8 digests, carried out on reduced and carboxymethylated samples, with the lysyl endopeptidase digest of GGF-II carried out on material eluted from the 55–65 RD region of a 11% SDS-PAGE (MW relative to the above-quoted markers).

A total of 21 peptide sequences (see FIG. 9) were obtained for GGF-I, of which 12 peptides (see FIG. 10) are not present in current protein databases and therefore represent unique-sequences. A total of 12 peptide sequences (see FIG. 11) were obtained for GGF-II, of which 10 peptides (see FIG. 12) are not present in current protein databases and therefore represent unique sequences (an exception is peptide GGF-II 06 (SEQ ID No. 38) which shows identical sequences in many proteins which are probably of no significance given the small number of residues). These novel sequences are extremely likely to correspond to portions of the true amino acid sequences of GGFs I and II.

Particular attention can be drawn to the sequences of GGF-I 07 (SEQ ID No. 39) and GGF-II 12 (SEQ ID No. 44), which are clearly highly related. The similarities indicate that the sequences of these peptides are almost certainly those of the assigned GGF species, and are most unlikely to be derived from contaminant proteins.

In addition, in peptide GGF-II 02 (SEQ ID No. 34), the sequence X S S is consistent with the presence of an N linked carbohydrate moiety on an asparagine at the position denoted by X.

In general, in FIGS. 9 and 11, X represents an unknown residue denoting a sequencing cycle where a single position could not be called with certainty either because there was more than one signal of equal size in the cycle or because no signal was present. As asterisk denotes those peptides where the last amino acid called corresponds to the last amino acid present in that peptide. In the remaining peptides, the signal strength after the last amino acid called was insufficient to continue sequence calling to the end of that peptide. The right hand column indicates the results of a computer database search using the GCG package FASTA and TFASTA programs to analyze the NBRF and EMBL sequence databases. The name of a protein in this column denotes identity of a portion of its sequence with the peptide amino acid sequence called allowing a maximum of two mismatches. A question mark denotes three mismatches allowed. The abbreviations used are as follows:

HMG-1 High Mobility Group protein-1
HMG-2 High Mobility Group protein-2
LH-alpha Luteinizing hormone alpha subunit
LH-beta Luteinizing hormone beta subunit

EXAMPLE 3

Mitogenic Activity of Purified GGF-I and GGF-II

The mitogenic activity of a highly purified sample containing both GGFs I and II was studied using a quantitative method, which allows a single microculture to be examined for DNA synthesis, cell morphology, cell number and expression of cell antigens. This technique has been modified from a method previously reported by Muir et al. ((1990) Analytical Biochemistry 185:377–382). The main modifications are: 1) the use of uncoated microtiter plates, 2) the cell number per well, 3) the use of 5% Fetal Bovine Plasma (FBP) instead of 10% Fetal Calf Serum (FCS), and 4) the time of incubation in presence of mitogens and bromodeoxyuridine (BrdU), added simultaneously to the cultures. In addition the cell monolayer was not washed before fixation to avoid loss of cells, and the incubation time of monoclonal mouse anti-BrdU antibody and peroxidase conjugated goat anti-mouse immunoglobulin (IgG) antibody were doubled to increase the sensitivity of the assay. The assay, optimized for rat sciatic nerve Schwann cells, has also been used for several cell lines, after appropriate modifications to the cell culture conditions.

I. Methods of Mitogenesis Testing

On day 1, purified Schwann cells were plated onto uncoated 96 well plates in 5% FBP/Dulbecco's Modified Eagle Medium (DMEM) (5,000 cells/well). On day 2, GGFs or other test factors were added to the cultures, as well as BrdU at a final concentration of 10 mm. After 48 hours (day 4) BrdU incorporation was terminated by aspirating the medium and cells were fixed with 200 μl/well of 70% ethanol for 20 min at room temperature. Next, the cells were washed with water and the DNA denatured by incubation with 100 μl 2N HCl for 10 min at 37° C. Following aspiration, residual acid was neutralized by filling the wells with 0.1M borate buffer, pH 9.0, and the cells were washed with phosphate buffered saline (PBS). Cells were then treated with 50 μl of blocking buffer (PBS containing 0.1% Triton X 100 and 2% normal goat serum) for 15 min at 37° C. After aspiration, monoclonal mouse anti-BrdU antibody (Dako Corp., Santa Barbara, Calif.) (50 μl/well, 1.4 mg/ml diluted in blocking buffer) was added and incubated for two hours at 37° C. Unbound antibodies were removed by three washes in PBS containing 0.1% Triton X-100 and peroxidase-conjugated goat anti-mouse IgG antibody (Dako Corp., Santa Barbara, Calif.) (50 μl/well, 2 mg/ml diluted in blocking buffer) was added and incubated for one hour at 37° C. After three washes in PBS/Triton and a final rinse in PBS, wells received 100 μl/well of 50 mM phosphate/citrate buffer, pH 5.0, containing 0.05% of the soluble chromogen o-phenylenediamine (OPD) and 0.02% $H_2O_2$. The reaction was terminated after 5–20 min at room temperature, by pipetting 80 μl from each well to a clean plate containing 40 μl/well of 2N sulfuric acid. The absorbance was recorded at 490 nm using a plate reader (Dynatech Labs). The assay plates containing the cell monolayers were washed twice with PBS and immunocytochemically stained for BrdU-DNA by adding 100 μl/well of the substrate diaminobenzidine (DAB) and 0.02% $H_2O_2$ to generate an insoluble product. After 10–20 min the staining reaction was stopped by washing with water, and BrdU-positive nuclei observed and counted using an inverted microscope. Occasionally, negative nuclei were counterstained with 0–001% Toluidine blue and counted as before.

II. Cell Lines used for Mitogenesis Assays

Swiss 3T3 Fibroblasts

Cells, from Flow Labs, were maintained in DMEM supplemented with 10% FCS, penicillin and streptomycin, at 37° C. in a humidified atmosphere of 10% $CO_2$ in air. Cells were fed or subcultured every two days. For mitogenic assay, cells were plated at a density of 5,000 cells/well in complete medium and incubated for a week until cells were confluent and quiescent. The serum containing medium was removed and the cell monolayer washed twice with serum free-medium. 100 μl of serum free medium containing mitogens and 10 μM BrdU were added to each well and incubated for 48 hours. Dose responses to GGFs and serum or PDGF (as a positive control) were performed.

BHK (Baby Hamster Kidney) 21 C13 Fibroblasts

Cells from European Collection of Animal Cell Cultures (ECACC), were maintained in Glasgow Modified Eagle Medium (GMEM) supplemented with 5% tryptose phosphate broth, 5% FCS, penicillin and streptomycin, at 37° C. in a humidified atmosphere of 5% $CO_2$ in air. Cells were fed or subcultured every two to three days. For mitogenic assay, cells were plated at a density of 2,000 cell/well in complete medium for 24 hours. The serum containing medium was then removed and after washing with serum free medium, replaced with 100 μl of 0.1% FCS containing GMEM or GMEM alone. GGFs and FCS or BFGF as positive controls were added, coincident with 10 μM BrdU, and incubated for 48 hours. Cell cultures were then processed as described for Schwann cells.

C6 Rat Glioma Cell Line

Cells, obtained at passage 39, were maintained in DMEM containing 5% FCS, 5% Horse serum (HS), penicillin and streptomycin, at 37° C. in a humidified atmosphere of 10% $CO_2$ in air. Cells were fed or subcultured every three days. For mitogenic assay, cells were plated at a density of 2,000 cells/well in complete medium and incubated for 24 hours. Then medium was replaced with a mixture of 1:1 DMEM and F12 medium containing 0.1% FCS, after washing in serum free medium. Dose responses to GGFS, FCS and AFGF were then performed and cells were processed through the ELISA as previously described for the other cell types.

PC12 (Rat Adrenal Pheochromocytoma Cells)

Cells from ECACC, were maintained in RPMI 1640 supplemented with 10% HS, 5% FCS, penicillin and streptomycin, in collagen coated flasks, at 37° C. in a humidified atmosphere of 5% $CO_2$ in air. Cells were fed every three days by replacing 80% of the medium. For mitogenic assay, cells were plated at a density of 3,000 cells/well in complete medium, on collagen coated plates (50 μl/well collagen, Vitrogen Collagen Corp., diluted 1:50, 30 min at 37° C.) and incubated for 24 hours. The medium was then placed with fresh RPMI either alone or containing 1 mM insulin or 1% FCS. Dose responses to FCS/HS (1:2) as positive control and to GGFs were performed as before. After 48 hours cells were fixed and the ELISA performed as previously described.

III. Results of Mitogenesis Assays

All the experiments presented in this Example were performed using a highly purified sample from a Superose 12 chromatography purification step (see Example 1, section D) containing a mixture of GGF-I and GGF-II (GGFs).

Firstly, the results obtained with the BrdU incorporation assay were compared with the classical mitogenic assay for Schwann cells based on $^{125}$I-UDR incorporation into DNA of dividing cells, described by J. P.Brockes ((1987) Methods Enzymol. 147:217).

Figure 1:
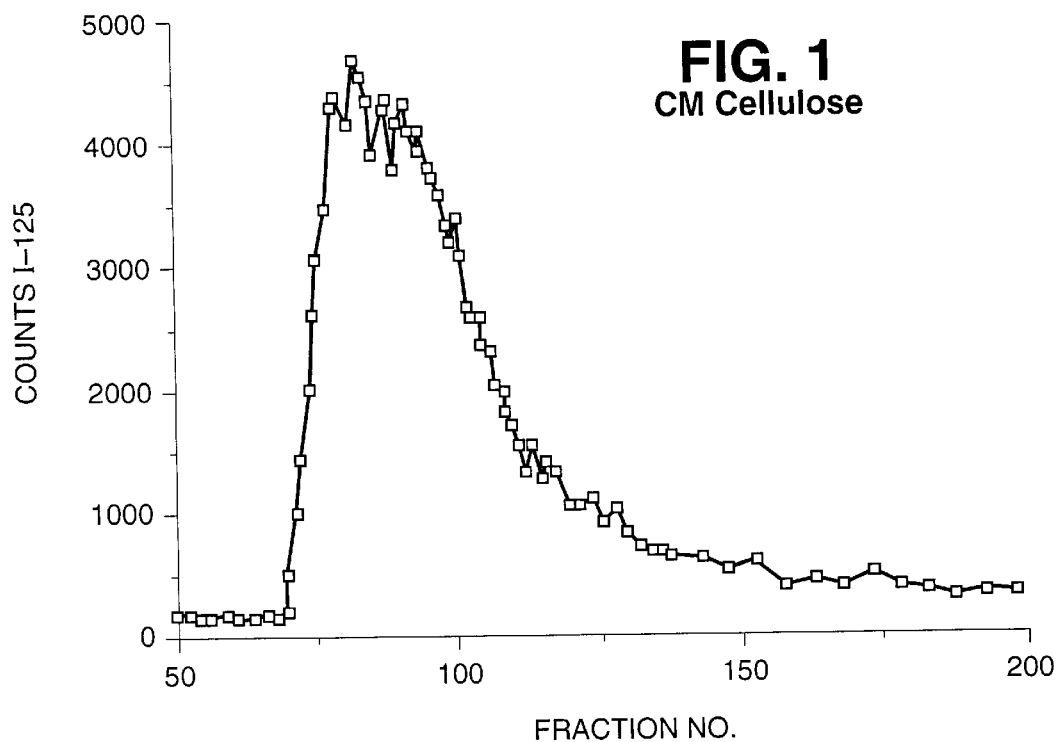
Figure 2:
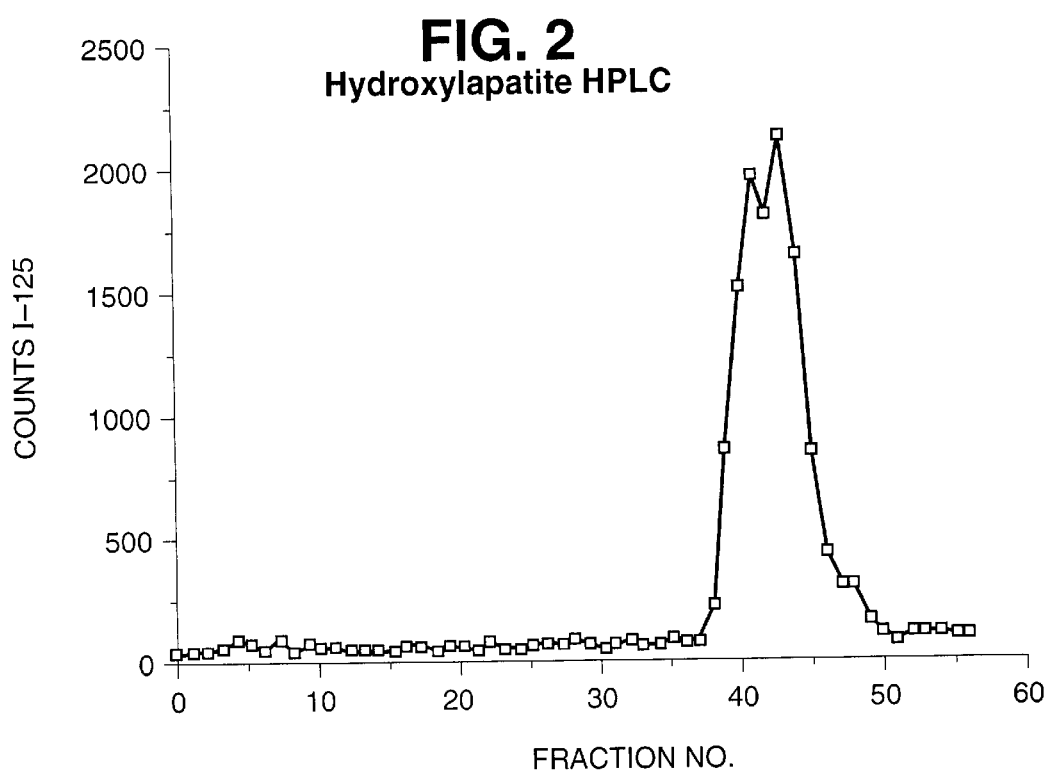
Figure 5:
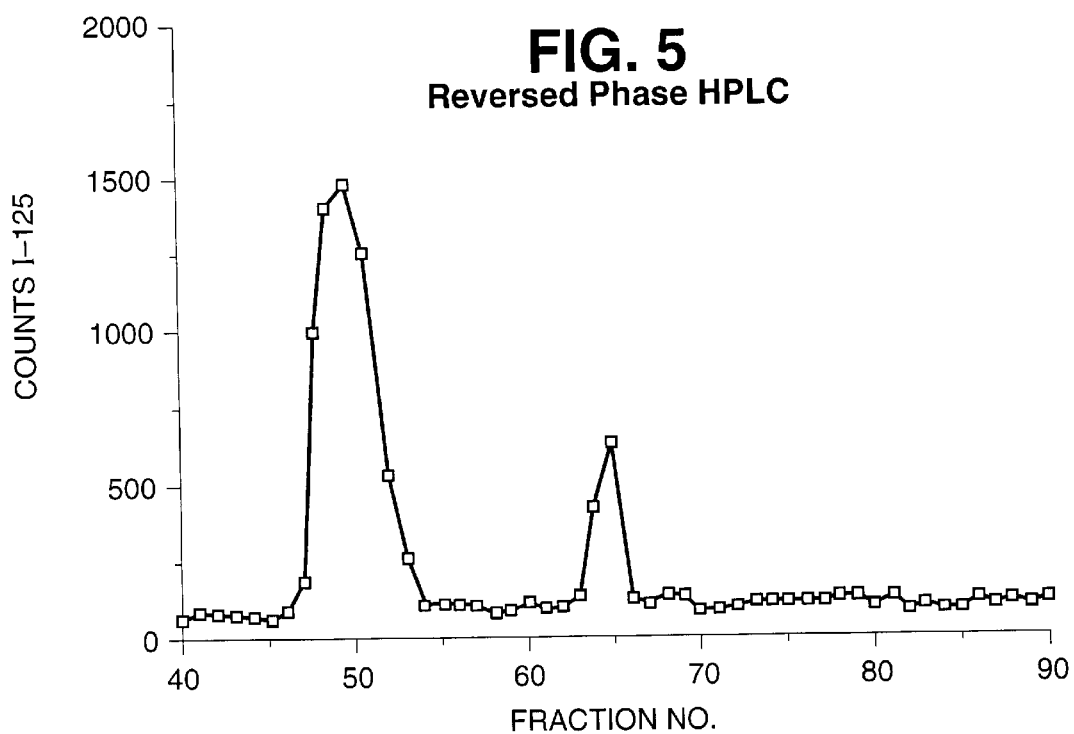
Figure 6:
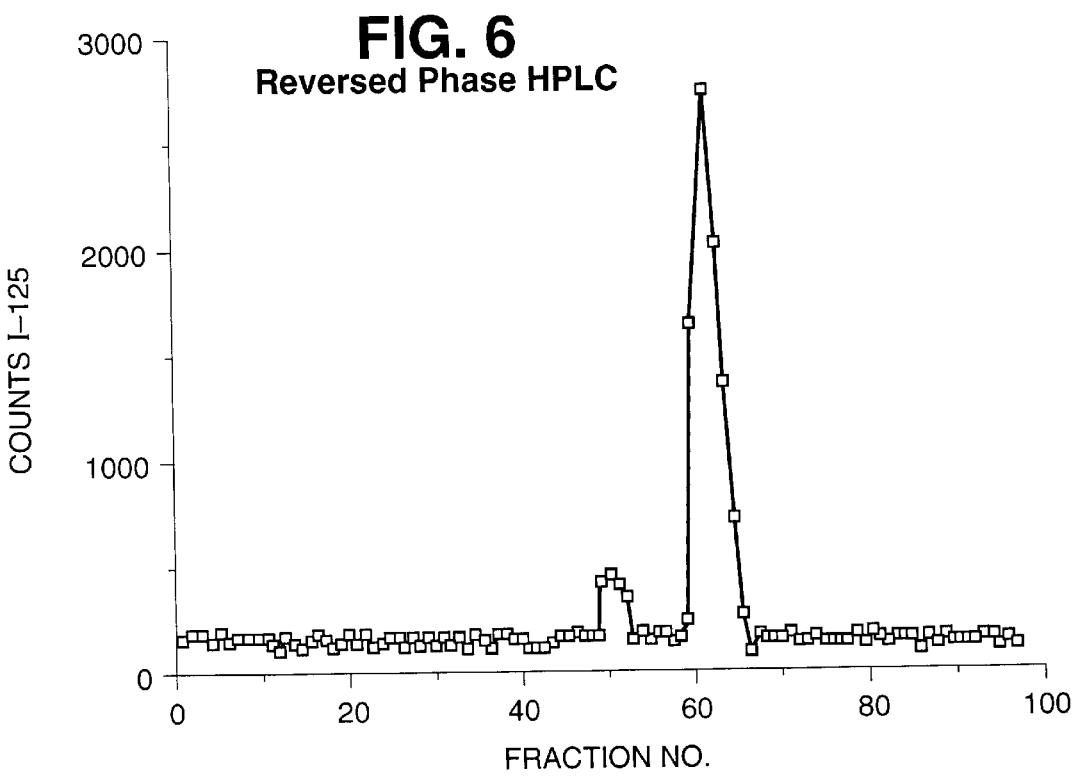
Figure 13:
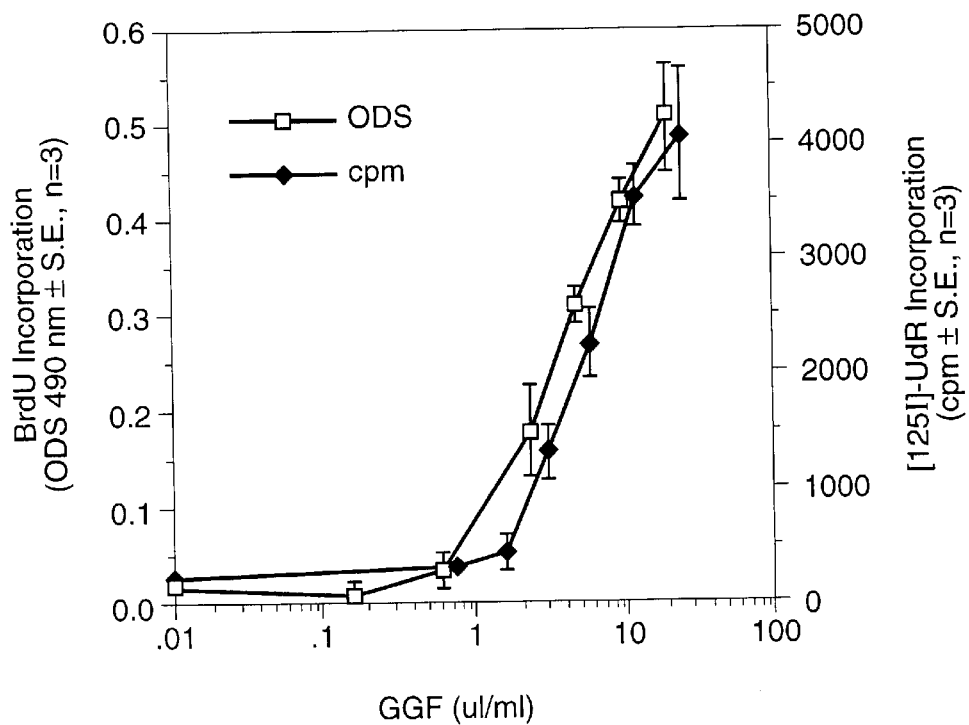

FIG. 13 shows the comparison of data obtained with the two assays, performed in the same cell culture conditions (5,000 cells/well, in 5% FBP/DMEM, incubated in presence of GGFs for 48hrs). As clearly shown, the results are comparable, but BrdU incorporation assay appears to be slightly more sensitive, as suggested by the shift of the curve to the left of the graph, i.e. to lower concentrations of GGFS.

As described under the section "Methods", after the immunoreactive BrdU-DNA has been quantitated by reading the intensity of the soluble product of the OPD peroxidase reaction, the original assay plates containing cell monolayers can undergo the second reaction resulting in the insoluble DAB product, which stains the BrdU positive nuclei. The microcultures can then be examined under an inverted microscope, and cell morphology and the numbers of BrdU-positive and negative nuclei can be observed.

Figure 14A:
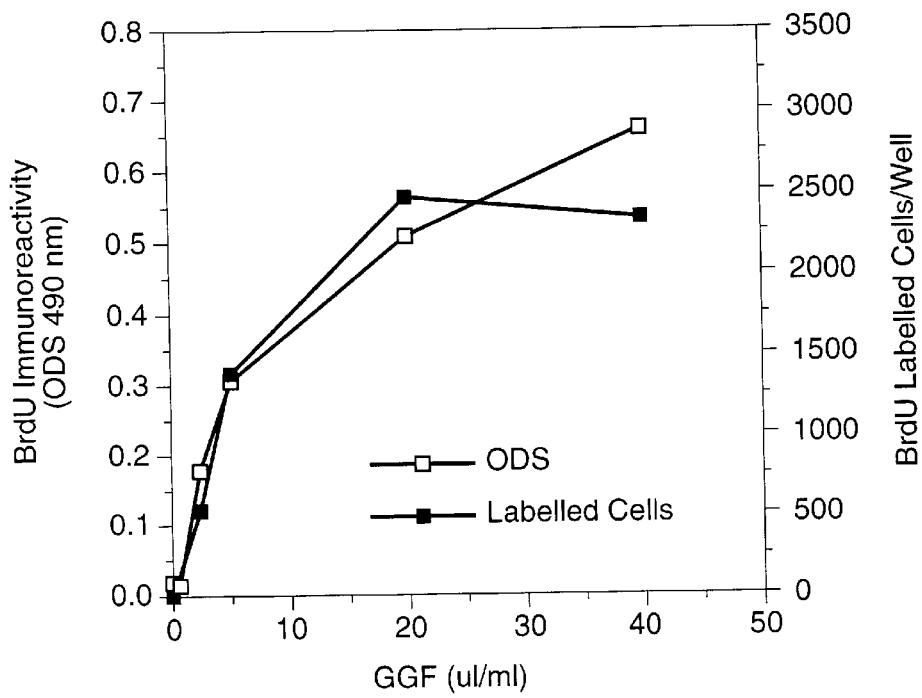
FIGS. 14A and 14B show graphs comparing Br-UdR immunoreactivity with the number of Br-UdR-labeled cells.
Figure 14B:
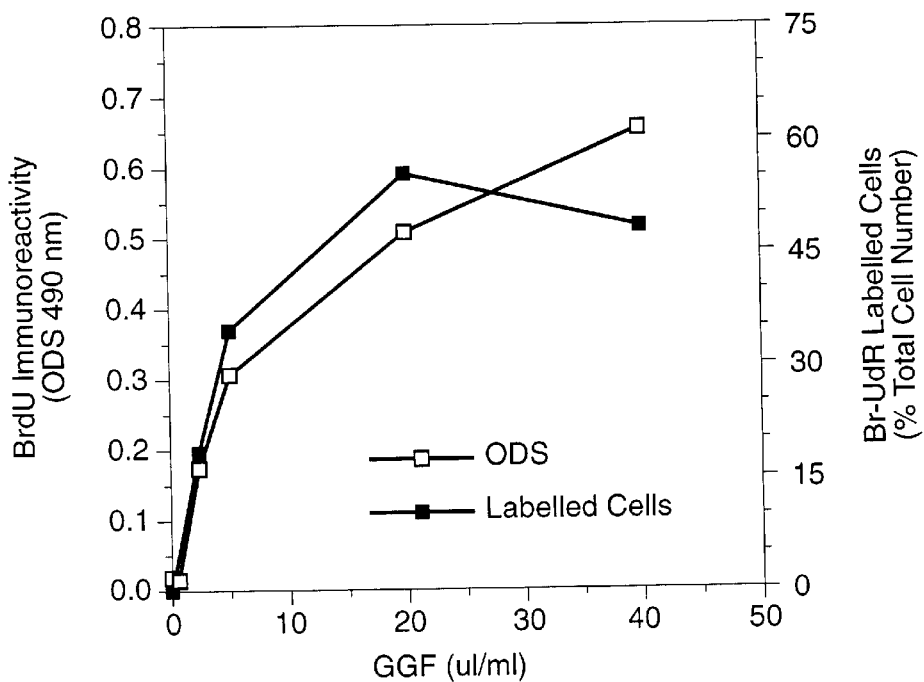

In FIG. 14a and FIG. 14b the BrdU-DNA immunoreactivity, evaluated by reading absorbance at 490 nm, is compared to the number of BrdU-positive nuclei and to the percentage of BrdU-positive nuclei on the total number of cells per well, counted in the same cultures. Standard deviations were less than 10%. The two evaluation methods show a very good correlation and the discrepancy between the values at the highest dose of GGFs can be explained by the different extent of DNA synthesis in cells detected as BrdU-positive.

Figure 15:
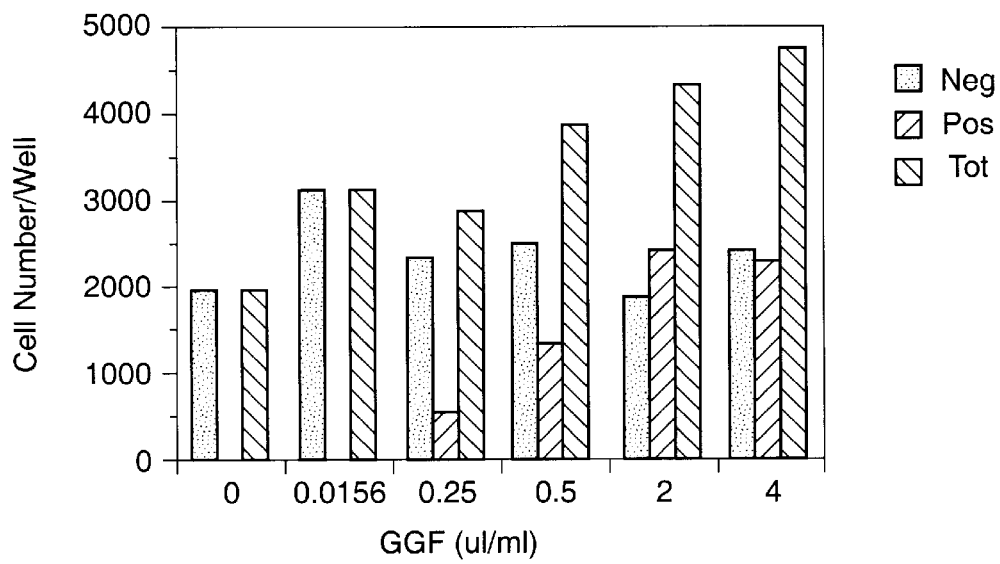

The BrdU incorporation assay can therefore provide additional useful information about the biological activity of GGFs on Schwann cells when compared to the $^{125}$I-UDR incorporation assay. For example, the data reported in FIG. 15 show that GGFs can act on Schwann cells to induce DNA synthesis, but at lower doses to increase the number of negative cells present in the microculture after 48 hours.

Figure 16:
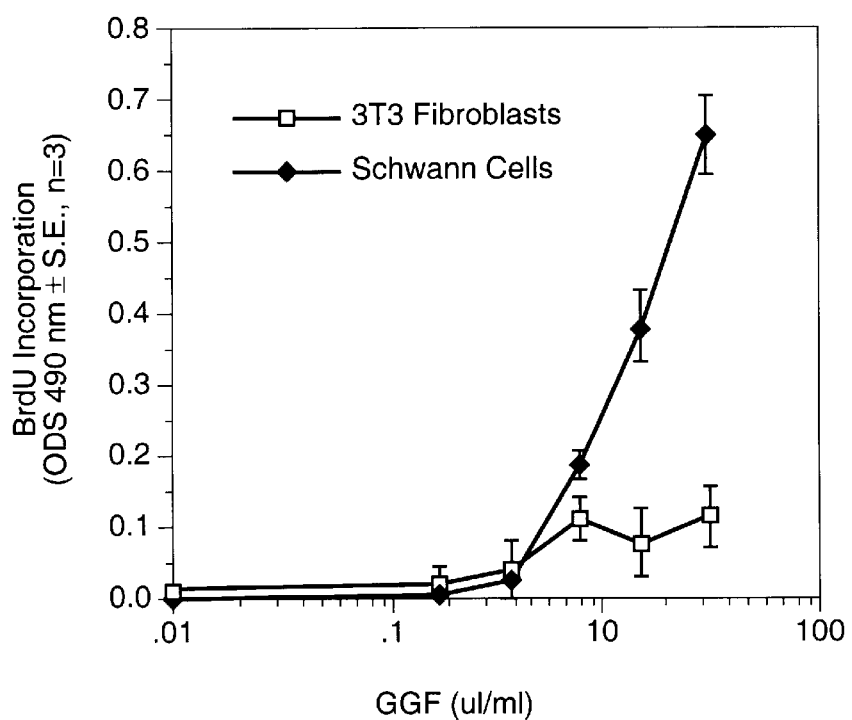

The BrdU incorporation assay has been used on several cell lines of different origin. In FIG. 16 the mitogenic responses of Schwann cells and Swiss 3T3 fibroblasts to GGFs are compared; despite the weak response obtained in 3T3 fibroblasts, some clearly BrdU-positive nuclei were detected in these cultures. Control cultures were run in parallel in presence of several doses of FCS or human recombinant PDGF, showing that the cells could respond to appropriate stimuli (not shown).

Figure 17:
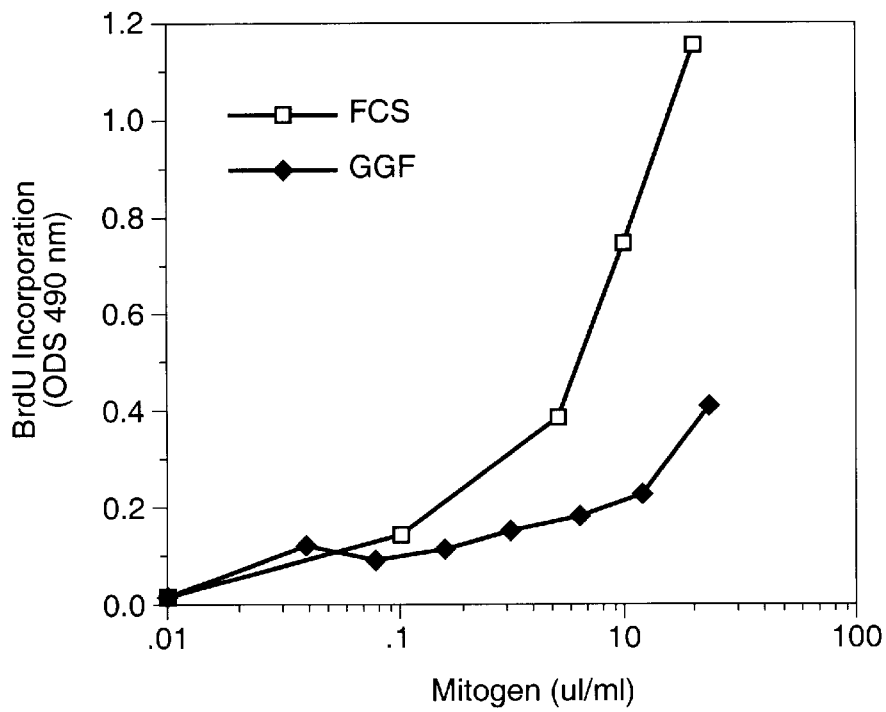
Figure 18:
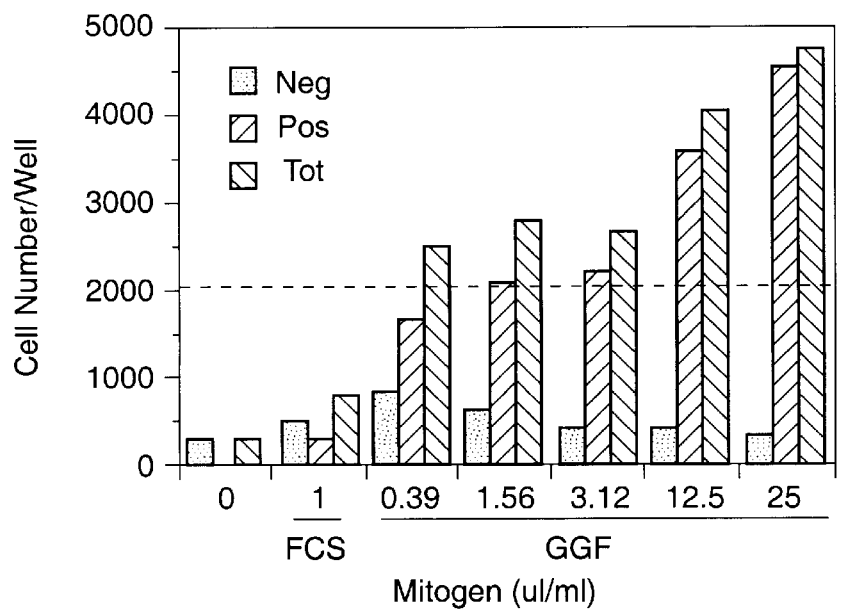

The ability of fibroblasts to respond to GGFs was further investigated using the BHK 21 C13 cell line. These fibroblasts, derived from kidney, do not exhibit contact inhibition or reach a quiescent state when confluent. Therefore the experimental conditions were designed to have a very low background proliferation without comprising the cell viability. GGFs have a significant mitogenic activity on BHK21 C13 cells as shown by FIG. 17 and FIG. 18. FIG. 17 shows the Brdu incorporation into DNA by BHK 21 C13 cells stimulated by GGFS in the presence of 0.1% FCS. The good mitogenic response to FCS indicates that cell culture conditions were not limiting. In FIG. 18 the mitogenic effect of GGFs is expressed as the number of BrdU-positive and BrdU-negative cells and as the total number of cells counted per well. Data are representative of two experiments run in duplicates; at least three fields per well were counted. As observed for Schwann cells in addition to a proliferative effect at low doses, GGFs also increase the numbers of nonresponding cells surviving. The percentage of BrdU positive cells is proportional to the increasing amounts of GGFs added to the cultures. The total number of cells after 48 hours in presence of higher doses of GGFs is at least doubled, confirming that GGFs induce DNA synthesis and proliferation in BHK21 C13 cells. Under the same conditions, cells maintained for 48 hours in the presence of 2% FCS showed an increase of about six fold (not shown).

Figure 19:
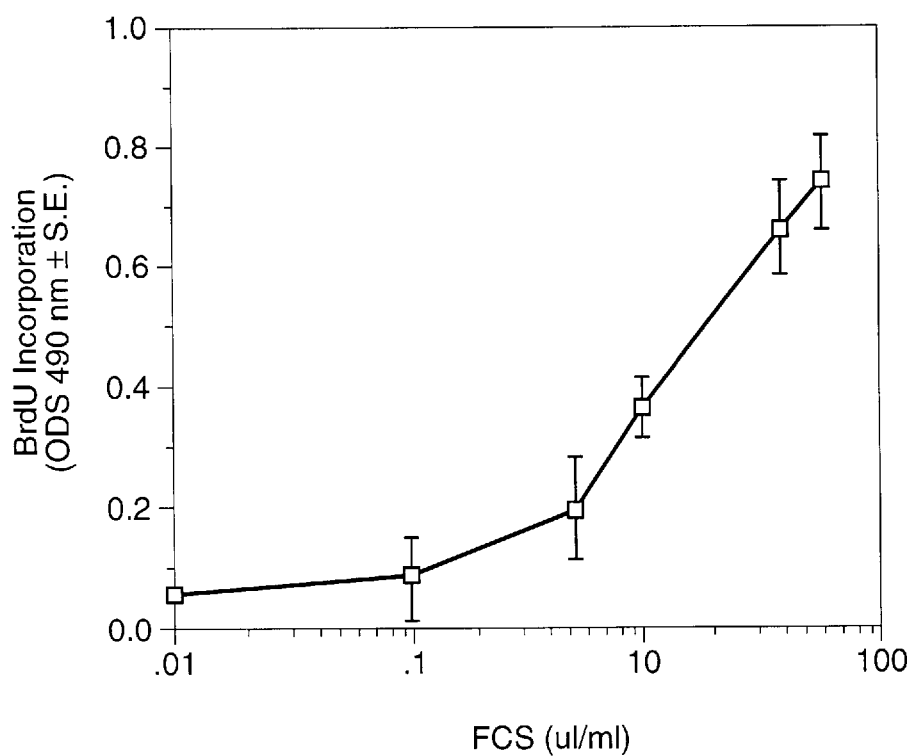

C6 glioma cells have provided a useful model to study glial cell properties. The phenotype expressed seems to be dependent on the cell passage, the cells more closely resembling an astrocyte phenotype at an early stage, and an oligodendrocyte phenotype at later stages (beyond passage 70). C6 cells used in these experiments were from passage 39 to passage 52. C6 cells are a highly proliferating population, therefore the experimental conditions were optimized to have a very low background of BrdU incorporation. The presence of 0.1% serum was necessary to maintain cell viability without significantly affecting the mitogenic responses, as shown by the dose response to FCS (FIG. 19).

In FIG. 20 the mitogenic responses to aFGF (acidic Fibroblast growth factor) and GGFs are expressed as the percentages of maximal BrdU incorporation obtained in the presence of FCS (8%). Values are averages of two experiments, run in duplicates. The effect of GGFs was comparable to that of a pure preparation of aFGF. aFGF has been described as a specific growth factor for C6 cells (Lim R. et al. (1990) Cell Regulation 1:741–746) and for that reason it was used as a positive control. The direct counting of BrdU positive and negative cells was not possible because of the high cell density in the microcultures. In contrast to the cell lines so far reported, PC12 cells did not show any evident responsiveness to GGFS, when treated under culture conditions in which PC12 could respond to sera (mixture of FCS and HS as used routinely for cell maintenance) Nevertheless the number of cells plated per well seems to affect the behavior of PC12 cells, and therefore further experiments are required.

EXAMPLE 4

Isolation and Cloning of Nucleotide Sequences Encoding Proteins Containing GGF-I and GGF-II Peptides Isolation and cloning of the GGF-II nucleotide sequences was performed as outlined herein, using peptide sequence information and library screening, and was performed as set out below. It will be appreciated that the peptides of FIGS. 4 and 5 can be used as the starting point for isolation and cloning of GGF-I sequences by following the techniques described herein. Indeed, FIG. 21, (SEQ ID No. 54–88) shows possible degenerate oligonucleotide probes for this purpose, and FIG. 23, (SEQ ID Nos. 90–119), lists possible PCR primers. DNA sequence and polypeptide sequence should be obtainable by this means as with GGF-II, and also DNA constructs and expression vectors incorporating such DNA sequence, host cells genetically altered by incorporating such constructs/vectors, and protein obtainable by cultivating such host cells. The invention envisages such subject matter.

I. Design and Synthesis of oligonucleotide Probes and Primers

Degenerate DNA oligomer probes were designed by backtranslating the amino acid sequences (derived from the peptides generated from purified GGF protein) into nucleotide sequences. Oligomers represented either the coding strand or the non-coding strand of the DNA sequence. When serine, arginine or leucine were included in the oligomer design, then two separate syntheses were prepared to avoid ambiguities. For example, serine was encoded by either TCN or AGY as in 537 and 538 or 609 and 610. Similar codon splitting was done for arginine or leucine (e.g. 544, 545). DNA oligomers were synthesized on a Biosearch 8750 4-column DNA synthesizer using β cyanoethyl chemistry operated at 0.2 micromole scale synthesis. Oligomers were cleaved off the column (500 angstrom CpG resins) and deprotected in concentrated ammonium hydroxide for 6–24 hours at 55°–60°' C. Deprotected oligomers were dried under vacuum (Speedvac) and purified by electrophoresis in gels of 15% acrylamide (20 mono: 1 bis), 50 mM Tris-borate-EDTA buffer containing 7M urea. Full length oligomers were detected in the gels by UV shadowing, then the bands were excised and DNA oligomers eluted into 1.5 μls H20 for 4–16 hours with shaking. The eluate was dried, redissolved in 0.1 μl $H_2O$ and absorbance measurements were taken at 260 nm.

Concentrations were determined according to the following formula:

$$(A260 \times units/\mu l)(60.6/length) = x\mu M$$

All oligomers were adjusted to 50 μM concentration by addition of $H_2O$.

Degenerate probes designed as above are shown in FIG. 21, (SEQ ID Nos. 54–88).

PCR primers were prepared by essentially the same procedures that were used for probes with the following modifications. Linkers of thirteen nucleotides containing restriction sites were included at the 5' ends of the degenerate oligomers for use in cloning into vectors. DNA synthesis was performed at 1 micromole scale using 1,000 angstrom CpG resins and inosine was used at positions where all four nucleotides were incorporated normally into degenerate probes. Purifications of PCR primers included an ethanol precipitation following the gel electrophoresis purification.

II. Library Construction and Screening

A bovine genomic DNA library was purchased from Stratagene (Catalogue Number: 945701). The library contained $2 \times 10^6$ 15–20 kb Sau3Al partial bovine DNA fragments cloned into the vector lambda DashII. A bovine total brain cDNA library was purchased from Clonetech (Catalogue Number: BL 10139). Complementary DNA libraries were constructed (In Vitrogen; Stratagene) from mRNA prepared from bovine total brain, from bovine pituitary and from bovine posterior pituitary. In Vitrogen prepared two cDNA libraries: one library was in the vector lambda g10, the other in vector pcDNAI (a plasmid library). The Stratagene libraries were prepared in the vector lambda unizap. Collectively, the cDNA libraries contained 14 million primary recombinant phage.

The bovine genomic library was plated on *E. coli* K12 host strain LE392 on 23×23 cm plates (Nunc) at 150,000 to 200,000 phage plaques per plate. Each plate represented approximately one bovine genome equivalent. Following an overnight incubation at 37° C., the plates were chilled and replicate filters were prepared according to procedures of Grunstein and Hogness ((1975) PNAS (USA) 72:3961). Four plaque lifts were prepared from each plate onto uncharged nylon membranes (Pall Biodyne A or MSI Nitropure). The DNA was immobilized onto the membranes by cross-linking under UV light for 5 minutes or, by baking at 80° C. under vacuum for two hours. DNA probes were labelled using T4 polynucleotide kinase (New England Biolabs) with gamma $^{32}$p ATP (New England Nuclear; 6500 Ci/mmol) according to the specifications of the suppliers. Briefly, 50 pmols of degenerate DNA oligomer were incubated in the presence of 600 $\mu$Ci gamma $^{32}$P-ATP and 5 units T4 polynucleotide kinase for 30 minutes at 37° C. Reactions were terminated, gel electrophoresis loading buffer was added and then radiolabelled probes were purified by electrophoresis. $^{32}$P labelled probes were excised from gel slices and eluted into water. Alternatively, DNA probes were labelled via PCR amplification by incorporation of $\alpha^{32}$P-dATP or $\alpha^{32}$P dCTP according to the protocol of Schowalter and Sommer ((1989) Anal. Biochem 177:90–94). Probes labelled in PCR reactions were purified by desalting on Sephadex G-150 columns.

Prehybridization and hybridization were performed in GMC buffer (0.52M NaPi, 7% SDS, 1% BSA, 1.5 mM EDTA, 0.1M NaCl 10 $\mu$g/$\mu$l TRNA). Washing was performed in buffer A oligowash (160 $\mu$l 1M Na2HPO$_4$, 200 $\mu$l 20% SDS, 8.0 $\mu$l 0.5m EDTA, 100 $\mu$l 5M NaCl, 3632 $\mu$l H20). Typically, 20 filters (400 sq. centimetres each) representing replicate copies of ten bovine genome equivalents were incubated in 200 $\mu$l hybridization solution with 100 pmols of degenerate oligonucleotide probe (128–512 fold degenerate). Hybridization was allowed to occur overnight at 5° C. below the minimum melting temperature calculated for the degenerate probe. The calculation of minimum melting temperature assumes 2° C. for an AT pair and 4° C. for a GC pair.

Filters were washed in repeated changes of oligowash at the hybridization temperatures for four to five hours and finally, in 3.2M tetramethylammonium chloride, 1% SDS twice for 30 min at a temperature dependent on the DNA probe length. For 20 mers, the final wash temperature was 60° C. Filters were mounted, then exposed to X-ray film (Kodak XAR5) using intensifying screens (Dupont Cronex Lightening Plus). Usually, a three to five day film exposure at minus 80° C. was sufficient to detect duplicate signals in these library screens. Following analysis of the results, filters could be stripped and reprobed. Filters were stripped by incubating through two successive cycles of fifteen minutes in a microwave oven at full power in a solution of 1% SDS containing 10 mM EDTA pH8. Filters were taken through at least three to four cycles of stripping and reprobing with various probes.

III. Recombinant Phage Isolation, Growth and DNA Preparation

These procedures followed standard protocol as described in Recombinant DNA (Maniatis et al. Recombinant DNA 2:60–62:81).

IV. Analysis of Isolated Clones Using DNA Digestion and Southern Blots

Recombinant Phage DNA samples (2 micrograms) were digested according to conditions recommended by the restriction endonuclease supplier (New England Biolabs). Following a four hour incubation at 37° C., the reactions products were precipitated in the presence of 0.1M sodium acetate and three volumes of ethanol. Precipitated DNA was collected by centrifugation, rinsed in 75% ethanol and dried. All resuspended samples were loaded onto agarose gels (typically 1% in TAE buffer; 0.04M Tris acetate, 0. 002M EDTA). Gel runs were at 1 volt per centimetre from 4 to 20 hours. Markers included lambda Hind III DNA fragments and/or $\phi$X174HaeIII DNA fragments (New England Biolabs). The gels were stained with 0.5 micrograms/$\mu$l of ethidium bromide and photographed. For southern blotting, DNA was first depurinated in the gel by treatment with 0.125N HCl, denatured in 0.5N NaOH and transferred in 20x SSC (3M sodium chloride, 0.03M sodium citrate) to uncharged nylon membranes. Blotting was done for 6 hours up to 24 hours, then the filters were neutralized in 0.5M Tris HCl pH 7.5, 0.15M sodium chloride, then rinsed briefly in 50 mM Tris-borate EDTA.

For cross-linking, the filters were wrapped first in transparent plastic wrap, then the DNA side exposed for five minutes to an ultraviolet light. Hybridization and washing was performed as described for library screening (see section 2 of this Example). For hybridization analysis to determine whether similar genes exist in other species slight modifications were made. The DNA filter was purchased from Clonetech (Catalogue Number 7753-1) and contains 5 micrograms of EcoRI digested DNA from various species per lane. The probe was labelled by PCR amplification reactions as described in section 2 above, and hybridizations were done in 80% buffer B(2 g polyvinylpyrrolidine, 2 g Ficoll-400, 2 g bovine serum albumin, 50 $\mu$l 1M Tris-HCl (pH 7.5) 58 g NaCl, 1 g sodium pyrophosphate, log sodium dodecyl sulfate, 950 $\mu$l H$_2$O) containing 10% dextran sulfate. The probes were denatured by boiling for ten minutes then rapidly cooling in ice water. The probe was added to the hybridization buffer at $10^6$ dpm $^{32}$p per $\mu$l and incubated overnight at 60° C. The filters were washed at 60° C. first in buffer B followed by 2x SSC, 0.1% SDS then in 1x SSC, 0.1% SDS. For high stringency, experiments, final washes were done in 0.1x SSC, 1% SDS and the temperature raised to 65° C.

Southern blot data were used to prepare a restriction map of the genomic clone and to indicate which subfragments hybridized to the GGF probes (candidates for subcloning).

V. Subcloning of Pieces of DNA Homologous to Hybridization Probes

DNA digests (e.g. 5 micrograms) were loaded onto 1% agarose gels then appropriate fragments excised from the gels following staining. The DNA was purified by adsorption onto glass beads followed by elution using the protocol described by the supplier (Bio 101). Recovered DNA fragments—(100–200 ng) were ligated into linearized dephosphorylated vectors, e.g. pT3T7 (Ambion), which is a derivative of pUC18, using T4 ligase (New England Biolabs). This vector carries the E. coli β lactamase gene, hence, transformants can be selected on plates containing ampicillin. The vector also supplies β-galactosidase complementation to the host cell, therefore non-recombinants (blue) can be detected using isopropylthiogaloctoside and Bluogal (Bethesda Research Labs). A portion of the ligation reactions was used to transform E. coli K12 XL1 blue competent cells (Stratagene Catalogue Number: 200236) and then the transformants were selected on LB plates containing 50 micrograms per $\mu$l ampicillin. White colonies were selected and plasmid mini preps were prepared for DNA digestion and for DNA sequence analysis. Selected clones were retested to determine if their insert DNA hybridized with the GGF probes.

VI. DNA Sequencing

Double stranded plasmid DNA templates were prepared from double stranded plasmids isolated from 5 µl cultures according to standard protocols. Sequencing was by the dideoxy chain termination method using Sequenase 2.0 and a dideoxynucleotide sequencing kit (US Biochemical) according to the manufacturers protocol (a modification of Sanger et al. (1977) PNAS (USA) 74:5463). Alternatively, sequencing was done in a DNA thermal cycler (Perkin Elmer, model 4800) using a cycle sequencing kit (New England Biolabs; Bethesda Research Laboratories) and was performed according to manufacturers instructions using a 5'-end labelled primer. Sequence primers were either those supplied with the sequencing kits or were synthesized according to sequence determined from the clones. Sequencing reactions were loaded on and resolved on 0.4 mm thick sequencing gels of 6% polyacylamide. Gels were dried and exposed to X-Ray film. Typically, 35S was incorporated when standard sequencing kits were used and a $^{32}p$ end labelled primer was used for cycle sequencing reactions. Sequences were read into a DNA sequence editor from the bottom of the gel to the top (5' direction to 3') and data were analyzed using programs supplied by Genetics Computer Group (GCG, University of Wisconsin).

VII. RNA Preparation and PCR Amplification

Open reading frames detected in the genomic DNA and which contained sequence encoding GGF peptides were extended via PCR amplification of pituitary RNA. RNA was prepared from frozen bovine tissue (Pelfreeze) according to the guanidine neutral-CsCl chloride procedure (Chirgwin et. al. (1979) Biochemistry 18:5294). Polyadenylated RNA was selected by oligo-dT cellulose column chromatography (Aviv and Leder. (1972) PNAS (USA) 69:1408).

Specific target nucleotide sequences were amplified beginning with either total RNA or polyadenylated RNA samples that had been converted to cDNA using the Perkin Elmer PCR/RNA Kit Number: N808-0017. First strand reverse transcription reactions used 1 µg template RNA and either primers of oligo dT with restriction enzyme recognition site linkers attached or specific antisense primers determined from cloned sequences with restriction sites attached. To produce the second strand, the primers either were plus strand unique sequences as used in 3' RACE reactions (Frohman et. al. (1988) PNAS (USA) 85:8998) or were oligo dT primers with restriction sites attached if the second target site had been added by terminal transferase tailing first strand reaction products with dATP (e.g. 5' race reactions, Frohman et. al., ibid). Alternatively, as in anchored PCR reactions the second strand primers were degenerate, hence, representing particular peptide sequences.

The amplification profiles followed the following general scheme: 1) five minutes soak file at 95° C.; 2) thermal cycle file of 1 minute, 95° C.; 1 minute ramped down to an annealing temperature of 45° C., 50° C. or 55° C.; maintain the annealing temperature for one minute; ramp up to 72° C. over one minute; extend at 72° C. for one minute or for one minute plus a 10 second auto extension; 3) extension cycle at 72° C., five minutes, and; 4) soak file 40° C. for infinite time. Thermal cycle files (#2) usually were run for 30 cycles. Sixteen µl of each 100 µl amplification reaction was analyzed by electrophoresis in 2% Nusieve 1% agarose gels run in TAE buffer at 4 volts per centimetre for three hours. The gels were stained, then blotted to uncharged nylon membranes which were probed with labelled DNA probes that were internal to the primers.

Specific sets of DNA amplification products could be identified in the blotting experiments and their positions used as a guide to purification and reamplification. When appropriate, the remaining portions of selected samples were loaded onto preparative gels, then following electrophoresis four to five slices of 0.5 mm thickness (bracketing the expected position of the specific product) were taken from the gel. The agarose was crushed, then soaked in 0.5 µl of electrophoresis buffer from 2–16 hours at 40° C. The crushed agarose was centrifuged for two minutes and the supernate was transferred to fresh tubes.

Reamplification was done on five microlitres (roughly 1% of the product) of the eluted material using the same sets of primers and the reaction profiles as in the original reactions. When the reamplification reactions were completed, samples were extracted with chloroform and transferred to fresh tubes. Concentrated restriction enzyme buffers and enzymes were added to the reactions in order to cleave at the restriction sites present in the linkers. The digested PCR products were purified by gel electrophoresis, then subcloned into vectors as described in the subcloning section above. DNA sequencing was done described as above.

VII. DNA Sequence Analysis

DNA sequences were assembled using a fragment assembly program and the amino acid sequences deduced by the GCG programs GelAssemble, Map and Translate. The deduced protein sequences were used as a query sequence to search protein sequence databases using WordSearch. Analysis was done on a VAX Station 3100 workstation operating under VMS 5.1. The database search was done on SwissProt release number 21 using GCG Version 7.0.

VII. Results

As indicated, to identify the DNA sequence encoding bovine GGF-II degenerate oligonucleotide probes were designed from GGF-II peptide sequences. GGF-II 12 (SEQ ID No. 44), a peptide generated via lysyl endopeptidase digestion of a purified GGF-II preparation (see FIGS. 11 and 12) showed strong amino acid sequence homology with GGF-I 07 (SEQ ID No. 39), a tryptic peptide generated from a purified GGF-I preparation. GGF-II 12 was thus used to create ten degenerate oligonucleotide probes (see oligos 609, 610 and 649 to 656 in FIG. 21, SEQ ID Nos. 69–71 and 79, respectively). A duplicate set of filters were probed with two sets (set 1=609, 610; set 2=649–656) of probes encoding two overlapping portions of GGF-II 12. Hybridization signals were observed, however, only one clone hybridized to both probe sets. The clone (designated GGF2BG1) was purified.

Southern blot analysis of DNA from the phage clone GGF2BG1 confirmed that both sets of probes hybridized with that bovine DNA sequence, and showed further that both probes reacted with the same set of DNA fragments within the clone. Based on those experiments a 4 kb EcoRI sub-fragment of the original clone was identified, subcloned and partially sequenced. FIG. 22 shows the nucleotide sequence and the deduced amino acid sequence (SEQ ID No. 89) of the initial DNA sequence readings that included the hybridization sites of probes 609 and 650, and confirmed that a portion of this bovine genomic DNA encoded peptide 12 (KASLADSGEYM).

Further sequence analysis demonstrated that GGF-II 12 resided on a 66 amino acid open reading frame (see below) which has become the starting point for the isolation of overlapping sequences representing a putative bovine GGF-II gene and a cDNA.

Several PCR procedures were used to obtain additional coding sequences for the putative bovine GGF-II gene. Total RNA and oligo dT-selected (poly A containing) RNA samples were prepared from bovine total pituitary, anterior pituitary, posterior pituitary, and hypothalamus. Using primers from the list shown in FIG. 23 (SEQ ID No. 109–119) one-sided PCR reactions (RACE) were used to amplify cDNA ends in both the 3' and 5' directions, and anchored PCR reactions were performed with degenerate oligonucleotide primers representing additional GGF-II peptides. FIG. 24 summarizes the contiguous DNA structures and sequences obtained in those experiments. From the 3' RACE reactions, three alternatively spliced cDNA sequences were produced, which have been cloned and sequenced. A 5' RACE reaction led to the discovery of an additional exon containing coding sequence for at least 52 amino acids. Analysis of that deduced amino acid sequence revealed peptides GGF-II-6 and a sequence similar to GGF-I-18 (see below). The anchored PCR reactions led to the identification of (cDNA) coding sequences of peptides GGF-II-1, 2, 3 and 10 contained within an additional cDNA segment of 300 bp. The 5' limit of this segment (i.e. segment E, see FIG. 31) is defined by the oligonucleotide which encodes peptide GGF-II-1 and which is used in the PCR reaction. (Additional 5' sequence data exists as described for the human clone in Example 6.) Thus this clone contains nucleotide sequences encoding six out of the existing total of nine novel GGF-II peptide sequences.

The cloned gene was characterized first by constructing a physical map of GGF2BG1 that allowed positioning the coding sequences as they were found (see below, FIG. 25). DNA probes from the coding sequences described above have been used to identify further DNA fragments containing the exons on this phage clone and to identify clones that overlap in both directions. The putative bovine GGF-II gene is divided into at least 5 coding segments, but only coding segments A and B have been defined as exons and sequenced and mapped thus far. The summary of the contiguous coding sequences identified is shown in FIG. 26. The exons are listed (alphabetically) in the order of their discovery. It is apparent from the intron/exon boundaries that exon B may be included in cDNAs that connect coding segment E and coding segment A. That is, exon B cannot be spliced out without compromising the reading frame. Therefore, we suggest that three alternative splicing patterns can produce putative bovine GGF-II cDNA sequences 1, 2 and 3. The coding sequences of these, designated GGF2BPP1. CDS, GGF2BPP2. CDS and GGF2BPP3. CDS, respectively, are given in FIGS. 28a (SEQ ID No. 133), 28b (SEQ ID No. 134) and 28c (SEQ ID No. 135), respectively. The deduced amino acid sequence of the three cDNAs is also given in FIGS. 28a, 28b and 28c (SEQ ID Nos. 133–135, respectively).

The three deduced structures encode proteins of lengths 206, 281 and 257 amino acids. The first 183 residues of the deduced protein sequence are identical in all three gene products. At position 184 the clones differ significantly. A codon for glycine GGT in GGF2BPP1 also serves as a splice donor for GGF2BPP2 and GGF2BPP3, which alternatively add on exons C, C/D, C/D' and D or C, C/D and D, respectively shown in FIG. 33 (SEQ ID No. 149). GGF2BPP1 is a truncated gene product which is generated by reading past the coding segment a splice junction into the following intervening sequence (intron). This represents coding segment A' in FIG. 31 (SEQ ID Nos. 140, 168). The transcript ends adjacent to a canonical AATAAA polyadenylation sequence, and we suggest that this truncated gene product represents a bona fide mature transcript. The other two longer gene products share the same 3' untranslated sequence and polyadenylation site.

All three of these molecules contain six of the nine novel GGF-II peptide sequences (see FIG. 12) and another peptide is highly homologous to GGF-I-18 (see FIG. 27). This finding gives a high probability that this recombinant molecule encodes at least a portion of bovine GGF-II. Furthermore, the calculated isoelectric points for the three peptides are consistent with the physical properties of GGF-I and II. Since the molecular size of GGF-2 is roughly 60 kd, the longest of the three cDNAs should encode a protein with nearly one-half of the predicted number of amino acids.

A probe encompassing the B and A exons was labelled via PCR amplification and used to screen a cDNA library made from RNA isolated from bovine posterior pituitary. One clone (GGF2BPP5) showed the pattern indicated in FIG. 30 and contained an additional DNA coding segment (G) between coding segments A and C. The entire nucleic acid sequence is shown in FIG. 32 (SEQ ID No. 148). The predicted translation product from the longest open reading frame is 241 amino acids. A portion of a second cDNA (GGF2BPP4) was also isolated from the bovine posterior pituitary library using the probe described above. This clone showed the pattern indicated in FIG. 30. This clone is incomplete at the 5' end, but is a splicing variant in the sense that it lacks coding segments G and D. BPP4 also displays a novel 3' end with regions H, K and L beyond region C/D. The sequence of BPP4 is shown in FIG. 34 (SEQ ID No. 150).

EXAMPLE 5

GGF Sequences in Various Species

Computer database searching has not revealed any meaningful similarities between any predicted GGF translation products and known protein sequences. This suggests that GGF-II is the first member of a new family or superfamily of proteins. In high stringency cross hybridization studies (DNA blotting experiments) with other mammalian DNAs we have shown clearly that DNA probes from this bovine recombinant molecule can readily detect specific sequences in a variety of samples tested. A highly homologous sequence is also detected in human genomic DNA. The autoradiogram is shown in FIG. 29. The signals in the lanes containing rat and human DNA represent the rat and human equivalents of GGF, the sequences of which have been recently reported by Holmes et al. ((1992) Science 256:1205) and Wen et al. ((1992) Cell 69:559).

EXAMPLE 6

Isolation of a Human Sequence Encoding Human GGF2

Several human clones containing sequences homologous to the bovine GGFII coding segment E were isolated by screening a human cDNA library prepared from brain stem (Stratagene catalog #935206). This strategy was pursued based upon the strong link between most of the GGF2 peptides (unique to GGF2) and the predicted peptide sequence from clones containing the bovine E segment. This library was screened as described in Example 4, Section II using the oligonucleotide probes 914–919 listed below.

914 TCGGGCTCCATGAAGAAGATGTA (SEQ ID NO: 42)
915 TCCATGAAGAAGATGTACCTGCT (SEQ ID NO: 43)
916 ATGTACCTGCTGTCCTCCTTGA (SEQ ID NO: 44)
917 TTGAAGAAGGACTCGCTGCTCA (SEQ ID NO: 77)
918 AAAGCCGGGGGCTTGAAGAA (SEQ ID NO: 183)
919 ATGARGTGTGGGCGGCGAAA (SEQ ID NO: 184)

Clones detected with these probes were further analyzed by hybridization. A probe derived from coding segment A (see FIG. 21), which was produced by labeling a polymerase chain reaction (PCR) product from segment A, was also used to screen the primary library. Several clones that hybridized with both A and E derived probes were selected and one particular clone, GGF2HBS5, was selected for further analysis. This clone is represented by the pattern of coding segments (EBACC/D'D as shown in FIG. 31). The E segment in this clone is the human equivalent of the truncated bovine version of E shown in FIG. 37. GGF2HBS5 is the most likely candidate to encode GGFII of all the "putative" GGFII candidates described. The length of coding sequence segment E is 786 nucleotides plus 264 bases of untranslated sequence. The predicted size of the protein encoded by GGF2HBS5 is approximately 423 amino acids (approximately 45 kilodaltons), which is similar to the size of the deglycosylated form of GGF (see Example 15). Additionally, seven of the GGFII peptides listed in FIG. 27 have equivalent sequences which fall within the protein sequence predicted from region E. Peptides II-6 and II-12 are exceptions, which fall in coding segment B and coding segment A, respectively. RNA encoding the GGF2HBS5 protein was produced in an in vitro transcription system driven by the bacteriophage T7 promoter resident in the vector (Bluescript SK [Stratagene Inc.] see FIG. 44) containing the GGF2HBS5 insert. This RNA can be translated in a cell free (rabbit reticulocyte) translation system and the size of the protein product was 45 Kd. Additionally, the cell-free product has been assayed in a Schwann cell mitogenic assay to confirm biological activity. Schwann cells treated with conditioned medium show both increased proliferation as measured by incorporation of $^{125}$-Uridine and phosphorylation on tyrosine of a protein in the 185 kilodalton range.

Thus the size of the product encoded by GGF2HBS5 and the presence of DNA sequences which encode human peptides highly homologous to the bovine peptides shown in FIG. 12 confirm that GGF2HBS5 encodes the human equivalent of bovine GGF2. The fact that conditioned media prepared from cells transformed with this clone elicits Schwann cell mitogenic activity confirms that the GGFII-HBS5 gene product (unlike the BPP5 gene product) is secreted. Additionally the GGFBPP5 gene product seems to mediate the Schwann cell proliferation response via a receptor tyrosine kinase such as p185$^{erbB2}$ or a closely related receptor (see Example 13).

EXAMPLE 7

Isolation of Human Sequences Related to Bovine GGF

The result in Example 5 indicates that GGF related sequences from human sources can also be easily isolated by using DNA probes derived from bovine GGF sequences. Alternatively, the procedure described by Holmes et al. ((1992) Science 256:1205) can be used. In this example a human protein (heregulin a) which binds to and activates the p185$^{erbB2}$ receptor (and is related to GGF) is purified from a tumor cell line and the derived peptide sequence is used to produce oligonucleotide probes which were utilized to clone the cDNAs encoding heregulin. This is a similar approach to that used in examples 1–4 for the cloning of GGF sequences from pituitary cDNAs. The heregulin protein and complementary DNAs were isolated according to the following procedures. Heregulin was purified from medium conditioned by MDA-MB-231 breast cancer cells (ATCC #HTB 26) grown on Percell Biolytica microcarrier beads (Hyclone Labs). The medium (10 liters) was concentrated ~25-fold by filtration through a membrane (10-kD cutoff) (Millipore) and clarified by centrifugation and filtration through a filter (0.22 μm). The filtrate was applied to a heparin Sepharose column (Pharmacia) and the proteins were eluted with steps of 0.3, 0.6, and 0.9M NaCl in phosphate-buffered saline. Activity in the various chromatographic fractions was measured by quantifying the increase in tyrosine phosphorylation of p185$^{erbB2}$ in MCF-7 breast tumor cells (ATCC # HTB 22). MCF-7 cells were plated in 24-well Costar plates in F12 (50%) Dulbecco's minimum essential medium (50%) containing serum (10%) (10$^5$ cells per well), and allowed to attach for at least 24 hours. Prior to assay, cells were transferred into medium without serum for a minimum of 1 hour. Column fractions (10 to 100 μl) were incubated for 30 min. at 37°. Supernatants were then aspirated and the reaction was stopped by the addition of SDS-PAGE sample buffer 100 μl). Samples were heated for 5 min. at 100° C., and portions (10 to 15 μl) were applied to a tris-glycine gel (4 to 20%) (Novex). After electrophoresis, proteins were electroblotted onto a polyvinylidenedifluoride (PVDF) membrane and then blocked with bovine serum albumin (5%) in tris-buffered saline containing Tween-20 (0.05%) (TBST). Blots were probed with a monoclonal antibody (1:1000 dilution) to phosphotyrosine (Upstate Biotechnology) for a minimum of 1 hour at room temperature. Blots were washed with TBST, probed with an antibody to mouse immunoglobulin G conjugated to alkaline phosphatase (Promega) (diluted 1:7500) for a minimum of 30 min. at room temperature. Reactive bands were visualized with 5-bromo-4-chloro-3-indoyl-1-phosphate and nitro-blue tetrazolium. Immunoblots were scanned with a Scan Jet Plus (Hewlett-Packard) densitometer. Signal intensities for unstimulated MCF-7 cells were 20 to 30 units. Fully stimulated p185$^{erbB2}$ yielded signals of 180 to 200 units. The 0.6M NaCl pool, which contained most of the activity, was applied to a polyaspartic acid (PolyLC) column equilibrated in 17 mM sodium phosphate (pH 6.8) containing ethanol (30%). A linear gradient from 0.3M to 0.6M NaCl in the equilibration buffer was used to elute bound proteins. A peak of activity (at ~0.45M NaCl) was further fractionated on a C4 reversed-phase column (SynChropak RP-4) equilibrated in buffer containing TFA (0.1%) and acetonitrile (15%). Proteins were eluted from this column with an acetonitrile gradient from 25 to 40% over 60 min. Fractions (1 μl) were collected, assayed for activity, and analyzed by SDS-PAGE on tris-glycine gels (4–20%, Novex).

HPLC-purified HRG-α was digested with lysine C in SDS (0.1%), 10 mM dithiothreitol, 0.1M NH$_4$HCO$_3$ (pH 8.0) for 20 hours at 37° C. and the resultant fragments were resolved on a Synchrom C4 column (4000Å, 0.2 by 10 cm). The column was equilibrated in 0.1% TFA and eluted with a 1-propanol gradient in 0.1% TFA (Henzel et al. (1989) J. Biol. Chem. 264:15905). Peaks from the chromatographic run were dried under vacuum and sequenced. One of the peptides (eluting at ~24% 1-propanol) gave the sequence [A]AEKEKTF[C]VNGGEXFMVKDLXNP (SEQ ID Nos 162). Residues in brackets were uncertain and an X represents a cycle in which it was not possible to identify the amino acid. The initial yield was 8.5 pmol and the sequence did not correspond to any known protein. Residues 1, 9, 15, and 22 were later identified in the cDNA sequence as cysteine. Direct sequencing of the ~45-kD band from a gel that had been overloaded and blotted onto a PVDF membrane revealed a low abundance sequence XEXKE[G][R]GK[G]K[G]KKKEXGXG[K] (SEQ ID No. 169) with a very low initial yield (0.2 pmol). This corresponded to amino acid residues 2 to 22 of heregulin-α (FIG. 31), suggesting that serine 2 is the NH$_2$-terminus of proHRG-α. Although the NH$_2$ terminus was blocked, it was observed that occasionally a small amount of a normally blocked protein may not be post-translationally modified. The NH$_2$ terminal assignment was confirmed by mass spectrometry of the protein after digestion with cyanogen bromide. The COOH-terminus of the isolated protein has not been definitely identified; however, by mixture sequencing of proteolytic digests, the mature sequence does not appear to extend past residue 241. Abbreviations for amino residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T. Thr; V, Val; W, Trp; and Y, Tyr.

As a source of cDNA clones, an oligo(dT)-primed λgt10 (Hurn et al. (1984) λgt10 and λgt11 DNA Cloning Techniques: A Practical Approach) cDNA library was constructed (Gubler and Hoffman. (1983) Gene 25:263) with mRNA purified (Chirwin et al. (1979) Biochemistry 18:5294) from MDA-MB-231 cells. The following eightfold degenerate antisense deoxyoligonucleotide encoding the 13-amino acid sequence AEKEKTFCVNGGE (SEQ ID No. 164) was designed on the basis of human codon frequency optima (Lathe. (1985) J. Mol. Biol. 183:1) and chemically synthesized:

5'-CTCGCC (G OR T) CC (A OR G) TTCAC (A OR G) CAGAAGGTCTTCTCCTTCTCAGC-3' (SEQ ID No. 165). For the purpose of probe design a cysteine was assigned to an unknown residue in the amino acid sequence. The probe was labeled by phosphorylation and hybridized under low-stringency conditions to the cDNA library. The proHRG-α protein was identified in this library. HRB-β1 cDNA was identified by probing a second oligo(dT)-primed λgt10 library made from MDA-MB-231 cell mRNA with sequences derived from both the 5' and 3' ends of proHRG. Clone 13 (FIG. 2A) was a product of screening a primed (5'-CCTCGCTCCTTCTTCTTGCCCTTC-3' primer; proHRG-α antisense nucleotides 33 to 56) MDA-MB-231 λgt10 library with 5' HRG sequence. A sequence corresponding to the 5' end of clone 13 as the probe was used to identify proHRGβ2 and proHRGβ3 in a third oligo(dT)-primed λgt10 library derived from MDA-MB-231 cell mRNA. Two cDNA clones encoding each of the four HRGs were sequenced (Sanger et al. (1977) PNAS (USA) 74:5463). Another cDNA designated clone 84 has an amino acid sequence identical to proHRGβ2 through amino acid 420. A stop codon at position 421 is followed by a different 3'-untranslated sequence.

EXAMPLE 8

Isolation of a Further Splicing Variant

The methods in Example 7 produced four closely related sequences (heregulin α, β1, β2, β3) which arise as a result of splicing variation. Peles et al. ((1992) Cell 69:205) and Wen et al. ((1992) Cell 69:559) have isolated another splicing variant (from rat) using a similar purification and cloning approach to that described in Examples 1–4 and 7 involving a protein which binds to p185$^{erbB}$2. The cDNA clone was obtained as follows (via the purification and sequencing of a p185$^{erbB2}$ binding protein from a transformed rat fibroblast cell line).

A p185$^{erbB2}$ binding protein was purified from conditioned medium as follows. Pooled conditioned medium from three harvests of 500 roller bottles (120 liters total) was cleared by filtration through 0.2 μfilters and concentrated 31-fold with a Pelicon ultrafiltration system using membranes with a 20 kd molecular size cutoff. All the purification steps were performed by using a Pharmacia fast protein liquid chromatography system. The concentrated material was directly loaded on a column of heparin-Sepharose (150 μl, preequilibrated with phosphate-buffered saline (PBS)). The column was washed with PBS containing 0.2M NaCl until no absorbance at 280 nm wavelength could be detected. Bound proteins were then eluted with a continuous gradient (250 μl) of NaCl (from 0.2M to 1.0M), and 5 μl fractions were collected. Samples (0.01 μl of the collected fractions) were used for the quantitative assay of the kinase stimulatory activity. Active fractions from three column runs (total volume=360 μl) were pooled, concentrated to 25 μl by using a YM10 ultrafiltration membrane (Amicon, Danvers, Mass.), and ammonium sulfate was added to reach a concentration of 1.7M. After clearance by centrifugation (10,000×g, 15 min.), the pooled material was loaded on a phenyl-Superose column (HR10/10, Pharmacia). The column was developed with a 45 μl gradient of $(NH_4)_2SO_4$ (from 1.7M to no salt) in 0.1M $Na_2PO_4$ (pH 7.4), and 2 μl fractions were collected and assayed (0.002 μl per sample) for kinase stimulation (as described in Example 7). The major peak of activity was pooled and dialyzed against 50 mM sodium phosphate buffer (pH 7.3). A Mono-S cation-exchange column (HR5/5, Pharmacia) was preequilibrated with 50 mM sodium phosphate. After loading the active material (0.884 mg of protein; 35 μl), the column was washed with the starting buffer and then developed at a rate of 1 μl/min. with a gradient of NaCl. The kinase stimulatory activity was recovered at 0.45–0.55M salt and was spread over four fractions of 2 μl each. These were pooled and loaded directly on a Cu$^{+2}$ chelating columns (1.6 μl, HR2/5 chelating Superose, Pharmacia). Most of the proteins adsorbed to the resin, but they gradually eluted with a 30 μl linear gradient of ammonium chloride (0–1M). The activity eluted in a single peak of protein at the range of 0.05 to 0.2M NH$_4$Cl. Samples from various steps of purification were analyzed by gel electrophoresis followed by silver staining using a kit from ICN (Costa Mesa, Calif.), and their protein contents were determined with a Coomassie blue dye binding assay using a kit from Bio-Rad (Richmond, Calif.).

The p44 protein (10 μg) was reconstituted in 200 μl of 0.1M ammonium bicarbonate buffer (pH 7.8). Digestion was conducted with L-1-tosyl-amide 2-phenylethyl chloromethyl ketone-treated trypsin (Serva) at 37° C. for 18 hr. at an enzyme-to-substrate ratio of 1:10. The resulting peptide mixture was separated by reverse phase HPLC and monitored at 215 nm using a Vydac C4 micro column (2.1 mm i.d.×15 cm, 300) and an HP 1090 liquid chromatographic system equipped with a diode-array detector and a workstation. The column was equilibrated with 0.1% trifluoroacetic acid (mobile phase A), and elution was effected with a linear gradient from 0%–55% mobile phase B (90% acetonitrile in 0.1% trifluoroacetic acid) over 70 min. The flow rate was 0.2 μl/min. and the column temperature was controlled at 25° C. One-third aliquots of the peptide peaks collected manually from the HPLC system were characterized by N-terminal sequence analysis by Edman degradation. The fraction eluted after 27.7 min. (T27.7) contained mixed amino acid sequences and was further rechromatographed after reduction as follows: A 70% aliquot of the peptide fraction was dried in vacuo and reconstituted in 100 μl of 0.2M ammonium bicarbonate buffer (pH 7.8). DTT (final concentration 2 mM) was added to the solution, which was then incubated at 37° C. for 30 min. The reduced peptide mixture was then separated by reverse-phase HPLC using a Vydac column (2.1 mm i.d.×15 cm). Elution conditions and flow rat were identical to those described above. Amino acid sequence analysis of the peptide was performed with a Model 477 protein sequencer (Applied Biosystems, Inc., Foster City, Calif.) equipped with an on-line phenylthiohydantoin (PTH) amino acid analyzer and a Model 900 data analysis system (Hunkapiller et al. (1986)). The protein was loaded onto a trifluoroacetic acid-treated glass fiber disc precycled with polybrene and NaCl. The PTH-amino acid analysis was performed with a micro liquid chromatography system (Model 120) using dual syringe pumps and reverse-phase (C-18) narrow bore columns (Applied Biosystems, 2.1 mm×250 mm).

RNA was isolated from Rat1-EJ cells by standard procedures (Maniatis et al. (1982) Molecular Cloning: A Laboratory Manual) and poly (A)$^+$ was selected using an mRNA Separator kit (Clontech Lab, Inc., Palo, Alto, Calif.). cDNA was synthesized with the Superscript kit (from BRL Life Technologies, Inc., Bethesda, Miss.). Column-fractionated double-strand cDNA was ligated into an SalI- and NacI-digested pJT-2 plasmid vector, a derivative of the pCD-X vector (Okayama and Berg (1983) Mol. Cell Biol. 3:280) and transformed into DH10B *E. coli* cells by electroporation (Dower et al. (1988) Nucl. Acids Res. 16:6127). Approximately $5\times10^5$ primary transformants were screened with two oligonucleotide probes that were derived from the protein sequences of the N-terminus of NDF (residues 5–24) and the T40.4 tryptic peptide (residues 7–12). Their respective sequences were as follows (N indicates all 4 nt):

```
(1) 5'-ATA GGG AAG GGC GGG GGA AGG GTC NCC CTC NGC
                                   A       T
            AGG GCC GGG CTT GCC TCT GGA GCC TCT-3'

(2) 5'-TTT ACA CAT ATA TTC NCC-3'
       C   G       G   C
```

(1: SEQ ID No. 167; 2: SEQ ID No. 168)

The synthetic oligonucleotides were end-labeled with [γ-$^{32}$P]ATP with T4 polynucleotide kinase and used to screen replicate sets of nitrocellulose filters. The hybridization solution contained 6× SSC, 50 mM sodium phosphate (pH 6.8), 0.1% sodium pyrophosphate, 2× Denhardt's solution, 50 μg/ml salmon sperm DNA, and 20% formamide (for probe 1) or no formamide (for probe 2). The filters were washed at either 50° C. with 0.5× SSC, 0.2% SDS, 2 mM EDTA (for probe 1) or at 37° C. with 2× SSC, 0.2% SDS, 2 mM EDTA (for probe 2). Autoradiography of the filters gave ten clones that hybridized with both probes. These clones were purified by replating and probe hybridization as described above.

The cDNA clones were sequenced using an Applied Biosystems 373A automated DNA sequencer and Applied Biosystems Taq DyeDeoxy™ Terminator cycle sequencing kits following the manufacture's instructions. In some instances, sequences were obtained using [$^{35}$S]dATP (Amersham) and Sequenase™ kits from U.S. Biochemicals following the manufacturer's instructions. Both strands of the cDNA clone 44 were sequenced by using synthetic oligonucleotides as primers. The sequence of the most 5' 350 nt was determined in seven independent cDNA clones. The resultant clone demonstrated the pattern shown in FIG. 30 (NDF).

EXAMPLE 9

Other Possible Splicing Variants

Alignment of the deduced amino acid sequences of the cDNA clones and PCR products of the bovine, and the published human (FIG. 31) and rat sequences show a high level of similarity, indicating that these sequences are derived from homologous genes within the three species. The variable number of messenger RNA transcripts detectable at the cDNA/PCR product level is probably due to extensive tissue-specific splicing. The patterns obtained and shown in FIG. 30 suggests that other splicing variants exist. A list of probable splicing variants is indicated as followed. Many of these variants can be obtained by coding segment specific probing of cDNA libraries derived from different tissues. Alternatively, the variants can be assembled from specific (excised from) cDNA clones, PCR products or genomic DNA regions via cutting and splicing techniques known to one skilled in the art. These variant sequences can be expressed in recombinant systems and the recombinant products can be assayed to determine their level of Schwann cell mitogenic activity as well as their ability to bind and activate the p185$^{erbB2}$ receptor.

EXAMPLE 10

Functional Elements of GGF

The deduced structures of family of GGF sequences indicate that the longest forms (as represented by GGF2BPP4) encode transmembrane proteins where the extracellular part contains a domain which resembles epidermal growth factor (see Carpenter and Wahl in Peptide Growth Factors and Their Receptors I pp. 69–133, Springer-Verlag, N.Y. 1991). The positions of the cysteine residues in coding segments C and C/D or C/D' peptide sequence are conserved with respect to the analogous residues in the epidermal growth factor (EGF) peptide sequence. This suggests that the extracellular domain functions as a receptor recognition and biological activation sites. Several of the variant forms lack the H, K, and L coding segments and thus may be expressed as secreted, diffusible biologically active proteins. Likely structures are shown in FIG. 35.

Membrane bound versions of this protein may induce Schwann cell proliferation if expressed on the surface of neurons during embryogenesis or during nerve regeneration (where the surfaces of neurons are intimately associated with the surfaces of proliferating Schwann cells).

Secreted (non membrane bound) GGF's may act as classically diffusible factors which can interact with Schwann cells at some distance from their point of secretion. An example of a secreted GGF is the protein encoded by GGF2HBS5 (see example 6) Other GGFs such as that encoded by GGF2BPP5 seem to be non-secreted (see example 6). These GGFs may be injury response forms which are released as a consequence of tissue damage.

EXAMPLE 11

Splicing Variants with Antiproliferative Action

One particular splicing variant (GGF2BPP1) is described in Example 4. GGF2BPP1 is a truncated gene product which is generated by reading past the coding segment A splice junction into the adjoining genomic sequence. This represents coding segment A' in FIG. 31. The transcript ends near to a canonical AATAAA polyadenylation sequence. This splicing variant contains regions F, E, B and A'. Other possible variants of this may lack region E (F, B, A'). As described in Example 10 regions C, C/D, or C/D' are homologous to EGF and are most likely to be the sites which are responsible for biological activity. GGF2BPP1 could retain receptor binding activity yet lack the ability to activate the receptor. Such a ligand would function as an antagonist since it would compete with active GGF/p185 erbB2 ligands (eg. GGF2BPP5) for receptor binding. Other splicing variants such as those containing region E may also function as antagonists as described above. The presence of an extra domain such as that which is encoded by region E may result in structural differences which would interfere with biological activity following receptor binding. GGF2BPP2 may also be an inhibitor molecule. The presence of region C/D' in addition to region C/D in GGF2BPP2 adds sequence to the EGF related region which could potentially result in a protein which lacks biological activity. GGF2HBS11 is another potential inhibitor molecule. This clone was isolated from a human brainstem library using the same methods and probes as described in Example 6 for the isolation of GGF2HBS5. The GGF2HBS11 clone contains a portion of region E which is flanked by new sequence which is not contained in any other known region. The lack of region C, C/D or C/D' suggests that GGF2HBS11 would also lack biological activity.

EXAMPLE 12

Purification of Antiproliferative Factors from Recombinant Cells

In order to obtain antiproliferative factors to assay for biological activity, the proteins can be overproduced using cloned DNA. Several approaches can be used. A recombinant *E. coli* cell containing the sequences described in example 11 can be constructed. Expression systems such as pNH8a (Stratagene, Inc.) can be used for this purpose by following manufacturers procedures. Alternatively, these sequences can be inserted in a mammalian expression vector and an overproducing cell line can be constructed. As an example, for this purpose DNA encoding GGF2BPP1 can be expressed in COS cells or can be expressed in Chinese hamster ovary cells using the pMSXND expression vector (Lee and Nathans, J. Biol. Chem. 263, 3521–3527, (1981)). This vector containing GGF DNA sequences can be transfected into host cells using established procedures.

Transient expression can be examined or G418-resistant clones can be grown in the presence of methotrexate to select for cells that amplify the DHFR gene (contained on the pMSXND vector) and, in the process, co-amplify the adjacent protein encoding sequence. Because CHO cells can be maintained in a totally protein-free medium (Hamilton and Ham, in Vitro 13, 537–547 (1977)), the desired protein can be purified from the medium. Western analysis using the antisera produced in Example 9 can be used to detect the presence of the desired protein in the conditioned medium of the overproducing cells.

The desired protein can be purified from the *E. coli* lysate or the CHO cell conditioned medium using the types of procedures described in Example 1. The protein may be assayed at various points in the procedure using a Western blot assay.

EXAMPLE 13

Design and Assay of Antiproliferative Factors

As indicated above and in FIGS. 35 and 39–45, the GGF coding segments include regions with EGF-like homology. These EGF-like domains can be required for the activation of mitogenesis in the binding reaction between GGF ligands containing such domains and the erbB2 receptor. Comparisons of naturally occurring products of the GGF coding sequences which confer mitogenic activity versus those which confer antiproliferative activity, as disclosed above, provide additional support for this. Consequently, preferred antiproliferative factors are those which lack these EGF-like domains. Antiproliferative factors designed in this manner will lack all or part of the C, C/D, or C/D' coding segments. Examples of such factors likely to have antiproliferative activity using this design strategy are shown in FIG. 37 and described in the summary of the invention.

The recombinant proteins produced in Example 12 using the criterion described above may be assayed as described hereafter. The Schwann cell mitogenic assay described herein may be used to assay the expressed product of the full length clone or any biologically active portions thereof. Any member of the family of splicing variant complementary DNA's derived from the GGF gene (including the Heregulins) can be expressed in this manner and assayed in the Schwann cell proliferation assay by one skilled in the art. Antiproliferative activity in the GGF assay can be examined by a competition assay (Chan et al., Science 254:1383 (1991)). Varying concentrations of recombinant antiproliferative GGF variants (such as GGF2BPP1) can be added to Schwann cell cultures in the presence of GGF. The extent of antiproliferative activity can be measured by comparing mitogenic activity of the cultures to controls treated only with GGF. This will provide a measure of dose dependent inhibition. The specificity of the response can be measured by examining the effect of varying concentrations of antiproliferative factor on the mitogenic activity of other growth factors and their target cells (e.g. EGF). Antiproliferative activity of recombinant GGF variants can also be examined in breast tumour cells. Cell lines such as SK-BR-3 which proliferate in response to GGF's/p185$^{erbB2}$ ligands can be assayed in a similar manner to that described above for Schwann cells.

Crosslinking studies can be performed to determine whether $I^{125}$ labelled GGF variants, which show antiproliferative activity (as described above), bind to the erbB2 receptor (Chan et al., Science 254:1383 (1991)). Binding can be demonstrated by immunoprecipitation of the crosslinked protein with an antibody to the erbB2 receptor.

I claim:

1. A method for producing an antibody specific for a polypeptide, said method comprising
 i) immunizing a mammal with a polypeptide comprising the E amino acid sequence (SEQ ID NOS. 137 or 163), and
 ii) purifying said antibody from tissue of said mammal, or from a hybridoma made using said tissue.

* * * * *

SEQUENCE LISTING ( 1 ) GENERAL INFORMATION:

( i i i ) NUMBER OF SEQUENCES: 184

( 2 ) INFORMATION FOR SEQ ID NO: 1:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( x i ) SEQUENCE DESCRIPTION: SEQ ID NO: 1:

Phe Lys Gly Asp Ala His Thr Glu
 1              5

( 2 ) INFORMATION FOR SEQ ID NO: 2:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine; Xaa in position 12 is
            unknown.

( x i ) SEQUENCE DESCRIPTION: SEQ ID NO: 2:

Xaa Ala Ser Leu Ala Asp Glu Tyr Glu Tyr Met Xaa Lys
 1              5                     10

( 2 ) INFORMATION FOR SEQ ID NO: 3:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine; Xaa in position 10 is
            unknown.

( x i ) SEQUENCE DESCRIPTION: SEQ ID NO: 3:

Xaa Thr Glu Thr Ser Ser Ser Gly Leu Xaa Leu Lys
 1              5                  10

( 2 ) INFORMATION FOR SEQ ID NO: 4:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine.

( x i ) SEQUENCE DESCRIPTION: SEQ ID NO: 4:

Xaa Lys Leu Gly Glu Met Trp Ala Glu
 1              5

( 2 ) INFORMATION FOR SEQ ID NO: 5:

( i ) SEQUENCE CHARACTERISTICS:
        ( A ) LENGTH: 7
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine.

( x i ) SEQUENCE DESCRIPTION: SEQ ID NO: 5:

Xaa Leu Gly Glu Lys Arg Ala
 1               5

( 2 ) INFORMATION FOR SEQ ID NO: 6:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine.

( x i ) SEQUENCE DESCRIPTION: SEQ ID NO: 6:

Xaa Ile Lys Ser Glu His Ala Gly Leu Ser Ile Gly Asp Thr Ala Lys
 1               5                   1 0                     1 5

( 2 ) INFORMATION FOR SEQ ID NO: 7:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine.

( x i ) SEQUENCE DESCRIPTION: SEQ ID NO: 7:

Xaa Ala Ser Leu Ala Asp Glu Tyr Glu Tyr Met Arg Lys
 1               5                   1 0

( 2 ) INFORMATION FOR SEQ ID NO: 8:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine.

( x i ) SEQUENCE DESCRIPTION: SEQ ID NO: 8:

Xaa Ile Lys Gly Glu His Pro Gly Leu Ser Ile Gly Asp Val Ala Lys
 1               5                   1 0                     1 5

( 2 ) INFORMATION FOR SEQ ID NO: 9:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine and Xaa in position 12 is unknown.

( x i ) SEQUENCE DESCRIPTION: SEQ ID NO: 9:

Xaa Met Ser Glu Tyr Ala Phe Phe Val Gln Thr Xaa Arg
 1               5                          10

( 2 ) INFORMATION FOR SEQ ID NO: 10:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 10:

Xaa Ser Glu His Pro Gly Leu Ser Ile Gly Asp Thr Ala Lys
 1               5                          10

( 2 ) INFORMATION FOR SEQ ID NO: 11:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine; Xaa in position 8 is unknown.

( x i ) SEQUENCE DESCRIPTION: SEQ ID NO: 11:

Xaa Ala Gly Tyr Phe Ala Glu Xaa Ala Arg
 1               5                          10

( 2 ) INFORMATION FOR SEQ ID NO: 12:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine; Xaa in position 7 is unknown.

( x i ) SEQUENCE DESCRIPTION: SEQ ID NO: 12:

Xaa Lys Leu Glu Phe Leu Xaa Ala Lys
 1               5

( 2 ) INFORMATION FOR SEQ ID NO: 13:

( i ) SEQUENCE CHARACTERISTICS:
        ( A ) LENGTH: 11
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 13:

Xaa Thr Thr Glu Met Ala Ser Glu Gln Gly Ala ( 2 ) INFORMATION FOR SEQ ID NO: 14:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 14:

Xaa Ala Lys Glu Ala Leu Ala Ala Leu Lys
1               5                   10

( 2 ) INFORMATION FOR SEQ ID NO: 15:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 15:

Xaa Phe Val Leu Gln Ala Lys Lys
1               5

( 2 ) INFORMATION FOR SEQ ID NO: 16:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 16:

Xaa Leu Gly Glu Met Trp
1               5

( 2 ) INFORMATION FOR SEQ ID NO: 17:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( x i ) SEQUENCE DESCRIPTION: SEQ ID NO: 17:

Glu Tyr Lys Cys Leu Lys Phe Lys Trp Phe Lys Lys Ala Thr Val Met
1               5                   10                  15

( 2 ) INFORMATION FOR SEQ ID NO: 18:

( i ) SEQUENCE CHARACTERISTICS:
        ( A ) LENGTH: 10
        ( B ) TYPE: amino acid
        ( C ) STRANDEDNESS:
        ( D ) TOPOLOGY: linear ( i x ) FEATURE:

( D ) OTHER INFORMATION: Xaa in position 8 is unknown.

( x i ) SEQUENCE DESCRIPTION: SEQ ID NO: 18:

```
Glu Ala Lys Tyr Phe Ser Lys Xaa Asp Ala
1               5                   10
```

( 2 ) INFORMATION FOR SEQ ID NO: 19:

( i ) SEQUENCE CHARACTERISTICS:
        ( A ) LENGTH: 7
        ( B ) TYPE: amino acid
        ( C ) STRANDEDNESS:
        ( D ) TOPOLOGY: linear ( i x ) FEATURE:
        ( D ) OTHER INFORMATION: Xaa in position 2 is unknown.

( x i ) SEQUENCE DESCRIPTION: SEQ ID NO: 19:

```
Glu Xaa Lys Phe Tyr Val Pro
1               5
```

( 2 ) INFORMATION FOR SEQ ID NO: 20:

( i ) SEQUENCE CHARACTERISTICS:
        ( A ) LENGTH: 26
        ( B ) TYPE: amino acid
        ( C ) STRANDEDNESS:
        ( D ) TOPOLOGY: linear ( x i ) SEQUENCE DESCRIPTION: SEQ ID NO: 20:

```
Glu Leu Ser Phe Ala Ser Val Arg Leu Pro Gly Cys Pro Pro Gly Val
1               5                   10                  15
Asp Pro Met Val Ser Phe Pro Val Ala Leu
            20                  25
```

( 2 ) INFORMATION FOR SEQ ID NO: 21:

( i ) SEQUENCE CHARACTERISTICS:
        ( A ) LENGTH: 2003
        ( B ) TYPE: nucleic acid
        ( C ) STRANDEDNESS: double
        ( D ) TOPOLOGY: linear ( i x ) FEATURE:
        ( D ) OTHER INFORMATION: N in positions 31 and 32 could be
        either A or G.

( x i ) SEQUENCE DESCRIPTION: SEQ ID NO: 21:

```
GGAATTCCTT TTTTTTTTTT TTTTTTTCTT NNTTTTTTTT TGCCCTTATA CCTCTTCGCC      60

TTTCTGTGGT TCCATCCACT TCTTCCCCCT CCTCCTCCCA TAAACAACTC TCCTACCCCT     120

GCACCCCCAA TAAATAAATA AAAGGAGGAG GGCAAGGGGG GAGGAGGAGG AGTGGTGCTG     180

CGAGGGGAAG GAAAAGGGAG GCAGCGCGAG AAGAGCCGGG CAGAGTCCGA ACCGACAGCC     240

AGAAGCCCGC ACGCACCTCG CACC ATG AGA TGG CGA CGC GCC CCG CGC CGC       291
                              Met Arg Trp Arg Arg Ala Pro Arg Arg
                              1                   5

TCC GGG CGT CCC GGC CCC CGG GCC CAG CGC CCC GGC TCC GCC GCC CGC      339
Ser Gly Arg Pro Gly Pro Arg Ala Gln Arg Pro Gly Ser Ala Ala Arg
10                  15                  20                  25

TCG TCG CCG CCG CTG CCG CTG CTG CCA CTA CTG CTG CTG CTG GGG ACC      387
Ser Ser Pro Pro Leu Pro Leu Leu Pro Leu Leu Leu Leu Leu Gly Thr
                30                  35                  40

GCG GCC CTG GCG CCG GGG GCG GCG GCC GGC AAC GAG GCG GCT CCC GCG      435
Ala Ala Leu Ala Pro Gly Ala Ala Ala Gly Asn Glu Ala Ala Pro Ala
            45                  50                  55
```

```
GGG GCC TCG GTG TGC TAC TCG TCC CCG CCC AGC GTG GGA TCG GTG CAG         483
Gly Ala Ser Val Cys Tyr Ser Ser Pro Pro Ser Val Gly Ser Val Gln
            60              65              70

GAG CTA GCT CAG CGC GCC GCG GTG GTG ATC GAG GGA AAG GTG CAC CCG         531
Glu Leu Ala Gln Arg Ala Ala Val Val Ile Glu Gly Lys Val His Pro
        75              80              85

CAG CGG CGG CAG CAG GGG GCA CTC GAC AGG AAG GCG GCG GCG GCG GCG         579
Gln Arg Arg Gln Gln Gly Ala Leu Asp Arg Lys Ala Ala Ala Ala Ala
    90              95             100                         105

GGC GAG GCA GGG GCG TGG GGC GGC GAT CGC GAG CCG CCA GCC GCG GGC         627
Gly Glu Ala Gly Ala Trp Gly Gly Asp Arg Glu Pro Pro Ala Ala Gly
                    110             115             120

CCA CGG GCG CTG GGG CCG CCC GCC GAG GAG CCG CTG CTC GCC GCC AAC         675
Pro Arg Ala Leu Gly Pro Pro Ala Glu Glu Pro Leu Leu Ala Ala Asn
                125             130             135

GGG ACC GTG CCC TCT TGG CCC ACC GCC CCG GTG CCC AGC GCC GGC GAG         723
Gly Thr Val Pro Ser Trp Pro Thr Ala Pro Val Pro Ser Ala Gly Glu
            140             145             150

CCC GGG GAG GAG GCG CCC TAT CTG GTG AAG GTG CAC CAG GTG TGG GCG         771
Pro Gly Glu Glu Ala Pro Tyr Leu Val Lys Val His Gln Val Trp Ala
    155             160             165

GTG AAA GCC GGG GGC TTG AAG AAG GAC TCG CTG CTC ACC GTG CGC CTG         819
Val Lys Ala Gly Gly Leu Lys Lys Asp Ser Leu Leu Thr Val Arg Leu
170             175             180             185

GGG ACC TGG GGC CAC CCC GCC TTC CCC TCC TGC GGG AGG CTC AAG GAG         867
Gly Thr Trp Gly His Pro Ala Phe Pro Ser Cys Gly Arg Leu Lys Glu
                190             195             200

GAC AGC AGG TAC ATC TTC TTC ATG GAG CCC GAC GCC AAC AGC ACC AGC         915
Asp Ser Arg Tyr Ile Phe Phe Met Glu Pro Asp Ala Asn Ser Thr Ser
            205             210             215

CGC GCG CCG GCC GCC TTC CGA GCC TCT TTC CCC CCT CTG GAG ACG GGC         963
Arg Ala Pro Ala Ala Phe Arg Ala Ser Phe Pro Pro Leu Glu Thr Gly
        220             225             230

CGG AAC CTC AAG AAG GAG GTC AGC CGG GTG CTG TGC AAG CGG TGC GCC        1011
Arg Asn Leu Lys Lys Glu Val Ser Arg Val Leu Cys Lys Arg Cys Ala
    235             240             245

TTG CCT CCC CAA TTG AAA GAG ATG AAA AGC CAG GAA TCG GCT GCA GGT        1059
Leu Pro Pro Gln Leu Lys Glu Met Lys Ser Gln Glu Ser Ala Ala Gly
250             255             260             265

TCC AAA CTA GTC CTT CGG TGT GAA ACC AGT TCT GAA TAC TCC TCT CTC        1107
Ser Lys Leu Val Leu Arg Cys Glu Thr Ser Ser Glu Tyr Ser Ser Leu
                270             175             180

AGA TTC AAG TGG TTC AAG AAT GGG AAT GAA TTG AAT CGA AAA AAC AAA        1155
Arg Phe Lys Trp Phe Lys Asn Gly Asn Glu Leu Asn Arg Lys Asn Lys
        185             190             195

CCA CAA AAT ATC AAG ATA CAA AAA AAG CCA GGG AAG TCA GAA CTT CGC        1203
Pro Gln Asn Ile Lys Ile Gln Lys Lys Pro Gly Lys Ser Glu Leu Arg
            200             205             210

ATT AAC AAA GCA TCA CTG GCT GAT TCT GGA GAG TAT ATG TGC AAA GTG        1251
Ile Asn Lys Ala Ser Leu Ala Asp Ser Gly Glu Tyr Met Cys Lys Val
215             220             225

ATC AGC AAA TTA GGA AAT GAC AGT GCC TCT GCC AAT ATC ACC ATC GTG        1299
Ile Ser Lys Leu Gly Asn Asp Ser Ala Ser Ala Asn Ile Thr Ile Val
        230             235             240             245

GAA TCA AAC GCT ACA TCT ACA TCC ACC ACT GGG ACA AGC CAT CTT GTA        1347
Glu Ser Asn Ala Thr Ser Thr Ser Thr Thr Gly Thr Ser His Leu Val
                250             255             260

AAA TGT GCG GAG AAG GAG AAA ACT TTC TGT GTG AAT GGA GGG GAG TGC        1395
Lys Cys Ala Glu Lys Glu Lys Thr Phe Cys Val Asn Gly Gly Glu Cys
            265             270             275
```

| TTC | ATG | GTG | AAA | GAC | CTT | TCA | AAC | CCC | TCG | AGA | TAC | TTG | TGC | AAG | TGC | 1443 |
| Phe | Met | Val | Lys | Asp | Leu | Ser | Asn | Pro | Ser | Arg | Tyr | Leu | Cys | Lys | Cys | |
| | | 280 | | | | | 285 | | | | | 290 | | | | |

| CCA | AAT | GAG | TTT | ACT | GGT | GAT | CGC | TGC | CAA | AAC | TAC | GTA | ATG | GCC | AGC | 1491 |
| Pro | Asn | Glu | Phe | Thr | Gly | Asp | Arg | Cys | Gln | Asn | Tyr | Val | Met | Ala | Ser | |
| | 295 | | | | | 300 | | | | | 305 | | | | | |

| TTC | TAC | AGT | ACG | TCC | ACT | CCC | TTT | CTG | TCT | CTG | CCT | GAA | | | | 1530 |
| Phe | Tyr | Ser | Thr | Ser | Thr | Pro | Phe | Leu | Ser | Leu | Pro | Glu | | | | |
| 400 | | | | | 405 | | | | | 410 | | | | | | |

```
TAGGAGCATG  CTCAGTTGGT  GCTGCTTTCT  TGTTGCTGCA  TCTCCCCTCA  GATTCCACCT    1590

AGAGCTAGAT  GTGTCTTACC  AGATCTAATA  TTGACTGCCT  CTGCCTGTCG  CATGAGAACA    1650

TTAACAAAAG  CAATTGTATT  ACTTCCTCTG  TTCGCGACTA  GTTGGCTCTG  AGATACTAAT    1710

AGGTGTGTGA  GGCTCCGGAT  GTTTCTGGAA  TTGATATTGA  ATGATGTGAT  ACAAATTGAT    1770

AGTCAATATC  AAGCAGTGAA  ATATGATAAT  AAAGGCATTT  CAAAGTCTCA  CTTTTATTGA    1830

TAAAATAAAA  ATCATTCTAC  TGAACAGTCC  ATCTTCTTTA  TACAATGACC  ACATCCTGAA    1890

AAGGGTGTTG  CTAAGCTGTA  ACCGATATGC  ACTTGAAATG  ATGGTAAGTT  AATTTTGATT    1950

CAGAATGTGT  TATTTGTCAC  AAATAAACAT  AATAAAGGA   AAAAAAAAA   AAA           2003
```

(2) INFORMATION FOR SEQ ID NO: 22:

(i) SEQUENCE CHARACTERISTICS:
        (A) LENGTH: 12
        (B) TYPE: amino acid
        (C) STRANDEDNESS:
        (D) TOPOLOGY: linear (ix) FEATURE:
        (D) OTHER INFORMATION: Xaa in position 11 is unknown.

(xi) SEQUENCE DESCRIPTION: SEQ ID NO: 22:

| Ala | Ser | Leu | Ala | Asp | Glu | Tyr | Glu | Tyr | Met | Xaa | Lys |
| 1 | | | | 5 | | | | | 10 | | |

(2) INFORMATION FOR SEQ ID NO: 23:

(i) SEQUENCE CHARACTERISTICS:
        (A) LENGTH: 11
        (B) TYPE: amino acid
        (C) STRANDEDNESS:
        (D) TOPOLOGY: linear (ix) FEATURE:
        (D) OTHER INFORMATION: Xaa in position 9 is unknown.

(xi) SEQUENCE DESCRIPTION: SEQ ID NO: 23:

| Thr | Glu | Thr | Ser | Ser | Ser | Gly | Leu | Xaa | Leu | Lys |
| 1 | | | | 5 | | | | | 10 | |

(2) INFORMATION FOR SEQ ID NO: 24:

(i) SEQUENCE CHARACTERISTICS:
        (A) LENGTH: 12
        (B) TYPE: amino acid
        (C) STRANDEDNESS:
        (D) TOPOLOGY: linear (xi) SEQUENCE DESCRIPTION: SEQ ID NO: 24:

| Ala | Ser | Leu | Ala | Asp | Glu | Tyr | Glu | Tyr | Met | Arg | Lys |
| 1 | | | | 5 | | | | | 10 | | |

(2) INFORMATION FOR SEQ ID NO: 25:

(i) SEQUENCE CHARACTERISTICS:

(A) LENGTH: 9
(B) TYPE: amino acid
(C) STRANDEDNESS:
(D) TOPOLOGY: linear (ix) FEATURE:
(D) OTHER INFORMATION: Xaa in position 7 is unknown.

(xi) SEQUENCE DESCRIPTION: SEQ ID NO: 25:

Ala Gly Tyr Phe Ala Glu Xaa Ala Arg
 1               5

(2) INFORMATION FOR SEQ ID NO: 26:

(i) SEQUENCE CHARACTERISTICS:
(A) LENGTH: 10
(B) TYPE: amino acid
(C) STRANDEDNESS:
(D) TOPOLOGY: linear (xi) SEQUENCE DESCRIPTION: SEQ ID NO: 26:

Thr Thr Glu Met Ala Ser Glu Gln Gly Ala
 1               5                   10

(2) INFORMATION FOR SEQ ID NO: 27:

(i) SEQUENCE CHARACTERISTICS:
(A) LENGTH: 9
(B) TYPE: amino acid
(C) STRANDEDNESS:
(D) TOPOLOGY: linear (xi) SEQUENCE DESCRIPTION: SEQ ID NO: 27:

Ala Lys Glu Ala Leu Ala Ala Leu Lys
 1               5

(2) INFORMATION FOR SEQ ID NO: 28:

(i) SEQUENCE CHARACTERISTICS:
(A) LENGTH: 7
(B) TYPE: amino acid
(C) STRANDEDNESS:
(D) TOPOLOGY: linear (xi) SEQUENCE DESCRIPTION: SEQ ID NO: 28:

Phe Val Leu Gln Ala Lys Lys
 1               5

(2) INFORMATION FOR SEQ ID NO: 29:

(i) SEQUENCE CHARACTERISTICS:
(A) LENGTH: 21
(B) TYPE: amino acid
(C) STRANDEDNESS:
(D) TOPOLOGY: linear (xi) SEQUENCE DESCRIPTION: SEQ ID NO: 29:

Glu Thr Gln Pro Asp Pro Gly Gln Ile Leu Lys Lys Val Pro Met Val
 1               5                   10                  15
Ile Gly Ala Tyr Thr
                20

(2) INFORMATION FOR SEQ ID NO: 30:

(i) SEQUENCE CHARACTERISTICS:
(A) LENGTH: 21
(B) TYPE: amino acid
(C) STRANDEDNESS:
(D) TOPOLOGY: linear ( i x ) FEATURE:
    ( D ) OTHER INFORMATION: Xaa in positions 1, 3, 17 and 19 is
        unknown.

( x i ) SEQUENCE DESCRIPTION: SEQ ID NO: 30:

```
Xaa Glu Xaa Lys Glu Gly Arg Gly Lys Gly Lys Gly Lys Lys Lys Glu
 1               5                  10                      15
Xaa Gly Xaa Gly Lys
             20
```

( 2 ) INFORMATION FOR SEQ ID NO: 31:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( x i ) SEQUENCE DESCRIPTION: SEQ ID NO: 31:

```
Ala Glu Lys Glu Lys Thr Phe Cys Val Asn Gly Gly Glu
 1               5                  10
```

( 2 ) INFORMATION FOR SEQ ID NO: 32:

( i ) SEQUENCE CHARACTERISTICS:
        ( A ) LENGTH: 8
        ( B ) TYPE: amino acid
        ( C ) STRANDEDNESS:
        ( D ) TOPOLOGY: linear ( i x ) FEATURE:
        ( D ) OTHER INFORMATION: Xaa in position 6 is unknown.

( x i ) SEQUENCE DESCRIPTION: SEQ ID NO: 32:

```
Lys Leu Glu Phe Leu Xaa Ala Lys
 1               5
```

( 2 ) INFORMATION FOR SEQ ID NO: 33:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine.

( x i ) SEQUENCE DESCRIPTION: SEQ ID NO: 33:

```
Xaa Val His Gln Val Trp Ala Ala Lys
 1               5
```

( 2 ) INFORMATION FOR SEQ ID NO: 34:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or
            Arginine, Xaa in position 11 is
            unknown.

( x i ) SEQUENCE DESCRIPTION: SEQ ID NO: 34:

```
Xaa Tyr Ile Phe Phe Met Glu Pro Glu Ala Xaa Ser Ser Gly
 1               5                  10
```

( 2 ) INFORMATION FOR SEQ ID NO: 35:

( i ) SEQUENCE CHARACTERISTICS:
        ( A ) LENGTH: 14
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine, Xaa in position 13 is unknown.

( x i ) SEQUENCE DESCRIPTION: SEQ ID NO: 35:

```
Xaa Leu Gly Ala Trp Gly Pro Pro Ala Phe Pro Val Xaa Tyr
 1               5                   10
```

( 2 ) INFORMATION FOR SEQ ID NO: 36:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 36:

```
Xaa Trp Phe Val Val Ile Glu Gly Lys
 1               5
```

( 2 ) INFORMATION FOR SEQ ID NO: 37:

( i ) SEQUENCE CHARACTERISTICS:
        ( A ) LENGTH: 16
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 37:

```
Xaa Ala Ser Pro Val Ser Val Gly Ser Val Gln Glu Leu Val Gln Arg
 1               5                   10                  15
```

( 2 ) INFORMATION FOR SEQ ID NO: 38:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 1 is Lysine or Arginine.

( x i ) SEQUENCE DESCRIPTION: SEQ ID NO: 38:

```
Xaa Val Cys Leu Leu Thr Val Ala Ala Leu Pro Pro Thr
 1               5                   10
```

( 2 ) INFORMATION FOR SEQ ID NO: 39:

( i ) SEQUENCE CHARACTERISTICS:
        ( A ) LENGTH: 7
        ( B ) TYPE: amino acid (C) STRANDEDNESS:
(D) TOPOLOGY: linear (ix) FEATURE:
(D) OTHER INFORMATION: Xaa in position 1 is Lysine or Arginine; Xaa in position 6 is unknown.

(xi) SEQUENCE DESCRIPTION: SEQ ID NO: 39:

Xaa Asp Leu Leu Leu Xaa Val
1               5

(2) INFORMATION FOR SEQ ID NO: 40:

(i) SEQUENCE CHARACTERISTICS:
(A) LENGTH: 39
(B) TYPE: amino acid
(C) STRANDEDNESS:
(D) TOPOLOGY: linear (xi) SEQUENCE DESCRIPTION: SEQ ID NO: 40:

Cys Thr Cys Gly Cys Cys Lys Cys Cys Arg Thr Thr Cys Ala Cys Arg
1               5                   10                  15
Cys Ala Gly Ala Ala Gly Gly Thr Cys Thr Cys Thr Cys Cys Thr
            20                  25                  30
Thr Cys Thr Cys Ala Gly Cys
            35

(2) INFORMATION FOR SEQ ID NO: 41:

(i) SEQUENCE CHARACTERISTICS:
(A) LENGTH: 24
(B) TYPE: amino acid
(C) STRANDEDNESS:
(D) TOPOLOGY: linear (xi) SEQUENCE DESCRIPTION: SEQ ID NO: 41:

Cys Cys Thr Cys Gly Cys Thr Cys Cys Thr Cys Thr Thr Cys Thr
1               5                   10                  15
Thr Gly Cys Cys Cys Thr Thr Cys
            20

(2) INFORMATION FOR SEQ ID NO: 42:

(i) SEQUENCE CHARACTERISTICS:
(A) LENGTH: 23
(B) TYPE: nucliec acid
(C) STRANDEDNESS: double
(D) TOPOLOGY: linear (xi) SEQUENCE DESCRIPTION: SEQ ID NO: 42:

TCGGGCTCCA TGAAGAAGAT GTA                                                                    23

(2) INFORMATION FOR SEQ ID NO: 43:

(i) SEQUENCE CHARACTERISTICS:
(A) LENGTH: 23
(B) TYPE: nucleic acid
(C) STRANDEDNESS: double
(D) TOPOLOGY: linear (xi) SEQUENCE DESCRIPTION: SEQ ID NO: 43:

TCCATGAAGA AGATGTACCT GCT                                                                    23

(2) INFORMATION FOR SEQ ID NO: 44:

(i) SEQUENCE CHARACTERISTICS:

(A) LENGTH: 22
(B) TYPE: nucleic acid
(C) STRANDEDNESS: double
(D) TOPOLOGY: linear (xi) SEQUENCE DESCRIPTION: SEQ ID NO: 44:

ATGTACCTGC TGTCCTCCTT GA  22

(2) INFORMATION FOR SEQ ID NO: 45:

(i) SEQUENCE CHARACTERISTICS:
(A) LENGTH: 8
(B) TYPE: amino acid
(C) STRANDEDNESS:
(D) TOPOLOGY: linear (xi) SEQUENCE DESCRIPTION: SEQ ID NO: 45:

Val His Gln Val Trp Ala Ala Lys
 1               5

(2) INFORMATION FOR SEQ ID NO: 46:

(i) SEQUENCE CHARACTERISTICS:
(A) LENGTH: 13
(B) TYPE: amino acid
(C) STRANDEDNESS:
(D) TOPOLOGY: linear (ix) FEATURE:
(D) OTHER INFORMATION: Xaa in position 10 is unknown.

(xi) SEQUENCE DESCRIPTION: SEQ ID NO: 46:

Tyr Ile Phe Phe Met Glu Pro Glu Ala Xaa Ser Ser Gly
 1               5                   10

(2) INFORMATION FOR SEQ ID NO: 47:

(i) SEQUENCE CHARACTERISTICS:
(A) LENGTH: 13
(B) TYPE: amino acid
(C) STRANDEDNESS:
(D) TOPOLOGY: linear (ix) FEATURE:
(D) OTHER INFORMATION: Xaa in position 12 is unknown.

(xi) SEQUENCE DESCRIPTION: SEQ ID NO: 47:

Leu Gly Ala Trp Gly Pro Pro Ala Phe Pro Val Xaa Tyr
 1               5                   10

(2) INFORMATION FOR SEQ ID NO: 48:

(i) SEQUENCE CHARACTERISTICS:
(A) LENGTH: 8
(B) TYPE: amino acid
(C) STRANDEDNESS:
(D) TOPOLOGY: linear (xi) SEQUENCE DESCRIPTION: SEQ ID NO: 48:

Trp Phe Val Val Ile Glu Gly Lys
 1               5

(2) INFORMATION FOR SEQ ID NO: 49:

(i) SEQUENCE CHARACTERISTICS:
(A) LENGTH: 15
(B) TYPE: amino acid
(C) STRANDEDNESS:
(D) TOPOLOGY: linear ( x i ) SEQUENCE DESCRIPTION: SEQ ID NO: 49:

Ala Ser Pro Val Ser Val Gly Ser Val Gln Glu Leu Val Gln Arg
 1               5                  10                 15

( 2 ) INFORMATION FOR SEQ ID NO: 50:

( i ) SEQUENCE CHARACTERISTICS:
        ( A ) LENGTH: 12
        ( B ) TYPE: amino acid
        ( C ) STRANDEDNESS:
        ( D ) TOPOLOGY: linear ( x i ) SEQUENCE DESCRIPTION: SEQ ID NO: 50:

Val Cys Leu Leu Thr Val Ala Ala Leu Pro Pro Thr
 1               5                  10

( 2 ) INFORMATION FOR SEQ ID NO: 51:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( x i ) SEQUENCE DESCRIPTION: SEQ ID NO: 51:

Lys Val His Gln Val Trp Ala Ala Lys
 1               5

( 2 ) INFORMATION FOR SEQ ID NO: 52:

( i ) SEQUENCE CHARACTERISTICS:
        ( A ) LENGTH: 13
        ( B ) TYPE: amino acid
        ( C ) STRANDEDNESS:
        ( D ) TOPOLOGY: linear ( i x ) FEATURE:
        ( D ) OTHER INFORMATION: Xaa in position 12 is unknown.

( x i ) SEQUENCE DESCRIPTION: SEQ ID NO: 52:

Lys Ala Ser Leu Ala Asp Ser Gly Glu Tyr Met Xaa Lys
 1               5                  10

( 2 ) INFORMATION FOR SEQ ID NO: 53:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i x ) FEATURE:
        ( D ) OTHER INFORMATION: Xaa in position 5 is unknown.

( x i ) SEQUENCE DESCRIPTION: SEQ ID NO: 53:

Asp Leu Leu Leu Xaa Val
 1               5

( 2 ) INFORMATION FOR SEQ ID NO: 54:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 54:

TTYAARGGNG AYGCNCAYAC         20

( 2 ) INFORMATION FOR SEQ ID NO: 55:

( i ) SEQUENCE CHARACTERISTICS:
    ( A ) LENGTH: 21
    ( B ) TYPE: nucleic acid
    ( C ) STRANDEDNESS: double
    ( D ) TOPOLOGY: linear ( x i ) SEQUENCE DESCRIPTION: SEQ ID NO: 55:

CATRTAYTCR TAYTCRTCNG C                                                                 21

( 2 ) INFORMATION FOR SEQ ID NO: 56:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( x i ) SEQUENCE DESCRIPTION: SEQ ID NO: 56:

TGYTCNGANG CCATYTCNGT                                                                   20

( 2 ) INFORMATION FOR SEQ ID NO: 57:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( x i ) SEQUENCE DESCRIPTION: SEQ ID NO: 57:

TGYTCRCTNG CCATYTCNGT                                                                   20

( 2 ) INFORMATION FOR SEQ ID NO: 58:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( x i ) SEQUENCE DESCRIPTION: SEQ ID NO: 58:

CCDATNACCA TNGGNACYTT                                                                   20

( 2 ) INFORMATION FOR SEQ ID NO: 59:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( x i ) SEQUENCE DESCRIPTION: SEQ ID NO: 59:

GCNGCCCANA CYTGRTGNAC                                                                   20

( 2 ) INFORMATION FOR SEQ ID NO: 60:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( x i ) SEQUENCE DESCRIPTION: SEQ ID NO: 60:

GCYTCNGGYT CCATRAARAA                                                                   20

( 2 ) INFORMATION FOR SEQ ID NO: 61:

( i ) SEQUENCE CHARACTERISTICS:
  ( A ) LENGTH: 20
  ( B ) TYPE: nucleic acid
  ( C ) STRANDEDNESS: double
  ( D ) TOPOLOGY: linear ( x i ) SEQUENCE DESCRIPTION: SEQ ID NO: 61:

CCYTCDATNA CNACRAACCA 20

( 2 ) INFORMATION FOR SEQ ID NO: 62:

( i ) SEQUENCE CHARACTERISTICS:
  ( A ) LENGTH: 17
  ( B ) TYPE: nucleic acid
  ( C ) STRANDEDNESS: double
  ( D ) TOPOLOGY: linear ( x i ) SEQUENCE DESCRIPTION: SEQ ID NO: 62:

TCNGCRAART ANCCNGC 17

( 2 ) INFORMATION FOR SEQ ID NO: 63:

( i ) SEQUENCE CHARACTERISTICS:
  ( A ) LENGTH: 20
  ( B ) TYPE: nucleic acid
  ( C ) STRANDEDNESS: double
  ( D ) TOPOLOGY: linear ( x i ) SEQUENCE DESCRIPTION: SEQ ID NO: 63:

GCNGCNAGNG CYTCYTTNGC 20

( 2 ) INFORMATION FOR SEQ ID NO: 64:

( i ) SEQUENCE CHARACTERISTICS:
  ( A ) LENGTH: 20
  ( B ) TYPE: nucleic acid
  ( C ) STRANDEDNESS: double
  ( D ) TOPOLOGY: linear ( x i ) SEQUENCE DESCRIPTION: SEQ ID NO: 64:

GCNGCYAANG CYTCYTTNGC 20

( 2 ) INFORMATION FOR SEQ ID NO: 65:

( i ) SEQUENCE CHARACTERISTICS:
  ( A ) LENGTH: 20
  ( B ) TYPE: nucleic acid
  ( C ) STRANDEDNESS: double
  ( D ) TOPOLOGY: linear ( x i ) SEQUENCE DESCRIPTION: SEQ ID NO: 65:

TTYTTNGCYT GNAGNACRAA 20

( 2 ) INFORMATION FOR SEQ ID NO: 66:

( i ) SEQUENCE CHARACTERISTICS:
  ( A ) LENGTH: 20
  ( B ) TYPE: nucleic acid
  ( C ) STRANDEDNESS: double
  ( D ) TOPOLOGY: linear ( x i ) SEQUENCE DESCRIPTION: SEQ ID NO: 66:

TTYTTNGCYT GYAANACRAA 20

( 2 ) INFORMATION FOR SEQ ID NO: 67:

( i ) SEQUENCE CHARACTERISTICS:

(A) LENGTH: 17
            (B) TYPE: nucleic acid
            (C) STRANDEDNESS: double
            (D) TOPOLOGY: linear (xi) SEQUENCE DESCRIPTION: SEQ ID NO: 67:

TGNACNAGYT CYTGNAC 17

(2) INFORMATION FOR SEQ ID NO: 68:

(i) SEQUENCE CHARACTERISTICS:
            (A) LENGTH: 17
            (B) TYPE: nucleic acid
            (C) STRANDEDNESS: double
            (D) TOPOLOGY: linear (xi) SEQUENCE DESCRIPTION: SEQ ID NO: 68:

TGNACYAAYT CYTGNAC 17

(2) INFORMATION FOR SEQ ID NO: 69:

(i) SEQUENCE CHARACTERISTICS:
            (A) LENGTH: 21
            (B) TYPE: nucleic acid
            (C) STRANDEDNESS: double
            (D) TOPOLOGY: linear (xi) SEQUENCE DESCRIPTION: SEQ ID NO: 69:

CATRTAYTCN CCNGARTCNG C 21

(2) INFORMATION FOR SEQ ID NO: 70:

(i) SEQUENCE CHARACTERISTICS:
            (A) LENGTH: 21
            (B) TYPE: nucleic acid
            (C) STRANDEDNESS: double
            (D) TOPOLOGY: linear (xi) SEQUENCE DESCRIPTION: SEQ ID NO: 70:

CATRTAYTCN CCRCTRTCNG C 21

(2) INFORMATION FOR SEQ ID NO: 71:

(i) SEQUENCE CHARACTERISTICS:
            (A) LENGTH: 21
            (B) TYPE: nucleic acid
            (C) STRANDEDNESS: double
            (D) TOPOLOGY: linear (xi) SEQUENCE DESCRIPTION: SEQ ID NO: 71:

NGARTCNGCY AANGANGCYT T 21

(2) INFORMATION FOR SEQ ID NO: 72:

(i) SEQUENCE CHARACTERISTICS:
            (A) LENGTH: 21
            (B) TYPE: nucleic acid
            (C) STRANDEDNESS: double
            (D) TOPOLOGY: linear (xi) SEQUENCE DESCRIPTION: SEQ ID NO: 72:

NGARTCNGCN AGNGANGCYT T 21

(2) INFORMATION FOR SEQ ID NO: 73:

(i) SEQUENCE CHARACTERISTICS:
            (A) LENGTH: 21
            (B) TYPE: nucleic acid ( C ) STRANDEDNESS: double
                    ( D ) TOPOLOGY: linear ( x i ) SEQUENCE DESCRIPTION: SEQ ID NO: 73:

RCTRTCNGCY AANGANGCYT T                                                           21

( 2 ) INFORMATION FOR SEQ ID NO: 74:

( i ) SEQUENCE CHARACTERISTICS:
                    ( A ) LENGTH: 21
                    ( B ) TYPE: nucleic acid
                    ( C ) STRANDEDNESS: double
                    ( D ) TOPOLOGY: linear ( x i ) SEQUENCE DESCRIPTION: SEQ ID NO: 74:

RCTRTCNGCN AGNGANGCYT T                                                           21

( 2 ) INFORMATION FOR SEQ ID NO: 75:

( i ) SEQUENCE CHARACTERISTICS:
                    ( A ) LENGTH: 21
                    ( B ) TYPE: nucleic acid
                    ( C ) STRANDEDNESS: double
                    ( D ) TOPOLOGY: linear ( x i ) SEQUENCE DESCRIPTION: SEQ ID NO: 75:

NGARTCNGCY AARCTNGCYT T                                                           21

( 2 ) INFORMATION FOR SEQ ID NO: 76:

( i ) SEQUENCE CHARACTERISTICS:
                    ( A ) LENGTH: 21
                    ( B ) TYPE: nucleic acid
                    ( C ) STRANDEDNESS: double
                    ( D ) TOPOLOGY: linear ( x i ) SEQUENCE DESCRIPTION: SEQ ID NO: 76:

NGARTCNGCN AGRCTNGCYT T                                                           21

( 2 ) INFORMATION FOR SEQ ID NO: 77:

( i ) SEQUENCE CHARACTERISTICS:
                    ( A ) LENGTH: 22
                    ( B ) TYPE: nucleic acid
                    ( C ) STRANDEDNESS: double
                    ( D ) TOPOLOGY: linear ( x i ) SEQUENCE DESCRIPTION: SEQ ID NO: 77:

TTGAAGAAGG ACTCGCTGCT CA                                                          22

( 2 ) INFORMATION FOR SEQ ID NO: 78:

( i ) SEQUENCE CHARACTERISTICS:
                    ( A ) LENGTH: 21
                    ( B ) TYPE: nucleic acid
                    ( C ) STRANDEDNESS: double
                    ( D ) TOPOLOGY: linear ( x i ) SEQUENCE DESCRIPTION: SEQ ID NO: 78:

RCTRTCNGCY AARCTNGCYT T                                                           21

( 2 ) INFORMATION FOR SEQ ID NO: 79:

( i ) SEQUENCE CHARACTERISTICS:
                    ( A ) LENGTH: 21
                    ( B ) TYPE: nucleic acid
                    ( C ) STRANDEDNESS: double
                    ( D ) TOPOLOGY: linear ( x i ) SEQUENCE DESCRIPTION: SEQ ID NO: 79:

RCTRCTNGCN AGRCTNGCYT T                                                                                      21

( 2 ) INFORMATION FOR SEQ ID NO: 80:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 80:

ACNACNGARA TGGCTCNNGA                                                                                        20

( 2 ) INFORMATION FOR SEQ ID NO: 81:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 81:

ACNACNGARA TGGCAGYNGA                                                                                        20

( 2 ) INFORMATION FOR SEQ ID NO: 82:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 82:

CAYCARGTNT GGGCNGCNAA                                                                                        20

( 2 ) INFORMATION FOR SEQ ID NO: 83:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 83:

TTYGTNGTNA THGARGGNAA                                                                                        20

( 2 ) INFORMATION FOR SEQ ID NO: 84:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 84:

AARGGNGAYG CNCAYACNGA                                                                                        20

( 2 ) INFORMATION FOR SEQ ID NO: 85:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 85:

```
GARGCNYTNG  CNGCNYTNAA                                                                          20
```

( 2 ) INFORMATION FOR SEQ ID NO: 86:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 86:

```
GTNGGNTCNG  TNCARGARYT                                                                          20
```

( 2 ) INFORMATION FOR SEQ ID NO: 87:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( x i ) SEQUENCE DESCRIPTION: SEQ ID NO: 87:

```
GTNGGNAGYG  TNCARGARYT                                                                          20
```

( 2 ) INFORMATION FOR SEQ ID NO: 88:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( x i ) SEQUENCE DESCRIPTION: SEQ ID NO: 88:

```
NACYTTYTTN  ARDATYTGNC  C                                                                       21
```

( 2 ) INFORMATION FOR SEQ ID NO: 89:

( i ) SEQUENCE CHARACTERISTICS:
        ( A ) LENGTH: 417
        ( B ) TYPE: nucleic acid
        ( C ) STRANDEDNESS: double
        ( D ) TOPOLOGY: linear ( i x ) FEATURE:
        ( D ) OTHER INFORMATION: Xaa in positions 14, 23, 90, 100,
            126, and 135 is a stop codon.

( x i ) SEQUENCE DESCRIPTION: SEQ ID NO: 89:

```
TCTAA AAC TAC AGA GAC TGT ATT TTC ATG ATC ATC ATA GTT CTG TGA AAT ATA    53
      Asn Tyr Arg Asp Cys Ile Phe Met Ile Ile Ile Val Leu Xaa Asn Ile
       1               5                  10                  15

CTT AAA CCG CTT TGG TCC TGA TCT TGT AGG AAG TCA GAA CTT CGC ATT         101
Leu Lys Pro Leu Trp Ser Xaa Ser Cys Arg Lys Ser Glu Leu Arg Ile
             20                  25                  30

AGC AAA GCG TCA CTG GCT GAT TCT GGA GAA TAT ATG TGC AAA GTG ATC         149
Ser Lys Ala Ser Leu Ala Asp Ser Gly Glu Ser Met Cys Lys Val Ile
         35                  40                  45

AGC AAA CTA GGA AAT GAC AGT GCC TCT GCC AAC ATC ACC ATT GTG GAG         197
Ser Lys Leu Gly Asn Asp Ser Ala Ser Ala Asn Ile Arg Ile Val Glu
     50                  55                  60

TCA AAC GGT AAG AGA TGC CTA CTG CGT GCT ATT TCT CAG TCT CTA AGA         245
Ser Asn Gly Lys Arg Cys Leu Leu Arg Ala Ile Ser Gln Ser Leu Arg
 65                  70                  75                  80

GGA GTG ATC AAG GTA TGT GGT CAC ACT TGA ATC ACG CAG GTG TGT GAA         293
Gly Val Ile Lys Val Cys Gly His Thr Xaa Ile Thr Gln Val Cys Glu
                 85                  90                  95
```

| ATC | TCA | TTG | TGA | ACA | AAT | AAA | AAT | CAT | GAA | AGG | AAA | ACT | CTA | TGT | TTG | 341 |
| Ile | Ser | Cys | Xaa | Thr | Asn | Lys | Asn | His | Glu | Arg | Lys | Thr | Leu | Cys | Leu | |
| | | | 100 | | | | | 105 | | | | | 110 | | | |

| AAA | TAT | CTT | ATG | GGT | CCT | CCT | GTA | AAG | CTC | TTC | ACT | CCA | TAA | GGT | GAA | 389 |
| Lys | Tyr | Leu | Met | Gly | Pro | Pro | Val | Lys | Leu | Phe | Thr | Pro | Xaa | Gly | Glu | |
| | | 115 | | | | | 120 | | | | | 125 | | | | |

| ATA | GAC | CTG | AAA | TAT | ATA | TAG | ATT | ATT | T | | | | | | | 417 |
| Ile | Asp | Leu | Lys | Tyr | Ile | Xaa | Ile | Ile | | | | | | | | |
| | 130 | | | | | 135 | | | | | | | | | | |

( 2 ) INFORMATION FOR SEQ ID NO: 90:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
        ( D ) OTHER INFORMATION: N at positions 19, 25, and 31 is
            Inosine. Y can be cytidine or
            thymidine.

( x i ) SEQUENCE DESCRIPTION: SEQ ID NO: 90:

CCGAATTCTG CAGGARACNC ARCCNGAYCC NGG          33

( 2 ) INFORMATION FOR SEQ ID NO: 91:

( i ) SEQUENCE CHARACTERISTICS:
        ( A ) LENGTH: 37
        ( B ) TYPE: nucleic acid
        ( C ) STRANDEDNESS: double
        ( D ) TOPOLOGY: linear ( i x ) FEATURE:
        ( D ) OTHER INFORMATION: N at positions 14, 20, 23, 29, and
            35 is Inosine.

( x i ) SEQUENCE DESCRIPTION: SEQ ID NO: 91:

AAGGATCCTG CAGNGTRTAN GCNCCDATNA CCATNGG          37

( 2 ) INFORMATION FOR SEQ ID NO: 92:

( i ) SEQUENCE CHARACTERISTICS:
        ( A ) LENGTH: 34
        ( B ) TYPE: nucleic acid
        ( C ) STRANDEDNESS: double
        ( D ) TOPOLOGY: linear ( i x ) FEATURE:
        ( D ) OTHER INFORMATION: N at positions 16, 21, and 24 is
            Inosine. Y can be cytidine or
            thymidine.

( x i ) SEQUENCE DESCRIPTION: SEQ ID NO: 92:

CCGAATTCTG CAGGCNGAYT CNGGNGARTA YATG          34

( 2 ) INFORMATION FOR SEQ ID NO: 93:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
        ( D ) OTHER INFORMATION: N at positions 16 and 25 is Inosine.
            Y can be cytidine or thymidine.

( x i ) SEQUENCE DESCRIPTION: SEQ ID NO: 93:

```
CCGAATTCTG  CAGGCNGAYA  GYGGNGARTA  YAT                                    33
```

( 2 ) INFORMATION FOR SEQ ID NO: 94:

( i ) SEQUENCE CHARACTERISTICS:
        ( A ) LENGTH: 34
        ( B ) TYPE: nucleic acid
        ( C ) STRANDEDNESS: double
        ( D ) TOPOLOGY: linear ( i x ) FEATURE:
        ( D ) OTHER INFORMATION: N at positions 14, 15, 16, 26, and 29 is Inosine. Y can be cytidine or thymidine.

( x i ) SEQUENCE DESCRIPTION: SEQ ID NO: 94:

```
AAGGATCCTG  CAGNNNCATR  TAYTCNCCNG  ARTC                                   34
```

( 2 ) INFORMATION FOR SEQ ID NO: 95:

( i ) SEQUENCE CHARACTERISTICS:
        ( A ) LENGTH: 34
        ( B ) TYPE: nucleic acid
        ( C ) STRANDEDNESS: double
        ( D ) TOPOLOGY: linear ( i x ) FEATURE:
        ( D ) OTHER INFORMATION: N at positions 14, 15, 16, and 26 is Inosine. Y can be cytidine or thymidine.

( x i ) SEQUENCE DESCRIPTION: SEQ ID NO: 95:

```
AAGGATCCTG  CAGNNNCATR  TAYTCNCCRC  TRTC                                   34
```

( 2 ) INFORMATION FOR SEQ ID NO: 96:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
        ( D ) OTHER INFORMATION: N at positions 21, 28, and 31 is Inosine. Y can be cytidine or thymidine.

( x i ) SEQUENCE DESCRIPTION: SEQ ID NO: 96:

```
CCGAATTCTG  CAGCAYCARG  TNTGGGCNGC  NAA                                    33
```

( 2 ) INFORMATION FOR SEQ ID NO: 97:

( i ) SEQUENCE CHARACTERISTICS:
        ( A ) LENGTH: 35
        ( B ) TYPE: nucleic acid
        ( C ) STRANDEDNESS: double
        ( D ) TOPOLOGY: linear ( i x ) FEATURE:
        ( D ) OTHER INFORMATION: N at position 31 is Inosine. Y can be cytidine or thymidine.

( x i ) SEQUENCE DESCRIPTION: SEQ ID NO: 97:

```
CCGAATTCTG  CAGATHTTYT  TYATGGARCC  NGARG                                  35
```

( 2 ) INFORMATION FOR SEQ ID NO: 98:

( i ) SEQUENCE CHARACTERISTICS:
        ( A ) LENGTH: 35
        ( B ) TYPE: nucleic acid ( C ) STRANDEDNESS: double
( D ) TOPOLOGY: linear ( i x ) FEATURE:
( D ) OTHER INFORMATION: N at positions 18, 21, 24, 27, and
33 is Inosine. Y can be cytidine or
thymidine.

( x i ) SEQUENCE DESCRIPTION: SEQ ID NO: 98:

CCGAATTCTG CAGGGGGNCC NCCNGCNTTY CCNGT                35

( 2 ) INFORMATION FOR SEQ ID NO: 99:

( i ) SEQUENCE CHARACTERISTICS:
( A ) LENGTH: 33
( B ) TYPE: nucleic acid
( C ) STRANDEDNESS: double
( D ) TOPOLOGY: linear ( i x ) FEATURE:
( D ) OTHER INFORMATION: N at positions 21 and 24 is Inosine.
Y can be cytidine or thymidine.

( x i ) SEQUENCE DESCRIPTION: SEQ ID NO: 99:

CCGAATTCTG CAGTGGTTYG TNGTNATHGA RGG                  33

( 2 ) INFORMATION FOR SEQ ID NO: 100:

( i ) SEQUENCE CHARACTERISTICS:
( A ) LENGTH: 35
( B ) TYPE: nucleic acid
( C ) STRANDEDNESS: double
( D ) TOPOLOGY: linear ( i x ) FEATURE:
( D ) OTHER INFORMATION: N at positions 17, 20, and 26 is
Inosine. Y can be cytidine or
thymidine.

( x i ) SEQUENCE DESCRIPTION: SEQ ID NO: 100:

AAGGATCCTG CAGYTTNGCU NGCCCANACY TGRTG                35

( 2 ) INFORMATION FOR SEQ ID NO: 101:

( i ) SEQUENCE CHARACTERISTICS:
( A ) LENGTH: 33
( B ) TYPE: nucleic acid
( C ) STRANDEDNESS: double
( D ) TOPOLOGY: linear ( i x ) FEATURE:
( D ) OTHER INFORMATION: N at position 19 is Inosine. Y can
be cytidine or thymidine.

( x i ) SEQUENCE DESCRIPTION: SEQ ID NO: 101:

AAGGATCCTG CAGGCYTCNG GYTCCATRAA RAA                  33

( 2 ) INFORMATION FOR SEQ ID NO: 102:

( i ) SEQUENCE CHARACTERISTICS:
( A ) LENGTH: 33
( B ) TYPE: nucleic acid
( C ) STRANDEDNESS: double
( D ) TOPOLOGY: linear ( i x ) FEATURE:
( D ) OTHER INFORMATION: N at positions 16, 22, 25, 28, and
31 is Inosine.

( x i ) SEQUENCE DESCRIPTION: SEQ ID NO: 102:

AAGGATCCTG CAGACNGGRA ANGCNGGNGG NCC                  33

( 2 ) INFORMATION FOR SEQ ID NO: 103:

( i ) SEQUENCE CHARACTERISTICS:
        ( A ) LENGTH: 35
        ( B ) TYPE: nucleic acid
        ( C ) STRANDEDNESS: double
        ( D ) TOPOLOGY: linear ( i x ) FEATURE:
        ( D ) OTHER INFORMATION: N at positions 17, 26, and 29 is
            Inosine. Y can be cytidine or
            thymidine.

( x i ) SEQUENCE DESCRIPTION: SEQ ID NO: 103:

AAGGATCCTG CAGYTTNCCY TCDATNACNA CRAAC                                  35

( 2 ) INFORMATION FOR SEQ ID NO: 104:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
        ( D ) OTHER INFORMATION: N at position 18 is Inosine. Y can
            be cytidine or thymidine.

( x i ) SEQUENCE DESCRIPTION: SEQ ID NO: 104:

CATRTAYTCR TAYTCTCNGC AAGGATCCTG CAG                                    33

( 2 ) INFORMATION FOR SEQ ID NO: 105:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
        ( D ) OTHER INFORMATION: N at position 19, 25, and 31 is
            Inosine. Y can be cytidine or
            thymidine.

( x i ) SEQUENCE DESCRIPTION: SEQ ID NO: 105:

CCGAATTCTG CAGAARGGNG AYGCNCAYAC NGA                                    33

( 2 ) INFORMATION FOR SEQ ID NO: 106:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
        ( D ) OTHER INFORMATION: N at position 3 and 18 is Inosine. Y
            can be cytidine or thymidine.

( x i ) SEQUENCE DESCRIPTION: SEQ ID NO: 106:

GCNGCYAANG CYTCYTTNGC AAGGATCCTG CAG                                    33

( 2 ) INFORMATION FOR SEQ ID NO: 107:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( i x ) FEATURE:
  ( D ) OTHER INFORMATION: N at position 3, 6, 9, and 18 is
   Inosine. Y can be cytidine or
   thymidine.

( x i ) SEQUENCE DESCRIPTION: SEQ ID NO: 107:

GCNGCNAGNG CYTCYTTNGC AAGGATCCTG CAG    33

( 2 ) INFORMATION FOR SEQ ID NO: 108:

( i ) SEQUENCE CHARACTERISTICS:
  ( A ) LENGTH: 30
  ( B ) TYPE: nucleic acid
  ( C ) STRANDEDNESS: double
  ( D ) TOPOLOGY: linear ( i x ) FEATURE:
  ( D ) OTHER INFORMATION: N at position 3, 12, and 15 is
   Inosine. Y can be cytidine or
   thymidine.

( x i ) SEQUENCE DESCRIPTION: SEQ ID NO: 108:

TCNGCRAART ANCCNGCAAG GATCCTGCAG    30

( 2 ) INFORMATION FOR SEQ ID NO: 109:

( i ) SEQUENCE CHARACTERISTICS:
  ( A ) LENGTH: 38
  ( B ) TYPE: nucleic acid
  ( C ) STRANDEDNESS: double
  ( D ) TOPOLOGY: linear ( x i ) SEQUENCE DESCRIPTION: SEQ ID NO: 109:

CATCGATCTG CAGGCTGATT CTGGAGAATA TATGTGCA    38

( 2 ) INFORMATION FOR SEQ ID NO: 110:

( i ) SEQUENCE CHARACTERISTICS:
  ( A ) LENGTH: 37
  ( B ) TYPE: nucleic acid
  ( C ) STRANDEDNESS: double
  ( D ) TOPOLOGY: linear ( x i ) SEQUENCE DESCRIPTION: SEQ ID NO: 110:

AAGGATCCTG CAGCCACATC TCGAGTCGAC ATCGATT    37

( 2 ) INFORMATION FOR SEQ ID NO: 111:

( i ) SEQUENCE CHARACTERISTICS:
  ( A ) LENGTH: 37
  ( B ) TYPE: nucleic acid
  ( C ) STRANDEDNESS: double
  ( D ) TOPOLOGY: linear ( x i ) SEQUENCE DESCRIPTION: SEQ ID NO: 111:

CCGAATTCTG CAGTGATCAG CAAACTAGGA AATGACA    37

( 2 ) INFORMATION FOR SEQ ID NO: 112:

( i ) SEQUENCE CHARACTERISTICS:
  ( A ) LENGTH: 37
  ( B ) TYPE: nucleic acid
  ( C ) STRANDEDNESS: double
  ( D ) TOPOLOGY: linear ( x i ) SEQUENCE DESCRIPTION: SEQ ID NO: 112:

CATCGATCTG CAGCCTAGTT TGCTGATCAC TTTGCAC    37

( 2 ) INFORMATION FOR SEQ ID NO: 113:

( i ) SEQUENCE CHARACTERISTICS:
        ( A ) LENGTH: 37
        ( B ) TYPE: nucleic acid
        ( C ) STRANDEDNESS: double
        ( D ) TOPOLOGY: linear ( x i ) SEQUENCE DESCRIPTION: SEQ ID NO: 113:

AAGGATCCTG CAGTATATTC TCCAGAATCA GCCAGTG 37

( 2 ) INFORMATION FOR SEQ ID NO: 114:

( i ) SEQUENCE CHARACTERISTICS:
        ( A ) LENGTH: 34
        ( B ) TYPE: nucleic acid
        ( C ) STRANDEDNESS: double
        ( D ) TOPOLOGY: linear ( x i ) SEQUENCE DESCRIPTION: SEQ ID NO: 114:

AAGGATCCTG CAGGCACGCA GTAGGCATCT CTTA 34

( 2 ) INFORMATION FOR SEQ ID NO: 115:

( i ) SEQUENCE CHARACTERISTICS:
        ( A ) LENGTH: 35
        ( B ) TYPE: nucleic acid
        ( C ) STRANDEDNESS: double
        ( D ) TOPOLOGY: linear ( x i ) SEQUENCE DESCRIPTION: SEQ ID NO: 115:

CCGAATTCTG CAGCAGAACT TCGCATTAGC AAAGC 35

( 2 ) INFORMATION FOR SEQ ID NO: 116:

( i ) SEQUENCE CHARACTERISTICS:
        ( A ) LENGTH: 33
        ( B ) TYPE: nucleic acid
        ( C ) STRANDEDNESS: double
        ( D ) TOPOLOGY: linear ( x i ) SEQUENCE DESCRIPTION: SEQ ID NO: 116:

CATCCCGGGA TGAAGAGTCA GGAGTCTGTG GCA 33

( 2 ) INFORMATION FOR SEQ ID NO: 117:

( i ) SEQUENCE CHARACTERISTICS:
        ( A ) LENGTH: 39
        ( B ) TYPE: nucleic acid
        ( C ) STRANDEDNESS: double
        ( D ) TOPOLOGY: linear ( x i ) SEQUENCE DESCRIPTION: SEQ ID NO: 117:

ATACCCGGGC TGCAGACAAT GAGATTTCAC ACACCTGCG 39

( 2 ) INFORMATION FOR SEQ ID NO: 118:

( i ) SEQUENCE CHARACTERISTICS:
        ( A ) LENGTH: 36
        ( B ) TYPE: nucleic acid
        ( C ) STRANDEDNESS: double
        ( D ) TOPOLOGY: linear ( x i ) SEQUENCE DESCRIPTION: SEQ ID NO: 118:

AAGGATCCTG CAGTTTGGAA CCTGCCACAG ACTCCT 36

( 2 ) INFORMATION FOR SEQ ID NO: 119:

( i ) SEQUENCE CHARACTERISTICS:
  ( A ) LENGTH: 39
  ( B ) TYPE: nucleic acid
  ( C ) STRANDEDNESS: double
  ( D ) TOPOLOGY: linear ( x i ) SEQUENCE DESCRIPTION: SEQ ID NO: 119:

ATACCCGGGC TGCAGATGAG ATTTCACACA CCTGCGTGA    39

( 2 ) INFORMATION FOR SEQ ID NO: 120:

( i ) SEQUENCE CHARACTERISTICS:
  ( A ) LENGTH: 12
  ( B ) TYPE: amino acid
  ( C ) STRANDEDNESS:
  ( D ) TOPOLOGY: linear ( x i ) SEQUENCE DESCRIPTION: SEQ ID NO: 120:

His Gln Val Trp Ala Ala Lys Ala Ala Gly Leu Lys
 1               5                  10

( 2 ) INFORMATION FOR SEQ ID NO: 121:

( i ) SEQUENCE CHARACTERISTICS:
  ( A ) LENGTH: 16
  ( B ) TYPE: amino acid
  ( C ) STRANDEDNESS:
  ( D ) TOPOLOGY: linear ( x i ) SEQUENCE DESCRIPTION: SEQ ID NO: 121:

Gly Gly Leu Lys Lys Asp Ser Leu Leu Thr Val Arg Leu Gly Ala Asn
 1               5                  10                  15

( 2 ) INFORMATION FOR SEQ ID NO: 122:

( i ) SEQUENCE CHARACTERISTICS:
  ( A ) LENGTH: 13
  ( B ) TYPE: amino acid
  ( C ) STRANDEDNESS:
  ( D ) TOPOLOGY: linear ( i x ) FEATURE:
  ( D ) OTHER INFORMATION: Xaa in position 12 is unknown.

( x i ) SEQUENCE DESCRIPTION: SEQ ID NO: 122:

Leu Gly Ala Trp Gly Pro Pro Ala Phe Pro Val Xaa Tyr
 1               5                  10

( 2 ) INFORMATION FOR SEQ ID NO: 123:

( i ) SEQUENCE CHARACTERISTICS:
  ( A ) LENGTH: 23
  ( B ) TYPE: amino acid
  ( C ) STRANDEDNESS:
  ( D ) TOPOLOGY: linear ( x i ) SEQUENCE DESCRIPTION: SEQ ID NO: 123:

Leu Leu Thr Val Arg Leu Gly Ala Trp Gly His Pro Ala Phe Pro Ser
 1               5                  10                  15
Cys Gly Arg Leu Lys Glu Asp
                20

( 2 ) INFORMATION FOR SEQ ID NO: 124:

( i ) SEQUENCE CHARACTERISTICS:
  ( A ) LENGTH: 13
  ( B ) TYPE: amino acid
  ( C ) STRANDEDNESS:
  ( D ) TOPOLOGY: linear ( i x ) FEATURE:
   ( D ) OTHER INFORMATION: Xaa in position 10 is unknown.

( x i ) SEQUENCE DESCRIPTION: SEQ ID NO: 124:

Tyr Ile Phe Phe Met Glu Pro Glu Ala Xaa Ser Ser Gly
1               5                   10

( 2 ) INFORMATION FOR SEQ ID NO: 125:

( i ) SEQUENCE CHARACTERISTICS:
    ( A ) LENGTH: 23
    ( B ) TYPE: amino acid
    ( C ) STRANDEDNESS:
    ( D ) TOPOLOGY: linear ( x i ) SEQUENCE DESCRIPTION: SEQ ID NO: 125:

Lys Glu Asp Ser Arg Tyr Ile Phe Phe Met Glu Pro Glu Ala Asn Ser
1               5                   10                  15
Ser Gly Gly Pro Gly Arg Leu
            20

( 2 ) INFORMATION FOR SEQ ID NO: 126:

( i ) SEQUENCE CHARACTERISTICS:
    ( A ) LENGTH: 14
    ( B ) TYPE: amino acid
    ( C ) STRANDEDNESS:
    ( D ) TOPOLOGY: linear ( x i ) SEQUENCE DESCRIPTION: SEQ ID NO: 126:

Val Ala Gly Ser Lys Leu Val Leu Arg Cys Glu Thr Ser Ser
1               5                   10

( 2 ) INFORMATION FOR SEQ ID NO: 127:

( i ) SEQUENCE CHARACTERISTICS:
    ( A ) LENGTH: 16
    ( B ) TYPE: amino acid
    ( C ) STRANDEDNESS:
    ( D ) TOPOLOGY: linear ( x i ) SEQUENCE DESCRIPTION: SEQ ID NO: 127:

Glu Tyr Lys Cys Leu Lys Phe Lys Trp Phe Lys Lys Ala Thr Val Met
1               5                   10                  15

( 2 ) INFORMATION FOR SEQ ID NO: 128:

( i ) SEQUENCE CHARACTERISTICS:
    ( A ) LENGTH: 26
    ( B ) TYPE: amino acid
    ( C ) STRANDEDNESS:
    ( D ) TOPOLOGY: linear ( x i ) SEQUENCE DESCRIPTION: SEQ ID NO: 128:

Cys Glu Thr Ser Ser Glu Tyr Ser Ser Leu Lys Phe Lys Trp Phe Lys
1               5                   10                  15
Asn Gly Ser Glu Leu Ser Arg Lys Asn Lys
            20                  25

( 2 ) INFORMATION FOR SEQ ID NO: 129:

( i ) SEQUENCE CHARACTERISTICS:
    ( A ) LENGTH: 13
    ( B ) TYPE: amino acid
    ( C ) STRANDEDNESS:
    ( D ) TOPOLOGY: linear ( i x ) FEATURE:
   ( D ) OTHER INFORMATION: Xaa in position 12 is unknown.

( x i ) SEQUENCE DESCRIPTION: SEQ ID NO: 129:

Lys Ala Ser Leu Ala Asp Ser Gly Glu Tyr Met Xaa Lys
 1               5                   10

( 2 ) INFORMATION FOR SEQ ID NO: 130:

( i ) SEQUENCE CHARACTERISTICS:
      ( A ) LENGTH: 23
      ( B ) TYPE: amino acid
      ( C ) STRANDEDNESS:
      ( D ) TOPOLOGY: linear ( x i ) SEQUENCE DESCRIPTION: SEQ ID NO: 130:

Glu Leu Arg Ile Ser Lys Ala Ser Leu Ala Asp Ser Gly Glu Tyr Met
 1               5                   10                  15
Cys Lys Val Ile Ser Lys Leu
               20

( 2 ) INFORMATION FOR SEQ ID NO: 131:

( i ) SEQUENCE CHARACTERISTICS:
      ( A ) LENGTH: 12
      ( B ) TYPE: amino acid
      ( C ) STRANDEDNESS:
      ( D ) TOPOLOGY: linear ( x i ) SEQUENCE DESCRIPTION: SEQ ID NO: 131:

Ala Ser Leu Ala Asp Glu Tyr Glu Tyr Met Arg Lys
 1               5                   10

( 2 ) INFORMATION FOR SEQ ID NO: 132:

( i ) SEQUENCE CHARACTERISTICS:
      ( A ) LENGTH: 22
      ( B ) TYPE: amino acid
      ( C ) STRANDEDNESS:
      ( D ) TOPOLOGY: linear ( x i ) SEQUENCE DESCRIPTION: SEQ ID NO: 132:

Leu Arg Ile Ser Lys Ala Ser Leu Ala Asp Ser Gly Glu Tyr Met Cys
 1               5                   10                  15
Lys Val Ile Ser Lys Leu
               20

( 2 ) INFORMATION FOR SEQ ID NO: 133:

( i ) SEQUENCE CHARACTERISTICS:
      ( A ) LENGTH: 744
      ( B ) TYPE: nucleic acid
      ( C ) STRANDEDNESS: double
      ( D ) TOPOLOGY: linear ( x i ) SEQUENCE DESCRIPTION: SEQ ID NO: 133:

CCTGCAG CAT CAA GTG TGG GCG GCG AAA GCC GGG GGC TTG AAG AAG GAC TCG CT    55
        His Gln Val Trp Ala Ala Lys Ala Gly Gly Leu Lys Lys Asp Ser Leu
         1               5                   10                  15

CTC ACC GTG CGC CTG GGC GCC TGG GGC CAC CCC GCC TTC CCC TCC TGC          103
Leu Thr Val Arg Leu Gly Ala Trp Gly His Pro Ala Phe Pro Ser Cys
             20                  25                  30

GGG CGC CTC AAG GAG GAC AGC AGG TAC ATC TTC TTC ATG GAG CCC GAG          151
Gly Arg Leu Lys Glu Asp Ser Arg Tyr Ile Phe Phe Met Glu Pro Glu
         35                  40                  45

GCC AAC AGC AGC GGC GGG CCC GGC CGC CTT CCG AGC CTC CTT CCC CCC          199

| | | | | | | | | | | | | | | | | |
|---|---|---|---|---|---|---|---|---|---|---|---|---|---|---|---|---|
| Ala | Asn | Ser | Ser | Gly | Gly | Pro | Gly | Arg | Leu | Pro | Ser | Leu | Leu | Pro | Pro | |
| | 50 | | | | 55 | | | | | 60 | | | | | | |

```
TCT  CGA  GAC  GGG  CCG  GAA  CCT  CAA  GAA  GGA  GGT  CAG  CCG  GGT  GCT  GTG      247
Ser  Arg  Asp  Gly  Pro  Glu  Pro  Gln  Glu  Gly  Gly  Gln  Pro  Gly  Ala  Val
65                  70                       75                       80

CAA  CGG  TGC  GCC  TTG  CCT  CCC  CGC  TTG  AAA  GAG  ATG  AAG  AGT  CAG  GAG      295
Gln  Arg  Cys  Ala  Leu  Pro  Pro  Arg  Leu  Lys  Glu  Met  Lys  Ser  Gln  Glu
                    85                       90                       95

TCT  GTG  GCA  GGT  TCC  AAA  CTA  GTG  CTT  CGG  TGC  GAG  ACC  AGT  TCT  GAA      343
Ser  Val  Ala  Gly  Ser  Lys  Leu  Val  Leu  Arg  Cys  Glu  Thr  Ser  Ser  Glu
               100                      105                      110

TAC  TCC  TCT  CTC  AAG  TTC  AAG  TGG  TTC  AAG  AAT  GGG  AGT  GAA  TTA  AGC      391
Tyr  Ser  Ser  Leu  Lys  Phe  Lys  Trp  Phe  Lys  Asn  Gly  Ser  Glu  Leu  Ser
               115                      120                      125

CGA  AAG  AAC  AAA  CCA  GAA  AAC  ATC  AAG  ATA  CAG  AAA  AGG  CCG  GGG  AAG      439
Arg  Lys  Asn  Lys  Pro  Glu  Asn  Ile  Lys  Ile  Gln  Lys  Arg  Pro  Gly  Lys
          130                      135                      140

TCA  GAA  CTT  CGC  ATT  AGC  AAA  GCG  TCA  CTG  GCT  GAT  TCT  GGA  GAA  TAT      487
Ser  Glu  Leu  Arg  Ile  Ser  Lys  Ala  Ser  Leu  Ala  Asp  Ser  Gly  Glu  Tyr
145                      150                      155                      160

ATG  TGC  AAA  GTG  ATC  AGC  AAA  CTA  GGA  AAT  GAC  AGT  GCC  TCT  GCC  AAC      535
Met  Cys  Lys  Val  Ile  Ser  Lys  Leu  Gly  Asn  Asp  Ser  Ala  Ser  Ala  Asn
                    165                      170                      175

ATC  ACC  ATT  GTG  GAG  TCA  AAC  GGT  AAG  AGA  TGC  CTA  CTG  CGT  GCT  ATT      583
Ile  Thr  Ile  Val  Glu  Ser  Asn  Gly  Lys  Arg  Cys  Leu  Leu  Arg  Ala  Ile
               180                      185                      190

TCT  CAG  TCT  CTA  AGA  GGA  GTG  ATC  AAG  GTA  TGT  GGT  CAC  ACT                625
Ser  Gln  Ser  Leu  Arg  Gly  Val  Ile  Lys  Val  Cys  Gly  His  Thr
          195                      200                      205

TGAATCACGC  AGGTGTGTGA  AATCTCATTG  TGAACAAATA  AAAATCATGA  AAGGAAAAAA            685

AAAAAAAAAA  AATCGATGTC  GACTCGAGAT  GTGGCTGCAG  GTCGACTCTA  GAGGATCCC            744
```

( 2 ) INFORMATION FOR SEQ ID NO: 134:

( i ) SEQUENCE CHARACTERISTICS:
        ( A ) LENGTH: 1193
        ( B ) TYPE: nucleic acid
        ( C ) STRANDEDNESS: double
        ( D ) TOPOLOGY: linear ( x i ) SEQUENCE DESCRIPTION: SEQ ID NO: 134:

```
CCTGCAG  CAT  CAA  GTG  TGG  GCG  GCG  AAA  GCC  GGG  GGC  TTG  AAG  AAG  GAC  TCG  CT   55
         His  Gln  Val  Trp  Ala  Ala  Lys  Ala  Gly  Gly  Leu  Lys  Lys  Asp  Ser  Leu
         1                   5                        10                      15

CTC  ACC  GTG  CGC  CTG  GGC  GCC  TGG  GGC  CAC  CCC  GCC  TTC  CCC  TCC  TGC       103
Leu  Thr  Val  Arg  Leu  Gly  Ala  Trp  Gly  His  Pro  Ala  Phe  Pro  Ser  Cys
               20                       25                       30

GGG  CGC  CTC  AAG  GAG  GAC  AGC  AGG  TAC  ATC  TTC  TTC  ATG  GAG  CCC  GAG       151
Gly  Arg  Leu  Lys  Glu  Asp  Ser  Arg  Tyr  Ile  Phe  Phe  Met  Glu  Pro  Glu
          35                       40                       45

GCC  AAC  AGC  AGC  GGC  GGG  CCC  GGC  CGC  CTT  CCG  AGC  CTC  CTT  CCC  CCC       199
Ala  Lys  Ser  Ser  Gly  Gly  Pro  Gly  Arg  Leu  Pro  Ser  Leu  Leu  Pro  Pro
     50                       55                       60

TCT  CGA  GAC  GGG  CCG  GAA  CCT  CAA  GAA  GGA  GGT  CAG  CCG  GGT  GCT  GTG       247
Ser  Arg  Asp  Gly  Pro  Glu  Pro  Gln  Glu  Gly  Gly  Gln  Pro  Gly  Ala  Val
65                  70                       75                       80

CAA  CGG  TGC  GCC  TTG  CCT  CCC  CGC  TTG  AAA  GAG  ATG  AAG  AGT  CAG  GAG       295
Gln  Arg  Cys  Ala  Leu  Pro  Pro  Arg  Leu  Lys  Glu  Met  Lys  Ser  Gln  Glu
                    85                       90                       95

TCT  GTG  GCA  GGT  TCC  AAA  CTA  GTG  CTT  CGG  TGC  GAG  ACC  AGT  TCT  GAA       343
Ser  Val  Ala  Gly  Ser  Lys  Leu  Val  Leu  Arg  Cys  Glu  Thr  Ser  Ser  Glu
```

```
                          100                            105                           110
TAC   TCC   TCT   CTC   AAG   TTC   AAG   TGG   TTC   AAG   AAT   GGG   AGT   GAA   TTA   AGC         391
Tyr   Ser   Ser   Leu   Lys   Phe   Lys   Trp   Phe   Lys   Asn   Gly   Ser   Glu   Leu   Ser
            115                     120                           125

CGA   AAG   AAC   AAA   CCA   GAA   AAC   ATC   AAG   ATA   CAG   AAA   AGG   CCG   GGG   AAG         439
Arg   Lys   Asn   Lys   Gly   Gly   Asn   Ile   Lys   Ile   Gln   Lys   Arg   Pro   Gly   Lys
      130                           135                           140

TCA   GAA   CTT   CGC   ATT   AGC   AAA   GCG   TCA   CTG   GCT   GAT   TCT   GGA   GAA   TAT         487
Ser   Glu   Leu   Arg   Ile   Ser   Lys   Ala   Ser   Leu   Ala   Asp   Ser   Gly   Glu   Tyr
145                           150                           155                           160

ATG   TGC   AAA   GTG   ATC   AGC   AAA   CTA   GGA   AAT   GAC   AGT   GCC   TCT   GCC   AAC         535
Met   Cys   Lys   Val   Ile   Ser   Lys   Leu   Gly   Asn   Asp   Ser   Ala   Ser   Ala   Asn
                        165                           170                           175

ATC   ACC   ATT   GTG   GAG   TCA   AAC   GCC   ACA   TCC   ACA   TCT   ACA   GCT   GGG   ACA         583
Ile   Thr   Ile   Val   Glu   Ser   Asn   Ala   Thr   Ser   Thr   Ser   Thr   Ala   Gly   Thr
                  180                           185                           190

AGC   CAT   CTT   GTC   AAG   TGT   GCA   GAG   AAG   GAG   AAA   ACT   TTC   TGT   GTG   AAT         631
Ser   His   Leu   Val   Lys   Ser   Ala   Glu   Lys   Glu   Lys   Thr   Phe   Cys   Val   Asn
            195                           200                           205

GGA   GGC   GAG   TGC   TTC   ATG   GTG   AAA   GAC   CTT   TCA   AAT   CCC   TCA   AGA   TAC         679
Gly   Gly   Glu   Cys   Phe   Met   Val   Lys   Asp   Leu   Ser   Asn   Pro   Ser   Arg   Tyr
      210                           215                           220

TTG   TGC   AAG   TGC   CAA   CCT   GGA   TTC   ACT   GGA   GCG   AGA   TGT   ACT   GAG   AAT         727
Leu   Cys   Lys   Cys   Gln   Pro   Gly   Phe   Thr   Gly   Ala   Arg   Cys   Thr   Glu   Asn
225                           230                           235                           240

GTG   CCC   ATG   AAA   GTC   CAA   ACC   CAA   GAA   AGT   GCC   CAA   ATG   AGT   TTA   CTG         775
Val   Pro   Met   Lys   Val   Gln   Thr   Gln   Glu   Ser   Ala   Gln   Met   Ser   Leu   Leu
                        245                           250                           255

GTG   ATC   GCT   GCC   AAA   ACT   ACG   TAATGGCAG   CTTCTACAGT   ACGTCCACTC                          826
Val   Ile   Ala   Ala   Lys   Thr   Thr
                  260

CCTTTCTGTC   TCTGCCTGAA   TAGCGCATCT   CAGTCGGTGC   CGCTTTCTTG   TTGCCGCATC                           886

TCCCCTCAGA   TTCCTCCTAG   AGCTAGATGC   GTTTTACCAG   GTCTAACATT   GACTGCCTCT                           946

GCCTGTCGCA   TGAGAACATT   AACACAAGCG   ATTGTATGAC   TTCCTCTGTC   CGTGACTAGT                           1006

GGGCTCTGAG   CTACTCGTAG   GTGCGTAAGG   CTCCAGTGTT   TCTGAAATTG   ATCTTGAATT                           1066

ACTGTGATAC   GACATGATAG   TCCCTCTCAC   CCAGTGCAAT   GACAATAAAG   GCCTTGAAAA                           1126

GTCAAAAAAA   AAAAAAAAAA   AAAAAATCGA   TGTCGACTCG   AGATGTGGCT   GCAGGTCGAC                           1186

TCTAGAG                                                                                             1193
```

( 2 ) INFORMATION FOR SEQ ID NO: 135:

( i ) SEQUENCE CHARACTERISTICS:
        ( A ) LENGTH: 1108
        ( B ) TYPE: nucleic acid
        ( C ) STRANDEDNESS: double
        ( D ) TOPOLOGY: linear ( x i ) SEQUENCE DESCRIPTION: SEQ ID NO: 135:

```
CCTGCAG   CAT   CAA   GTG   TGG   GCG   GCG   AAA   GCC   GGG   GGC   TTG   AAG   AAG   GAC   TCG   CT   55
          His   Gln   Val   Trp   Ala   Ala   Lys   Ala   Gly   Gly   Leu   Lys   Lys   Asp   Ser   Leu
          1                       5                       10                          15

CTC   ACC   GTG   CGC   CTG   GGC   GCC   TGG   GGC   CAC   CCC   GCC   TTC   CCC   TCC   TGC                103
Leu   Thr   Val   Arg   Leu   Gly   Ala   Trp   Gly   His   Pro   Ala   Phe   Pro   Ser   Cys
                  20                          25                          30

GGG   CGC   CTC   AAG   GAG   GAC   AGC   AGG   TAC   ATC   TTC   TTC   ATG   GAG   CCC   GAG                151
Gly   Arg   Leu   Lys   Glu   Asp   Ser   Arg   Tyr   Ile   Phe   Phe   Met   Glu   Pro   Glu
            35                          40                          45

GCC   AAC   AGC   AGC   GGC   GGG   CCC   GGC   CGC   CTT   CCG   AGC   CTC   CTT   CCC   CCC                199
```

|     |     |     |     |     |     |     |     |     |     |     |     |     |     |     |
|-----|-----|-----|-----|-----|-----|-----|-----|-----|-----|-----|-----|-----|-----|-----|
| Ala | Asn | Ser | Ser | Gly | Gly | Pro | Gly | Arg | Leu | Pro | Ser | Leu | Leu | Pro | Pro |
|     | 50  |     |     |     | 55  |     |     |     | 60  |     |     |     |     |     |

```
TCT CGA GAC GGG CCG GAA CCT CAA GAA GGA GGT CAG CCG GGT GCT GTG    247
Ser Arg Asp Gly Pro Glu Pro Gln Glu Gly Gly Gln Pro Gly Ala Val
65              70                  75                  80

CAA CGG TGC GCC TTG CCT CCC CGC TTG AAA GAG ATG AAG AGT CAG GAG    295
Gln Arg Cys Ala Leu Pro Pro Arg Leu Lys Glu Met Lys Ser Gln Glu
                85                  90                  95

TCT GTG GCA GGT TCC AAA CTA GTG CTT CGG TGC GAG ACC AGT TCT GAA    343
Ser Val Ala Gly Ser Lys Leu Val Leu Arg Cys Glu Thr Ser Ser Glu
            100                 105                 110

TAC TCC TCT CTC AAG TTC AAG TGG TTC AAG AAT GGG AGT GAA TTA AGC    391
Tyr Ser Ser Leu Lys Phe Lys Trp Phe Lys Asn Gly Ser Glu Leu Ser
        115                 120                 125

CGA AAG AAC AAA CCA GAA AAC ATC AAG ATA CAG AAA AGG CCG GGG AAG    439
Arg Lys Asn Lys Pro Glu Asn Ile Lys Ile Gln Lys Arg Pro Pro Lys
    130                 135                 140

TCA GAA CTT CGC ATT AGC AAA GCG TCA CTG GCT GAT TCT GGA GAA TAT    487
Ser Glu Leu Arg Ile Ser Lys Ala Ser Leu Ala Asp Ser Gly Glu Tyr
145                 150                 155                 160

ATG TGC AAA GTG ATC AGC AAA CTA GGA AAT GAC AGT GCC TCT GCC AAC    535
Met Cys Lys Val Ile Ser Lys Leu Gly Asn Asp Ser Ala Ser Ala Asn
                165                 170                 175

ATC ACC ATT GTG GAG TCA AAC GCC ACA TCC ACA TCT ACA GCT GGG ACA    583
Ile Arg Ile Val Glu Ser Asn Ala Thr Ser Thr Ser Thr Ala Gly Thr
            180                 185                 190

AGC CAT CTT GTC AAG TGT GCA GAG AAG GAG AAA ACT TTC TGT GTG AAT    631
Ser His Leu Val Lys Cys Ala Glu Lys Glu Lys Thr Phe Cys Val Asn
        195                 200                 205

GGA GGC GAG TGC TTC ATG GTG AAA GAC CTT TCA AAT CCC TCA AGA TAC    679
Gly Gly Glu Cys Phe Met Val Lys Asp Leu Ser Asn Pro Ser Arg Tyr
    210                 215                 220

TTG TGC AAG TGC CCA AAT GAG TTT ACT GGT GAT CGC TGC CAA AAC TAC    727
Leu Cys Lys Cys Pro Asn Glu Phe Thr Gly Asp Arg Cys Gln Asn Tyr
225                 230                 235                 240

GTA ATG GCC AGC TTC TAC AGT ACG TCC ACT CCC TTT CTG TCT CTG CCT    775
Val Met Ala Ser Phe Tyr Ser Thr Ser Thr Pro Phe Leu Ser Leu Pro
                245                 250                 255

GAA TAGCGCATCT CAGTCGGTGC CGCTTTCTTG TTGCCGCATC TCCCCTCAGA TTCCGCCTAG 838
Glu

AGCTAGATGC GTTTTACCAG GTCTAACATT GACTGCCTCT GCCTGTCGCA TGAGAACATT      898

AACACAAGCG ATTGTATGAC TTCCTCTGTC CGTGACTAGT GGGCTCTGAG CTACTCGTAG      958

GTGCGTAAGG CTCCAGTGTT TCTGAAATTG ATCTTGAATT ACTGTGATAC GACATGATAG     1018

TCCCTCTCAC CCAGTGCAAT GACAATAAAG GCCTTGAAAA GTCAAAAAAA AAAAAAAAA      1078

AAAATCGAT GTCGACTCGA GATGTGGCTG                                      1108
```

( 2 ) INFORMATION FOR SEQ ID NO: 136:

( i ) SEQUENCE CHARACTERISTICS:
        ( A ) LENGTH: 559
        ( B ) TYPE: nucleic acid
        ( C ) STRANDEDNESS: double
        ( D ) TOPOLOGY: linear ( i x ) FEATURE:
        ( D ) OTHER INFORMATION: N in position 214 is unknown.

( x i ) SEQUENCE DESCRIPTION: SEQ ID NO: 136:

```
AGTTTCCCCC CCCAACTTGT CGGAACTCTG GGCTCGCGCG CAGGGCAGGA GCGGAGCGGC    60
```

```
GGCGGCTGCC  CAGGCGATGC  GAGCGCGGGC  CGGACGGTAA  TCGCCTCTCC  CTCCTCGGGC      120

TGCGAGCGCG  CCGGACCGAG  GCAGCGACAG  GAGCGGACCG  CGGCGGGAAC  CGAGGACTCC      180

CCAGCGGCGC  GCCAGCAGGA  GCCACCCCGC  GAGNCGTGCG  ACCGGGACGG  AGCGCCCGCC      240

AGTCCCAGGT  GGCCCGGACC  GCACGTTGCG  TCCCCGCGCT  CCCCGCCGGC  GACAGGAGAC      300

GCTCCCCCCC  ACGCCGCGCG  CGCCTCGGCC  CGGTCGCTGG  CCCGCCTCCA  CTCCGGGGAC      360

AAACTTTTCC  CGAAGCCGAT  CCCAGCCCTC  GGACCCAAAC  TTGTCGCGCG  TCGCCTTCGC      420

CGGGAGCCGT  CCGCGCAGAG  CGTGCACTTC  TCGGGCGAG  ATG  TCG  GAG  CGC  AGA      474
                                               Met  Ser  Glu  Arg  Arg
                                                1                     5

GAA  GGC  AAA  GGC  AAG  GGG  AAG  GGC  GGC  AAG  AAG  GAC  CGA  GGC  TCC  GGG    522
Glu  Gly  Lys  Gly  Lys  Gly  Lys  Gly  Gly  Lys  Lys  Asp  Arg  Gly  Ser  Gly
                    10                        15                        20

AAG  AAG  CCC  GTG  CCC  GCG  GCT  GGC  GGC  CCG  AGC  CCA  G                     559
Lys  Lys  Pro  Val  Pro  Ala  Ala  Gly  Gly  Pro  Ser  Pro  Ala
               25                        30
```

( 2 ) INFORMATION FOR SEQ ID NO: 137:

( i ) SEQUENCE CHARACTERISTICS:
        ( A ) LENGTH: 252
        ( B ) TYPE: nucleic acid
        ( C ) STRANDEDNESS: double
        ( D ) TOPOLOGY: linear ( i x ) FEATURE:
        ( D ) OTHER INFORMATION: N in position 8 could be either A or
        G.

( x i ) SEQUENCE DESCRIPTION: SEQ ID NO: 137:

```
CC  CAT  CAN  GTG  TGG  GCG  GCG  AAA  GCC  GGG  GGC  TTG  AAG  AAG  GAC  TCG     47
    His  Gln  Val  Trp  Ala  Ala  Lys  Ala  Gly  Gly  Leu  Lys  Lys  Asp  Ser
     1                   5                        10                       15

CTG  CTC  ACC  GTG  CGC  CTG  GGC  GCC  TGG  GGC  CAC  CCC  GCC  TTC  CCC  TCC    95
Leu  Leu  Thr  Val  Arg  Leu  Gly  Ala  Trp  Gly  His  Pro  Ala  Phe  Pro  Ser
                    20                        25                        30

TGC  GGG  CGC  CTC  AAG  GAG  GAC  AGC  AGG  TAC  ATC  TTC  TTC  ATG  GAG  CCC   143
Cys  Gly  Arg  Leu  Lys  Glu  Asp  Ser  Arg  Tyr  Ile  Phe  Phe  Met  Glu  Pro
               35                        40                        45

GAG  GCC  AAC  AGC  AGC  GGC  GGG  CCC  GGC  CGC  CTT  CCG  AGC  CTC  CTT  CCC   191
Glu  Ala  Asn  Ser  Ser  Gly  Gly  Pro  Gly  Arg  Leu  Pro  Ser  Leu  Leu  Pro
          50                        55                        60

CCC  TCT  CGA  GAC  GGG  CCG  GAA  CCT  CAA  GAA  GGA  GGT  CAG  CCG  GGT  GCT   239
Pro  Ser  Arg  Asp  Gly  Pro  Glu  Pro  Gln  Glu  Gly  Gly  Gln  Pro  Gly  Ala
     65                        70                        75

GTG  CAA  CGG  TGC  G                                                            252
Val  Gln  Arg  Cys
 80
```

( 2 ) INFORMATION FOR SEQ ID NO: 138:

( i ) SEQUENCE CHARACTERISTICS:
        ( A ) LENGTH: 178
        ( B ) TYPE: nucleic acid
        ( C ) STRANDEDNESS: double
        ( D ) TOPOLOGY: linear ( x i ) SEQUENCE DESCRIPTION: SEQ ID NO: 138:

```
CCT  TGC  CTC  CCC  GCT  TGA  AAG  AGA  TGA  AGA  GTC  AGG  AGT  CTG  TGG  CAG    48
Leu  Pro  Pro  Arg  Leu  Lys  Glu  His  Lys  Ser  Gln  Glu  Ser  Val  Ala  Gly
 1                    5                        10                       15

GTT  CCA  AAC  TAG  TGC  TTC  GGT  GCG  AGA  CCA  GTT  CTG  AAT  ACT  CCT  CTC    96
Ser  Lys  Leu  Val  Leu  Arg  Cys  Glu  Thr  Ser  Ser  Glu  Tyr  Ser  Ser  Leu
```

```
                             20                          25                           30
TCA  AGT  TCA  AGT  GGT  TCA  AGA  ATG  GGA  GTG  AAT  TAA  GCC  GAA  AGA  ACA         144
Lys  Phe  Lys  Trp  Phe  Lys  Asn  Gly  Ser  Glu  Leu  Ser  Arg  Lys  Asn  Lys
               35                        40                       45

AAC  CAC  AAA  ACA  TCA  AGA  TAC  AGA  AAA  GGC  CGG  G                              178
Pro  Gly  Asn  Ile  Lys  Ile  Gln  Lys  Arg  Pro  Gly
          50                        55
```

( 2 ) INFORMATION FOR SEQ ID NO: 139:

( i ) SEQUENCE CHARACTERISTICS:
        ( A ) LENGTH: 122
        ( B ) TYPE: nucleic acid
        ( C ) STRANDEDNESS: double
        ( D ) TOPOLOGY: linear ( x i ) SEQUENCE DESCRIPTION: SEQ ID NO: 139:

```
G  AAG  TCA  GAA  CTT  CGC  ATT  AGC  AAA  GCG  TCA  CTG  GCT  GAT  TCT  GGA          46
   Lys  Ser  Glu  Leu  Arg  Ile  Ser  Lys  Ala  Ser  Leu  Ala  Asp  Ser  Gly
    1                   5                        10                       15

GAA  TAT  ATG  TGC  AAA  GTG  ATC  AGC  AAA  CTA  GGA  AAT  GAC  AGT  GCC  TCT         94
Glu  Tyr  Met  Cys  Lys  Val  Ile  Ser  Lys  Leu  Gly  Asn  Asp  Ser  Ala  Ser
               20                       25                            30

GCC  AAC  ATC  ACC  ATT  GTG  GAG  TCA  AAC  G                                        122
Ala  Asn  Ile  Thr  Ile  Val  Glu  Ser  Asn  Ala
               35
```

( 2 ) INFORMATION FOR SEQ ID NO: 140:

( i ) SEQUENCE CHARACTERISTICS:
        ( A ) LENGTH: 417
        ( B ) TYPE: nucleic acid
        ( C ) STRANDEDNESS: double
        ( D ) TOPOLOGY: linear ( x i ) SEQUENCE DESCRIPTION: SEQ ID NO: 140:

```
TCTAAAACTA  CAGAGACTGT  ATTTTCATGA  TCATCATAGT  TCTGTGAAAT  ATACTTAAAC                60

CGCTTTGGTC  CTGATCTTGT  AGG  AAG  TCA  GAA  CTT  CGC  ATT  AGC  AAA  GCG              110
                            Lys  Ser  Glu  Leu  Arg  Ile  Ser  Lys  Ala
                             1                   5

TCA  CTG  GCT  GAT  TCT  GGA  GAA  TAT  ATG  TGC  AAA  GTG  ATC  AGC  AAA  CTA         158
Ser  Leu  Ala  Asp  Ser  Gly  Glu  Tyr  Met  Cys  Lys  Val  Ile  Ser  Lys  Leu
 10                  15                       20                            25

GGA  AAT  GAC  AGT  GCC  TCT  GCC  AAC  ATC  ACC  ATT  GTG  GAG  TCA  AAC  GGT         206
Gly  Asn  Asp  Ser  Ala  Ser  Ala  Asn  Ile  Thr  Ile  Val  Glu  Ser  Asn  Gly
               30                        35                            40

AAG  AGA  TGC  CTA  CTG  CGT  GCT  ATT  TCT  CAG  TCT  CTA  AGA  GGA  GTG  ATC         254
Lys  Arg  Cys  Leu  Leu  Arg  Ala  Ile  Ser  Gln  Ser  Leu  Arg  Gly  Val  Ile
               45                        50                            55

AAG  GTA  TGT  GGT  CAC  ACT  TGAATCACGC  AGGTGTGTGA  AATCTCATTG                      302
Lys  Val  Cys  Gly  His  Thr
               60

TGAACAAATA  AAAATCATGA  AAGGAAAACT  CTATGTTTGA  AATATCTTAT  GGGTCCTCCT                362

GTAAAGCTCT  TCACTCCATA  AGGTGAAATA  GACCTGAAAT  ATATATAGAT  TATTT                     417
```

( 2 ) INFORMATION FOR SEQ ID NO: 141:

( i ) SEQUENCE CHARACTERISTICS:
        ( A ) LENGTH: 102
        ( B ) TYPE: nucleic acid
        ( C ) STRANDEDNESS: double
        ( D ) TOPOLOGY: linear ( x i ) SEQUENCE DESCRIPTION: SEQ ID NO: 141:

```
AG  ATC ACC ACT GGC ATG CCA GCC TCA ACT GAG ACA GCG TAT GTG TCT       47
Glu Ile Thr Thr Gly Met Pro Ala Ser Thr Glu Thr Ala Tyr Val Ser
1                 5                 10                  15

TCA GAG TCT CCC ATT AGA ATA TCA GTA TCA ACA GAA GGA ACA AAT ACT       95
Ser Glu Ser Pro Ile Arg Ile Ser Val Ser Thr Glu Gly Thr Asn Thr
            20                  25                  30

TCT TCA T                                                            102
Ser Ser Ser
        35
```

( 2 ) INFORMATION FOR SEQ ID NO: 142:

( i ) SEQUENCE CHARACTERISTICS:
        ( A ) LENGTH: 69
        ( B ) TYPE: nucleic acid
        ( C ) STRANDEDNESS: double
        ( D ) TOPOLOGY: linear ( x i ) SEQUENCE DESCRIPTION: SEQ ID NO: 142:

```
AAG TGC CAA CCT GGA TTC ACT GGA GCG AGA TGT ACT GAG AAT GTG CCC       48
Lys Cys Gln Pro Gly Phe Thr Gly Ala Arg Cys Thr Glu Asn Val Pro
1                 5                 10                  15

ATG AAA GTC CAA ACC CAA GAA                                           69
Met Lys Val Gln Thr Gln Glu
            20
```

( 2 ) INFORMATION FOR SEQ ID NO: 143:

( i ) SEQUENCE CHARACTERISTICS:
        ( A ) LENGTH: 60
        ( B ) TYPE: nucleic acid
        ( C ) STRANDEDNESS: double
        ( D ) TOPOLOGY: linear ( x i ) SEQUENCE DESCRIPTION: SEQ ID NO: 143:

```
AAG TGC CCA AAT GAG TTT ACT GGT GAT CGC TGC CAA AAC TAC GTA ATG       48
Lys Cys Pro Asn Glu Phe Thr Gly Asp Arg Cys Gln Asn Tyr Val Met
1                 5                 10                  15

GCC AGC TTC TAC                                                       60
Ala Ser Phe Tyr
            20
```

( 2 ) INFORMATION FOR SEQ ID NO: 144:

( i ) SEQUENCE CHARACTERISTICS:
        ( A ) LENGTH: 36
        ( B ) TYPE: nucleic acid
        ( C ) STRANDEDNESS: double
        ( D ) TOPOLOGY: linear ( x i ) SEQUENCE DESCRIPTION: SEQ ID NO: 144:

```
AGT ACG TCC ACT CCC TTT CTG TCT CTG CCT GAA TAG                       36
Ser Thr Ser Thr Pro Phe Leu Ser Leu Pro Glu
1               5                   10
```

( 2 ) INFORMATION FOR SEQ ID NO: 145:

( i ) SEQUENCE CHARACTERISTICS:
        ( A ) LENGTH: 27
        ( B ) TYPE: nucleic acid
        ( C ) STRANDEDNESS: double
        ( D ) TOPOLOGY: linear ( x i ) SEQUENCE DESCRIPTION: SEQ ID NO: 145:

```
AAG CAT CTT GGG ATT GAA TTT ATG GAG                                   27
Lys His Leu Gly Ile Glu Phe Met Glu
1               5
```

( 2 ) INFORMATION FOR SEQ ID NO: 146:

( i ) SEQUENCE CHARACTERISTICS:
    ( A ) LENGTH: 569
    ( B ) TYPE: nucleic acid
    ( C ) STRANDEDNESS: double
    ( D ) TOPOLOGY: linear ( x i ) SEQUENCE DESCRIPTION: SEQ ID NO: 146:

```
AAA  GCG  GAG  GAG  CTC  TAC  CAG  AAG  AGA  GTG  CTC  ACC  ATT  ACC  GGC  ATT        48
Lys  Ala  Glu  Glu  Leu  Tyr  Gln  Lys  Arg  Val  Leu  Thr  Ile  Thr  Gly  Ile
 1                    5                        10                       15

TGC  ATC  GCG  CTG  CTC  GTG  GTT  GGC  ATC  ATG  TGT  GTG  GTG  GTC  TAC  TGC        96
Cys  Ile  Ala  Leu  Leu  Val  Val  Gly  Ile  Met  Cys  Val  Val  Val  Tyr  Cys
               20                       25                       30

AAA  ACC  AAG  AAA  CAA  CGG  AAA  AAG  CTT  CAT  GAC  CGG  CTT  CGG  CAG  AGC       144
Lys  Thr  Lys  Lys  Gln  Arg  Lys  Lys  Leu  His  Asp  Arg  Leu  Arg  Gln  Ser
          35                        40                        45

CTT  CGG  TCT  GAA  AGA  AAC  ACC  ATG  ATG  AAC  GTA  GCC  AAC  GGG  CCC  CAC       192
Leu  Arg  Ser  Glu  Arg  Asn  Thr  Met  Met  Asn  Val  Ala  Asn  Gly  Pro  His
     50                        55                        60

CAC  CCC  AAT  CCG  CCC  CCC  GAG  AAC  GTG  CAG  CTG  GTG  AAT  CAA  TAC  GTA       240
His  Pro  Asn  Pro  Pro  Pro  Glu  Asn  Val  Gln  Leu  Val  Asn  Gln  Tyr  Val
 65                       70                        75                       80

TCT  AAA  AAT  GTC  ATC  TCT  AGC  GAG  CAT  ATT  GTT  GAG  AGA  GAG  GCG  GAG       288
Ser  Lys  Asn  Val  Ile  Ser  Ser  Glu  His  Ile  Val  Glu  Arg  Glu  Ala  Glu
                    85                        90                       95

AGC  TCT  TTT  TCC  ACC  AGT  CAC  TAC  ACT  TCG  ACA  GCT  CAT  CAT  TCC  ACT       336
Ser  Ser  Phe  Ser  Thr  Ser  His  Tyr  Thr  Ser  Thr  Ala  His  His  Ser  Thr
               100                      105                      110

ACT  GTC  ACT  CAG  ACT  CCC  AGT  CAC  AGC  TGG  AGC  AAT  GGA  CAC  ACT  GAA       384
Thr  Val  Thr  Gln  Thr  Pro  Ser  His  Ser  Trp  Ser  Asn  Gly  His  Thr  Glu
          115                      120                      125

AGC  ATC  ATT  TCG  GAA  AGC  CAC  TCT  GTC  ATC  GTG  ATG  TCA  TCC  GTA  GAA       432
Ser  Ile  Ile  Ser  Glu  Ser  His  Ser  Val  Ile  Val  Met  Ser  Ser  Val  Glu
     130                      135                      140

AAC  AGT  AGG  CAC  AGC  AGC  CCG  ACT  GGG  GGC  CCG  AGA  GGA  CGT  CTC  AAT       480
Asn  Ser  Arg  His  Ser  Ser  Pro  Thr  Gly  Gly  Pro  Arg  Gly  Arg  Leu  Asn
145                      150                      155                      160

GGC  TTG  GGA  GGC  CCT  CGT  GAA  TGT  AAC  AGC  TTC  CTC  AGG  CAT  GCC  AGA       528
Gly  Leu  Gly  Gly  Pro  Arg  Glu  Cys  Asn  Ser  Phe  Leu  Arg  His  Ala  Arg
               165                      170                      175

GAA  ACC  CCT  GAC  TCC  TAC  CGA  GAC  TCT  CCT  CAT  AGT  G AAAG                   569
Glu  Thr  Pro  Asp  Ser  Tyr  Arg  Asp  Ser  Pro  His  Ser
          180                      185
```

( 2 ) INFORMATION FOR SEQ ID NO: 147:

( i ) SEQUENCE CHARACTERISTICS:
    ( A ) LENGTH: 730
    ( B ) TYPE: nucleic acid
    ( C ) STRANDEDNESS: double
    ( D ) TOPOLOGY: linear ( x i ) SEQUENCE DESCRIPTION: SEQ ID NO: 147:

```
G  TAT  GTA  TCA  GCA  ATG  ACC  ACC  CCG  GCT  CGT  ATG  TCA  CCT  GTA  GAT         46
   Tyr  Val  Ser  Ala  Met  Thr  Thr  Pro  Ala  Arg  Met  Ser  Pro  Val  Asp
    1                    5                       10                       15

TTC  CAC  ACG  CCA  AGC  TCC  CCC  AAG  TCA  CCC  CCT  TCG  GAA  ATG  TCC  CCG        94
Phe  His  Thr  Pro  Ser  Ser  Pro  Lys  Ser  Pro  Pro  Ser  Glu  Met  Ser  Pro
               20                        25                       30

CCC  GTG  TCC  AGC  ACG  ACG  GTC  TCC  ATG  CCC  TCC  ATG  GCG  GTC  AGT  CCC       142
```

```
                        Pro  Val  Ser  Ser  Thr  Thr  Val  Ser  Met  Pro  Ser  Met  Ala  Val  Ser  Pro
                                       35                  40                      45

TTC  GTG  GAA  GAG  GAG  AGA  CCC  CTG  CTC  CTT  GTG  ACG  CCA  CCA  CGG  CTG                              190
Phe  Val  Glu  Glu  Glu  Arg  Pro  Leu  Leu  Leu  Val  Thr  Pro  Pro  Arg  Leu
          50                       55                       60

CGG  GAG  AAG  TAT  GAC  CAC  CAC  GCC  CAG  CAA  TTC  AAC  TCG  TTC  CAC  TGC                              238
Arg  Glu  Lys  Tyr  Asp  His  His  Ala  Gln  Gln  Phe  Asn  Ser  Phe  His  Cys
          65                       70                       75

AAC  CCC  GCG  CAT  GAG  AGC  AAC  AGC  CTG  CCC  CCC  AGC  CCC  TTG  AGG  ATA                              286
Asn  Pro  Ala  His  Glu  Ser  Asn  Ser  Leu  Pro  Pro  Ser  Pro  Leu  Arg  Ile
     80                       85                       90                       95

GTG  GAG  GAT  GAG  GAA  TAT  GAA  ACG  ACC  CAG  GAG  TAC  GAA  CCA  GCT  CAA                              334
Val  Glu  Asp  Glu  Glu  Tyr  Glu  Thr  Thr  Gln  Glu  Tyr  Glu  Pro  Ala  Gln
                    100                      105                      110

GAG  CCG  GTT  AAG  AAA  CTC  ACC  AAC  AGC  AGC  CGG  CGG  GCC  AAA  AGA  ACC                              382
Glu  Pro  Val  Lys  Lys  Leu  Thr  Asn  Ser  Ser  Arg  Arg  Ala  Lys  Arg  Thr
               115                      120                      125

AAG  CCC  AAT  GGT  CAC  ATT  GCC  CAC  AGG  TTG  GAA  ATG  GAC  AAC  AAC  ACA                              430
Lys  Pro  Asn  Gly  His  Ile  Ala  His  Arg  Leu  Glu  Met  Asp  Asn  Asn  Thr
          130                      135                      140

GGC  GCT  GAC  AGC  AGT  AAC  TCA  GAG  AGC  GAA  ACA  GAG  GAT  GAA  AGA  GTA                              478
Gly  Ala  Asp  Ser  Ser  Asn  Ser  Glu  Ser  Glu  Thr  Glu  Asp  Glu  Arg  Val
     145                      150                      155

GGA  GAA  GAT  ACG  CCT  TTC  CTG  GCC  ATA  CAG  AAC  CCC  CTG  GCA  GCC  AGT                              526
Gly  Glu  Asp  Thr  Pro  Phe  Leu  Ala  Ile  Gln  Asn  Pro  Leu  Ala  Ala  Ser
160                      165                      170                      175

CTC  GAG  GCG  GCC  CCT  GCC  TTC  CGC  CTG  GTC  GAC  AGC  AGG  ACT  AAC  CCA                              574
Leu  Glu  Ala  Ala  Pro  Ala  Phe  Arg  Leu  Val  Asp  Ser  Arg  Thr  Asn  Pro
                    180                      185                      190

ACA  GGC  GGC  TTC  TCT  CCG  CAG  GAA  GAA  TTG  CAG  GCC  AGG  CTC  TCC  GGT                              622
Thr  Gly  Gly  Phe  Ser  Pro  Gln  Glu  Glu  Leu  Gln  Ala  Arg  Leu  Ser  Gly
               195                      200                      205

GTA  ATC  GCT  AAC  CAA  GAC  CCT  ATC  GCT  GTC  TAAAACGAA  ATACACCCAT                                     672
Val  Ile  Ala  Asn  Gln  Asp  Pro  Ile  Ala  Val
          210                      215

AGATTCACCT GTAAAACTTT ATTTTATATA ATAAAGTATT CCACCTTAAA TTAAACAA                                             730
```

( 2 ) INFORMATION FOR SEQ ID NO: 148:

( i ) SEQUENCE CHARACTERISTICS:
        ( A ) LENGTH: 1652
        ( B ) TYPE: nucleic acid
        ( C ) STRANDEDNESS: double
        ( D ) TOPOLOGY: linear ( x i ) SEQUENCE DESCRIPTION: SEQ ID NO: 148:

```
AGTTTCCCCC  CCCAACTTGT  CGGAACTCTG  GGCTCGCGCG  CAGGGCAGGA  GCGGAGCGGC          60

GGCGGCTGCC  CAGGCGATGC  GAGCGCGGGC  CGGACGGTAA  TCGCCTCTCC  CTCCTCGGGC         120

TGCGAGCGCG  CCGGACCGAG  GCAGCGACAG  GAGCGGACCG  CGGCGGGAAC  CGAGGACTCC         180

CCAGCGGCGC  GCCAGCAGGA  GCCACCCCGC  GAGCGTGCGA  CCGGGACGGA  GCGCCCGCCA         240

GTCCCAGGTG  GCCCGGACCG  CACGTTGCGT  CCCCGCGCTC  CCGCCGGCG  ACAGGAGACG          300

CTCCCCCCCA  CGCCGCGCGC  GCCTCGGCCC  GGTCGCTGGC  CCGCCTCCAC  TCGGGGACA          360

AACTTTTCCC  GAAGCCGATC  CCAGCCCTCG  GACCCAAACT  TGTCGCGCGT  CGCCTTCGCC         420

GGGAGCCGTC  CGCGCAGAGC  GTGCACTTCT  CGGGCGAG  ATG  TCG  GAG  CGC  AGA           473
                                              Met  Ser  Glu  Arg  Arg
                                               1                     5

GAA  GGC  AAA  GGC  AAG  GGG  AAG  GGC  GGC  AAG  AAG  GAC  CGA  GGC  TCC  GGG                              521
Glu  Gly  Lys  Gly  Lys  Gly  Lys  Gly  Gly  Lys  Lys  Asp  Arg  Gly  Ser  Gly
```

| | | | | | | | | | | | | | | | | |
|---|---|---|---|---|---|---|---|---|---|---|---|---|---|---|---|---|
| AAG | AAG | CCC | GTG | CCC | GCG | GCT | GGC | GGC | CCG | AGC | CCA | GCC | TTG | CCT | CCC | 569 |
| Lys | Lys | Pro | Val 25 | Pro | Ala | Ala | Gly | Gly 30 | Pro | Ser | Pro | Ala | Leu 35 | Pro | Pro | |
| CGC | TTG | AAA | GAG | ATG | AAG | ATG | CAG | GAG | TCT | GTG | GCA | GGT | TCC | AAA | CTA | 617 |
| Arg | Leu | Lys 40 | Glu | Met | Lys | Ser | Gln 45 | Glu | Ser | Val | Ala | Gly 50 | Ser | Lys | Leu | |
| GTG | CTT | CGG | TGC | GAG | ACC | AGT | TCT | GAA | TAC | TCC | TCT | CTC | AAG | TTC | AAG | 665 |
| Val | Leu 55 | Arg | Cys | Glu | Thr | Ser 60 | Ser | Glu | Tyr | Ser | Ser 65 | Leu | Lys | Phe | Lys | |
| TGG | TTC | AAG | AAT | GGG | AGT | GAA | TTA | AGC | CGA | AAG | AAC | AAA | CCA | CAA | AAC | 713 |
| Trp 70 | Phe | Lys | Asn | Gly | Ser 75 | Glu | Leu | Ser | Arg | Lys 80 | Asn | Lys | Pro | Gln | Asn 85 | |
| ATC | AAG | ATA | CAG | AAA | AGG | CCG | GGG | AAG | TCA | GAA | CTT | CGC | ATT | AGC | AAA | 761 |
| Ile | Lys | Ile | Gln | Lys 90 | Arg | Pro | Gly | Lys | Ser 95 | Glu | Leu | Arg | Ile | Ser 100 | Lys | |
| GCG | TCA | CTG | GCT | GAT | TCT | GGA | GAA | TAT | ATG | TGC | AAA | GTG | ATC | AGC | AAA | 809 |
| Ala | Ser | Leu | Ala 105 | Asp | Ser | Gly | Glu | Tyr 110 | Met | Cys | Lys | Val | Ile 115 | Ser | Lys | |
| CTA | GGA | AAT | GAC | AGT | GCC | TCT | GCC | AAC | ATC | ACC | ATT | GTG | GAG | TCA | AAC | 857 |
| Leu | Gly | Asn 120 | Asp | Ser | Ala | Ser | Ala 125 | Asn | Ile | Thr | Ile | Val 130 | Glu | Ser | Asn | |
| GAG | ATC | ACC | ACT | GGC | ATG | CCA | GCC | TCA | ACT | GAG | ACA | GCG | TAT | GTG | TCT | 905 |
| Glu | Ile | Thr 135 | Thr | Gly | Met | Pro | Ala 140 | Ser | Thr | Glu | Thr | Ala 145 | Tyr | Val | Ser | |
| TCA | GAG | TCT | CCC | ATT | AGA | ATA | TCA | GTA | TCA | ACA | GAA | GGA | ACA | AAT | ACT | 953 |
| Ser | Glu | Ser 150 | Pro | Ile | Arg | Ile | Ser 155 | Val | Ser | Thr | Glu 160 | Gly | Thr | Asn | Thr 165 | |
| TCT | TCA | TCC | ACA | TCC | ACA | TCT | ACA | GCT | GGG | ACA | AGC | CAT | CTT | GTC | AAG | 1001 |
| Ser | Ser | Ser | Thr | Ser 170 | Thr | Ser | Thr | Ala | Gly 175 | Thr | Ser | His | Leu | Val 180 | Lys | |
| TGT | GCA | GAG | AAG | GAG | AAA | ACT | TTC | TGT | GTG | AAT | GGA | GGC | GAG | TGC | TTC | 1049 |
| Cys | Ala | Glu | Lys 185 | Glu | Lys | Thr | Phe | Cys 190 | Val | Asn | Gly | Gly | Glu 195 | Cys | Phe | |
| ATG | GTG | AAA | GAC | CTT | TCA | AAT | CCC | TCA | AGA | TAC | TTG | TGC | AAG | TGC | CCA | 1097 |
| Met | Val | Lys 200 | Asp | Leu | Ser | Asn | Pro 205 | Ser | Arg | Tyr | Leu | Cys 210 | Lys | Cys | Pro | |
| AAT | GAG | TTT | ACT | GGT | GAT | CGC | TGC | CAA | AAC | TAC | GTA | ATG | GCC | AGC | TTC | 1145 |
| Asn | Glu | Phe 215 | Thr | Gly | Asp | Arg | Cys 220 | Gln | Asn | Tyr | Val | Met 225 | Ala | Ser | Phe | |
| TAC | AGT | ACG | TCC | ACT | CCC | TTT | CTG | TCT | CTG | CCT | GAA | TAGGCGCATG | | | | 1191 |
| Tyr | Ser | Thr 230 | Ser | Thr | Pro | Phe | Leu 235 | Ser | Leu | Pro | Glu 240 | | | | | |

| | | | | | |
|---|---|---|---|---|---|
| CTCAGTCGGT | GCCGCTTTCT | TGTTGCCGCA | TCTCCCCTCA | GATTCAACCT | AGAGCTAGAT | 1251 |
| GCGTTTTACC | AGGTCTAACA | TTGACTGCCT | CTGCCTGTCG | CATGAGAACA | TTAACACAAG | 1311 |
| CGATTGTATG | ACTTCCTCTG | TCCGTGACTA | GTGGGCTCTG | AGCTACTCGT | AGGTGCGTAA | 1371 |
| GGCTCCAGTG | TTTCTGAAAT | TGATCTTGAA | TTACTGTGAT | ACGACATGAT | AGTCCCTCTC | 1431 |
| ACCCAGTGCA | ATGACAATAA | AGGCCTTGAA | AAGTCTCACT | TTTATTGAGA | AAATAAAAAT | 1491 |
| CGTTCCACGG | GACAGTCCCT | CTTCTTTATA | AAATGACCCT | ATCCTTGAAA | AGGAGGTGTG | 1551 |
| TTAAGTTGTA | ACCAGTACAC | ACTTGAAATG | ATGGTAAGTT | CGCTTCGGTT | CAGAATGTGT | 1611 |
| TCTTTCTGAC | AAATAAACAG | AATAAAAAAA | AAAAAAAAA | A | | 1652 |

( 2 ) INFORMATION FOR SEQ ID NO: 149:

( i ) SEQUENCE CHARACTERISTICS:
        ( A ) LENGTH: 1140
        ( B ) TYPE: nucleic acid (C) STRANDEDNESS: double
(D) TOPOLOGY: linear (xi) SEQUENCE DESCRIPTION: SEQ ID NO: 149:

```
CAT CAN GTG TGG GCG GCG AAA GCC GGG GGC TTG AAG AAG GAC TCG CTG    48
His Gln Val Trp Ala Ala Lys Ala Gly Gly Leu Lys Lys Asp Ser Leu
1               5                   10                  15

CTC ACC GTG CGC CTG GGC GCC TGG GGC CAC CCC GCC TTC CCC TCC TGC    96
Leu Thr Val Arg Leu Gly Ala Trp Gly His Pro Ala Phe Pro Ser Cys
                20                  25                  30

GGG CGC CTC AAG GAG GAC AGC AGG TAC ATC TTC TTC ATG GAG CCC GAG   144
Gly Arg Leu Lys Glu Asp Ser Arg Tyr Ile Phe Phe Met Glu Pro Glu
            35                  40                  45

GCC AAC AGC AGC GGC GGG CCC GGC CGC CTT CCG AGC CTC CTT CCC CCC   192
Ala Asn Ser Ser Gly Gly Pro Gly Arg Leu Pro Ser Leu Leu Pro Pro
        50                  55                  60

TCT CGA GAC GGG CCG GAA CCT CAA GAA GGA GGT CAG CCG GGT GCT GTG   240
Ser Arg Asp Gly Pro Glu Pro Gln Glu Gly Gly Gln Pro Gly Ala Val
65                  70                  75                  80

CAA CGG TGC GCC TTG CCT CCC CGC TTG AAA GAG ATG AAG AGT CAG GAG   288
Gln Arg Cys Ala Leu Pro Pro Arg Leu Lys Glu Met Lys Ser Gln Glu
                85                  90                  95

TCT GTG GCA GGT TCC AAA CTA GTG CTT CGG TGC GAG ACC AGT TCT GAA   336
Ser Val Ala Gly Ser Lys Leu Val Leu Arg Cys Glu Thr Ser Ser Glu
            100                 105                 110

TAC TCC TCT CTC AAG TTC AAG TGG TTC AAG AAT GGG AGT GAA TTA AGC   384
Tyr Ser Ser Leu Lys Phe Lys Trp Phe Lys Asn Gly Ser Glu Leu Ser
        115                 120                 125

CGA AAG AAC AAA CCA GAA AAC ATC AAG ATA CAG AAA AGG CCG GGG AAG   432
Arg Lys Asn Lys Pro Glu Asn Ile Lys Ile Gln Lys Arg Pro Gly Lys
        130                 135                 140

TCA GAA CTT CGC ATT AGC AAA GCG TCA CTG GCT GAT TCT GGA GAA TAT   480
Ser Glu Leu Arg Ile Ser Lys Ala Ser Leu Ala Asp Ser Gly Glu Tyr
145                 150                 155                 160

ATG TGC AAA GTG ATC AGC AAA CTA GGA AAT GAC AGT GCC TCT GCC AAC   528
Met Cys Lys Val Ile Ser Lys Leu Gly Asn Asp Ser Ala Ser Ala Asn
                165                 170                 175

ATC ACC ATT GTG GAG TCA AAC GCC ACA TCC ACA TCT ACA GCT GGG ACA   576
Ile Thr Ile Val Glu Ser Asn Ala Thr Ser Thr Ser Thr Ala Gly Thr
            180                 185                 190

AGC CAT CTT GTC AAG TGT GCA GAG AAG GAG AAA ACT TTC TGT GTG AAT   624
Ser His Leu Val Lys Cys Ala Glu Lys Glu Lys Thr Phe Cys Val Asn
        195                 200                 205

GGA GGC GAG TGC TTC ATG GTG AAA GAC CTT TCA AAT CCC TCA AGA TAC   672
Gly Gly Glu Cys Phe Met Val Lys Asp Leu Ser Asn Pro Ser Arg Tyr
    210                 215                 220

TTG TGC AAG TGC CAA CCT GGA TTC ACT GGA GCG AGA TGT ACT GAG AAT   720
Leu Cys Lys Cys Gln Pro Gly Phe Thr Gly Ala Arg Cys Thr Glu Asn
225                 230                 235                 240

GTG CCC ATG AAA GTC CAA ACC CAA GAA AAG TGC CCA AAT GAG TTT ACT   768
Val Pro Met Lys Val Gln Thr Gln Glu Lys Cys Pro Asn Glu Phe Thr
                245                 250                 255

GGT GAT CGC TGC CAA AAC TAC GTA ATG GCC AGC TTC TAC AGT ACG TCC   816
Gly Asp Arg Cys Gln Asn Tyr Val Met Ala Ser Phe Tyr Ser Thr Ser
            260                 265                 270

ACT CCC TTT CTG TCT CTG CCT GAA TAGCGCATCT CAGTCGGTGC CGCTTTCTTG   870
Thr Pro Phe Leu Ser Leu Pro Glu
        275                 280

TTGCCGCATC TCCCCTCAGA TTCCNCCTAG AGCTAGATGC GTTTTACCAG GTCTAACATT    930

GACTGCCTCT GCCTGTCGCA TGAGAACATT AACACAAGCG ATTGTATGAC TTCCTCTGTC    990
```

CGTGACTAGT GGGCTCTGAG CTACTCGTAG GTGCGTAAGG CTCCAGTGTT TCTGAAATTG    1050

ATCTTGAATT ACTGTGATAC GACATGATAG TCCCTCTCAC CCAGTGCAAT GACAATAAAG    1110

GCCTTGAAAA GTCAAAAAAA AAAAAAAAA                                      1140

( 2 ) INFORMATION FOR SEQ ID NO: 150:

( i ) SEQUENCE CHARACTERISTICS:
        ( A ) LENGTH: 1764
        ( B ) TYPE: nucleic acid
        ( C ) STRANDEDNESS: double
        ( D ) TOPOLOGY: linear ( x i ) SEQUENCE DESCRIPTION: SEQ ID NO: 150:

```
G   AAG TCA GAA CTT CGC ATT AGC AAA GCG TCA CTG GCT GAT TCT GGA GAA      49
    Lys Ser Glu Leu Arg Ile Ser Lys Ala Ser Leu Ala Asp Ser Gly Glu
    1               5                   10                  15

TAT ATG TGC AAA GTG ATC AGC AAA CTA GGA AAT GAC AGT GCC TCT GCC          97
Tyr Met Cys Lys Val Ile Ser Lys Leu Gly Asn Asp Ser Ala Ser Ala
            20                  25                  30

AAC ATC ACC ATT GTG GAG TCA AAC GCC ACA TCC ACA TCT ACA GCT GGG         145
Asn Ile Thr Ile Val Glu Ser Asn Ala Thr Ser Thr Ser Thr Ala Gly
        35                  40                  45

ACA AGC CAT CTT GTC AAG TGT GCA GAG AAG GAG AAA ACT TTC TGT GTG         193
Thr Ser His Leu Val Lys Cys Ala Glu Lys Glu Lys Thr Phe Cys Val
    50                  55                  60

AAT GGA GGC GAC TGC TTC ATG GTG AAA GAC CTT TCA AAT CCC TCA AGA         241
Asn Gly Gly Asp Cys Phe Met Val Lys Asp Leu Ser Asn Pro Ser Arg
65                  70                  75                  80

TAC TTG TGC AAG TGC CAA CCT GGA TTC ACT GGA GCG AGA TGT ACT GAG         289
Tyr Leu Cys Lys Cys Gln Pro Gly Phe Thr Gly Ala Arg Cys Thr Glu
                85                  90                  95

AAT GTG CCC ATG AAA GTC CAA ACC CAA GAA AAA GCG GAG GAG CTC TAC         337
Asn Val Pro Met Lys Val Gln Thr Gln Glu Lys Ala Glu Glu Leu Tyr
            100                 105                 110

CAG AAG AGA GTG CTC ACC ATT ACC GGC ATT TGC ATC GCG CTG CTC GTG         385
Gln Lys Arg Val Leu Thr Ile Thr Gly Ile Cys Ile Ala Leu Leu Val
        115                 120                 125

GTT GGC ATC ATG TGT GTG GTG GTC TAC TGC AAA ACC AAG AAA CAA CGG         433
Val Gly Ile Met Cys Val Val Val Tyr Cys Lys Thr Lys Lys Gln Arg
    130                 135                 140

AAA AAG CTT CAT GAC CGG CTT CGG CAG AGC CTT CGG TCT GAA AGA AAC         481
Lys Lys Leu His Asp Arg Leu Arg Gln Ser Leu Arg Ser Glu Arg Asn
145                 150                 155                 160

ACC ATG ATG AAC GTA GCC AAC GGG CCC CAC CAC CCC AAT CCG CCC CCC         529
Thr Met Met Asn Val Ala Asn Gly Pro His His Pro Asn Pro Pro Pro
                165                 170                 175

GAG AAC GTG CAG CTG GTG AAT CAA TAC GTA TCT AAA AAT GTC ATC TCT         577
Glu Asn Val Gln Leu Val Asn Gln Tyr Val Ser Lys Asn Val Ile Ser
            180                 185                 190

AGC GAG CAT ATT GTT GAG AGA GAG GCG GAG AGC TCT TTT TCC ACC AGT         625
Ser Glu His Ile Val Glu Arg Glu Ala Glu Ser Ser Phe Ser Thr Ser
        195                 200                 205

CAC TAC ACT TCG ACA GCT CAT CAT TCC ACT ACT GTC ACT CAG ACT CCC         673
His Tyr Thr Ser Thr Ala His His Ser Thr Thr Val Thr Gln Thr Pro
    210                 215                 220

AGT CAC AGC TGG AGC AAT GGA CAC ACT GAA AGC ATC ATT TCG GAA AGC         721
Ser His Ser Trp Ser Asn Gly His Thr Glu Ser Ile Ile Ser Glu Ser
225                 230                 235                 240

CAC TCT GTC ATC GTG ATG TCA TCC GTA GAA AAC AGT AGG CAC AGC AGC         769
His Ser Val Ile Val Met Ser Ser Val Glu Asn Ser Arg His Ser Ser
```

-continued

|     |     |     |     |     |     | 245 |     |     |     |     |     | 250 |     |     |     |     | 255 |      |
|-----|-----|-----|-----|-----|-----|-----|-----|-----|-----|-----|-----|-----|-----|-----|-----|-----|-----|------|
| CCG | ACT | GGG | GGC | CCG | AGA | GGA | CGT | CTC | AAT | GGC | TTG | GGA | GGC | CCT | CGT |     |     | 817  |
| Pro | Thr | Gly | Gly | Pro | Arg | Gly | Arg | Leu | Asn | Gly | Leu | Gly | Gly | Pro | Arg |     |     |      |
|     |     |     | 260 |     |     |     |     | 265 |     |     |     |     | 270 |     |     |     |     |      |

```
CCG ACT GGG GGC CCG AGA GGA CGT CTC AAT GGC TTG GGA GGC CCT CGT                817
Pro Thr Gly Gly Pro Arg Gly Arg Leu Asn Gly Leu Gly Gly Pro Arg
        260                 265                 270

GAA TGT AAC AGC TTC CTC AGG CAT GCC AGA GAA ACC CCT GAC TCC TAC                865
Glu Cys Asn Ser Phe Leu Arg His Ala Arg Glu Thr Pro Asp Ser Tyr
            275                 280                 285

CGA GAC TCT CCT CAT AGT GAA AGA CAT AAC CTT ATA GCT GAG CTA AGG                913
Arg Asp Ser Pro His Ser Glu Arg His Asn Leu Ile Ala Glu Leu Arg
        290                 295                 300

AGA AAC AAG GCC CAC AGA TCC AAA TGC ATG CAG ATC CAG CTT TCC GCA                961
Arg Asn Lys Ala His Arg Ser Lys Cys Met Gln Ile Gln Leu Ser Ala
305                 310                 315                 320

ACT CAT CTT AGA GCT TCT TCC ATT CCC CAT TGG GCT TCA TTC TCT AAG               1009
Thr His Leu Arg Ala Ser Ser Ile Pro His Trp Ala Ser Phe Ser Lys
                325                 330                 335

ACC CCT TGG CCT TTA GGA AGG TAT GTA TCA GCA ATG ACC ACC CCG GCT               1057
Thr Pro Trp Pro Leu Gly Arg Tyr Val Ser Ala Met Thr Thr Pro Ala
            340                 345                 350

CGT ATG TCA CCT GTA GAT TTC CAC ACG CCA AGC TCC CCC AAG TCA CCC               1105
Arg Met Ser Pro Val Asp Phe His Thr Pro Ser Ser Pro Lys Ser Pro
        355                 360                 365

CCT TCG GAA ATG TCC CCG CCC GTG TCC AGC ACG ACG GTC TCC ATG CCC               1153
Pro Ser Glu Met Ser Pro Pro Val Ser Ser Thr Thr Val Ser Met Pro
370                 375                 380

TCC ATG GCG GTC AGT CCC TTC GTG GAA GAG GAG AGA CCC CTG CTC CTT               1201
Ser Met Ala Val Ser Pro Phe Val Glu Glu Glu Arg Pro Leu Leu Leu
385                 390                 395                 400

GTG ACG CCA CCA CGG CTG CGG GAG AAG TAT GAC CAC CAC GCC CAG CAA               1249
Val Thr Pro Pro Arg Leu Arg Glu Lys Tyr Asp His His Ala Gln Gln
                405                 410                 415

TTC AAC TCG TTC CAC TGC AAC CCC GCG CAT GAG AGC AAC AGC CTG CCC               1297
Phe Asn Ser Phe His Cys Asn Pro Ala His Glu Ser Asn Ser Leu Pro
            420                 425                 430

CCC AGC CCC TTG AGG ATA GTG GAG GAT GAG GAA TAT GAA ACG ACC CAG               1345
Pro Ser Pro Leu Arg Ile Val Glu Asp Glu Glu Tyr Glu Thr Thr Gln
        435                 440                 445

GAG TAC GAA CCA GCT CAA GAG CCG GTT AAG AAA CTC ACC AAC AGC AGC               1393
Glu Tyr Glu Pro Ala Gln Glu Pro Val Lys Lys Leu Thr Asn Ser Ser
450                 455                 460

CGG CGG GCC AAA AGA ACC AAG CCC AAT GGT CAC ATT GCC CAC AGG TTG               1441
Arg Arg Ala Lys Arg Thr Lys Pro Asn Gly His Ile Ala His Arg Leu
465                 470                 475                 480

GAA ATG GAC AAC AAC ACA GGC GCT GAC AGC AGT AAC TCA GAG AGC GAA               1489
Glu Met Asp Asn Asn Thr Gly Ala Asp Ser Ser Asn Ser Glu Ser Glu
                485                 490                 495

ACA GAG GAT GAA AGA GTA GGA GAA GAT ACG CCT TTC CTG GCC ATA CAG               1537
Thr Glu Asp Glu Arg Val Gly Glu Asp Thr Pro Phe Leu Ala Ile Gln
            500                 505                 510

AAC CCC CTG GCA GCC AGT CTC GAG GCG GCC CCT GCC TTC CGC CTG GTC               1585
Asn Pro Leu Ala Ala Ser Leu Glu Ala Ala Pro Ala Phe Arg Leu Val
        515                 520                 525

GAC AGC AGG ACT AAC CCA ACA GGC GGC TTC TCT CCG CAG GAA GAA TTG               1633
Asp Ser Arg Thr Asn Pro Thr Gly Gly Phe Ser Pro Gln Glu Glu Leu
        530                 535                 540

CAG GCC AGG CTC TCC GGT GTA ATC GCT AAC CAA GAC CCT ATC GCT GTC               1681
Gln Ala Arg Leu Ser Gly Val Ile Ala Asn Gln Asp Pro Ile Ala Val
545                 550                 555                 560

TAAAACCGAA ATACACCCAT AGATTCACCT GTAAAACTTT ATTTTATATA ATAAAGTATT            1741
```

CCACCTTAAA TTAAACAAAA AAA 1764

( 2 ) INFORMATION FOR SEQ ID NO: 151:

( i ) SEQUENCE CHARACTERISTICS:
        ( A ) LENGTH: 50
        ( B ) TYPE: amino acid
        ( C ) STRANDEDNESS:
        ( D ) TOPOLOGY: linear ( x i ) SEQUENCE DESCRIPTION: SEQ ID NO: 151:

```
Lys Cys Ala Glu Lys Glu Lys Thr Phe Cys Val Asn Gly Gly Glu Cys
 1               5                  10                      15
Phe Met Val Lys Asp Leu Ser Asn Pro Ser Arg Tyr Leu Cys Lys Cys
                20                  25                  30
Pro Asn Glu Phe Thr Gly Asp Arg Cys Gln Asn Tyr Val Met Ala Ser
            35                  40                  45
Phe Tyr
    50
```

( 2 ) INFORMATION FOR SEQ ID NO: 152:

( i ) SEQUENCE CHARACTERISTICS:
        ( A ) LENGTH: 50
        ( B ) TYPE: amino acid
        ( C ) STRANDEDNESS:
        ( D ) TOPOLOGY: linear ( x i ) SEQUENCE DESCRIPTION: SEQ ID NO: 152:

```
Lys Cys Ala Glu Lys Glu Lys Thr Phe Cys Val Asn Gly Gly Glu Cys
 1               5                  10                      15
Phe Met Val Lys Asp Leu Ser Asn Pro Ser Arg Tyr Leu Cys Lys Cys
                20                  25                  30
Gln Pro Gly Phe Thr Gly Ala Arg Cys Thr Glu Asn Val Pro Met Lys
            35                  40                  45
Val Gln
    50
```

( 2 ) INFORMATION FOR SEQ ID NO: 153:

( i ) SEQUENCE CHARACTERISTICS:
        ( A ) LENGTH: 46
        ( B ) TYPE: amino acid
        ( C ) STRANDEDNESS:
        ( D ) TOPOLOGY: linear ( x i ) SEQUENCE DESCRIPTION: SEQ ID NO: 153:

```
Glu Cys Leu Arg Lys Tyr Lys Asp Phe Cys Ile His Gly Glu Cys Lys
 1               5                  10                      15
Tyr Val Lys Glu Leu Arg Ala Pro Ser Cys Lys Cys Gln Gln Glu Tyr
                20                  25                  30
Phe Gly Glu Arg Cys Gly Glu Lys Ser Asn Lys Thr His Ser
            35                  40                  45
```

( 2 ) INFORMATION FOR SEQ ID NO: 154:

( i ) SEQUENCE CHARACTERISTICS:
        ( A ) LENGTH: 198
        ( B ) TYPE: nucleic acid
        ( C ) STRANDEDNESS: double
        ( D ) TOPOLOGY: linear ( x i ) SEQUENCE DESCRIPTION: SEQ ID NO: 154:

AGC CAT CTT GTC AAG TGT GCA GAG AAG GAG AAA ACT TTC TGT GTG AAT 48

```
Ser  His  Leu  Val  Lys  Cys  Ala  Glu  Lys  Glu  Lys  Thr  Phe  Cys  Val  Asn
1               5                   10                       15

GGA  GGC  GAG  TGC  TTC  ATG  GTG  AAA  GAC  CTT  TCA  AAT  CCC  TCA  AGA  TAC        96
Gly  Gly  Glu  Cys  Phe  Met  Val  Lys  Asp  Leu  Ser  Asn  Pro  Ser  Arg  Tyr
               20                   25                       30

TTG  TGC  AAG  TGC  CCA  AAT  GAG  TTT  ACT  GGT  GAT  CGC  TGC  CAA  AAC  TAC       144
Leu  Cys  Lys  Cys  Pro  Asn  Glu  Phe  Thr  Gly  Asp  Arg  Cys  Gln  Asn  Tyr
          35                        40                       45

GTA  ATG  GCC  AGC  TTC  TAC  AGT  ACG  TCC  ACT  CCC  TTT  CTG  TCT  CTG  CCT       192
Val  Met  Ala  Ser  Phe  Tyr  Ser  Thr  Ser  Thr  Pro  Phe  Leu  Ser  Leu  Pro
     50                        55                       60

GAA  TAG                                                                             198
Glu
65
```

( 2 ) INFORMATION FOR SEQ ID NO: 155:

( i ) SEQUENCE CHARACTERISTICS:
        ( A ) LENGTH: 192
        ( B ) TYPE: nucleic acid
        ( C ) STRANDEDNESS: double
        ( D ) TOPOLOGY: linear ( x i ) SEQUENCE DESCRIPTION: SEQ ID NO: 155:

```
AGC  CAT  CTT  GTC  AAG  TGT  GCA  GAG  AAG  GAG  AAA  ACT  TTC  TGT  GTG  AAT        48
Ser  His  Leu  Val  Lys  Cys  Ala  Glu  Lys  Glu  Lys  Thr  Phe  Cys  Val  Asn
1               5                   10                       15

GGA  GGC  GAG  TGC  TTC  ATG  GTG  AAA  GAC  CTT  TCA  AAT  CCC  TCA  AGA  TAC        96
Gly  Gly  Glu  Cys  Phe  Met  Val  Lys  Asp  Leu  Ser  Asn  Pro  Ser  Arg  Tyr
               20                   25                       30

TTG  TGC  AAG  TGC  CAA  CCT  GGA  TTC  ACT  GGA  GCG  AGA  TGT  ACT  GAG  AAT       144
Leu  Cys  Lys  Cys  Gln  Pro  Gly  Phe  Thr  Gly  Ala  Arg  Cys  Thr  Glu  Asn
          35                        40                       45

GTG  CCC  ATG  AAA  GTC  CAA  ACC  CAA  GAA  AAA  GCG  GAG  GAG  CTC  TAC  TAA       192
Val  Pro  Met  Lys  Val  Gln  Thr  Gln  Glu  Lys  Ala  Glu  Glu  Leu  Tyr
     50                        55                       60
```

( 2 ) INFORMATION FOR SEQ ID NO: 156:

( i ) SEQUENCE CHARACTERISTICS:
        ( A ) LENGTH: 183
        ( B ) TYPE: nucleic acid
        ( C ) STRANDEDNESS: double
        ( D ) TOPOLOGY: linear ( x i ) SEQUENCE DESCRIPTION: SEQ ID NO: 156:

```
AGC  CAT  CTT  GTC  AAG  TGT  GCA  GAG  AAG  GAG  AAA  ACT  TTC  TGT  GTG  AAT        48
Ser  His  Leu  Val  Lys  Cys  Ala  Glu  Lys  Glu  Lys  Thr  Phe  Cys  Val  Asn
1               5                   10                       15

GGA  GGC  GAG  TGC  TTC  ATG  GTG  AAA  GAC  CTT  TCA  AAT  CCC  TCA  AGA  TAC        96
Gly  Gly  Glu  Cys  Phe  Met  Val  Lys  Asp  Leu  Ser  Asn  Pro  Ser  Arg  Tyr
               20                   25                       30

TTG  TGC  AAG  TGC  CCA  AAT  GAG  TTT  ACT  GGT  GAT  CGC  TGC  CAA  AAC  TAC       144
Leu  Cys  Lys  Cys  Pro  Asn  Glu  Phe  Thr  Gly  Asp  Arg  Cys  Gln  Asn  Tyr
          35                        40                       45

GTA  ATG  GCC  AGC  TTC  TAC  AAA  GCG  GAG  GAG  CTC  TAC  TAA                      183
Val  Met  Ala  Ser  Phe  Tyr  Lys  Ala  Glu  Glu  Leu  Tyr
     50                        55                       60
```

( 2 ) INFORMATION FOR SEQ ID NO: 157:

( i ) SEQUENCE CHARACTERISTICS:
        ( A ) LENGTH: 210
        ( B ) TYPE: nucleic acid ( C ) STRANDEDNESS: double
( D ) TOPOLOGY: linear ( x i ) SEQUENCE DESCRIPTION: SEQ ID NO: 157:

```
AGC CAT CTT GTC AAG TGT GCA GAG AAG GAG AAA ACT TTC TGT GTG AAT      48
Ser His Leu Val Lys Cys Ala Glu Lys Glu Lys Thr Phe Cys Val Asn
 1               5                  10                  15

GGA GGC GAG TGC TTC ATG GTG AAA GAC CTT TCA AAT CCC TCA AGA TAC      96
Gly Gly Glu Cys Phe Met Val Lys Asp Leu Ser Asn Pro Ser Arg Tyr
             20                  25                  30

TTG TGC AAG TGC CCA AAT GAG TTT ACT GGT GAT CGC TGC CAA AAC TAC     144
Leu Cys Lys Cys Pro Asn Glu Phe Thr Gly Asp Arg Cys Gln Asn Tyr
         35                  40                  45

GTA ATG GCC AGC TTC TAC AAG CAT CTT GGG ATT GAA TTT ATG GAG AAA     192
Val Met Ala Ser Phe Tyr Lys His Leu Gly Ile Glu Phe Met Glu Lys
     50                  55                  60

GCG GAG GAG CTC TAC TAA                                             210
Ala Glu Glu Leu Tyr
 65
```

( 2 ) INFORMATION FOR SEQ ID NO: 158:

( i ) SEQUENCE CHARACTERISTICS:
        ( A ) LENGTH: 267
        ( B ) TYPE: nucleic acid
        ( C ) STRANDEDNESS: double
        ( D ) TOPOLOGY: linear ( x i ) SEQUENCE DESCRIPTION: SEQ ID NO: 158:

```
AGC CAT CTT GTC AAG TGT GCA GAG AAG GAG AAA ACT TTC TGT GTG AAT      48
Ser His Leu Val Lys Cys Ala Glu Lys Glu Lys Thr Phe Cys Val Asn
 1               5                  10                  15

GGA GGC GAG TGC TTC ATG GTG AAA GAC CTT TCA AAT CCC TCA AGA TAC      96
Gly Gly Glu Cys Phe Met Val Lys Asp Leu Ser Asn Pro Ser Arg Tyr
             20                  25                  30

TTG TGC AAG TGC CAA CCT GGA TTC ACT GGA GCG AGA TGT ACT GAG AAT     144
Leu Cys Lys Cys Gln Pro Gly Phe Thr Gly Ala Arg Cys Thr Glu Asn
         35                  40                  45

GTG CCC ATG AAA GTC CAA ACC CAA GAA AAG TGC CCA AAT GAG TTT ACT     192
Val Pro Met Lys Val Gln Thr Gln Glu Lys Cys Pro Asn Glu Phe Thr
     50                  55                  60

GGT GAT CGC TGC CAA AAC TAC GTA ATG GCC AGC TTC TAC AGT ACG TCC     240
Gly Asp Arg Cys Gln Asn Tyr Val Met Ala Ser Phe Tyr Ser Thr Ser
 65                  70                  75                  80

ACT CCC TTT CTG TCT CTG CCT GAA TAG                                 267
Thr Pro Phe Leu Ser Leu Pro Glu
                 85
```

( 2 ) INFORMATION FOR SEQ ID NO: 159:

( i ) SEQUENCE CHARACTERISTICS:
        ( A ) LENGTH: 252
        ( B ) TYPE: nucleic acid
        ( C ) STRANDEDNESS: double
        ( D ) TOPOLOGY: linear ( x i ) SEQUENCE DESCRIPTION: SEQ ID NO: 159:

```
AGC CAT CTT GTC AAG TGT GCA GAG AAG GAG AAA ACT TTC TGT GTG AAT      48
Ser His Leu Val Lys Cys Ala Glu Lys Glu Lys Thr Phe Cys Val Asn
 1               5                  10                  15

GGA GGC GAG TGC TTC ATG GTG AAA GAC CTT TCA AAT CCC TCA AGA TAC      96
Gly Gly Glu Cys Phe Met Val Lys Asp Leu Ser Asn Pro Ser Arg Tyr
             20                  25                  30

TTG TGC AAG TGC CAA CCT GGA TTC ACT GGA GCG AGA TGT ACT GAG AAT     144
```

```
Leu  Cys  Lys  Cys  Gln  Pro  Gly  Phe  Thr  Gly  Ala  Arg  Cys  Thr  Glu  Asn
          35                       40                      45

GTG  CCC  ATG  AAA  GTC  CAA  ACC  CAA  GAA  AAG  TGC  CCA  AAT  GAG  TTT  ACT        192
Val  Pro  Met  Lys  Val  Gln  Thr  Gln  Glu  Lys  Cys  Pro  Asn  Glu  Phe  Thr
     50                       55                      60

GGT  GAT  CGC  TGC  CAA  AAC  TAC  GTA  ATG  GCC  AGC  TTC  TAC  AAA  GCG  GAG        240
Gly  Asp  Arg  Cys  Gln  Asn  Tyr  Val  Met  Ala  Ser  Phe  Tyr  Lys  Ala  Glu
65                       70                      75                           80

GAG  CTC  TAC  TAA                                                                    252
Glu  Leu  Tyr
```

( 2 ) INFORMATION FOR SEQ ID NO: 160:

( i ) SEQUENCE CHARACTERISTICS:
        ( A ) LENGTH: 128
        ( B ) TYPE: nucleic acid
        ( C ) STRANDEDNESS: double
        ( D ) TOPOLOGY: linear ( x i ) SEQUENCE DESCRIPTION: SEQ ID NO: 160:

```
CC  ACA  TCC  ACA  TCT  ACA  GCT  GGG  ACA  AGC  CAT  CTT  GTC  AAG  TGT  GCA         47
    Thr  Ser  Thr  Ser  Thr  Ala  Gly  Thr  Ser  His  Leu  Val  Lys  Cys  Ala
    1                        5                       10                      15

GAG  AAG  GAG  AAA  ACT  TTC  TGT  GTG  AAT  GGA  GGC  GAG  TGC  TTC  ATG  GTG        95
Glu  Lys  Glu  Lys  Thr  Phe  Cys  Val  Asn  Gly  Gly  Glu  Cys  Phe  Met  Val
                         20                      25                      30

AAA  GAC  CTT  TCA  AAT  CCC  TCA  AGA  TAC  TTG  T  GC                              128
Lys  Asp  Leu  Ser  Asn  Pro  Ser  Arg  Tyr  Leu
               35                      40
```

( 2 ) INFORMATION FOR SEQ ID NO: 161:

( i ) SEQUENCE CHARACTERISTICS:
        ( A ) LENGTH: 141
        ( B ) TYPE: nucleic acid
        ( C ) STRANDEDNESS: double
        ( D ) TOPOLOGY: linear ( x i ) SEQUENCE DESCRIPTION: SEQ ID NO: 161:

```
A  CAT  AAC  CTT  ATA  GCT  GAG  CTA  AGG  AGA  AAC  AAG  GCC  CAC  AGA  TCC         46
   His  Asn  Leu  Ile  Ala  Glu  Leu  Arg  Arg  Asn  Lys  Ala  His  Arg  Ser
   1                   5                       10                      15

AAA  TGC  ATG  CAG  ATC  CAG  CTT  TCC  GCA  ACT  CAT  CTT  AGA  GCT  TCT  TCC        94
Lys  Cys  Met  Gln  Ile  Gln  Leu  Ser  Ala  Thr  His  Leu  Arg  Ala  Ser  Ser
                    20                      25                      30

ATT  CCC  CAT  TGG  GCT  TCA  TTC  TCT  AAG  ACC  CCT  TGG  CCT  TTA  GGA  AG        141
Ile  Pro  His  Trp  Ala  Ser  Phe  Ser  Lys  Thr  Pro  Trp  Pro  Leu  Gly  Arg
               35                      40                      45
```

( 2 ) INFORMATION FOR SEQ ID NO: 162:

( i ) SEQUENCE CHARACTERISTICS:
        ( A ) LENGTH: 24
        ( B ) TYPE: amino acid
        ( C ) STRANDEDNESS:
        ( D ) TOPOLOGY: linear ( i x ) FEATURE:
        ( D ) OTHER INFORMATION: Xaa in positions 15 and 22 is
        unknown.

( x i ) SEQUENCE DESCRIPTION: SEQ ID NO: 162:

```
Ala  Ala  Glu  Lys  Glu  Lys  Thr  Phe  Cys  Val  Asn  Gly  Gly  Glu  Xaa  Phe
1                   5                        10                      15

Met  Val  Lys  Asp  Leu  Xaa  Asn  Pro
                    20
```

( 2 ) INFORMATION FOR SEQ ID NO: 163:

( i ) SEQUENCE CHARACTERISTICS:
        ( A ) LENGTH: 745
        ( B ) TYPE: nucleic acid
        ( C ) STRANDEDNESS: double
        ( D ) TOPOLOGY: linear ( x i ) SEQUENCE DESCRIPTION: SEQ ID NO: 163:

```
ATG AGA TGG CGA CGC GCC CCG CGC CGC TCC GGG CGT CCC GGC CCC CGG        48
Met Arg Trp Arg Arg Ala Pro Arg Arg Ser Gly Arg Pro Gly Pro Arg
 1           5                  10                  15

GCC CAG CGC CCC GGC TCC GCC GCC CGC TCG TCG CCG CCG CTG CCG CTG        96
Ala Gln Arg Pro Gly Ser Ala Ala Arg Ser Ser Pro Pro Leu Pro Leu
             20                  25                  30

CTG CCA CTA CTG CTG CTG CTG GGG ACC GCG GCC CTG GCG CCG GGG GCG       144
Leu Pro Leu Leu Leu Leu Leu Gly Thr Ala Ala Leu Ala Pro Gly Ala
         35                  40                  45

GCG GCC GGC AAC GAG GCG GCT CCC GCG GGG GCC TCG GTG TGC TAC TCG       192
Ala Ala Gly Asn Glu Ala Ala Pro Ala Gly Ala Ser Val Cys Tyr Ser
     50                  55                  60

TCC CCG CCC AGC GTG GGA TCG GTG CAG GAG CTA GCT CAG CGC GCC GCG       240
Ser Pro Pro Ser Val Gly Ser Val Gln Glu Leu Ala Gln Arg Ala Ala
 65                  70                  75                  80

GTG GTG ATC GAG GGA AAG GTG CAC CCG CAG CGG CGG CAG CAG GGG GCA       288
Val Val Ile Glu Gly Lys Val His Pro Gln Arg Arg Gln Gln Gly Ala
                 85                  90                  95

CTC GAC AGG AAG GCG GCG GCG GCG GCG GGC GAG GCA GGG GCG TGG GGC       336
Leu Asp Arg Lys Ala Ala Ala Ala Ala Gly Glu Ala Gly Ala Trp Gly
            100                 105                 110

GGC GAT CGC GAG CCG CCA GCC GCG GGC CCA CGG GCG CTG GGG CCG CCC       384
Gly Asp Arg Glu Pro Pro Ala Ala Gly Pro Arg Ala Leu Gly Pro Pro
        115                 120                 125

GCC GAG GAG CCG CTG CTC GCC GCC AAC GGG ACC GTG CCC TCT TGG CCC       432
Ala Glu Glu Pro Leu Leu Ala Ala Asn Gly Thr Val Pro Ser Trp Pro
    130                 135                 140

ACC GCC CCG GTG CCC AGC GCC GGC GAG CCC GGG GAG GAG GCG CCC TAT       480
Thr Ala Pro Val Pro Ser Ala Gly Glu Pro Gly Glu Glu Ala Pro Tyr
145                 150                 155                 160

CTG GTG AAG GTG CAC CAG GTG TGG GCG GTG AAA GCC GGG GGC TTG AAG       528
Leu Val Lys Val His Gln Val Trp Ala Val Lys Ala Gly Gly Leu Lys
                165                 170                 175

AAG GAC TCG CTG CTC ACC GTG CGC CTG GGG ACC TGG GGC CAC CCC GCC       576
Lys Asp Ser Leu Leu Thr Val Arg Leu Gly Thr Trp Gly His Pro Ala
            180                 185                 190

TTC CCC TCC TGC GGG AGG CTC AAG GAG GAC AGC AGG TAC ATC TTC TTC       624
Phe Pro Ser Cys Gly Arg Leu Lys Glu Asp Ser Arg Tyr Ile Phe Phe
        195                 200                 205

ATG GAG CCC GAC GCC AAC AGC ACC AGC CGC GCG CCG GCC GCC TTC CGA       672
Met Glu Pro Asp Ala Asn Ser Thr Ser Arg Ala Pro Ala Ala Phe Arg
    210                 215                 220

GCC TCT TTC CCC CCT CTG GAG ACG GGC CGG AAC CTC AAG AAG GAG GTC       720
Ala Ser Phe Pro Pro Leu Glu Thr Gly Arg Asn Leu Lys Lys Glu Val
225                 230                 235                 240

AGC CGG GTG CTG TGC AAG CGG TGC G                                     745
Ser Arg Val Leu Cys Lys Arg Cys
                245
```

( 2 ) INFORMATION FOR SEQ ID NO: 164:

( i ) SEQUENCE CHARACTERISTICS:

(A) LENGTH: 12
                (B) TYPE: amino acid
                (C) STRANDEDNESS:
                (D) TOPOLOGY: linear (ix) FEATURE:
                (D) OTHER INFORMATION: Xaa in position 1 is unknown.

(xi) SEQUENCE DESCRIPTION: SEQ ID NO: 164:

Xaa  Ala  Leu  Ala  Ala  Ala  Gly  Tyr  Asp  Val  Glu  Lys
 1              5                        10

(2) INFORMATION FOR SEQ ID NO: 165:

(i) SEQUENCE CHARACTERISTICS:
                (A) LENGTH: 5
                (B) TYPE: amino acid
                (C) STRANDEDNESS:
                (D) TOPOLOGY: linear (ix) FEATURE:
                (D) OTHER INFORMATION: Xaa in position 1 is unknown.

(xi) SEQUENCE DESCRIPTION: SEQ ID NO: 165:

Xaa  Leu  Val  Leu  Arg
 1              5

(2) INFORMATION FOR SEQ ID NO: 166:

(i) SEQUENCE CHARACTERISTICS:
                (A) LENGTH: 11
                (B) TYPE: amino acid
                (C) STRANDEDNESS:
                (D) TOPOLOGY: linear (ix) FEATURE:
                (D) OTHER INFORMATION: Xaa in positions 1, 2, and 3 is
                        unknown.

(xi) SEQUENCE DESCRIPTION: SEQ ID NO: 166:

Xaa  Xaa  Xaa  Tyr  Pro  Gly  Gln  Ile  Thr  Ser  Asn
 1              5                        10

(2) INFORMATION FOR SEQ ID NO: 167:

(i) SEQUENCE CHARACTERISTICS:
                (A) LENGTH: 60
                (B) TYPE: nucleic acid
                (C) STRANDEDNESS: double
                (D) TOPOLOGY: linear (ix) FEATURE:
                (D) OTHER INFORMATION: N in positions 25 and 36 is unknown.

(xi) SEQUENCE DESCRIPTION: SEQ ID NO: 167:

ATAGGGAAGG  GCGGGGGAAG  GGTCNCCCTC  NGCAGGGCCG  GGCTTGCCTC  TGGAGCCTCT                60

(2) INFORMATION FOR SEQ ID NO: 168:

(i) SEQUENCE CHARACTERISTICS:
                (A) LENGTH: 18
                (B) TYPE: nucleic acid
                (C) STRANDEDNESS: double
                (D) TOPOLOGY: linear (ix) FEATURE:
                (D) OTHER INFORMATION: N in position 16 is unknown.

(xi) SEQUENCE DESCRIPTION: SEQ ID NO: 168:

TTTACACATA  TATTCNCC                                                                   18

( 2 ) INFORMATION FOR SEQ ID NO: 169:

( i ) SEQUENCE CHARACTERISTICS:
        ( A ) LENGTH: 21
        ( B ) TYPE: amino acid
        ( C ) STRANDEDNESS:
        ( D ) TOPOLOGY: linear ( x i ) SEQUENCE DESCRIPTION: SEQ ID NO: 169:

```
Glu Thr Gln Pro Asp Pro Gly Gln Ile Leu Lys Lys Val Pro Met Val
 1               5                  10                  15
Ile Gly Ala Tyr Thr
            20
```

( 2 ) INFORMATION FOR SEQ ID NO: 170:

( i ) SEQUENCE CHARACTERISTICS:
        ( A ) LENGTH: 422
        ( B ) TYPE: amino acid
        ( C ) STRANDEDNESS:
        ( D ) TOPOLOGY: linear ( x i ) SEQUENCE DESCRIPTION: SEQ ID NO: 170:

```
Met Arg Trp Arg Arg Ala Pro Arg Arg Ser Gly Arg Pro Gly Pro Arg
 1               5                  10                  15
Ala Gln Arg Pro Gly Ser Ala Ala Arg Ser Ser Pro Pro Leu Pro Leu
                20                  25                  30
Leu Pro Leu Leu Leu Leu Leu Gly Thr Ala Ala Leu Ala Pro Gly Ala
                35                  40                  45
Ala Ala Gly Asn Glu Ala Ala Pro Ala Gly Ala Ser Val Cys Tyr Ser
        50                  55                  60
Ser Pro Pro Ser Val Gly Ser Val Gln Glu Leu Ala Gln Arg Ala Ala
65                  70                  75                  80
Val Val Ile Glu Gly Lys Val His Pro Gln Arg Arg Gln Gln Gly Ala
                85                  90                  95
Leu Asp Arg Lys Ala Ala Ala Ala Ala Gly Glu Ala Gly Ala Trp Gly
                100                 105                 110
Gly Asp Arg Glu Pro Pro Ala Ala Gly Pro Arg Ala Leu Gly Pro Pro
                115                 120                 125
Ala Glu Glu Pro Leu Leu Ala Ala Asn Gly Thr Val Pro Ser Trp Pro
        130                 135                 140
Thr Ala Pro Val Pro Ser Ala Gly Glu Pro Gly Glu Glu Ala Pro Tyr
145                 150                 155                 160
Leu Val Lys Val His Gln Val Trp Ala Val Lys Ala Gly Gly Leu Lys
                165                 170                 175
Lys Asp Ser Leu Leu Thr Val Arg Leu Gly Thr Trp Gly His Pro Ala
                180                 185                 190
Phe Pro Ser Cys Gly Arg Leu Lys Glu Asp Ser Arg Tyr Ile Phe Phe
                195                 200                 205
Met Glu Pro Asp Ala Asn Ser Thr Ser Arg Ala Pro Ala Ala Phe Arg
        210                 215                 220
Ala Ser Phe Pro Pro Leu Glu Thr Gly Arg Asn Leu Lys Lys Glu Val
225                 230                 235                 240
Ser Arg Val Leu Cys Lys Arg Cys Ala Leu Pro Pro Gln Leu Lys Glu
                245                 250                 255
Met Lys Ser Gln Glu Ser Ala Ala Gly Ser Lys Leu Val Leu Arg Cys
                260                 265                 270
Glu Thr Ser Ser Glu Tyr Ser Ser Leu Arg Phe Lys Trp Phe Lys Asn
```

275                          280                          285
Gly Asn Glu Leu Asn Arg Lys Asn Lys Pro Gln Asn Ile Lys Ile Gln
    290                          295                 300

Lys Lys Pro Gly Lys Ser Glu Leu Arg Ile Asn Lys Ala Ser Leu Ala
305                 310                 315                          320

Asp Ser Gly Glu Tyr Met Cys Lys Val Ile Ser Lys Leu Gly Asn Asp
                325                 330                     335

Ser Ala Ser Ala Asn Ile Thr Ile Val Glu Ser Asn Ala Thr Ser Thr
                340              345                 350

Ser Thr Thr Gly Thr Ser His Leu Val Lys Cys Ala Glu Lys Glu Lys
        355                 360                 365

Thr Phe Cys Val Asn Gly Gly Glu Cys Phe Met Val Lys Asp Leu Ser
    370                 375                 380

Asn Pro Ser Arg Tyr Leu Cys Lys Cys Pro Asn Glu Phe Thr Gly Asp
385                 390                 395                     400

Arg Cys Gln Asn Tyr Val Met Ala Ser Phe Tyr Ser Thr Ser Thr Pro
                405                 410                 415

Phe Leu Ser Leu Pro Glu
                420

( 2 ) INFORMATION FOR SEQ ID NO: 171:

( i ) SEQUENCE CHARACTERISTICS:
        ( A ) LENGTH: 69
        ( B ) TYPE: amino acid
        ( C ) STRANDEDNESS:
        ( D ) TOPOLOGY: linear ( x i ) SEQUENCE DESCRIPTION: SEQ ID NO: 171:

Met Ser Glu Arg Lys Glu Gly Arg Gly Lys Gly Lys Gly Lys Lys Lys
1               5                   10                      15

Glu Arg Gly Ser Gly Lys Lys Pro Glu Ser Ala Ala Gly Ser Gln Ser
                20                  25                  30

Pro Arg Glu Ile Ile Thr Gly Met Pro Ala Ser Thr Glu Gly Ala Tyr
            35                  40                  45

Val Ser Ser Glu Ser Pro Ile Arg Ile Ser Val Ser Thr Glu Gly Ala
        50                  55                  60

Asn Thr Ser Ser Ser
65

( 2 ) INFORMATION FOR SEQ ID NO: 172:

( i ) SEQUENCE CHARACTERISTICS:
        ( A ) LENGTH: 19
        ( B ) TYPE: amino acid
        ( C ) STRANDEDNESS:
        ( D ) TOPOLOGY: linear ( x i ) SEQUENCE DESCRIPTION: SEQ ID NO: 172:

Arg Lys Gly Asp Val Pro Gly Pro Arg Val Lys Ser Ser Arg Ser Thr
1               5                   10                      15

Thr Thr Ala ( 2 ) INFORMATION FOR SEQ ID NO: 173:

( i ) SEQUENCE CHARACTERISTICS:
        ( A ) LENGTH: 231
        ( B ) TYPE: nucleic acid
        ( C ) STRANDEDNESS: double
        ( D ) TOPOLOGY: linear (xi) SEQUENCE DESCRIPTION: SEQ ID NO: 173:

```
CGCGAGCGCC  TCAGCGCGGC  CGCTCGCTCT  CCCCCTCGAG  GGACAAACTT  TTCCCAAACC    60
CGATCCGAGC  CCTTGGACCA  AACTCGCCTG  CGCCGAGAGC  CGTCCGCGTA  GAGCGCTCCG   120
TCTCCGGCGA  GATGTCCGAG  CGCAAAGAAG  GCAGAGGCAA  AGGGAAGGGC  AAGAAGAAGG   180
AGCGAGGCTC  CGGCAAGAAG  CCGGAGTCCG  CGGCGGGCAG  CCAGAGCCCA  G            231
```

(2) INFORMATION FOR SEQ ID NO: 174:

(i) SEQUENCE CHARACTERISTICS:
        (A) LENGTH: 178
        (B) TYPE: nucleic acid
        (C) STRANDEDNESS: double
        (D) TOPOLOGY: linear (xi) SEQUENCE DESCRIPTION: SEQ ID NO: 174:

```
CCTTGCCTCC  CCGATTGAAA  GAGATGAAAA  GCCAGGAATC  GGCTGCAGGT  TCCAAACTAG    60
TCCTTCGGTG  TGAAACCAGT  TCTGAATACT  CCTCTCTCAG  ATTCAAGTGG  TTCAAGAATG   120
GGAATGAATT  GAATCGAAAA  AACAAACCAC  AAAATATCAA  GATACAAAAA  AAGCCAGG     178
```

(2) INFORMATION FOR SEQ ID NO: 175:

(i) SEQUENCE CHARACTERISTICS:
        (A) LENGTH: 122
        (B) TYPE: nucleic acid
        (C) STRANDEDNESS: double
        (D) TOPOLOGY: linear (xi) SEQUENCE DESCRIPTION: SEQ ID NO: 175:

```
GAAGTCAGAA  CTTCGCATTA  ACAAAGCATC  ACTGGCTGAT  TCTGGAGAGT  ATATGTGCAA    60
AGTGATCAGC  AAATTAGGAA  ATGACAGTGC  CTCTGCCAAT  ATCACCATCG  TGGAATCAAA   120
CG                                                                       122
```

(2) INFORMATION FOR SEQ ID NO: 176:

(i) SEQUENCE CHARACTERISTICS:
        (A) LENGTH: 102
        (B) TYPE: nucleic acid
        (C) STRANDEDNESS: double
        (D) TOPOLOGY: linear (xi) SEQUENCE DESCRIPTION: SEQ ID NO: 176:

```
AGATCATCAC  TGGTATGCCA  GCCTCAACTG  AAGGAGCATA  TGTGTCTTCA  GAGTCTCCCA    60
TTAGAATATC  AGTATCCACA  GAAGGAGCAA  ATACTTCTTC  AT                       102
```

(2) INFORMATION FOR SEQ ID NO: 177:

(i) SEQUENCE CHARACTERISTICS:
        (A) LENGTH: 128
        (B) TYPE: nucleic acid
        (C) STRANDEDNESS: double
        (D) TOPOLOGY: linear (xi) SEQUENCE DESCRIPTION: SEQ ID NO: 177:

```
CTACATCTAC  ATCCACCACT  GGGACAAGCC  ATCTTGTAAA  ATGTGCGGAG  AAGGAGAAAA    60
CTTTCTGTGT  GAATGGAGGG  GAGTGCTTCA  TGGTGAAAGA  CCTTTCAAAC  CCCTCGAGAT   120
ACTTGTGC                                                                 128
```

(2) INFORMATION FOR SEQ ID NO: 178:

(i) SEQUENCE CHARACTERISTICS:

( A ) LENGTH: 69
( B ) TYPE: nucleic acid
( C ) STRANDEDNESS: double
( D ) TOPOLOGY: linear ( x i ) SEQUENCE DESCRIPTION: SEQ ID NO: 178:

| | | | | | |
|---|---|---|---|---|---|
| AAGTGCCAAC | CTGGATTCAC | TGGAGCAAGA | TGTACTGAGA | ATGTGCCCAT | GAAAGTCCAA | 60
| AACCAAGAA | | | | | | 69

( 2 ) INFORMATION FOR SEQ ID NO: 179:

( i ) SEQUENCE CHARACTERISTICS:
        ( A ) LENGTH: 60
        ( B ) TYPE: nucleic acid
        ( C ) STRANDEDNESS: double
        ( D ) TOPOLOGY: linear ( x i ) SEQUENCE DESCRIPTION: SEQ ID NO: 179:

AAGTGCCCAA ATGAGTTTAC TGGTGATCGC TGCCAAAACT ACGTAATGGC CAGCTTCTAC        60

( 2 ) INFORMATION FOR SEQ ID NO: 180:

( i ) SEQUENCE CHARACTERISTICS:
        ( A ) LENGTH: 36
        ( B ) TYPE: nucleic acid
        ( C ) STRANDEDNESS: double
        ( D ) TOPOLOGY: linear ( x i ) SEQUENCE DESCRIPTION: SEQ ID NO: 180:

AGTACGTCCA CTCCCTTTCT GTCTCTGCCT GAATAG        36

( 2 ) INFORMATION FOR SEQ ID NO: 181:

( i ) SEQUENCE CHARACTERISTICS:
        ( A ) LENGTH: 569
        ( B ) TYPE: nucleic acid
        ( C ) STRANDEDNESS: double
        ( D ) TOPOLOGY: linear ( x i ) SEQUENCE DESCRIPTION: SEQ ID NO: 181:

| | | | | | |
|---|---|---|---|---|---|
| AAGGCGGAGG | AGCTGTACCA | GAAGAGAGTG | CTGACCATAA | CCGGCATCTG | CATCGCCCTC | 60
| CTTGTGGTCG | GCATCATGTG | TGTGGTGGCC | TACTGCAAAA | CCAAGAAACA | GCGGAAAAAG | 120
| CTGCATGACC | GTCTTCGGCA | GAGCCTTCGG | TCTGAACGAA | ACAATATGAT | GAACATTGCC | 180
| AATGGGCCTC | ACCATCCTAA | CCCACCCCCC | GAGAATGTCC | AGCTGGTGAA | TCAATACGTA | 240
| TCTAAAAACG | TCATCTCCAG | TGAGCATATT | GTTGAGAGAG | AAGCAGAGAC | ATCCTTTTCC | 300
| ACCAGTCACT | ATACTTCCAC | AGCCCATCAC | TCCACTACTG | TCACCCAGAC | TCCTAGCCAC | 360
| AGCTGGAGCA | ACGGACACAC | TGAAAGCATC | CTTTCGAAA | GCCACTCTGT | AATCGTGATG | 420
| TCATCCGTAG | AAAACAGTAG | GCACAGCAGC | CCAACTGGGG | GCCCAAGAGG | ACGTCTTAAT | 480
| GGCACAGGAG | GCCCTCGTGA | ATGTAACAGC | TTCCTCAGGC | ATGCCAGAGA | AACCCCTGAT | 540
| TCCTACCGAG | ACTCTCCTCA | TAGTGAAAG | | | | 569

( 2 ) INFORMATION FOR SEQ ID NO: 182:

( i ) SEQUENCE CHARACTERISTICS:
        ( A ) LENGTH: 730
        ( B ) TYPE: nucleic acid
        ( C ) STRANDEDNESS: double
        ( D ) TOPOLOGY: linear ( x i ) SEQUENCE DESCRIPTION: SEQ ID NO: 182:

GTATGTGTCA GCCATGACCA CCCCGGCTCG TATGTCACCT GTAGATTTCC ACACGCCAAG        60

| | | | | | |
|---|---|---|---|---|---|
|CTCCCCCAAA|TCGCCCCCTT|CGGAAATGTC|TCCACCCGTG|TCCAGCATGA|CGGTGTCCAT|120
|GCCTTCCATG|GCGGTCAGCC|CCTTCATGGA|AGAAGAGAGA|CCTCTACTTC|TCGTGACACC|180
|ACCAAGGCTG|CGGGAGAAGA|AGTTTGACCA|TCACCCTCAG|CAGTTCAGCT|CCTTCCACCA|240
|CAACCCCGCG|CATGACAGTA|ACAGCCTCCC|TGCTAGCCCC|TTGAGGATAG|TGGAGGATGA|300
|GGAGTATGAA|ACGACCCAAG|AGTACGAGCC|AGCCCAAGAG|CCTGTTAAGA|AACTCGCCAA|360
|TAGCCGGCGG|GCCAAAAGAA|CCAAGCCCAA|TGGCCACATT|GCTAACAGAT|TGGAAGTGGA|420
|CAGCAACACA|AGCTCCCAGA|GCAGTAACTC|AGAGAGTGAA|ACAGAAGATG|AAAGAGTAGG|480
|TGAAGATACG|CCTTTCCTGG|GCATACAGAA|CCCCCTGGCA|GCCAGTCTTG|AGGCAACACC|540
|TGCCTTCCGC|CTGGCTGACA|GCAGGACTAA|CCCAGCAGGC|CGCTTCTCGA|CACAGGAAGA|600
|AATCCAGGCC|AGGCTGTCTA|GTGTAATTGC|TAACCAAGAC|CCTATTGCTG|TATAAAACCT|660
|AAATAAACAC|ATAGATTCAC|CTGTAAAACT|TTATTTTATA|TAATAAAGTA|TTCCACCTTA|720
|AATTAAACAA| | | | | |730

(2) INFORMATION FOR SEQ ID NO: 183:

(i) SEQUENCE CHARACTERISTICS:
(A) LENGTH: 20
(B) TYPE: nucleic acid
(C) STRANDEDNESS: double
(D) TOPOLOGY: linear (xi) SEQUENCE DESCRIPTION: SEQ ID NO: 183:

AAAGCCGGGG GCTTGAAGAA                    20

(2) INFORMATION FOR SEQ ID NO: 184:

(i) SEQUENCE CHARACTERISTICS:
(A) LENGTH: 20
(B) TYPE: nucleic acid
(C) STRANDEDNESS: double
(D) TOPOLOGY: linear (xi) SEQUENCE DESCRIPTION: SEQ ID NO: 184:

ATGARGTGTG GGCGGCGAAA                    20